(12) United States Patent
Xiao et al.

(10) Patent No.: US 8,846,873 B2
(45) Date of Patent: Sep. 30, 2014

(54) ANTIBODIES DIRECTED TO GPNMB AND USES THEREOF

(75) Inventors: Feng Xiao, Union City, CA (US); Xiao-Chi Jia, Los Angeles, CA (US); Meina Liang, Fremont, CA (US); Orit Foord, Foster City, CA (US); Scott Klakamp, Fremont, CA (US); Kam Fai Tse, Clinton, CT (US); Vincent A. Pollack, Gales Ferry, CT (US); Luca Rastelli, Guilford, CT (US); John Herrmann, Bothell, WA (US); Henri Lichenstein, Guilford, CT (US); Michael Jeffers, Branford, CT (US); William LaRochelle, Madison, CT (US); Gulshan Ara, Northford, CT (US); Peter Mezes, Old Lyme, CT (US); Andrei Chapoval, Towson, MD (US); Cyrus Karkaria, Branford, CT (US); Michael Torgov, Middletown, CT (US); Juan Davagnino, Madison, CT (US)

(73) Assignees: Celldex Therapeutics, Inc., Needham, MA (US); Amgen Fremont, Inc., Fremont, CA (US)

( * ) Notice: Subject to any disclaimer, the term of this patent is extended or adjusted under 35 U.S.C. 154(b) by 0 days.

(21) Appl. No.: 13/355,366

(22) Filed: Jan. 20, 2012
(Under 37 CFR 1.47)

(65) Prior Publication Data
US 2013/0022597 A1 Jan. 24, 2013

Related U.S. Application Data

(63) Continuation of application No. 13/151,690, filed on Jun. 2, 2011, now abandoned, which is a continuation of application No. 12/911,269, filed on Oct. 25, 2010, now abandoned, which is a continuation of application No. 12/721,099, filed on Mar. 10, 2010, now abandoned, which is a continuation of application No. 12/506,029, filed on Jul. 20, 2009, now abandoned, which is a continuation of application No. 12/290,779, filed on Nov. 3, 2008, now abandoned, which is a continuation of application No. 11/792,032, filed as application No. PCT/US2005/043482 on Nov. 30, 2005, now abandoned.

(60) Provisional application No. 60/632,023, filed on Nov. 30, 2004, provisional application No. 60/733,779, filed on Nov. 7, 2005.

(51) Int. Cl.
| C07K 16/30 | (2006.01) |
| C07K 19/00 | (2006.01) |
| C07K 16/28 | (2006.01) |
| A61K 47/48 | (2006.01) |
| A61K 39/00 | (2006.01) |

(52) U.S. Cl.
CPC ....... *A61K 47/48438* (2013.01); *C07K 2317/94* (2013.01); *A61K 2039/545* (2013.01); *C07K 16/2809* (2013.01); *C07K 2317/62* (2013.01); *C07K 2317/732* (2013.01); *A61K 47/48569* (2013.01); *C07K 2317/31* (2013.01); *C07K 16/30* (2013.01); *C07K 2317/622* (2013.01); *C07K 2317/73* (2013.01); *C07K 2317/77* (2013.01); *A61K 47/48561* (2013.01); *C07K 2317/21* (2013.01); *A61K 2039/505* (2013.01)
USPC ............. 530/388.85; 530/387.3; 530/388.15; 530/391.7

(58) Field of Classification Search
None
See application file for complete search history.

(56) References Cited

U.S. PATENT DOCUMENTS

| 4,179,337 A | 12/1979 | Davis et al. |
| 4,301,144 A | 11/1981 | Iwashita et al. |
| 4,486,414 A | 12/1984 | Pettit |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,444 A | 3/1989 | Pettit et al. |
| 4,879,278 A | 11/1989 | Pettit et al. |
| 4,978,744 A | 12/1990 | Pettit et al. |
| 4,986,988 A | 1/1991 | Pettit et al. |
| 5,076,973 A | 12/1991 | Pettit et al. |

(Continued)

FOREIGN PATENT DOCUMENTS

| WO | WO-0246475 | 6/2002 |
| WO | WO-02062947 A2 | 8/2002 |

(Continued)

OTHER PUBLICATIONS

Paul, Fundamental Immunology, 3rd Edition, 1993, pp. 292-295.*

(Continued)

*Primary Examiner* — Sheela J Huff
*Assistant Examiner* — Jessica H Roark
(74) *Attorney, Agent, or Firm* — Mintz Levin Cohn Ferris Glovsky and Popeo, P.C.; Shovon Ashraf

(57) ABSTRACT

The present invention provides fully human monoclonal antibodies that specifically bind to GPNMB, and uses thereof. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDRs) are provided. The present invention also provides immunoconjugates comprising anti-GPNMB antibodies and methods of using such immunoconjugates. The present invention further provides bi-specific antibodies comprising an anti-GPNMB antibody component and an anti-CD3 component, and methods of using such bispecific antibodies.

27 Claims, 22 Drawing Sheets

(56) References Cited

U.S. PATENT DOCUMENTS

| | | | |
|---|---|---|---|
| 5,138,036 | A | 8/1992 | Pettit et al. |
| 5,410,024 | A | 4/1995 | Pettit et al. |
| 5,504,191 | A | 4/1996 | Pettit et al. |
| 5,521,284 | A | 5/1996 | Pettit et al. |
| 5,530,097 | A | 6/1996 | Pettit et al. |
| 5,545,806 | A | 8/1996 | Lonberg et al. |
| 5,545,807 | A | 8/1996 | Surani et al. |
| 5,554,725 | A | 9/1996 | Pettit |
| 5,591,669 | A | 1/1997 | Krimpenfort et al. |
| 5,599,902 | A | 2/1997 | Pettit et al. |
| 5,612,205 | A | 3/1997 | Kay et al. |
| 5,625,126 | A | 4/1997 | Lonberg et al. |
| 5,625,825 | A | 4/1997 | Rostoker et al. |
| 5,633,425 | A | 5/1997 | Lonberg et al. |
| 5,635,483 | A | 6/1997 | Pettit et al. |
| 5,643,763 | A | 7/1997 | Dunn et al. |
| 5,661,016 | A | 8/1997 | Lonberg et al. |
| 5,663,149 | A | 9/1997 | Pettit et al. |
| 5,665,860 | A | 9/1997 | Pettit et al. |
| 5,721,367 | A | 2/1998 | Kay et al. |
| 5,780,588 | A | 7/1998 | Pettit et al. |
| 5,789,215 | A | 8/1998 | Berns et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 5,939,598 | A | 8/1999 | Kucherlapati et al. |
| 5,981,175 | A | 11/1999 | Loring et al. |
| 6,034,065 | A | 3/2000 | Pettit et al. |
| 6,075,181 | A | 6/2000 | Kucherlapati et al. |
| 6,150,584 | A | 11/2000 | Kucherlapati et al. |
| 6,162,963 | A | 12/2000 | Kucherlapati et al. |
| 6,255,458 | B1 | 7/2001 | Lonberg et al. |
| 6,323,315 | B1 | 11/2001 | Pettit et al. |
| 7,115,265 | B1 | 10/2006 | Riggins et al. |
| 7,968,684 | B2 * | 6/2011 | Ghayur et al. ............. 530/387.1 |
| 8,067,544 | B2 * | 11/2011 | Landes et al. ............. 530/387.1 |
| 2002/0102264 | A1 | 8/2002 | Cheung |
| 2002/0151486 | A1 * | 10/2002 | Popoff et al. .................. 514/12 |
| 2003/0064947 | A1 | 4/2003 | Wang et al. |
| 2003/0083263 | A1 | 5/2003 | Doronina et al. |
| 2003/0100720 | A1 | 5/2003 | Baker et al. |
| 2003/0157730 | A1 | 8/2003 | Walker et al. |
| 2003/0202938 | A1 * | 10/2003 | Rameshwar ................. 424/1.49 |
| 2005/0026881 | A1 * | 2/2005 | Robinson et al. ............. 514/170 |
| 2005/0059087 | A1 * | 3/2005 | Weber et al. .................. 435/7.1 |
| 2013/0058948 | A1 * | 3/2013 | Jeffers et al. ............... 424/156.1 |
| 2013/0156784 | A1 * | 6/2013 | Jeffers et al. ............... 424/142.1 |

FOREIGN PATENT DOCUMENTS

| | | |
|---|---|---|
| WO | WO-02/088172 | 11/2002 |
| WO | WO-03/080856 | 10/2003 |
| WO | WO-2004/010957 | 2/2004 |
| WO | WO-2004073656 | 9/2004 |

OTHER PUBLICATIONS

Baeuerle et al., "Bispecific antibodies for polyclonal T-cell engagement" Curr. Opin. Mol. Ther. 5:413-419 (2003).

Bandari et al, "Hematopoietic growth factor inducible neurokinin-1 type: a transmembrane protein that is similar to neurokinin 1 interacts with substance P" Reg. Peptides 111:169-178), (2003).

Bird et al., "Single-Chain Antigen-Binding Proteins" Science 242:423-426 (1988).

Boulianne, et al. "Production of functional chimaeric mouse/human antibody" 1984 Nature 312:643-646.

Chapoval et al., "Anti-CD3 X Anti-Tumor F(ab'), Bifunctional Antibody Activates and Retargets Tumor-Infiltrating Lymphocytes" J. Immunol 155:1296-1303 (1995)).

Chen et al., "Immunoglobulin gene rearrangement in B cell deficient mice generated by targeted deletion of the JH locus" Int Immunol. Jun. 1993;5(6):647-656.

Choi et al., "Transgenic mice containing a human heavy chain immunoglobulin gene fragment cloned in a yeast artificial chromosome" Nat Genet. Jun. 1993;4(2):117-23. Erratum in: Nat Genet Jul. 1993;4(3):320.

de Haard, et al, "A Large Non-immunized Human Fab Fragment Phage Library That Permits Rapid Isolation and Kinetic Analysis of High Affinity Antibodies" 1999 J Biol. Chem. 274: 18218-18230.

Denzin et al., "Single-chain Site-specific Mutations of Fluorescein-Amino Acid Contact Residues in High Affinity Monoclonal Antibody 4-4-20*'" J Biol Chem. Jul. 25, 1991;266(21):14095-103.

Doronina S.O. et al, "Development of potent monoclonal antibody auristatin conjugates for cancer therapy" 2003 Nature Biotechnology 21(7):778-794.

Dykes et al., Development of human tumor xenograft models for in vivo evaluation of new antitumor drugs, in Immunodeficient mice in Oncology, vol. 42 (Fiebig HH and Berger DPe eds) pp. 1-22, Contrib. Oncol. Basel, Karger (1992).

Fishwild, et al, 1996 "High-avidity human monoclonal antibodies from a novel strain of minilocus transgenic mice" Nature Biotechnol 14:845-851.

Fogh et al., "One Hundred and Twenty-Seven Cultured Human Tumor Cell Lines Producing Tumors in Nude Mice" J. Natl. Cancer Inst. 59: 221-226 (1977.

Geran et al., "Protocols for Screening Chemical Agents and Natural Products Against Animal Tumors and Other Biological Systems (Third Edition): Melanotic Melanoma B16 " Cancer Chemother. Rep. 3:11 (1972).

Green and Jakobovits, 1998 "Regulation of B Cell Development by Variable Gene Complexity in Mice Reconstituted with Human Immunoglobulin Yeast Artificial Chromosomes" J. Exp. Med. 188:483-495.

Green et al. 1994 "Antigen-specific human monoclonal antibodies from mice engineered with human Ig heavy and light chain YACs" Nature Genetics 7:13-21.

Griffiths et al "Isolation of high affinity human antibodies directly from large synthetic repertoires" EMBO J. 13:3245-3260), (1994).

Hamblett et al., "Effects of Drug Loading on the Antitumor Activity of a Monoclonal Antibody Drug Conjugate" Clin. Cancer Res. 10: 7063-7070 (2004).

Hickman et al., "C-Terminal Epitope Tagging Facilitates Comparative Ligand Mapping from MHC Class I Positive Cells" Hum Immunol. Dec. 2000;61(12):1339-46.

Huston et al., "Protein engineering of antibody binding sites: Recovery of specific activity in an anti-digoxin single-chain Fv analogue produced in *Escherichia coli*" Proc. Natl. Acad. Sci. USA 85:5879-5883 (1988).

Jirik et al., "Cloning and sequence determination of a human rheumatoid factor light-chain gene" Proc Natl Acad Sci U S A. Apr. 1986;83(7):2195-9.

Johnson et al., "Relationships between drug activity in NCI preclinical in vitro and in vivo models and early clinical trials" Br J Cancer 84:1424-1431 (2001).

Jones, et al, 1986 "Replacing the complementarity-determining regions in a human antibody with those from a mouse" Nature 321: 522-525.

Kearney et al, "A New Mouse Myeloma Cell Line That Has Lost Immunoglobulin Expression But Permits the Construction of Antibody-Secreting Hybrid Cell Lines" J. Immunol. 123, 1979, 1548-1550.

Kipriyanov and Le Gall, "Recent advances in the generation of bispecific antibodies for tumor immunotherapy" Curr Opin Drug Discov Devel 7:233-242 (2004).

Kipriyanov et al., "Effect of Domain Order on the Activity of Bacterially Produced Bispecific Single-chain Fv Antibodies" J. Mol. Biol. 330:99-111 (2003).

Knappik, et al, 2000 "Fully Synthetic Human Combinatorial Antibody Libraries (HuCAL) Based on Modular Consensus Frameworks and CDRs Randomized with Trinucleotides" J. Mol. Biol. 296:57-86.

Kontermann, "Recombinant bispecific antibodies for cancer therapy" Acta Pharmacol Sin 26:1-9 (2005).

Kwon et al., 1991, "A melanocyte-specific gene, Pmel 17, maps near the silver coat color locus on mouse chromosome 10 and is in a syntenic region on human chromosome 12" PNAS 88:9228-9232).

(56) References Cited

OTHER PUBLICATIONS

Le Gall et al., "Effect of linker sequences between the antibody variable domains on the formation, stability and biological activity of a bispecific tandem diabody" Protein Eng. Des. Sel. 17:357-366 (2004).
Lobo et al., "Antibody Pharmacokinetics and Pharmacodynamics" J. Pharm. Sci. 93: 2645-2668 (2004).
Loging et al., 2000, "Identifying Potential Tumor Markers and Antigens by Database Mining and Rapid Expression Screening" Genome Research 10:1393-1402.
Lonberg et al., "Antigen-specific human antibodies from mice comprising four distinct genetic modifications" Nature. Apr. 28, 1994;368(6474):856-9.
Mack et al., "A small bispecific antibody construct expressed as a functional single-chain molecule with high tumor cell cytotoxicity" Proc Natl Acad Sci U S A. Jul. 18, 1995;92(15): 7021-5.
Mahmood and Green, "Pharmacokinetic and Pharmacodynamic Considerations in the Development of Therapeutic Proteins" Clin. Pharmacokinet 44: 331-347 (2005).
Mendez, et al, 1997 "Functional transplant of megabase human immunoglobulin loci recapitulates human antibody response in mice" Nature Genet. 15:146-156.
Morrison et al, 1984 "Chimeric human antibody molecules: Mouse antigen-binding domains with human constant region domains" PNAS USA 81:6851-6855).
Nicholson, et al, 1999 "Antibody Repertoires of Four- and Five-Feature Translocus Mice Carrying Human Immunoglobulin Heavy Chain and k and I Light Chain Yeast Artificial Chromosomes" J. Immunol 163, 6898-6906.
Owen et al., "Identification and Characterization of the Genes Encoding Human and Mouse Osteoactivin" Crit Rev Eukaryot Gene Expr 2003, 13(2-4):205-220.
Pantoliano et al., "Conformational Stability, Folding, and Ligand-Binding Affinity of Single-Chain Fv Immunoglobulin Fragments Expressed in *Escherichia coli*" Biochemistry 30:10117-10125 (1991).
Pavlinkova et al., "Radioimmunotherapy of Human Colon Cancer Xenografts Using a Dimeric Single-Chain Fv Antibody Construct" Clin Cancer Res. 5:2613-1619 (1999)).
Peipp and Valerius, "Bispecific antibodies targeting cancer cells" Biochem. Soc. Trans. 30:507-511 (2002).
Rich et al., "Bone-related Genes Expressed in Advanced Malignancies Induce Invasion and Metastasis in a Genetically Defined Human Cancer Model" J. Biol. Chem. 278:15951-15975 (2003).
Riechmann, et al, 1988 "Reshaping human antibodies for therapy" Nature 332:323-327.
Sanderson et al., "Efficient construction of a large nonimmune phage antibody library: The production of high afinity human single-chain antibodies to protein antigesn" Clin. Cancer Res. 11: 843-852 (2005).
Sheets, et al, 1998 "Efficient construction of a large nonimmune phage antibody library: The production of high-affinity human single-chain antibodies to protein antigens" PNAS USA 95:6157-6162.
Shernan et al., "Impact of Pexelizumab, an Anti-C5 Complement Antibody, on Total Mortality and Adverse Cardiovascular Outcomes in Cardiac Surgical Patients Undergoing Cardiopulmonary Bypass" Ann. Thorac Surg. 77:942-949 (2004)).
Shikano et al., 2001 "Molecular Cloning of a Dendritic Cell-associated Transmembrane Protein, DC-HIL, That Promotes RGD-dependent Adhesion of Endothelial Cells through Recognition of Heparan Sulfate Proteoglycans" Biol. Chem. 276:8125-8134.
Shimkets RA et. al. "Gene expression analysis by transcript profiling coupled to a gene database query" Nat Biotechnol., 1999. 17-8: 798-803.
Taylor et al., "Human immunoglobulin transgenes undergo rearrangement, somatic mutation and class switching in mice that lack endogenous IgM" Int Immunol. Apr. 1994;6(4):579-91.
Taylor et al., "A transgenic mouse that expresses a diversity of human sequence heavy and light chain immunoglobulins" Nucleic Acids Res. Dec. 11, 1992;20(23):6287-95.
Tuaillon et al., J Immunol. Jun. 15, 1995;154(12):6453-65.
Tuaillon et al., "Human immunoglobulin heavy-chain minilocus recombination in transgenic mice: Gene-segment use in ,u and y transcripts" Proc Natl Acad Sci USA. Apr. 15, 1993;90(8):3720-4.
Vaughan, et al, 1996 "Human Antibodies with Sub-nanomolar Affinities Isolated form a Large Non-immunized Phage Display Library" Nature Biotechnol 14:309-314.
Vaughan, et al, 1998 "Human antibodies by design" Nature Biotechnol. 16:535-539.
Verhoeyen, et al, 1988 "Reshaping Human Antibodies: Grafting an Antilysozyme Activity" Science 239:1534-1536.
Weterman et al., "nmb, A Novel Gene, Is Expressed in Low-Metastatic Human Melanoma Cell Lines and Xenografts" Int J Cancer 60:73-81, 1995.
Lutterbuese et al., GenBank Accession No. CAE85148.1, "unnamed protein product [unidentified]" Dec. 15, 2003.
Lenglet et al., GenBank Accession No. NM_002046, "Homo sapiens glyceraldehyde-3-phosphate dehydrogenase (GAPDH),transcript variant 1, mRNA", Jan. 9, 2014.
Weterman et al., GenBank Accession No. X76534, "H.sapiens NMB mRNA", Apr. 18, 2005.
Davis et al. "Transgenic Mice as a Source of Fully Human Antibodies for the Treatment of Cancer." *Cancer Metastasis Rev.* 18.4(1999):421-425.
Glabinski et al. "Chemokines and Chemokine Receptors in CNS Pathology." *J. NeuroVirol.* 5(1999):3-12.
Holt et al. "Domain Antibodies: Proteins for Therapy." *Trends Biotechnol.* 21.11(2003):484-490.
Kasahara et al. "IL-1 and TNF-α Induction of IL-8 and Monocyte Chemotactic and Activating Factor (MCAF) mRNA Expression in a Human Astrocytoma Cell Line." *Immunol.* 74.1(1991):60-67.
Kriangkum et al. "Bispecific and Bifunctional Single Chain Recombinant Antibodies." *Biomol. Eng.* 18.2(2001):31-40.
Kuan et al. "Monoclonal Antibodies Recognizing Human gpnmb$_{wt}$/gpnmb$_{sv}$ React with Human High-Grade Gliomas (HGL)." *Proceedings of the American Association for Cancer Research Annual Meeting.* 44(2003):1116-1117. (Abstract #5607).
Rudikoff et al. "Single Amino Acid Substitution Altering Antigen-Binding Specificity." *PNAS.* 79.6(1982):1979-1983.
Tse et al. "CR011, a Fully Human Monoclonal Antibody-Auristatin E Conjugate, for the Treatment of Melanoma." *Clin. Cancer Res.* 12.4(2006):1373-1382.
Tse et al. "CR011, a Potent Fully Human Monoclonal Antibody-Auristatin E Conjugate for the Treatment of Melanoma." *96th Annual Meeting of the American Association for Cancer Research in Anaheim, CA.* Apr. 16, 2005. (Abstract #557).
Van Meir et al. "Interleukin-8 is Produced in Neoplastic and Infectious Diseases of the Human Central Nervous System." *Cancer Res.* 52(1992):4297-4305.
Veltri et al. "Interleukin-8 Serum Levels in Patients with Benign Prostatic Hyperplasia and Prostate Cancer." *Urology.* 53.1(1999):139-147.

* cited by examiner

A.

B

C

A

B

Secondary Ab-PE alone (filled)
IgG$_2$ + Secondary Ab-PE (dotted line)
CR011+ Secondary Ab-PE (solid line)

C

A.

B.

A.

B.

C

SK-MEL-2

21.4-fold shift

XF-498

10-fold shift

U-118-MG

7.4-fold shift

SNB-78

8.6-fold shift

SF-539

5.4-fold shift

SF-268

1.5-fold shift

A

B

SEQUENCE LISTING

```
<160> NUMBER OF SEQ ID NOS: 395

<210> SEQ ID NO 1
<211> LENGTH: 347
<212> TYPE: DNA
<213> ORGANISM: Homo sapiens

<400> SEQUENCE: 1
aggtgcagct gcaggagtcg ggcccaggac tggtgaagcc ttcggagacc ctgtccctca      60
cctgcactgt ctctggtgac tccatcagta attactactg gagctggatc cggcagcccc     120
cagggaaggg actggagtgg attgggtatt ctattacag tgggagcacc aactacaacc      180
cctccctcaa gagtcgagtc accatatcag tagacacgtc caagaaccag ttctccctga     240
aactgagctc tgtgaccgct gcggacacgg ccgtgtatta ctgtgcgaga gatagggct      300 gggctgacta ctggggccag ggaaccctgg tcaccgtctc ctcagcc                   347

<210> SEQ ID NO 2
<211> LENGTH: 116
<212> TYPE: PRT
<213> ORGANISM: Homo sapiens

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Phe Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Asp Arg Gly Trp Ala Asp Tyr Trp Gly Gln Gly Thr Leu Val Thr
                100                 105                 110
Val Ser Ser Ala
        115

<210> SEQ ID NO 3
<211> LENGTH: 25
<212> TYPE: PRT
<213> ORGANISM: Homo sapiens

<400> SEQUENCE: 3

Gln Val Gln Leu Gln Glu Ser Gly Pro Gly Leu Val Lys Pro Ser Glu
1               5                   10                  15
Thr Leu Ser Leu Thr Cys Thr Val Ser
            20                  25

<210> SEQ ID NO 4
<211> LENGTH: 10
<212> TYPE: PRT
<213> ORGANISM: Homo sapiens

<400> SEQUENCE: 4

Gly Asp Ser Ile Ser Asn Tyr Tyr Trp Ser
1               5                   10

<210> SEQ ID NO 5
<211> LENGTH: 14
<212> TYPE: PRT
<213> ORGANISM: Homo sapiens

<400> SEQUENCE: 5

Trp Ile Arg Gln Pro Pro Gly Lys Gly Leu Glu Trp Ile Gly
1               5                   10

<210> SEQ ID NO 6
<211> LENGTH: 16
<212> TYPE: PRT
<213> ORGANISM: Homo sapiens

<400> SEQUENCE: 6

Tyr Phe Tyr Tyr Ser Gly Ser Thr Asn Tyr Asn Pro Ser Leu Lys Ser
1               5                   10                  15

<210> SEQ ID NO 7
<211> LENGTH: 32
<212> TYPE: PRT
<213> ORGANISM: Homo sapiens

<400> SEQUENCE: 7

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys Ala Arg
            20                  25                  30

<210> SEQ ID NO 8
<211> LENGTH: 7
<212> TYPE: PRT
<213> ORGANISM: Homo sapiens

<400> SEQUENCE: 8

Asp Arg Gly Trp Ala Asp Tyr
1               5
```

```
<210> SEQ ID NO 9
<211> LENGTH: 12
<212> TYPE: PRT
<213> ORGANISM: Homo sapiens

<400> SEQUENCE: 9

Trp Gly Gln Gly Thr Leu Val Thr Val Ser Ser Ala
1               5                   10

<210> SEQ ID NO 10
<211> LENGTH: 324
<212> TYPE: DNA
<213> ORGANISM: Homo sapiens

<400> SEQUENCE: 10
gaaattgtgt tgacgcagtc tccaggcacc ctgtctttgt ctccagggga aagggccacc      60
ctctcctgca gaaccagtca gagtattagc agcagctatt tagcctggta ccagcagaaa     120
cctggccagg ttcccaggct cctcatctat ggtgcttcca gcagggccac tggcatccca     180
gacaggttca gtggcagtgg gtctgggaca gacttcactc tcaccatcag cagactggag     240
cctgaagatt ttgcagtgta ttattgtcag cagtatggta gctcgatcac cttcggccaa     300
gggacacgac tggagattaa acga                                            324

<210> SEQ ID NO 11
<211> LENGTH: 108
<212> TYPE: PRT
<213> ORGANISM: Homo sapiens

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Thr Ser Gln Ser Ile Ser Ser Ser
            20                  25                  30

Tyr Leu Ala Trp Tyr Gln Gln Lys Pro Gly Gln Val Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ile
                85                  90                  95

Thr Phe Gly Gln Gly Thr Arg Leu Glu Ile Lys Arg
            100                 105

<210> SEQ ID NO 12
<211> LENGTH: 23
<212> TYPE: PRT
<213> ORGANISM: Homo sapiens

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 13
<211> LENGTH: 12
<212> TYPE: PRT
<213> ORGANISM: Homo sapiens
```

```
<400> SEQUENCE: 13

Arg Thr Ser Gln Ser Ile Ser Ser Ser Tyr Leu Ala
1               5                   10

<210> SEQ ID NO 14
<211> LENGTH: 15
<212> TYPE: PRT
<213> ORGANISM: Homo sapiens

<400> SEQUENCE: 14

Trp Tyr Gln Gln Lys Pro Gly Gln Val Pro Arg Leu Leu Ile Tyr
1               5                   10                  15

<210> SEQ ID NO 15
<211> LENGTH: 7
<212> TYPE: PRT
<213> ORGANISM: Homo sapiens

<400> SEQUENCE: 15

Gly Ala Ser Ser Arg Ala Thr
1               5

<210> SEQ ID NO 16
<211> LENGTH: 32
<212> TYPE: PRT
<213> ORGANISM: Homo sapiens

<400> SEQUENCE: 16

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 17
<211> LENGTH: 8
<212> TYPE: PRT
<213> ORGANISM: Homo sapiens

<400> SEQUENCE: 17

Gln Gln Tyr Gly Ser Ser Ile Thr
1               5

<210> SEQ ID NO 18
<211> LENGTH: 11
<212> TYPE: PRT
<213> ORGANISM: Homo sapiens

<400> SEQUENCE: 18

Phe Gly Gln Gly Thr Arg Leu Glu Ile Lys Arg
1               5                   10

<210> SEQ ID NO 19
<211> LENGTH: 360
<212> TYPE: DNA
<213> ORGANISM: Homo sapiens

<400> SEQUENCE: 19
caggtgcagc tgcaggagtc gggcccagga ctggtgaagc cttcacagac cctgtccctc       60
acctgcactg tctctggtgg ctccatcagc agttttaatt actactggag ctggatccgc      120
caccacccag ggaagggcct ggagtggatt gggtacatct attacagtgg gagcacctac      180
tccaacccgt ccctcaagag tcgagttacc atatcagtag acacgtctaa gaaccagttc      240
```

```
tccctgacgc tgagctctgt gactgccgcg gacacggccg tgtattactg tgcgagaggg    300
tataactgga actactttga ctactggggc cagggaaccc tggtcaccgt ctcctcagcc    360
```

<210> SEQ ID NO 20
<211> LENGTH: 120
<212> TYPE: PRT
<213> ORGANISM: Homo sapiens

<400> SEQUENCE: 20

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Asn Tyr Tyr Trp Ser Trp Ile Arg His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Gly Tyr Asn Trp Asn Tyr Phe Asp Tyr Trp Gly Gln Gly
            100                 105                 110

Thr Leu Val Thr Val Ser Ser Ala
        115                 120
```

<210> SEQ ID NO 21
<211> LENGTH: 30
<212> TYPE: PRT
<213> ORGANISM: Homo sapiens

<400> SEQUENCE: 21

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser
            20                  25                  30
```

<210> SEQ ID NO 22
<211> LENGTH: 7
<212> TYPE: PRT
<213> ORGANISM: Homo sapiens

<400> SEQUENCE: 22

```
Ser Phe Asn Tyr Tyr Trp Ser
1               5
```

<210> SEQ ID NO 23
<211> LENGTH: 14
<212> TYPE: PRT
<213> ORGANISM: Homo sapiens

<400> SEQUENCE: 23

```
Trp Ile Arg His His Pro Gly Lys Gly Leu Glu Trp Ile Gly
1               5                   10
```

<210> SEQ ID NO 24
<211> LENGTH: 16
<212> TYPE: PRT
<213> ORGANISM: Homo sapiens

<400> SEQUENCE: 24

Tyr Ile Tyr Tyr Ser Gly Ser Thr Tyr Ser Asn Pro Ser Leu Lys Ser
1               5                   10                  15

<210> SEQ ID NO 25
<211> LENGTH: 32
<212> TYPE: PRT
<213> ORGANISM: Homo sapiens

<400> SEQUENCE: 25

Arg Val Thr Ile Ser Val Asp Thr Ser Lys Asn Gln Phe Ser Leu Thr
1               5                   10                  15

Leu Ser Ser Val Thr Ala Ala Asp Thr Ala Val Tyr Tyr Cys Ala Arg
            20                  25                  30

<210> SEQ ID NO 26
<211> LENGTH: 9
<212> TYPE: PRT
<213> ORGANISM: Homo sapiens

<400> SEQUENCE: 26

Gly Tyr Asn Trp Asn Tyr Phe Asp Tyr
1               5

<210> SEQ ID NO 27
<211> LENGTH: 12
<212> TYPE: PRT
<213> ORGANISM: Homo sapiens

<400> SEQUENCE: 27

Trp Gly Gln Gly Thr Leu Val Thr Val Ser Ser Ala
1               5                   10

<210> SEQ ID NO 28
<211> LENGTH: 327
<212> TYPE: DNA
<213> ORGANISM: Homo sapiens

<400> SEQUENCE: 28
gaaatagtga tgacgcagtc tccagccacc ctgtctgtgt ctccagggga aagagccacc        60
ctctcctgca gggccagtca gagtgttgac aacaacttag tctggtacca gcagaaacct       120
ggccaggctc ccaggctcct catctatggt gcatccacca gggccactgg tatcccagcc       180
aggttcagtg gcagtgggtc tgggacagag ttcactctca ccatcagtag tctgcagtct       240
gaagattttg cagtttatta ctgtcagcag tataataact ggcctccgtg gacgttcggc       300
caagggacca aggtggaaat caaacga                                           327

<210> SEQ ID NO 29
<211> LENGTH: 109
<212> TYPE: PRT
<213> ORGANISM: Homo sapiens

<400> SEQUENCE: 29

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Asn Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg
            100                 105
```

<210> SEQ ID NO 30
<211> LENGTH: 23
<212> TYPE: PRT
<213> ORGANISM: Homo sapiens

<400> SEQUENCE: 30

```
Glu Ile Val Met Thr Gln Ser Pro Ala Thr Leu Ser Val Ser Pro Gly
1               5                   10                  15

Glu Arg Ala Thr Leu Ser Cys
            20
```

<210> SEQ ID NO 31
<211> LENGTH: 11
<212> TYPE: PRT
<213> ORGANISM: Homo sapiens

<400> SEQUENCE: 31

```
Arg Ala Ser Gln Ser Val Asp Asn Asn Leu Val
1               5                   10
```

<210> SEQ ID NO 32
<211> LENGTH: 15
<212> TYPE: PRT
<213> ORGANISM: Homo sapiens

<400> SEQUENCE: 32

```
Trp Tyr Gln Gln Lys Pro Gly Gln Ala Pro Arg Leu Leu Ile Tyr
1               5                   10                  15
```

<210> SEQ ID NO 33
<211> LENGTH: 7
<212> TYPE: PRT
<213> ORGANISM: Homo sapiens

<400> SEQUENCE: 33

```
Gly Ala Ser Thr Arg Ala Thr
1               5
```

<210> SEQ ID NO 34
<211> LENGTH: 32
<212> TYPE: PRT
<213> ORGANISM: Homo sapiens

<400> SEQUENCE: 34

```
Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30
```

<210> SEQ ID NO 35
<211> LENGTH: 10
<212> TYPE: PRT
<213> ORGANISM: Homo sapiens

<400> SEQUENCE: 35

```
Gln Gln Tyr Asn Asn Trp Pro Pro Trp Thr
1               5                   10
```

<210> SEQ ID NO 36
<211> LENGTH: 11
<212> TYPE: PRT
<213> ORGANISM: Homo sapiens

<400> SEQUENCE: 36

```
Phe Gly Gln Gly Thr Lys Val Glu Ile Lys Arg
1               5                   10
```

<210> SEQ ID NO 37
<211> LENGTH: 369
<212> TYPE: DNA
<213> ORGANISM: Homo sapiens

<400> SEQUENCE: 37

```
atcaccttga aggagtctgg tcctacgctg gtgaaaccca cacagaccct cacgctgacc      60
tgcaccttct ctgggttctc actcagcgct ggtggagtgg gtgtgggctg gatccgtcag     120
cccccaggaa aggccctgga gtggcttgca ctcatttatt ggaatgatga taagcgctac     180
agcccatctc tgaggagcag gctcaccatc accaaggaca cctccaaaaa ccaggtggtc     240
cttacaatta ccaacatgga ccctgtggac acagccacat attattgtgc acacagtcac     300
tatgattacg attgggggag ttactttgac tactggggcc agggaaccct ggtcaccgtc     360
tcctcagcc                                                            369
```

<210> SEQ ID NO 38
<211> LENGTH: 123
<212> TYPE: PRT
<213> ORGANISM: Homo sapiens

<400> SEQUENCE: 38

```
Ile Thr Leu Lys Glu Ser Gly Pro Thr Leu Val Lys Pro Thr Gln Thr
1               5                   10                  15

Leu Thr Leu Thr Cys Thr Phe Ser Gly Phe Ser Leu Ser Ala Gly Gly
                20                  25                  30

Val Gly Val Gly Trp Ile Arg Gln Pro Pro Gly Lys Ala Leu Glu Trp
            35                  40                  45

Leu Ala Leu Ile Tyr Trp Asn Asp Asp Lys Arg Tyr Ser Pro Ser Leu
        50                  55                  60

Arg Ser Arg Leu Thr Ile Thr Lys Asp Thr Ser Lys Asn Gln Val Val
65                  70                  75                  80

Leu Thr Ile Thr Asn Met Asp Pro Val Asp Thr Ala Thr Tyr Tyr Cys
                85                  90                  95

Ala His Ser His Tyr Asp Tyr Asp Trp Gly Ser Tyr Phe Asp Tyr Trp
                100                 105                 110

Gly Gln Gly Thr Leu Val Thr Val Ser Ser Ala
            115                 120
```

<210> SEQ ID NO 39
<211> LENGTH: 24
<212> TYPE: PRT
<213> ORGANISM: Homo sapiens

<400> SEQUENCE: 39

```
Ile Thr Leu Lys Glu Ser Gly Pro Thr Leu Val Lys Pro Thr Gln Thr
1               5                   10                  15
```

Leu Thr Leu Thr Cys Thr Phe Ser
            20

<210> SEQ ID NO 40
<211> LENGTH: 12
<212> TYPE: PRT
<213> ORGANISM: Homo sapiens

<400> SEQUENCE: 40

Gly Phe Ser Leu Ser Ala Gly Gly Val Gly Val Gly
1               5                   10

<210> SEQ ID NO 41
<211> LENGTH: 14
<212> TYPE: PRT
<213> ORGANISM: Homo sapiens

<400> SEQUENCE: 41

Trp Ile Arg Gln Pro Pro Gly Lys Ala Leu Glu Trp Leu Ala
1               5                   10

<210> SEQ ID NO 42
<211> LENGTH: 16
<212> TYPE: PRT
<213> ORGANISM: Homo sapiens

<400> SEQUENCE: 42

Leu Ile Tyr Trp Asn Asp Asp Lys Arg Tyr Ser Pro Ser Leu Arg Ser
1               5                   10                  15

<210> SEQ ID NO 43
<211> LENGTH: 32
<212> TYPE: PRT
<213> ORGANISM: Homo sapiens

<400> SEQUENCE: 43

Arg Leu Thr Ile Thr Lys Asp Thr Ser Lys Asn Gln Val Val Leu Thr
1               5                   10                  15

Ile Thr Asn Met Asp Pro Val Asp Thr Ala Thr Tyr Tyr Cys Ala His
            20                  25                  30

<210> SEQ ID NO 44
<211> LENGTH: 13
<212> TYPE: PRT
<213> ORGANISM: Homo sapiens

<400> SEQUENCE: 44

Ser His Tyr Asp Tyr Asp Trp Gly Ser Tyr Phe Asp Tyr
1               5                   10

<210> SEQ ID NO 45
<211> LENGTH: 12
<212> TYPE: PRT
<213> ORGANISM: Homo sapiens

<400> SEQUENCE: 45

Trp Gly Gln Gly Thr Leu Val Thr Val Ser Ser Ala
1               5                   10

<210> SEQ ID NO 46
<211> LENGTH: 342
<212> TYPE: DNA
<213> ORGANISM: Homo sapiens

<400> SEQUENCE: 46

```
gatattgtga tgacccagac tccactctcc ctgcccgtca ccctggaga gccggcctcc    60 atctcctgca ggtctagtca gagcctcttg gatagtgatg atggaaacac ctatttggac   120
tggtacctgc agaagccagg acagtctcca cagctcctga tctatacgct ttcctatcgg   180
gcctctggag tcccagacag gttcagtggc agtgggtcag gcactgattt cacactgaac   240
atcagcaggg tggaggctga ggatgttgga gtttattact gcatgcaacg tatagagttt   300
cctatcacct tcggccaagg gacacgactg gagattaaac ga                     342
```

<210> SEQ ID NO 47
<211> LENGTH: 114
<212> TYPE: PRT
<213> ORGANISM: Homo sapiens

<400> SEQUENCE: 47

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Asn
65                  70                  75                  80

Ile Ser Arg Val Glu Ala Glu Asp Val Gly Val Tyr Tyr Cys Met Gln
                85                  90                  95

Arg Ile Glu Phe Pro Ile Thr Phe Gly Gln Gly Thr Arg Leu Glu Ile
            100                 105                 110

Lys Arg

<210> SEQ ID NO 48
<211> LENGTH: 23
<212> TYPE: PRT
<213> ORGANISM: Homo sapiens

<400> SEQUENCE: 48

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 49
<211> LENGTH: 17
<212> TYPE: PRT
<213> ORGANISM: Homo sapiens

<400> SEQUENCE: 49

Arg Ser Ser Gln Ser Leu Leu Asp Ser Asp Asp Gly Asn Thr Tyr Leu
1               5                   10                  15

Asp

<210> SEQ ID NO 50
<211> LENGTH: 15
<212> TYPE: PRT
<213> ORGANISM: Homo sapiens

<400> SEQUENCE: 50

```
Trp Tyr Leu Gln Lys Pro Gly Gln Ser Pro Gln Leu Leu Ile Tyr
1               5                   10                  15
```

<210> SEQ ID NO 51
<211> LENGTH: 7
<212> TYPE: PRT
<213> ORGANISM: Homo sapiens

<400> SEQUENCE: 51

```
Thr Leu Ser Tyr Arg Ala Ser
1               5
```

<210> SEQ ID NO 52
<211> LENGTH: 32
<212> TYPE: PRT
<213> ORGANISM: Homo sapiens

<400> SEQUENCE: 52

```
Gly Val Pro Asp Arg Phe Ser Gly Ser Gly Ser Gly Thr Asp Phe Thr
1               5                   10                  15

Leu Asn Ile Ser Arg Val Glu Ala Glu Asp Val Gly Val Tyr Tyr Cys
            20                  25                  30
```

<210> SEQ ID NO 53
<211> LENGTH: 9
<212> TYPE: PRT
<213> ORGANISM: Homo sapiens

<400> SEQUENCE: 53

```
Met Gln Arg Ile Glu Phe Pro Ile Thr
1               5
```

<210> SEQ ID NO 54
<211> LENGTH: 11
<212> TYPE: PRT
<213> ORGANISM: Homo sapiens

<400> SEQUENCE: 54

```
Phe Gly Gln Gly Thr Arg Leu Glu Ile Lys Arg
1               5                   10
```

<210> SEQ ID NO 55
<211> LENGTH: 360
<212> TYPE: DNA
<213> ORGANISM: Homo sapiens

<400> SEQUENCE: 55

```
caggtgcagc tgcaggagtc gggcccagga ctggtgaagc cttcacagac cctgtccctc      60
acctgcactg tctctggtgg ctccatcagc agtgctaatt actactggac ctggatccgc     120
cagcacccag ggaagggcct ggagtggatt gggtacatct attacagtgg gagcacctac     180
tgcaacccgt ccctcaagag tcgagttatc atatcagtag acacgtctaa gaaccagttc     240
tccctgaagc tgagctctgt gactgccgcg gacacggccg tgtattactg tgcgagaggg     300
tataactgga actactttga ctactggggc cagggaaccc tggtcaccgt ctcctcagcc     360
```

<210> SEQ ID NO 56
<211> LENGTH: 120
<212> TYPE: PRT
<213> ORGANISM: Homo sapiens

<400> SEQUENCE: 56

```
Gln Val Gln Leu Gln Glu Ser Gly Pro Gly Leu Val Lys Pro Ser Gln
```

```
                1               5                  10                  15
            Thr Leu Ser Leu Thr Cys Thr Val Ser Gly Gly Ser Ile Ser Ser Ala
                        20                  25                  30

Asn Tyr Tyr Trp Thr Trp Ile Arg Gln His Pro Gly Lys Gly Leu Glu
                    35                  40                  45

Trp Ile Gly Tyr Ile Tyr Tyr Ser Gly Ser Thr Tyr Cys Asn Pro Ser
                50                  55                  60

Leu Lys Ser Arg Val Ile Ile Ser Val Asp Thr Ser Lys Asn Gln Phe
            65                  70                  75                  80

Ser Leu Lys Leu Ser Ser Val Thr Ala Ala Asp Thr Ala Val Tyr Tyr
                        85                  90                  95

Cys Ala Arg Gly Tyr Asn Trp Asn Tyr Phe Asp Tyr Trp Gly Gln Gly
                        100                 105                 110

Thr Leu Val Thr Val Ser Ser Ala
                        115                 120
```

<210> SEQ ID NO 57
<211> LENGTH: 24
<212> TYPE: PRT
<213> ORGANISM: Homo sapiens

<400> SEQUENCE: 57

```
Gln Val Gln Leu Gln Glu Ser Gly Pro Gly Leu Val Lys Pro Ser Gln
1               5                   10                  15

Thr Leu Ser Leu Thr Cys Thr Val
            20
```

<210> SEQ ID NO 58
<211> LENGTH: 12
<212> TYPE: PRT
<213> ORGANISM: Homo sapiens

<400> SEQUENCE: 58

```
Gly Gly Ser Ile Ser Ser Ala Asn Tyr Tyr Trp Thr
1               5                   10
```

<210> SEQ ID NO 59
<211> LENGTH: 14
<212> TYPE: PRT
<213> ORGANISM: Homo sapiens

<400> SEQUENCE: 59

```
Trp Ile Arg Gln His Pro Gly Lys Gly Leu Glu Trp Ile Gly
1               5                   10
```

<210> SEQ ID NO 60
<211> LENGTH: 16
<212> TYPE: PRT
<213> ORGANISM: Homo sapiens

<400> SEQUENCE: 60

```
Tyr Ile Tyr Tyr Ser Gly Ser Thr Tyr Cys Asn Pro Ser Leu Lys Ser
1               5                   10                  15
```

<210> SEQ ID NO 61
<211> LENGTH: 32
<212> TYPE: PRT
<213> ORGANISM: Homo sapiens

<400> SEQUENCE: 61

Arg Val Ile Ile Ser Val Asp Thr Ser Lys Asn Gln Phe Ser Leu Lys

```
                1               5                  10                 15
Leu Ser Ser Val Thr Ala Ala Asp Thr Ala Val Tyr Tyr Cys Ala Arg
                20                  25                 30
```

<210> SEQ ID NO 62
<211> LENGTH: 9
<212> TYPE: PRT
<213> ORGANISM: Homo sapiens

<400> SEQUENCE: 62

```
Gly Tyr Asn Trp Asn Tyr Phe Asp Tyr
1               5
```

<210> SEQ ID NO 63
<211> LENGTH: 12
<212> TYPE: PRT
<213> ORGANISM: Homo sapiens

<400> SEQUENCE: 63

```
Trp Gly Gln Gly Thr Leu Val Thr Val Ser Ser Ala
1               5                   10
```

<210> SEQ ID NO 64
<211> LENGTH: 330
<212> TYPE: DNA
<213> ORGANISM: Homo sapiens

<400> SEQUENCE: 64

```
gatatagtga tgacgcagtc tccagccacc ctgtctgtgt ctccagggga aagagccacc    60
ctctcctgca gggccagtca gagtgttagc agcaacttag cctggtacca ggagagacct   120
ggccaggctc ccagactcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataagt ggcctccgtg gacgttcggc   300
caagggacca aggtggaaat cgaacgaact                                    330
```

<210> SEQ ID NO 65
<211> LENGTH: 109
<212> TYPE: PRT
<213> ORGANISM: Homo sapiens

<400> SEQUENCE: 65

```
Asp Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
                20                  25                  30
Leu Ala Trp Tyr Gln Glu Arg Pro Gly Gln Ala Pro Arg Leu Leu Ile
            35                  40                  45
Tyr Gly Ala Ser Thr Arg Ala Thr Gly Ile Pro Ala Arg Phe Ser Gly
        50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Lys Trp Pro Pro
                85                  90                  95
Trp Thr Phe Gly Gln Gly Thr Lys Val Glu Ile Glu Arg
                100                 105
```

<210> SEQ ID NO 66
<211> LENGTH: 23

```
<212> TYPE: PRT
<213> ORGANISM: Homo sapiens

<400> SEQUENCE: 66

Asp Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 67
<211> LENGTH: 11
<212> TYPE: PRT
<213> ORGANISM: Homo sapiens

<400> SEQUENCE: 67

Arg Ala Ser Gln Ser Val Ser Ser Asn Leu Ala
1               5                   10

<210> SEQ ID NO 68
<211> LENGTH: 15
<212> TYPE: PRT
<213> ORGANISM: Homo sapiens

<400> SEQUENCE: 68

Trp Tyr Gln Glu Arg Pro Gly Gln Ala Pro Arg Leu Leu Ile Tyr
1               5                   10                  15

<210> SEQ ID NO 69
<211> LENGTH: 7
<212> TYPE: PRT
<213> ORGANISM: Homo sapiens

<400> SEQUENCE: 69

Gly Ala Ser Thr Arg Ala Thr
1               5

<210> SEQ ID NO 70
<211> LENGTH: 32
<212> TYPE: PRT
<213> ORGANISM: Homo sapiens

<400> SEQUENCE: 70

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 71
<211> LENGTH: 10
<212> TYPE: PRT
<213> ORGANISM: Homo sapiens

<400> SEQUENCE: 71

Gln Gln Tyr Asn Lys Trp Pro Pro Trp Thr
1               5                   10

<210> SEQ ID NO 72
<211> LENGTH: 11
<212> TYPE: PRT
<213> ORGANISM: Homo sapiens

<400> SEQUENCE: 72

Phe Gly Gln Gly Thr Lys Val Glu Ile Glu Arg
1               5                   10
```

<210> SEQ ID NO 73
<211> LENGTH: 378
<212> TYPE: DNA
<213> ORGANISM: Homo sapiens

<400> SEQUENCE: 73

```
cagctggtgg agtctggggg aggcgtggtc cagcctggga ggtccctgag actctcctgt      60
gcagcctctg gattcgcctt cagtagctat ggcatgcact gggtccgcca ggctccaggc     120
aaggggctgg agtgggtggc agttatatca tatgatggaa ataataaata ctatgcagac     180
tccgtgaagg gccgattcac catctccaga gacaattcca agaacacgct gtatctgcaa     240
atgaacagcc tgagagctga ggacacggct gtgtattact gtgcgagaga tctagtggtt     300
cggggaatta gggggtacta ctactacttc ggtatggacg tctggggcca agggaccacg     360
gtcaccgtct cctcagcc                                                    378
```

<210> SEQ ID NO 74
<211> LENGTH: 126
<212> TYPE: PRT
<213> ORGANISM: Homo sapiens

<400> SEQUENCE: 74

Gln Leu Val Glu Ser Gly Gly Gly Val Val Gln Pro Gly Arg Ser Leu
1               5                   10                  15
Arg Leu Ser Cys Ala Ala Ser Gly Phe Ala Phe Ser Ser Tyr Gly Met
            20                  25                  30
His Trp Val Arg Gln Ala Pro Gly Lys Gly Leu Glu Trp Val Ala Val
        35                  40                  45
Ile Ser Tyr Asp Gly Asn Asn Lys Tyr Tyr Ala Asp Ser Val Lys Gly
    50                  55                  60
Arg Phe Thr Ile Ser Arg Asp Asn Ser Lys Asn Thr Leu Tyr Leu Gln
65                  70                  75                  80
Met Asn Ser Leu Arg Ala Glu Asp Thr Ala Val Tyr Tyr Cys Ala Arg
                85                  90                  95
Asp Leu Val Val Arg Gly Ile Arg Gly Tyr Tyr Tyr Phe Gly Met
            100                 105                 110
Asp Val Trp Gly Gln Gly Thr Thr Val Thr Val Ser Ser Ala
        115                 120                 125

<210> SEQ ID NO 75
<211> LENGTH: 23
<212> TYPE: PRT
<213> ORGANISM: Homo sapiens

<400> SEQUENCE: 75

Gln Leu Val Glu Ser Gly Gly Gly Val Val Gln Pro Gly Arg Ser Leu
1               5                   10                  15
Arg Leu Ser Cys Ala Ala Ser
            20

<210> SEQ ID NO 76
<211> LENGTH: 10
<212> TYPE: PRT
<213> ORGANISM: Homo sapiens

<400> SEQUENCE: 76

Gly Phe Ala Phe Ser Ser Tyr Gly Met His
1               5                   10

<210> SEQ ID NO 77
<211> LENGTH: 14
<212> TYPE: PRT
<213> ORGANISM: Homo sapiens

<400> SEQUENCE: 77

Trp Val Arg Gln Ala Pro Gly Lys Gly Leu Glu Trp Val Ala
1               5                   10

<210> SEQ ID NO 78
<211> LENGTH: 17
<212> TYPE: PRT
<213> ORGANISM: Homo sapiens

<400> SEQUENCE: 78

Val Ile Ser Tyr Asp Gly Asn Asn Lys Tyr Tyr Ala Asp Ser Val Lys
1               5                   10                  15

Gly

<210> SEQ ID NO 79
<211> LENGTH: 32
<212> TYPE: PRT
<213> ORGANISM: Homo sapiens

<400> SEQUENCE: 79

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 80
<211> LENGTH: 18
<212> TYPE: PRT
<213> ORGANISM: Homo sapiens

<400> SEQUENCE: 80

Asp Leu Val Val Arg Gly Ile Arg Gly Tyr Tyr Tyr Tyr Phe Gly Met
1               5                   10                  15

Asp Val

<210> SEQ ID NO 81
<211> LENGTH: 12
<212> TYPE: PRT
<213> ORGANISM: Homo sapiens

<400> SEQUENCE: 81

Trp Gly Gln Gly Thr Thr Val Thr Val Ser Ser Ala
1               5                   10

<210> SEQ ID NO 82
<211> LENGTH: 339
<212> TYPE: DNA
<213> ORGANISM: Homo sapiens

<400> SEQUENCE: 82
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240

```
agcagagtgg aggctgagga tgttggggtt tattactgca tgcaaggtct acaaactccg    300
atcaccttcg ccaagggac acgactggag attaaacga                            339
```

<210> SEQ ID NO 83
<211> LENGTH: 113
<212> TYPE: PRT
<213> ORGANISM: Homo sapiens

<400> SEQUENCE: 83

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Ile Thr Phe Gly Gln Gly Thr Arg Leu Glu Ile Lys
            100                 105                 110

Arg

<210> SEQ ID NO 84
<211> LENGTH: 23
<212> TYPE: PRT
<213> ORGANISM: Homo sapiens

<400> SEQUENCE: 84

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 85
<211> LENGTH: 16
<212> TYPE: PRT
<213> ORGANISM: Homo sapiens

<400> SEQUENCE: 85

Arg Ser Ser Gln Ser Leu Leu His Ser Asn Gly Tyr Asn Tyr Leu Asp
1               5                   10                  15

<210> SEQ ID NO 86
<211> LENGTH: 15
<212> TYPE: PRT
<213> ORGANISM: Homo sapiens

<400> SEQUENCE: 86

Trp Tyr Leu Gln Lys Pro Gly Gln Ser Pro Gln Leu Leu Ile Tyr
1               5                   10                  15

<210> SEQ ID NO 87
<211> LENGTH: 7
<212> TYPE: PRT
<213> ORGANISM: Homo sapiens

<400> SEQUENCE: 87

```
Leu Gly Ser Asn Arg Ala Ser
1               5

<210> SEQ ID NO 88
<211> LENGTH: 32
<212> TYPE: PRT
<213> ORGANISM: Homo sapiens

<400> SEQUENCE: 88

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 89
<211> LENGTH: 9
<212> TYPE: PRT
<213> ORGANISM: Homo sapiens

<400> SEQUENCE: 89

Met Gln Gly Leu Gln Thr Pro Ile Thr
1               5

<210> SEQ ID NO 90
<211> LENGTH: 11
<212> TYPE: PRT
<213> ORGANISM: Homo sapiens

<400> SEQUENCE: 90

Phe Gly Gln Gly Thr Arg Leu Glu Ile Lys Arg
1               5                   10

<210> SEQ ID NO 91
<211> LENGTH: 366
<212> TYPE: DNA
<213> ORGANISM: Homo sapiens

<400> SEQUENCE: 91
caggtgcagc tggtggagtc tgggggaggc gtggtccagc ctggagggtc cctgagactc      60
tcctgtgcag cgtctggatt caccttcagt aactatggca ttcactgggt ccgccaggct     120
ccaggcaagg ggctggagtg ggtggcagtt atatggtttg atggacgtaa taaatactat     180
gcagactccg tgaagggccg attcaccatc tccagagaca attccaagaa cacgctgtat     240
ctgcaaatga acagcctgag agccgaggac gcggctgtgt attactgtgc gagagatccc     300
tttgactatg gtgactcctt ctttgactac tggggccagg gcaccctggt caccgtctcc     360
tcagcc                                                                366

<210> SEQ ID NO 92
<211> LENGTH: 122
<212> TYPE: PRT
<213> ORGANISM: Homo sapiens

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Val Ile Trp Phe Asp Gly Arg Asn Lys Tyr Tyr Ala Asp Ser Val
```

```
                   50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Arg Asp Pro Phe Asp Tyr Gly Asp Ser Phe Asp Tyr Trp Gly
            100                 105                 110

Gln Gly Thr Leu Val Thr Val Ser Ser Ala
        115                 120

<210> SEQ ID NO 93
<211> LENGTH: 25
<212> TYPE: PRT
<213> ORGANISM: Homo sapiens

<400> SEQUENCE: 93

Gln Val Gln Leu Val Glu Ser Gly Gly Val Val Gln Pro Gly Arg
 1               5                  10                  15

Ser Leu Arg Leu Ser Cys Ala Ala Ser
             20                  25

<210> SEQ ID NO 94
<211> LENGTH: 10
<212> TYPE: PRT
<213> ORGANISM: Homo sapiens

<400> SEQUENCE: 94

Gly Phe Thr Phe Ser Asn Tyr Gly Ile His
 1               5                  10

<210> SEQ ID NO 95
<211> LENGTH: 14
<212> TYPE: PRT
<213> ORGANISM: Homo sapiens

<400> SEQUENCE: 95

Trp Val Arg Gln Ala Pro Gly Lys Gly Leu Glu Trp Val Ala
 1               5                  10

<210> SEQ ID NO 96
<211> LENGTH: 17
<212> TYPE: PRT
<213> ORGANISM: Homo sapiens

<400> SEQUENCE: 96

Val Ile Trp Phe Asp Gly Arg Asn Lys Tyr Tyr Ala Asp Ser Val Lys
 1               5                  10                  15

Gly

<210> SEQ ID NO 97
<211> LENGTH: 32
<212> TYPE: PRT
<213> ORGANISM: Homo sapiens

<400> SEQUENCE: 97

Arg Phe Thr Ile Ser Arg Asp Asn Ser Lys Asn Thr Leu Tyr Leu Gln
 1               5                  10                  15

Met Asn Ser Leu Arg Ala Glu Asp Ala Ala Val Tyr Tyr Cys Ala Arg
             20                  25                  30

<210> SEQ ID NO 98
```

```
<211> LENGTH: 12
<212> TYPE: PRT
<213> ORGANISM: Homo sapiens

<400> SEQUENCE: 98

Asp Pro Phe Asp Tyr Gly Asp Ser Phe Phe Asp Tyr
1               5                   10

<210> SEQ ID NO 99
<211> LENGTH: 12
<212> TYPE: PRT
<213> ORGANISM: Homo sapiens

<400> SEQUENCE: 99

Trp Gly Gln Gly Thr Leu Val Thr Val Ser Ser Ala
1               5                   10

<210> SEQ ID NO 100
<211> LENGTH: 315
<212> TYPE: DNA
<213> ORGANISM: Homo sapiens

<400> SEQUENCE: 100
ctgactcagt ctccatcctc cctgtctgca tctgtaagag acagagtcac catcacttgc      60
cgggcgagtc aggacattag caattattta gcctggtatc agcagaaacc agggaaagtt     120
cctaatctcc tgatctatgc tgcatccact ttgcaatcag gggtcccatc tcggttcagt     180
ggcagtggat ctgggacaga tttcactctc accatcagca gcctgcagcc tgaagatgtt     240
gcaacttatt actgtcaaaa gtataacagt gccccgctca ctttcggcgg agggaccaag     300
gtggagatca aacga                                                     315

<210> SEQ ID NO 101
<211> LENGTH: 105
<212> TYPE: PRT
<213> ORGANISM: Homo sapiens

<400> SEQUENCE: 101

Leu Thr Gln Ser Pro Ser Ser Leu Ser Ala Ser Val Arg Asp Arg Val
1               5                   10                  15

Thr Ile Thr Cys Arg Ala Ser Gln Asp Ile Ser Asn Tyr Leu Ala Trp
            20                  25                  30

Tyr Gln Gln Lys Pro Gly Lys Val Pro Asn Leu Leu Ile Tyr Ala Ala
        35                  40                  45

Ser Thr Leu Gln Ser Gly Val Pro Ser Arg Phe Ser Gly Ser Gly Ser
    50                  55                  60

Gly Thr Asp Phe Thr Leu Thr Ile Ser Ser Leu Gln Pro Glu Asp Val
65                  70                  75                  80

Ala Thr Tyr Tyr Cys Gln Lys Tyr Asn Ser Ala Pro Leu Thr Phe Gly
                85                  90                  95

Gly Gly Thr Lys Val Glu Ile Lys Arg
            100                 105

<210> SEQ ID NO 102
<211> LENGTH: 20
<212> TYPE: PRT
<213> ORGANISM: Homo sapiens

<400> SEQUENCE: 102

Leu Thr Gln Ser Pro Ser Ser Leu Ser Ala Ser Val Arg Asp Arg Val
1               5                   10                  15
```

Thr Ile Thr Cys
        20

<210> SEQ ID NO 103
<211> LENGTH: 11
<212> TYPE: PRT
<213> ORGANISM: Homo sapiens

<400> SEQUENCE: 103

Arg Ala Ser Gln Asp Ile Ser Asn Tyr Leu Ala
1               5                   10

<210> SEQ ID NO 104
<211> LENGTH: 15
<212> TYPE: PRT
<213> ORGANISM: Homo sapiens

<400> SEQUENCE: 104

Trp Tyr Gln Gln Lys Pro Gly Lys Val Pro Asn Leu Leu Ile Tyr
1               5                   10                  15

<210> SEQ ID NO 105
<211> LENGTH: 6
<212> TYPE: PRT
<213> ORGANISM: Homo sapiens

<400> SEQUENCE: 105

Ala Ala Ser Thr Leu Gln
1               5

<210> SEQ ID NO 106
<211> LENGTH: 32
<212> TYPE: PRT
<213> ORGANISM: Homo sapiens

<400> SEQUENCE: 106

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 107
<211> LENGTH: 9
<212> TYPE: PRT
<213> ORGANISM: Homo sapiens

<400> SEQUENCE: 107

Gln Lys Tyr Asn Ser Ala Pro Leu Thr
1               5

<210> SEQ ID NO 108
<211> LENGTH: 11
<212> TYPE: PRT
<213> ORGANISM: Homo sapiens

<400> SEQUENCE: 108

Phe Gly Gly Gly Thr Lys Val Glu Ile Lys Arg
1               5                   10

<210> SEQ ID NO 109
<211> LENGTH: 366
<212> TYPE: DNA
<213> ORGANISM: Homo sapiens -continued

```
<400> SEQUENCE: 109
caggtgcagc tggtggagtc tgggggaggc ttggtcaagc ctggagggtc cctgagactc      60
tcctgtgcag cctctggatt caccttcagt gactactaca tgacctggat ccgccaggct     120
ccagggaagg ggctggagtg ggtttcatac attagtatta gtggtagtat cacacactac     180
gcagactcag tgaagggccg attcaccatg tccagggaca acgccaagaa ctcactgtat     240
ctgcaaatga acagcctgag agccgaggac acggccgtgt attactgtgc gagagacgga     300
gcagcagctg gtacggatgc ttttgatatc tggggccacg ggacaaaggt caccgtctct     360
tcagcc                                                               366

<210> SEQ ID NO 110
<211> LENGTH: 122
<212> TYPE: PRT
<213> ORGANISM: Homo sapiens

<400> SEQUENCE: 110

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Tyr Ile Ser Ile Ser Gly Ser Ile Thr His Tyr Ala Asp Ser Val
    50                  55                  60

Lys Gly Arg Phe Thr Met Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ala Ala Gly Thr Asp Ala Phe Asp Ile Trp Gly
            100                 105                 110

His Gly Thr Lys Val Thr Val Ser Ser Ala
        115                 120

<210> SEQ ID NO 111
<211> LENGTH: 25
<212> TYPE: PRT
<213> ORGANISM: Homo sapiens

<400> SEQUENCE: 111

Gln Val Gln Leu Val Glu Ser Gly Gly Gly Leu Val Lys Pro Gly Gly
 1               5                  10                  15

Ser Leu Arg Leu Ser Cys Ala Ala Ser
            20                  25

<210> SEQ ID NO 112
<211> LENGTH: 10
<212> TYPE: PRT
<213> ORGANISM: Homo sapiens

<400> SEQUENCE: 112

Gly Phe Thr Phe Ser Asp Tyr Tyr Met Thr
 1               5                  10

<210> SEQ ID NO 113
<211> LENGTH: 14
<212> TYPE: PRT
<213> ORGANISM: Homo sapiens
```

```
<400> SEQUENCE: 113

Trp Ile Arg Gln Ala Pro Gly Lys Gly Leu Glu Trp Val Ser
1               5                   10

<210> SEQ ID NO 114
<211> LENGTH: 17
<212> TYPE: PRT
<213> ORGANISM: Homo sapiens

<400> SEQUENCE: 114

Tyr Ile Ser Ile Ser Gly Ser Ile Thr His Tyr Ala Asp Ser Val Lys
1               5                   10                  15

Gly

<210> SEQ ID NO 115
<211> LENGTH: 32
<212> TYPE: PRT
<213> ORGANISM: Homo sapiens

<400> SEQUENCE: 115

Arg Phe Thr Met Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 116
<211> LENGTH: 12
<212> TYPE: PRT
<213> ORGANISM: Homo sapiens

<400> SEQUENCE: 116

Asp Gly Ala Ala Ala Gly Thr Asp Ala Phe Asp Ile
1               5                   10

<210> SEQ ID NO 117
<211> LENGTH: 12
<212> TYPE: PRT
<213> ORGANISM: Homo sapiens

<400> SEQUENCE: 117

Trp Gly His Gly Thr Lys Val Thr Val Ser Ser Ala
1               5                   10

<210> SEQ ID NO 118
<211> LENGTH: 321
<212> TYPE: DNA
<213> ORGANISM: Homo sapiens

<400> SEQUENCE: 118
gagatagtga tgacgcagtc tccagccacc ctatctgtgt ctccagggga cagagccacc      60
ctctcctgca gggccagtca gaatgttagc agcaacttgg cctggtacca gcagaaacct    120
ggccaggctc ccaggctcct catctttggt gcatccacca gggccactgg tatcccagcc    180
aggttcagtg gcagtgggtc tgggacagag ttcactctca ccatcagcag cctacagtct    240
gaagattttg cagtttatta ctgtcagcag tatcattact ggcccacttt cggccctggg    300
accaaagtgg atatcaaacg a                                              321

<210> SEQ ID NO 119
<211> LENGTH: 107
<212> TYPE: PRT
<213> ORGANISM: Homo sapiens
```

<400> SEQUENCE: 119

Glu Ile Val Met Thr Gln Ser Pro Ala Thr Leu Ser Val Ser Pro Gly
1               5                   10                  15

Asp Arg Ala Thr Leu Ser Cys Arg Ala Ser Gln Asn Val Ser Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Tyr Trp Pro Thr
                85                  90                  95

Phe Gly Pro Gly Thr Lys Val Asp Ile Lys Arg
            100                 105

<210> SEQ ID NO 120
<211> LENGTH: 23
<212> TYPE: PRT
<213> ORGANISM: Homo sapiens

<400> SEQUENCE: 120

Glu Ile Val Met Thr Gln Ser Pro Ala Thr Leu Ser Val Ser Pro Gly
1               5                   10                  15

Asp Arg Ala Thr Leu Ser Cys
            20

<210> SEQ ID NO 121
<211> LENGTH: 11
<212> TYPE: PRT
<213> ORGANISM: Homo sapiens

<400> SEQUENCE: 121

Arg Ala Ser Gln Asn Val Ser Ser Asn Leu Ala
1               5                   10

<210> SEQ ID NO 122
<211> LENGTH: 15
<212> TYPE: PRT
<213> ORGANISM: Homo sapiens

<400> SEQUENCE: 122

Trp Tyr Gln Gln Lys Pro Gly Gln Ala Pro Arg Leu Leu Ile Phe
1               5                   10                  15

<210> SEQ ID NO 123
<211> LENGTH: 7
<212> TYPE: PRT
<213> ORGANISM: Homo sapiens

<400> SEQUENCE: 123

Gly Ala Ser Thr Arg Ala Thr
1               5

<210> SEQ ID NO 124
<211> LENGTH: 32
<212> TYPE: PRT
<213> ORGANISM: Homo sapiens

<400> SEQUENCE: 124

```
Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30
```

<210> SEQ ID NO 125
<211> LENGTH: 8
<212> TYPE: PRT
<213> ORGANISM: Homo sapiens

<400> SEQUENCE: 125

```
Gln Gln Tyr His Tyr Trp Pro Thr
1               5
```

<210> SEQ ID NO 126
<211> LENGTH: 11
<212> TYPE: PRT
<213> ORGANISM: Homo sapiens

<400> SEQUENCE: 126

```
Phe Gly Pro Gly Thr Lys Val Asp Ile Lys Arg
1               5                   10
```

<210> SEQ ID NO 127
<211> LENGTH: 360
<212> TYPE: DNA
<213> ORGANISM: Homo sapiens

<400> SEQUENCE: 127

```
cagctggtgc agtctggggc tgaggtgaag aagcctgggg cctcagtgaa ggtctcctgc      60
aaggcttctg gatacacctt caccggcttc tatatgcact gggtgcgaca gaccccggga     120
caagggcttg agtggatggg atggatcaac cctaacagtg gtggcacata ttatgtacag     180
aagtttcagg gcagggtcac catgaccagg gacacgtcca tcagcacagt ctacatggag     240
ctgagcaggt tgagatctga cgacacggcc gtatattact gtgcgagaga tgggtatagc     300
agtggagagg actggttcga ccctgggggc cagggaaccc tggtcaccgt ctcctcagcc     360
```

<210> SEQ ID NO 128
<211> LENGTH: 120
<212> TYPE: PRT
<213> ORGANISM: Homo sapiens

<400> SEQUENCE: 128

```
Gln Leu Val Gln Ser Gly Ala Glu Val Lys Lys Pro Gly Ala Ser Val
1               5                   10                  15

Lys Val Ser Cys Lys Ala Ser Gly Tyr Thr Phe Thr Gly Phe Tyr Met
                20                  25                  30

His Trp Val Arg Gln Thr Pro Gly Gln Gly Leu Glu Trp Met Gly Trp
            35                  40                  45

Ile Asn Pro Asn Ser Gly Gly Thr Tyr Tyr Val Gln Lys Phe Gln Gly
        50                  55                  60

Arg Val Thr Met Thr Arg Asp Thr Ser Ile Ser Thr Val Tyr Met Glu
65                  70                  75                  80

Leu Ser Arg Leu Arg Ser Asp Asp Thr Ala Val Tyr Tyr Cys Ala Arg
                85                  90                  95

Asp Gly Tyr Ser Ser Gly Glu Asp Trp Phe Asp Pro Trp Gly Gln Gly
                100                 105                 110

Thr Leu Val Thr Val Ser Ser Ala
            115                 120
```

<210> SEQ ID NO 129
<211> LENGTH: 23
<212> TYPE: PRT
<213> ORGANISM: Homo sapiens

<400> SEQUENCE: 129

Gln Leu Val Gln Ser Gly Ala Glu Val Lys Lys Pro Gly Ala Ser Val
1               5                   10                  15

Lys Val Ser Cys Lys Ala Ser
            20

<210> SEQ ID NO 130
<211> LENGTH: 10
<212> TYPE: PRT
<213> ORGANISM: Homo sapiens

<400> SEQUENCE: 130

Gly Tyr Thr Phe Thr Gly Phe Tyr Met His
1               5                   10

<210> SEQ ID NO 131
<211> LENGTH: 14
<212> TYPE: PRT
<213> ORGANISM: Homo sapiens

<400> SEQUENCE: 131

Trp Val Arg Gln Thr Pro Gly Gln Gly Leu Glu Trp Met Gly
1               5                   10

<210> SEQ ID NO 132
<211> LENGTH: 17
<212> TYPE: PRT
<213> ORGANISM: Homo sapiens

<400> SEQUENCE: 132

Trp Ile Asn Pro Asn Ser Gly Gly Thr Tyr Tyr Val Gln Lys Phe Gln
1               5                   10                  15

Gly

<210> SEQ ID NO 133
<211> LENGTH: 32
<212> TYPE: PRT
<213> ORGANISM: Homo sapiens

<400> SEQUENCE: 133

Arg Val Thr Met Thr Arg Asp Thr Ser Ile Ser Thr Val Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 134
<211> LENGTH: 12
<212> TYPE: PRT
<213> ORGANISM: Homo sapiens

<400> SEQUENCE: 134

Asp Gly Tyr Ser Ser Gly Glu Asp Trp Phe Asp Pro
1               5                   10

<210> SEQ ID NO 135
<211> LENGTH: 12
<212> TYPE: PRT

<213> ORGANISM: Homo sapiens

<400> SEQUENCE: 135

Trp Gly Gln Gly Thr Leu Val Thr Val Ser Ser Ala
1               5                   10

<210> SEQ ID NO 136
<211> LENGTH: 339
<212> TYPE: DNA
<213> ORGANISM: Homo sapiens

<400> SEQUENCE: 136

```
gatattgtga tgacccagac tccactctct ctgtccgtca cccctggaca gccggcctcc     60
atctcctgca agtctagtca gagcctcctg catagtggtg aaagaccta tttgtattgg    120
tacctgcaga ggccaggcca gcctccacag ctcctgatct atgaagtttc caaccggttc    180
tctggagtgc cagataggtt cagtggcagc gggtcaggga cagatttcac actgaaaatc    240
agccgggtgg aggctgagga tgttggggtt tattactgca tgcaaagtat acaccttccg    300
ctcactttcg gcggagggac caaggtggag atcaaacga                           339
```

<210> SEQ ID NO 137
<211> LENGTH: 113
<212> TYPE: PRT
<213> ORGANISM: Homo sapiens

<400> SEQUENCE: 137

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Gly Gly Lys Thr Tyr Leu Tyr Trp Tyr Leu Gln Arg Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile His Leu Pro Leu Thr Phe Gly Gly Gly Thr Lys Val Glu Ile Lys
            100                 105                 110

Arg

<210> SEQ ID NO 138
<211> LENGTH: 23
<212> TYPE: PRT
<213> ORGANISM: Homo sapiens

<400> SEQUENCE: 138

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 139
<211> LENGTH: 16
<212> TYPE: PRT
<213> ORGANISM: Homo sapiens

<400> SEQUENCE: 139

```
Lys Ser Ser Gln Ser Leu Leu His Ser Gly Gly Lys Thr Tyr Leu Tyr
1               5                   10                  15

<210> SEQ ID NO 140
<211> LENGTH: 15
<212> TYPE: PRT
<213> ORGANISM: Homo sapiens

<400> SEQUENCE: 140

Trp Tyr Leu Gln Arg Pro Gly Gln Pro Pro Gln Leu Leu Ile Tyr
1               5                   10                  15

<210> SEQ ID NO 141
<211> LENGTH: 7
<212> TYPE: PRT
<213> ORGANISM: Homo sapiens

<400> SEQUENCE: 141

Glu Val Ser Asn Arg Phe Ser
1               5

<210> SEQ ID NO 142
<211> LENGTH: 32
<212> TYPE: PRT
<213> ORGANISM: Homo sapiens

<400> SEQUENCE: 142

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 143
<211> LENGTH: 9
<212> TYPE: PRT
<213> ORGANISM: Homo sapiens

<400> SEQUENCE: 143

Met Gln Ser Ile His Leu Pro Leu Thr
1               5

<210> SEQ ID NO 144
<211> LENGTH: 11
<212> TYPE: PRT
<213> ORGANISM: Homo sapiens

<400> SEQUENCE: 144

Phe Gly Gly Gly Thr Lys Val Glu Ile Lys Arg
1               5                   10

<210> SEQ ID NO 145
<211> LENGTH: 360
<212> TYPE: DNA
<213> ORGANISM: Homo sapiens

<400> SEQUENCE: 145
caggtgcagc tggagcagtc gggggggaggc ctggtcaagc ctgggggtc cctgagattc      60 tcctgtgcag cctctggatt caccttcagt agctatagca tgaactgggt ccgccaggct    120
ccagggaagg ggctggagtg ggtctcattc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gagagaggac    300
```
tgggtgggag ctacctttga ctactggggc cagggaaccc tggtcaccgt ctcctcagcc    360

<210> SEQ ID NO 146
<211> LENGTH: 120
<212> TYPE: PRT
<213> ORGANISM: Homo sapiens

<400> SEQUENCE: 146

Gln Val Gln Leu Glu Gln Ser Gly Gly Gly Leu Val Lys Pro Gly Gly
1               5                   10                  15

Ser Leu Arg Phe Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Phe Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Val Gly Ala Thr Phe Asp Tyr Trp Gly Gln Gly
            100                 105                 110

Thr Leu Val Thr Val Ser Ser Ala
        115                 120

<210> SEQ ID NO 147
<211> LENGTH: 25
<212> TYPE: PRT
<213> ORGANISM: Homo sapiens

<400> SEQUENCE: 147

Gln Val Gln Leu Glu Gln Ser Gly Gly Gly Leu Val Lys Pro Gly Gly
1               5                   10                  15

Ser Leu Arg Phe Ser Cys Ala Ala Ser
            20                  25

<210> SEQ ID NO 148
<211> LENGTH: 10
<212> TYPE: PRT
<213> ORGANISM: Homo sapiens

<400> SEQUENCE: 148

Gly Phe Thr Phe Ser Ser Tyr Ser Met Asn
1               5                   10

<210> SEQ ID NO 149
<211> LENGTH: 14
<212> TYPE: PRT
<213> ORGANISM: Homo sapiens

<400> SEQUENCE: 149

Trp Val Arg Gln Ala Pro Gly Lys Gly Leu Glu Trp Val Ser
1               5                   10

<210> SEQ ID NO 150
<211> LENGTH: 17
<212> TYPE: PRT
<213> ORGANISM: Homo sapiens

<400> SEQUENCE: 150

```
Phe Ile Ser Ser Ser Ser Ser Tyr Ile Tyr Tyr Ala Asp Ser Val Lys
1               5                   10                  15

Gly
```

<210> SEQ ID NO 151
<211> LENGTH: 32
<212> TYPE: PRT
<213> ORGANISM: Homo sapiens

<400> SEQUENCE: 151

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
                20                  25                  30
```

<210> SEQ ID NO 152
<211> LENGTH: 10
<212> TYPE: PRT
<213> ORGANISM: Homo sapiens

<400> SEQUENCE: 152

```
Glu Asp Trp Val Gly Ala Thr Phe Asp Tyr
1               5                   10
```

<210> SEQ ID NO 153
<211> LENGTH: 12
<212> TYPE: PRT
<213> ORGANISM: Homo sapiens

<400> SEQUENCE: 153

```
Trp Gly Gln Gly Thr Leu Val Thr Val Ser Ser Ala
1               5                   10
```

<210> SEQ ID NO 154
<211> LENGTH: 324
<212> TYPE: DNA
<213> ORGANISM: Homo sapiens

<400> SEQUENCE: 154

```
gacattcagc tgacccagtc tccatcctcc ctgtctgcat ctgtaggaga cagagtcacc      60
atcacttgtc gggcgagtca gggcattagg aattatttag cctggtatca gcagaaacca     120
gggaaagttc ctaagctcct gatctatgct gcttccgctt tgaaattagg ggtcccatct     180
cggttcagtg gcagtggatc tgggacagat ttcactctca ccatcagcag cctgcagcct     240
gaagatgttg caacttatta ctgtcaaaag tataacagtg ccccgatcac cttcggccaa     300
gggacacgac tggacattaa acga                                            324
```

<210> SEQ ID NO 155
<211> LENGTH: 108
<212> TYPE: PRT
<213> ORGANISM: Homo sapiens

<400> SEQUENCE: 155

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Val Pro Lys Leu Leu Ile
            35                  40                  45

Tyr Ala Ala Ser Ala Leu Lys Leu Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Ile
                 85                  90                  95

Thr Phe Gly Gln Gly Thr Arg Leu Asp Ile Lys Arg
            100                 105

<210> SEQ ID NO 156
<211> LENGTH: 23
<212> TYPE: PRT
<213> ORGANISM: Homo sapiens

<400> SEQUENCE: 156

Asp Ile Gln Leu Thr Gln Ser Pro Ser Ser Leu Ser Ala Ser Val Gly
 1               5                  10                  15

Asp Arg Val Thr Ile Thr Cys
             20

<210> SEQ ID NO 157
<211> LENGTH: 11
<212> TYPE: PRT
<213> ORGANISM: Homo sapiens

<400> SEQUENCE: 157

Arg Ala Ser Gln Gly Ile Arg Asn Tyr Leu Ala
 1               5                  10

<210> SEQ ID NO 158
<211> LENGTH: 15
<212> TYPE: PRT
<213> ORGANISM: Homo sapiens

<400> SEQUENCE: 158

Trp Tyr Gln Gln Lys Pro Gly Lys Val Pro Lys Leu Leu Ile Tyr
 1               5                  10                  15

<210> SEQ ID NO 159
<211> LENGTH: 7
<212> TYPE: PRT
<213> ORGANISM: Homo sapiens

<400> SEQUENCE: 159

Ala Ala Ser Ala Leu Lys Leu
 1               5

<210> SEQ ID NO 160
<211> LENGTH: 32
<212> TYPE: PRT
<213> ORGANISM: Homo sapiens

<400> SEQUENCE: 160

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Val Ala Thr Tyr Tyr Cys
             20                  25                  30

<210> SEQ ID NO 161
<211> LENGTH: 9
<212> TYPE: PRT
<213> ORGANISM: Homo sapiens

<400> SEQUENCE: 161
```

```
Gln Lys Tyr Asn Ser Ala Pro Ile Thr
1               5
```

<210> SEQ ID NO 162
<211> LENGTH: 11
<212> TYPE: PRT
<213> ORGANISM: Homo sapiens

<400> SEQUENCE: 162

```
Phe Gly Gln Gly Thr Arg Leu Asp Ile Lys Arg
1               5                   10
```

<210> SEQ ID NO 163
<211> LENGTH: 396
<212> TYPE: DNA
<213> ORGANISM: Homo sapiens

<400> SEQUENCE: 163

```
caggtgcagc tggagcagtc gggcccagga ctggtgaagc cttcacagaa cctgtccctc      60
acctgcactg tctctggtgg ctccatcagc agtggtggtt atttctggag ctggatccgc     120
cagcacccag ggaagggcct ggagtggatt gggtacatct attacagtgg gaacacctac     180
tacaacccgt ccctcaagag tcgagttacc atatcagttg acacgtctaa gaaccagttc     240
tccctgaaac tgagctctgt gactgccgcg gacacggccg tgtattactg tgcgagagac     300
tattactatg atactagtgg ttttttcctac cgttacgact ggtactacgg tatggacgtc     360
tggggccaag ggaccacggt caccgtctcc tcagcc                               396
```

<210> SEQ ID NO 164
<211> LENGTH: 132
<212> TYPE: PRT
<213> ORGANISM: Homo sapiens

<400> SEQUENCE: 164

```
Gln Val Gln Leu Glu Gln Ser Gly Pro Gly Leu Val Lys Pro Ser Gln
1               5                   10                  15
Asn Leu Ser Leu Thr Cys Thr Val Ser Gly Gly Ser Ile Ser Ser Gly
            20                  25                  30
Gly Tyr Phe Trp Ser Trp Ile Arg Gln His Pro Gly Lys Gly Leu Glu
        35                  40                  45
Trp Ile Gly Tyr Ile Tyr Tyr Ser Gly Asn Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Tyr Tyr Tyr Asp Thr Ser Gly Phe Ser Tyr Arg Tyr
            100                 105                 110
Asp Trp Tyr Tyr Gly Met Asp Val Trp Gly Gln Gly Thr Thr Val Thr
        115                 120                 125
Val Ser Ser Ala
    130
```

<210> SEQ ID NO 165
<211> LENGTH: 25
<212> TYPE: PRT
<213> ORGANISM: Homo sapiens

<400> SEQUENCE: 165

Gln Val Gln Leu Glu Gln Ser Gly Pro Gly Leu Val Lys Pro Ser Gln
1               5                   10                  15

Asn Leu Ser Leu Thr Cys Thr Val Ser
            20                  25

<210> SEQ ID NO 166
<211> LENGTH: 12
<212> TYPE: PRT
<213> ORGANISM: Homo sapiens

<400> SEQUENCE: 166

Gly Gly Ser Ile Ser Ser Gly Gly Tyr Phe Trp Ser
1               5                   10

<210> SEQ ID NO 167
<211> LENGTH: 14
<212> TYPE: PRT
<213> ORGANISM: Homo sapiens

<400> SEQUENCE: 167

Trp Ile Arg Gln His Pro Gly Lys Gly Leu Glu Trp Ile Gly
1               5                   10

<210> SEQ ID NO 168
<211> LENGTH: 16
<212> TYPE: PRT
<213> ORGANISM: Homo sapiens

<400> SEQUENCE: 168

Tyr Ile Tyr Tyr Ser Gly Asn Thr Tyr Tyr Asn Pro Ser Leu Lys Ser
1               5                   10                  15

<210> SEQ ID NO 169
<211> LENGTH: 32
<212> TYPE: PRT
<213> ORGANISM: Homo sapiens

<400> SEQUENCE: 169

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 170
<211> LENGTH: 21
<212> TYPE: PRT
<213> ORGANISM: Homo sapiens

<400> SEQUENCE: 170

Asp Tyr Tyr Tyr Asp Thr Ser Gly Phe Ser Tyr Arg Tyr Asp Trp Tyr
1               5                   10                  15

Tyr Gly Met Asp Val
            20

<210> SEQ ID NO 171
<211> LENGTH: 12
<212> TYPE: PRT
<213> ORGANISM: Homo sapiens

<400> SEQUENCE: 171

Trp Gly Gln Gly Thr Thr Val Thr Val Ser Ser Ala
1               5                   10

<210> SEQ ID NO 172
<211> LENGTH: 321
<212> TYPE: DNA
<213> ORGANISM: Homo sapiens

<400> SEQUENCE: 172

```
gacatccagc tgacccagtc tccatcctcc ctgtctgcat ctgtaggaga cagagtcacc      60
atcacttgcc gggcaagtca gggcattaga aatgatttag ctggtatca  gcagaaacca     120
gggaaagccc ctaagcgcct gatctatgct gcatccagtt tgcaaaatgg ggtcccatca     180
aggttcagcg gcagtggatc tgggacagaa ttcactctca caatcagcag cctgcagcct     240
gaagattttg caacttatta ctgtctacaa cataatactt acccggcgtt cggccaaggg     300
accaaggtgg aaatcaaacg a                                               321
```

<210> SEQ ID NO 173
<211> LENGTH: 107
<212> TYPE: PRT
<213> ORGANISM: Homo sapiens

<400> SEQUENCE: 173

Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Asn Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Thr Tyr Pro Ala
                85                  90                  95
Phe Gly Gln Gly Thr Lys Val Glu Ile Lys Arg
            100                 105

<210> SEQ ID NO 174
<211> LENGTH: 23
<212> TYPE: PRT
<213> ORGANISM: Homo sapiens

<400> SEQUENCE: 174

Asp Ile Gln Leu Thr Gln Ser Pro Ser Ser Leu Ser Ala Ser Val Gly
1               5                   10                  15
Asp Arg Val Thr Ile Thr Cys
            20

<210> SEQ ID NO 175
<211> LENGTH: 11
<212> TYPE: PRT
<213> ORGANISM: Homo sapiens

<400> SEQUENCE: 175

Arg Ala Ser Gln Gly Ile Arg Asn Asp Leu Gly
1               5                   10

<210> SEQ ID NO 176
<211> LENGTH: 15
<212> TYPE: PRT
<213> ORGANISM: Homo sapiens

<400> SEQUENCE: 176

Trp Tyr Gln Gln Lys Pro Gly Lys Ala Pro Lys Arg Leu Ile Tyr
1               5                   10                  15

<210> SEQ ID NO 177
<211> LENGTH: 7
<212> TYPE: PRT
<213> ORGANISM: Homo sapiens

<400> SEQUENCE: 177

Ala Ala Ser Ser Leu Gln Asn
1               5

<210> SEQ ID NO 178
<211> LENGTH: 32
<212> TYPE: PRT
<213> ORGANISM: Homo sapiens

<400> SEQUENCE: 178

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 179
<211> LENGTH: 8
<212> TYPE: PRT
<213> ORGANISM: Homo sapiens

<400> SEQUENCE: 179

Leu Gln His Asn Thr Tyr Pro Ala
1               5

<210> SEQ ID NO 180
<211> LENGTH: 11
<212> TYPE: PRT
<213> ORGANISM: Homo sapiens

<400> SEQUENCE: 180

Phe Gly Gln Gly Thr Lys Val Glu Ile Lys Arg
1               5                   10

<210> SEQ ID NO 181
<211> LENGTH: 354
<212> TYPE: DNA
<213> ORGANISM: Homo sapiens

<400> SEQUENCE: 181
cagctggtgc agtctggagc agaagtgaaa aagcccgggg agtctctgaa gatctcctgt      60
cagggttctg gatacatctt taccaactac tggatcggct gggtgcgcca gatgcccggg     120
aaaggcctgg agtggatggg ggtcatctat cctgatgact ctgataccag atacagcccg     180
tccttccaag gccaggtcac catctcagcc gacaagtcca tcagcaccgc ctacctgcag     240
tggagcagcc tgaaggcctc ggacaccgcc atatattact gtgcgagaca aaaatggcta     300
caacacccct ttgactactg gggccaggga accctggtca ccgtctcctc agcc           354

<210> SEQ ID NO 182
<211> LENGTH: 118
<212> TYPE: PRT
<213> ORGANISM: Homo sapiens

<400> SEQUENCE: 182

Gln Leu Val Gln Ser Gly Ala Glu Val Lys Lys Pro Gly Glu Ser Leu
1               5                   10                  15

Lys Ile Ser Cys Gln Gly Ser Gly Tyr Ile Phe Thr Asn Tyr Trp Ile
            20                  25                  30

Gly Trp Val Arg Gln Met Pro Gly Lys Gly Leu Glu Trp Met Gly Val
        35                  40                  45

Ile Tyr Pro Asp Asp Ser Asp Thr Arg Tyr Ser Pro Ser Phe Gln Gly
50                  55                  60

Gln Val Thr Ile Ser Ala Asp Lys Ser Ile Ser Thr Ala Tyr Leu Gln
65                  70                  75                  80

Trp Ser Ser Leu Lys Ala Ser Asp Thr Ala Ile Tyr Tyr Cys Ala Arg
                85                  90                  95

Gln Lys Trp Leu Gln His Pro Phe Asp Tyr Trp Gly Gln Gly Thr Leu
            100                 105                 110

Val Thr Val Ser Ser Ala
        115

<210> SEQ ID NO 183
<211> LENGTH: 23
<212> TYPE: PRT
<213> ORGANISM: Homo sapiens

<400> SEQUENCE: 183

Gln Leu Val Gln Ser Gly Ala Glu Val Lys Lys Pro Gly Glu Ser Leu
1               5                   10                  15

Lys Ile Ser Cys Gln Gly Ser
            20

<210> SEQ ID NO 184
<211> LENGTH: 10
<212> TYPE: PRT
<213> ORGANISM: Homo sapiens

<400> SEQUENCE: 184

Gly Tyr Ile Phe Thr Asn Tyr Trp Ile Gly
1               5                   10

<210> SEQ ID NO 185
<211> LENGTH: 14
<212> TYPE: PRT
<213> ORGANISM: Homo sapiens

<400> SEQUENCE: 185

Trp Val Arg Gln Met Pro Gly Lys Gly Leu Glu Trp Met Gly
1               5                   10

<210> SEQ ID NO 186
<211> LENGTH: 17
<212> TYPE: PRT
<213> ORGANISM: Homo sapiens

<400> SEQUENCE: 186

Val Ile Tyr Pro Asp Asp Ser Asp Thr Arg Tyr Ser Pro Ser Phe Gln
1               5                   10                  15

Gly

<210> SEQ ID NO 187
<211> LENGTH: 32
<212> TYPE: PRT

<213> ORGANISM: Homo sapiens

<400> SEQUENCE: 187

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Ile Tyr Tyr Cys Ala Arg
            20                  25                  30

<210> SEQ ID NO 188
<211> LENGTH: 10
<212> TYPE: PRT
<213> ORGANISM: Homo sapiens

<400> SEQUENCE: 188

Gln Lys Trp Leu Gln His Pro Phe Asp Tyr
1               5                   10

<210> SEQ ID NO 189
<211> LENGTH: 12
<212> TYPE: PRT
<213> ORGANISM: Homo sapiens

<400> SEQUENCE: 189

Trp Gly Gln Gly Thr Leu Val Thr Val Ser Ser Ala
1               5                   10

<210> SEQ ID NO 190
<211> LENGTH: 327
<212> TYPE: DNA
<213> ORGANISM: Homo sapiens

<400> SEQUENCE: 190
gaaattgtgt tgacgcagtc accaggcacc ctgtctttgt ctccagggga aagagtcacc      60
ctctcatgca gggccagtca gagtgttagc agcagatact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagttta ttactgtcag cagtatggta gctcacctcg acgttcggc     300 caagggacca aggtggaaat caaacga                                        327

<210> SEQ ID NO 191
<211> LENGTH: 109
<212> TYPE: PRT
<213> ORGANISM: Homo sapiens

<400> SEQUENCE: 191

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg
            100                 105

100                 105

<210> SEQ ID NO 192
<211> LENGTH: 23
<212> TYPE: PRT
<213> ORGANISM: Homo sapiens

<400> SEQUENCE: 192

Glu Ile Val Leu Thr Gln Ser Pro Gly Thr Leu Ser Leu Ser Pro Gly
1               5                   10                  15

Glu Arg Val Thr Leu Ser Cys
            20

<210> SEQ ID NO 193
<211> LENGTH: 12
<212> TYPE: PRT
<213> ORGANISM: Homo sapiens

<400> SEQUENCE: 193

Arg Ala Ser Gln Ser Val Ser Ser Arg Tyr Leu Ala
1               5                   10

<210> SEQ ID NO 194
<211> LENGTH: 15
<212> TYPE: PRT
<213> ORGANISM: Homo sapiens

<400> SEQUENCE: 194

Trp Tyr Gln Gln Lys Pro Gly Gln Ala Pro Arg Leu Leu Ile Tyr
1               5                   10                  15

<210> SEQ ID NO 195
<211> LENGTH: 7
<212> TYPE: PRT
<213> ORGANISM: Homo sapiens

<400> SEQUENCE: 195

Gly Ala Ser Ser Arg Ala Thr
1               5

<210> SEQ ID NO 196
<211> LENGTH: 31
<212> TYPE: PRT
<213> ORGANISM: Homo sapiens

<400> SEQUENCE: 196

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr
            20                  25                  30

<210> SEQ ID NO 197
<211> LENGTH: 9
<212> TYPE: PRT
<213> ORGANISM: Homo sapiens

<400> SEQUENCE: 197

Gln Gln Tyr Gly Ser Ser Pro Arg Thr
1               5

<210> SEQ ID NO 198
<211> LENGTH: 11
<212> TYPE: PRT
<213> ORGANISM: Homo sapiens

<400> SEQUENCE: 198

Phe Gly Gln Gly Thr Lys Val Glu Ile Lys Arg
1               5                   10

<210> SEQ ID NO 199
<211> LENGTH: 369
<212> TYPE: DNA
<213> ORGANISM: Homo sapiens

<400> SEQUENCE: 199
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccta acagtggtgg cacaaactat      180
gcacagaagt tccaggacag ggtcaccatg accaggaca cgtccatcag cacagcctac     240
atggagctga gcaggctgag atctgacgac acggccgtgt attactgtgc gagagatttc     300
tttggttcgg ggagtctcct ctactttgac tactggggcc agggaaccct ggtcaccgtc     360
tcctcagcc                                                             369

<210> SEQ ID NO 200
<211> LENGTH: 123
<212> TYPE: PRT
<213> ORGANISM: Homo sapiens

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Phe Phe Gly Ser Gly Ser Leu Leu Tyr Phe Asp Tyr Trp
            100                 105                 110

Gly Gln Gly Thr Leu Val Thr Val Ser Ser Ala
        115                 120

<210> SEQ ID NO 201
<211> LENGTH: 25
<212> TYPE: PRT
<213> ORGANISM: Homo sapiens

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 202
<211> LENGTH: 10
<212> TYPE: PRT
<213> ORGANISM: Homo sapiens

<400> SEQUENCE: 202

Gly Tyr Thr Phe Thr Gly Tyr Tyr Met His
1               5                   10

<210> SEQ ID NO 203
<211> LENGTH: 14
<212> TYPE: PRT
<213> ORGANISM: Homo sapiens

<400> SEQUENCE: 203

Trp Val Arg Gln Ala Pro Gly Gln Gly Leu Glu Trp Met Gly
1               5                   10

<210> SEQ ID NO 204
<211> LENGTH: 17
<212> TYPE: PRT
<213> ORGANISM: Homo sapiens

<400> SEQUENCE: 204

Trp Ile Asn Pro Asn Ser Gly Gly Thr Asn Tyr Ala Gln Lys Phe Gln
1               5                   10                  15

Asp

<210> SEQ ID NO 205
<211> LENGTH: 32
<212> TYPE: PRT
<213> ORGANISM: Homo sapiens

<400> SEQUENCE: 205

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 206
<211> LENGTH: 13
<212> TYPE: PRT
<213> ORGANISM: Homo sapiens

<400> SEQUENCE: 206

Asp Phe Phe Gly Ser Gly Ser Leu Leu Tyr Phe Asp Tyr
1               5                   10

<210> SEQ ID NO 207
<211> LENGTH: 12
<212> TYPE: PRT
<213> ORGANISM: Homo sapiens

<400> SEQUENCE: 207

Trp Gly Gln Gly Thr Leu Val Thr Val Ser Ser Ala
1               5                   10

<210> SEQ ID NO 208
<211> LENGTH: 339
<212> TYPE: DNA
<213> ORGANISM: Homo sapiens

<400> SEQUENCE: 208
gatattgtga tgacccagac tccactctct ctgtccgtca cccctggaca gccggcctcc      60
atctcctgca agtctagtca gagcctcctg catagtggtg aaagaccta tttgtattgg     120 tacctgcaga ggccaggcca gcctccacag ctcctgatct atgaagtttc caaccggttc    180

```
tctggagtgc cagataggtt cagtggcagc gggtcaggga cagatttcac actgaaaatc    240
agccgggtgg aggctgagga tgttggggtt tattactgca tgcaaagtat acaccttccg    300
ctcactttcg gcggagggac caaggtggag atcaaacga                           339
```

<210> SEQ ID NO 209
<211> LENGTH: 113
<212> TYPE: PRT
<213> ORGANISM: Homo sapiens

<400> SEQUENCE: 209

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Gly Gly Lys Thr Tyr Leu Tyr Trp Tyr Leu Gln Arg Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile His Leu Pro Leu Thr Phe Gly Gly Gly Thr Lys Val Glu Ile Lys
            100                 105                 110

Arg
```

<210> SEQ ID NO 210
<211> LENGTH: 23
<212> TYPE: PRT
<213> ORGANISM: Homo sapiens

<400> SEQUENCE: 210

```
Asp Ile Val Met Thr Gln Thr Pro Leu Ser Leu Ser Val Thr Pro Gly
1               5                   10                  15

Gln Pro Ala Ser Ile Ser Cys
            20
```

<210> SEQ ID NO 211
<211> LENGTH: 16
<212> TYPE: PRT
<213> ORGANISM: Homo sapiens

<400> SEQUENCE: 211

```
Lys Ser Ser Gln Ser Leu Leu His Ser Gly Gly Lys Thr Tyr Leu Tyr
1               5                   10                  15
```

<210> SEQ ID NO 212
<211> LENGTH: 15
<212> TYPE: PRT
<213> ORGANISM: Homo sapiens

<400> SEQUENCE: 212

```
Trp Tyr Leu Gln Arg Pro Gly Gln Pro Pro Gln Leu Leu Ile Tyr
1               5                   10                  15
```

<210> SEQ ID NO 213
<211> LENGTH: 7
<212> TYPE: PRT
<213> ORGANISM: Homo sapiens

<400> SEQUENCE: 213

Glu Val Ser Asn Arg Phe Ser
1               5

<210> SEQ ID NO 214
<211> LENGTH: 32
<212> TYPE: PRT
<213> ORGANISM: Homo sapiens

<400> SEQUENCE: 214

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 215
<211> LENGTH: 9
<212> TYPE: PRT
<213> ORGANISM: Homo sapiens

<400> SEQUENCE: 215

Met Gln Ser Ile His Leu Pro Leu Thr
1               5

<210> SEQ ID NO 216
<211> LENGTH: 11
<212> TYPE: PRT
<213> ORGANISM: Homo sapiens

<400> SEQUENCE: 216

Phe Gly Gly Gly Thr Lys Val Glu Ile Lys Arg
1               5                   10

<210> SEQ ID NO 217
<211> LENGTH: 366
<212> TYPE: DNA
<213> ORGANISM: Homo sapiens

<400> SEQUENCE: 217
caggtgcagc tggagcagtc ggggggaggc gtggtccagc ctgggaggtc cctgagactc      60
tcctgtgcag cgtctggatt caccttcaat aactatggca tgcactgggt ccgccaggct     120
ccaggcaagg ggctggagtg ggtggcagtt atatggtatg atggaagtaa taatactat     180 gcagactccg tgaagggccg attcaccatc tccagagaca attccaagaa cacgctgtat     240
ctgcaaatga acagcctgag agccgaggac acggctgtgt attactgtgc gaaagatgag     300
gaatactact atgtttcggg gcttgactac tggggccagg gaaccctggt caccgtctcc     360
tcagcc                                                                366

<210> SEQ ID NO 218
<211> LENGTH: 122
<212> TYPE: PRT
<213> ORGANISM: Homo sapiens

<400> SEQUENCE: 218

Gln Val Gln Leu Glu Gln Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val

```
            35                  40                  45
Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Glu Tyr Tyr Tyr Val Ser Gly Leu Asp Tyr Trp Gly
            100                 105                 110

Gln Gly Thr Leu Val Thr Val Ser Ala
            115                 120
```

<210> SEQ ID NO 219
<211> LENGTH: 25
<212> TYPE: PRT
<213> ORGANISM: Homo sapiens

<400> SEQUENCE: 219

```
Gln Val Gln Leu Glu Gln Ser Gly Gly Gly Val Val Gln Pro Gly Arg
1               5                   10                  15

Ser Leu Arg Leu Ser Cys Ala Ala Ser
            20                  25
```

<210> SEQ ID NO 220
<211> LENGTH: 10
<212> TYPE: PRT
<213> ORGANISM: Homo sapiens

<400> SEQUENCE: 220

```
Gly Phe Thr Phe Asn Asn Tyr Gly Met His
1               5                   10
```

<210> SEQ ID NO 221
<211> LENGTH: 14
<212> TYPE: PRT
<213> ORGANISM: Homo sapiens

<400> SEQUENCE: 221

```
Trp Val Arg Gln Ala Pro Gly Lys Gly Leu Glu Trp Val Ala
1               5                   10
```

<210> SEQ ID NO 222
<211> LENGTH: 17
<212> TYPE: PRT
<213> ORGANISM: Homo sapiens

<400> SEQUENCE: 222

```
Val Ile Trp Tyr Asp Gly Ser Asn Lys Tyr Tyr Ala Asp Ser Val Lys
1               5                   10                  15

Gly
```

<210> SEQ ID NO 223
<211> LENGTH: 32
<212> TYPE: PRT
<213> ORGANISM: Homo sapiens

<400> SEQUENCE: 223

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 224
<211> LENGTH: 12
<212> TYPE: PRT
<213> ORGANISM: Homo sapiens

<400> SEQUENCE: 224

Asp Glu Glu Tyr Tyr Tyr Val Ser Gly Leu Asp Tyr
1               5                   10

<210> SEQ ID NO 225
<211> LENGTH: 12
<212> TYPE: PRT
<213> ORGANISM: Homo sapiens

<400> SEQUENCE: 225

Trp Gly Gln Gly Thr Leu Val Thr Val Ser Ser Ala
1               5                   10

<210> SEQ ID NO 226
<211> LENGTH: 315
<212> TYPE: DNA
<213> ORGANISM: Homo sapiens

<400> SEQUENCE: 226
ctgactcagt ctccatcctc cctgtctgca tctgtaagag acagagtcac catcacttgc     60
cgggcgagtc aggacattag caattattta gcctggtatc agcagaaacc agggaaagtt    120
cctaatctcc tgatctatgc tgcatccact ttgcaatcag ggtcccatc tcggttcagt    180 ggcagtggat ctgggacaga tttcactctc accatcagca gcctgcagcc tgaagatgtt    240
gcaacttatt actgtcaaaa gtataacagt gccccgctca ctttcggcgg agggaccaag    300
gtggagatca aacga                                                    315

<210> SEQ ID NO 227
<211> LENGTH: 105
<212> TYPE: PRT
<213> ORGANISM: Homo sapiens

<400> SEQUENCE: 227

Leu Thr Gln Ser Pro Ser Ser Leu Ser Ala Ser Val Arg Asp Arg Val
1               5                   10                  15

Thr Ile Thr Cys Arg Ala Ser Gln Asp Ile Ser Asn Tyr Leu Ala Trp
            20                  25                  30

Tyr Gln Gln Lys Pro Gly Lys Val Pro Asn Leu Leu Ile Tyr Ala Ala
        35                  40                  45

Ser Thr Leu Gln Ser Gly Val Pro Ser Arg Phe Ser Gly Ser Gly Ser
    50                  55                  60

Gly Thr Asp Phe Thr Leu Thr Ile Ser Ser Leu Gln Pro Glu Asp Val
65                  70                  75                  80

Ala Thr Tyr Tyr Cys Gln Lys Tyr Asn Ser Ala Pro Leu Thr Phe Gly
                85                  90                  95

Gly Gly Thr Lys Val Glu Ile Lys Arg
            100                 105

<210> SEQ ID NO 228
<211> LENGTH: 20
<212> TYPE: PRT
<213> ORGANISM: Homo sapiens

<400> SEQUENCE: 228

```
Leu Thr Gln Ser Pro Ser Ser Leu Ser Ala Ser Val Arg Asp Arg Val
1               5                   10                  15

Thr Ile Thr Cys
            20
```

<210> SEQ ID NO 229
<211> LENGTH: 11
<212> TYPE: PRT
<213> ORGANISM: Homo sapiens

<400> SEQUENCE: 229

```
Arg Ala Ser Gln Asp Ile Ser Asn Tyr Leu Ala
1               5                   10
```

<210> SEQ ID NO 230
<211> LENGTH: 15
<212> TYPE: PRT
<213> ORGANISM: Homo sapiens

<400> SEQUENCE: 230

```
Trp Tyr Gln Gln Lys Pro Gly Lys Val Pro Asn Leu Leu Ile Tyr
1               5                   10                  15
```

<210> SEQ ID NO 231
<211> LENGTH: 6
<212> TYPE: PRT
<213> ORGANISM: Homo sapiens

<400> SEQUENCE: 231

```
Ala Ala Ser Thr Leu Gln
1               5
```

<210> SEQ ID NO 232
<211> LENGTH: 32
<212> TYPE: PRT
<213> ORGANISM: Homo sapiens

<400> SEQUENCE: 232

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
                20                  25                  30
```

<210> SEQ ID NO 233
<211> LENGTH: 9
<212> TYPE: PRT
<213> ORGANISM: Homo sapiens

<400> SEQUENCE: 233

```
Gln Lys Tyr Asn Ser Ala Pro Leu Thr
1               5
```

<210> SEQ ID NO 234
<211> LENGTH: 11
<212> TYPE: PRT
<213> ORGANISM: Homo sapiens

<400> SEQUENCE: 234

```
Phe Gly Gly Gly Thr Lys Val Glu Ile Lys Arg
1               5                   10
```

<210> SEQ ID NO 235
<211> LENGTH: 372

<212> TYPE: DNA
<213> ORGANISM: Homo sapiens

<400> SEQUENCE: 235

```
cagatcacct tgaaggagtc tggtcctacg ctggtgacac ccacacagac cctcacgctg      60
acctgcacct tctctgggtt ctcactcagc actggtggaa tgggtgtggg ctggatccgt     120
cagcccccag gaaaggccct ggactggctt acactcattt attggaatga tgataagcac     180
tacagcccat ctctgaagag caggcttacc atcaccaagg acacctccaa aaaccaggtg     240
gtccttagaa tgaccaacat ggaccctgtg gacacagcca cttattactg tgcacacctg     300
cattacgata ttttgactgg ttttaacttt gactactggg gccagggaac cctggtcacc     360
gtctcctcag cc                                                         372
```

<210> SEQ ID NO 236
<211> LENGTH: 124
<212> TYPE: PRT
<213> ORGANISM: Homo sapiens

<400> SEQUENCE: 236

Gln Ile Thr Leu Lys Glu Ser Gly Pro Thr Leu Val Thr Pro Thr Gln
1               5                   10                  15
Thr Leu Thr Leu Thr Cys Thr Phe Ser Gly Phe Ser Leu Ser Thr Gly
            20                  25                  30
Gly Met Gly Val Gly Trp Ile Arg Gln Pro Pro Gly Lys Ala Leu Asp
        35                  40                  45
Trp Leu Thr Leu Ile Tyr Trp Asn Asp Asp Lys His Tyr Ser Pro Ser
    50                  55                  60
Leu Lys Ser Arg Leu Thr Ile Thr Lys Asp Thr Ser Lys Asn Gln Val
65                  70                  75                  80
Val Leu Arg Met Thr Asn Met Asp Pro Val Asp Thr Ala Thr Tyr Tyr
                85                  90                  95
Cys Ala His Leu His Tyr Asp Ile Leu Thr Gly Phe Asn Phe Asp Tyr
            100                 105                 110
Trp Gly Gln Gly Thr Leu Val Thr Val Ser Ser Ala
        115                 120

<210> SEQ ID NO 237
<211> LENGTH: 25
<212> TYPE: PRT
<213> ORGANISM: Homo sapiens

<400> SEQUENCE: 237

Gln Ile Thr Leu Lys Glu Ser Gly Pro Thr Leu Val Thr Pro Thr Gln
1               5                   10                  15
Thr Leu Thr Leu Thr Cys Thr Phe Ser
            20                  25

<210> SEQ ID NO 238
<211> LENGTH: 12
<212> TYPE: PRT
<213> ORGANISM: Homo sapiens

<400> SEQUENCE: 238

Gly Phe Ser Leu Ser Thr Gly Gly Met Gly Val Gly
1               5                   10

<210> SEQ ID NO 239
<211> LENGTH: 14

<212> TYPE: PRT
<213> ORGANISM: Homo sapiens

<400> SEQUENCE: 239

Trp Ile Arg Gln Pro Pro Gly Lys Ala Leu Asp Trp Leu Thr
1               5                   10

<210> SEQ ID NO 240
<211> LENGTH: 16
<212> TYPE: PRT
<213> ORGANISM: Homo sapiens

<400> SEQUENCE: 240

Leu Ile Tyr Trp Asn Asp Asp Lys His Tyr Ser Pro Ser Leu Lys Ser
1               5                   10                  15

<210> SEQ ID NO 241
<211> LENGTH: 32
<212> TYPE: PRT
<213> ORGANISM: Homo sapiens

<400> SEQUENCE: 241

Arg Leu Thr Ile Thr Lys Asp Thr Ser Lys Asn Gln Val Val Leu Arg
1               5                   10                  15

Met Thr Asn Met Asp Pro Val Asp Thr Ala Thr Tyr Tyr Cys Ala His
            20                  25                  30

<210> SEQ ID NO 242
<211> LENGTH: 13
<212> TYPE: PRT
<213> ORGANISM: Homo sapiens

<400> SEQUENCE: 242

Leu His Tyr Asp Ile Leu Thr Gly Phe Asn Phe Asp Tyr
1               5                   10

<210> SEQ ID NO 243
<211> LENGTH: 12
<212> TYPE: PRT
<213> ORGANISM: Homo sapiens

<400> SEQUENCE: 243

Trp Gly Gln Gly Thr Leu Val Thr Val Ser Ser Ala
1               5                   10

<210> SEQ ID NO 244
<211> LENGTH: 342
<212> TYPE: DNA
<213> ORGANISM: Homo sapiens

<400> SEQUENCE: 244
gatattgtga tgacccagac tccactctcc ctgcccgtca cccctggaga gccggcctcc      60
atctcctgca ggtctagtca gagcctcttg gatagtgatg atggaaacac ctatttggac     120
tggtacctgc agaagccagg gcagtctcca cagctcctga tctatacgct ttcctatcgg     180
gcctctggag tcccagacag gttcagtggc agtgggtcag gcactgattt cacactgaaa     240
atcagcaggg tggaggctga ggatgttgga gtttattact gcatgcaacg tatagagttt     300
ccgctcactt tcggcggagg gaccaaggtg gagatcaaac ga                        342

<210> SEQ ID NO 245
<211> LENGTH: 114
<212> TYPE: PRT

<213> ORGANISM: Homo sapiens

<400> SEQUENCE: 245

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
            100                 105                 110

Lys Arg

<210> SEQ ID NO 246
<211> LENGTH: 23
<212> TYPE: PRT
<213> ORGANISM: Homo sapiens

<400> SEQUENCE: 246

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 247
<211> LENGTH: 17
<212> TYPE: PRT
<213> ORGANISM: Homo sapiens

<400> SEQUENCE: 247

Arg Ser Ser Gln Ser Leu Leu Asp Ser Asp Asp Gly Asn Thr Tyr Leu
1               5                   10                  15

Asp

<210> SEQ ID NO 248
<211> LENGTH: 15
<212> TYPE: PRT
<213> ORGANISM: Homo sapiens

<400> SEQUENCE: 248

Trp Tyr Leu Gln Lys Pro Gly Gln Ser Pro Gln Leu Leu Ile Tyr
1               5                   10                  15

<210> SEQ ID NO 249
<211> LENGTH: 7
<212> TYPE: PRT
<213> ORGANISM: Homo sapiens

<400> SEQUENCE: 249

Thr Leu Ser Tyr Arg Ala Ser
1               5

<210> SEQ ID NO 250
<211> LENGTH: 32

<212> TYPE: PRT
<213> ORGANISM: Homo sapiens

<400> SEQUENCE: 250

Gly Val Pro Asp Arg Phe Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 251
<211> LENGTH: 9
<212> TYPE: PRT
<213> ORGANISM: Homo sapiens

<400> SEQUENCE: 251

Met Gln Arg Ile Glu Phe Pro Leu Thr
1               5

<210> SEQ ID NO 252
<211> LENGTH: 11
<212> TYPE: PRT
<213> ORGANISM: Homo sapiens

<400> SEQUENCE: 252

Phe Gly Gly Gly Thr Lys Val Glu Ile Lys Arg
1               5                   10

<210> SEQ ID NO 253
<211> LENGTH: 94
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is E or Q
<220> FEATURE:
<221> NAME/KEY: VARIANT
<222> LOCATION: (12)..(12)
<223> OTHER INFORMATION: Xaa is T or N
<220> FEATURE:
<221> NAME/KEY: VARIANT
<222> LOCATION: (27)..(27)
<223> OTHER INFORMATION: Xaa is A, F or G
<220> FEATURE:
<221> NAME/KEY: VARIANT
<222> LOCATION: (28)..(28)
<223> OTHER INFORMATION: Xaa is N or G
<220> FEATURE:
<221> NAME/KEY: VARIANT
<222> LOCATION: (30)..(30)
<223> OTHER INFORMATION: Xaa is Y or F
<220> FEATURE:
<221> NAME/KEY: VARIANT
<222> LOCATION: (32)..(32)
<223> OTHER INFORMATION: Xaa is T or S
<220> FEATURE:
<221> NAME/KEY: VARIANT
<222> LOCATION: (36)..(36)
<223> OTHER INFORMATION: Xaa is Q or H
<220> FEATURE:
<221> NAME/KEY: VARIANT
<222> LOCATION: (53)..(53)
<223> OTHER INFORMATION: Xaa is S or N
<220> FEATURE:
<221> NAME/KEY: VARIANT
<222> LOCATION: (56)..(56)
<223> OTHER INFORMATION: Xaa is C, S, or Y
<220> FEATURE:
<221> NAME/KEY: VARIANT
<222> LOCATION: (65)..(65)
<223> OTHER INFORMATION: Xaa is I or T
<220> FEATURE:

```
<221> NAME/KEY: VARIANT
<222> LOCATION: (78)..(78)
<223> OTHER INFORMATION: Xaa is K or T

<400> SEQUENCE: 253

Xaa Ser Gly Pro Gly Leu Val Lys Pro Ser Gln Xaa Leu Ser Leu Thr
1               5                   10                  15

Cys Thr Val Ser Gly Gly Ser Ile Ser Ser Xaa Xaa Tyr Xaa Trp Xaa
            20                  25                  30

Trp Ile Arg Xaa His Pro Gly Lys Gly Leu Glu Trp Ile Gly Tyr Ile
        35                  40                  45

Tyr Tyr Ser Gly Xaa Thr Tyr Xaa Asn Pro Ser Leu Lys Ser Arg Val
    50                  55                  60

Xaa Ile Ser Val Asp Thr Ser Lys Asn Gln Phe Ser Leu Xaa Leu Ser
65                  70                  75                  80

Ser Val Thr Ala Ala Asp Thr Ala Val Tyr Tyr Cys Ala Arg
                85                  90

<210> SEQ ID NO 254
<211> LENGTH: 12
<212> TYPE: PRT
<213> ORGANISM: Homo sapiens
<220> FEATURE:
<221> NAME/KEY: VARIANT
<222> LOCATION: (7)..(7)
<223> OTHER INFORMATION: Xaa is A, F, or G
<220> FEATURE:
<221> NAME/KEY: VARIANT
<222> LOCATION: (8)..(8)
<223> OTHER INFORMATION: Xaa is N or G
<220> FEATURE:
<221> NAME/KEY: VARIANT
<222> LOCATION: (10)..(10)
<223> OTHER INFORMATION: Xaa is Y or F
<220> FEATURE:
<221> NAME/KEY: VARIANT
<222> LOCATION: (12)..(12)
<223> OTHER INFORMATION: Xaa is T or S

<400> SEQUENCE: 254

Gly Gly Ser Ile Ser Ser Xaa Xaa Tyr Xaa Trp Xaa
1               5                   10

<210> SEQ ID NO 255
<211> LENGTH: 16
<212> TYPE: PRT
<213> ORGANISM: Homo sapiens
<220> FEATURE:
<221> NAME/KEY: VARIANT
<222> LOCATION: (7)..(7)
<223> OTHER INFORMATION: Xaa is S or N
<220> FEATURE:
<221> NAME/KEY: VARIANT
<222> LOCATION: (10)..(10)
<223> OTHER INFORMATION: Xaa is C, S, or  Y

<400> SEQUENCE: 255

Tyr Ile Tyr Tyr Ser Gly Xaa Thr Tyr Xaa Asn Pro Ser Leu Lys Ser
1               5                   10                  15

<210> SEQ ID NO 256
<211> LENGTH: 96
<212> TYPE: PRT
<213> ORGANISM: Homo sapiens
<220> FEATURE:
<221> NAME/KEY: VARIANT
<222> LOCATION: (30)..(30)
<223> OTHER INFORMATION: Xaa is Y or F
```

```
<220> FEATURE:
<221> NAME/KEY: VARIANT
<222> LOCATION: (38)..(38)
<223> OTHER INFORMATION: Xaa is A or T
<220> FEATURE:
<221> NAME/KEY: VARIANT
<222> LOCATION: (57)..(57)
<223> OTHER INFORMATION: Xaa is N or Y
<220> FEATURE:
<221> NAME/KEY: VARIANT
<222> LOCATION: (59)..(59)
<223> OTHER INFORMATION: Xaa is A or V
<220> FEATURE:
<221> NAME/KEY: VARIANT
<222> LOCATION: (64)..(64)
<223> OTHER INFORMATION: Xaa is D or G
<220> FEATURE:
<221> NAME/KEY: VARIANT
<222> LOCATION: (77)..(77)
<223> OTHER INFORMATION: Xaa is A or V

<400> SEQUENCE: 256

Gln Leu Val Gln Ser Gly Ala Glu Val Lys Lys Pro Gly Ala Ser Val
1               5                   10                  15

Lys Val Ser Cys Lys Ala Ser Gly Tyr Thr Phe Thr Gly Xaa Tyr Met
            20                  25                  30

His Trp Val Arg Gln Xaa Pro Gly Gln Gly Leu Glu Trp Met Gly Trp
        35                  40                  45

Ile Asn Pro Asn Ser Gly Gly Thr Xaa Tyr Xaa Gln Lys Phe Gln Xaa
    50                  55                  60

Arg Val Thr Met Thr Arg Asp Thr Ser Ile Ser Thr Xaa Tyr Met Glu
65                  70                  75                  80

Leu Ser Arg Leu Arg Ser Asp Asp Thr Ala Val Tyr Tyr Cys Ala Arg
                85                  90                  95

<210> SEQ ID NO 257
<211> LENGTH: 10
<212> TYPE: PRT
<213> ORGANISM: Homo sapiens
<220> FEATURE:
<221> NAME/KEY: VARIANT
<222> LOCATION: (7)..(7)
<223> OTHER INFORMATION: Xaa is Y or F

<400> SEQUENCE: 257

Gly Tyr Thr Phe Thr Gly Xaa Tyr Met His
1               5                   10

<210> SEQ ID NO 258
<211> LENGTH: 17
<212> TYPE: PRT
<213> ORGANISM: Homo sapiens
<220> FEATURE:
<221> NAME/KEY: VARIANT
<222> LOCATION: (10)..(10)
<223> OTHER INFORMATION: Xaa is N or Y
<220> FEATURE:
<221> NAME/KEY: VARIANT
<222> LOCATION: (12)..(12)
<223> OTHER INFORMATION: Xaa is A or V
<220> FEATURE:
<221> NAME/KEY: VARIANT
<222> LOCATION: (17)..(17)
<223> OTHER INFORMATION: Xaa is D or G

<400> SEQUENCE: 258

Trp Ile Asn Pro Asn Ser Gly Gly Thr Xaa Tyr Xaa Gln Lys Phe Gln
1               5                   10                  15
```

Xaa

```
<210> SEQ ID NO 259
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is Y or D
<220> FEATURE:
<221> NAME/KEY: VARIANT
<222> LOCATION: (2)..(2)
<223> OTHER INFORMATION: Xaa is Y or F
<220> FEATURE:
<221> NAME/KEY: VARIANT
<222> LOCATION: (3)..(3)
<223> OTHER INFORMATION: Xaa is Y or F
<220> FEATURE:
<221> NAME/KEY: VARIANT
<222> LOCATION: (8)..(8)
<223> OTHER INFORMATION: Xaa is Y or L
<220> FEATURE:
<221> NAME/KEY: VARIANT
<222> LOCATION: (9)..(9)
<223> OTHER INFORMATION: Xaa is Y or L

<400> SEQUENCE: 259

Xaa Xaa Xaa Gly Ser Gly Ser Xaa Xaa
1               5

<210> SEQ ID NO 260
<211> LENGTH: 98
<212> TYPE: PRT
<213> ORGANISM: Homo sapiens
<220> FEATURE:
<221> NAME/KEY: VARIANT
<222> LOCATION: (12)..(12)
<223> OTHER INFORMATION: Xaa is K or T
<220> FEATURE:
<221> NAME/KEY: VARIANT
<222> LOCATION: (30)..(30)
<223> OTHER INFORMATION: Xaa is T or A
<220> FEATURE:
<221> NAME/KEY: VARIANT
<222> LOCATION: (31)..(31)
<223> OTHER INFORMATION: Xaa is S or G
<220> FEATURE:
<221> NAME/KEY: VARIANT
<222> LOCATION: (33)..(33)
<223> OTHER INFORMATION: Xaa is M or V
<220> FEATURE:
<221> NAME/KEY: VARIANT
<222> LOCATION: (47)..(47)
<223> OTHER INFORMATION: Xaa is D or E
<220> FEATURE:
<221> NAME/KEY: VARIANT
<222> LOCATION: (50)..(50)
<223> OTHER INFORMATION: Xaa is A or T
<220> FEATURE:
<221> NAME/KEY: VARIANT
<222> LOCATION: (59)..(59)
<223> OTHER INFORMATION: Xaa is R or H
<220> FEATURE:
<221> NAME/KEY: VARIANT
<222> LOCATION: (65)..(65)
<223> OTHER INFORMATION: Xaa is K or R
<220> FEATURE:
<221> NAME/KEY: VARIANT
<222> LOCATION: (82)..(82)
<223> OTHER INFORMATION: Xaa is T or R
<220> FEATURE:
<221> NAME/KEY: VARIANT
<222> LOCATION: (83)..(83)
<223> OTHER INFORMATION: Xaa is M or I
```

<400> SEQUENCE: 260

Ile Thr Leu Lys Glu Ser Gly Pro Thr Leu Val Xaa Pro Thr Gln Thr
1               5                   10                  15

Leu Thr Leu Thr Cys Thr Phe Ser Gly Phe Ser Leu Ser Xaa Xaa Gly
            20                  25                  30

Xaa Gly Val Gly Trp Ile Arg Gln Pro Pro Gly Lys Ala Leu Xaa Trp
        35                  40                  45

Leu Xaa Leu Ile Tyr Trp Asn Asp Asp Lys Xaa Tyr Ser Pro Ser Leu
    50                  55                  60

Xaa Ser Arg Leu Thr Ile Thr Lys Asp Thr Ser Lys Asn Gln Val Val
65                  70                  75                  80

Leu Xaa Xaa Thr Asn Met Asp Pro Val Asp Thr Ala Thr Tyr Tyr Cys
                85                  90                  95

Ala His

<210> SEQ ID NO 261
<211> LENGTH: 12
<212> TYPE: PRT
<213> ORGANISM: Homo sapiens
<220> FEATURE:
<221> NAME/KEY: VARIANT
<222> LOCATION: (6)..(6)
<223> OTHER INFORMATION: Xaa is T or A
<220> FEATURE:
<221> NAME/KEY: VARIANT
<222> LOCATION: (7)..(7)
<223> OTHER INFORMATION: Xaa is S or G
<220> FEATURE:
<221> NAME/KEY: VARIANT
<222> LOCATION: (9)..(9)
<223> OTHER INFORMATION: Xaa is M or V

<400> SEQUENCE: 261

Gly Phe Ser Leu Ser Xaa Xaa Gly Xaa Gly Val Gly
1               5                   10

<210> SEQ ID NO 262
<211> LENGTH: 16
<212> TYPE: PRT
<213> ORGANISM: Homo sapiens
<220> FEATURE:
<221> NAME/KEY: VARIANT
<222> LOCATION: (9)..(9)
<223> OTHER INFORMATION: Xaa is R or H
<220> FEATURE:
<221> NAME/KEY: VARIANT
<222> LOCATION: (15)..(15)
<223> OTHER INFORMATION: Xaa is K or R

<400> SEQUENCE: 262

Leu Ile Tyr Trp Asn Asp Asp Lys Xaa Tyr Ser Pro Ser Leu Xaa Ser
1               5                   10                  15

<210> SEQ ID NO 263
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is Y or H
<220> FEATURE:
<221> NAME/KEY: VARIANT
<222> LOCATION: (8)..(8)
<223> OTHER INFORMATION: Xaa is Y or F
<220> FEATURE:
<221> NAME/KEY: VARIANT

```
<222> LOCATION: (9)..(9)
<223> OTHER INFORMATION: Xaa is Y or N

<400> SEQUENCE: 263

Xaa Tyr Asp Ile Leu Thr Gly Xaa Xaa
1               5

<210> SEQ ID NO 264
<211> LENGTH: 7
<212> TYPE: PRT
<213> ORGANISM: Homo sapiens
<220> FEATURE:
<221> NAME/KEY: VARIANT
<222> LOCATION: (4)..(4)
<223> OTHER INFORMATION: Xaa is V or D

<400> SEQUENCE: 264

Tyr Asp Tyr Xaa Trp Gly Ser
1               5

<210> SEQ ID NO 265
<211> LENGTH: 98
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is V or E
<220> FEATURE:
<221> NAME/KEY: VARIANT
<222> LOCATION: (6)..(6)
<223> OTHER INFORMATION: Xaa is E or Q
<220> FEATURE:
<221> NAME/KEY: VARIANT
<222> LOCATION: (30)..(30)
<223> OTHER INFORMATION: Xaa is S or N
<220> FEATURE:
<221> NAME/KEY: VARIANT
<222> LOCATION: (31)..(31)
<223> OTHER INFORMATION: Xaa is S or N
<220> FEATURE:
<221> NAME/KEY: VARIANT
<222> LOCATION: (34)..(34)
<223> OTHER INFORMATION: Xaa is M or I
<220> FEATURE:
<221> NAME/KEY: VARIANT
<222> LOCATION: (53)..(53)
<223> OTHER INFORMATION: Xaa is Y or F
<220> FEATURE:
<221> NAME/KEY: VARIANT
<222> LOCATION: (56)..(56)
<223> OTHER INFORMATION: Xaa is S or R
<220> FEATURE:
<221> NAME/KEY: VARIANT
<222> LOCATION: (91)..(91)
<223> OTHER INFORMATION: Xaa is T or A
<220> FEATURE:
<221> NAME/KEY: VARIANT
<222> LOCATION: (98)..(98)
<223> OTHER INFORMATION: Xaa is R or K

<400> SEQUENCE: 265

Gln Val Gln Leu Xaa Xaa Ser Gly Gly Gly Val Val Gln Pro Gly Arg
1               5                   10                  15

Ser Leu Arg Leu Ser Cys Ala Ala Ser Gly Phe Thr Phe Xaa Xaa Tyr
            20                  25                  30

Gly Xaa His Trp Val Arg Gln Ala Pro Gly Lys Gly Leu Glu Trp Val
        35                  40                  45

Ala Val Ile Trp Xaa Asp Gly Xaa Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Xaa Ala Val Tyr Tyr Cys
                 85                  90                  95

Ala Xaa

<210> SEQ ID NO 266
<211> LENGTH: 10
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is S or N
<220> FEATURE:
<221> NAME/KEY: VARIANT
<222> LOCATION: (6)..(6)
<223> OTHER INFORMATION: Xaa is S or N
<220> FEATURE:
<221> NAME/KEY: VARIANT
<222> LOCATION: (9)..(9)
<223> OTHER INFORMATION: Xaa is M or I

<400> SEQUENCE: 266

Gly Phe Thr Phe Xaa Xaa Tyr Gly Xaa His
 1               5                  10

<210> SEQ ID NO 267
<211> LENGTH: 17
<212> TYPE: PRT
<213> ORGANISM: Homo sapiens
<220> FEATURE:
<221> NAME/KEY: VARIANT
<222> LOCATION: (4)..(4)
<223> OTHER INFORMATION: Xaa is Y or F
<220> FEATURE:
<221> NAME/KEY: VARIANT
<222> LOCATION: (7)..(7)
<223> OTHER INFORMATION: Xaa is S or R

<400> SEQUENCE: 267

Val Ile Trp Xaa Asp Gly Xaa Asn Lys Tyr Tyr Ala Asp Ser Val Lys
 1               5                  10                  15

Gly

<210> SEQ ID NO 268
<211> LENGTH: 7
<212> TYPE: PRT
<213> ORGANISM: Homo sapiens
<220> FEATURE:
<221> NAME/KEY: VARIANT
<222> LOCATION: (7)..(7)
<223> OTHER INFORMATION: Xaa is S or L

<400> SEQUENCE: 268

Tyr Tyr Tyr Gly Ser Gly Xaa
 1               5

<210> SEQ ID NO 269
<211> LENGTH: 5
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is Y or S

<400> SEQUENCE: 269
```

Asp Tyr Gly Asp Xaa
1               5

<210> SEQ ID NO 270
<211> LENGTH: 98
<212> TYPE: PRT
<213> ORGANISM: Homo sapiens
<220> FEATURE:
<221> NAME/KEY: VARIANT
<222> LOCATION: (31)..(31)
<223> OTHER INFORMATION: Xaa is D or S
<220> FEATURE:
<221> NAME/KEY: VARIANT
<222> LOCATION: (33)..(33)
<223> OTHER INFORMATION: Xaa is S or Y
<220> FEATURE:
<221> NAME/KEY: VARIANT
<222> LOCATION: (35)..(35)
<223> OTHER INFORMATION: Xaa is S or T
<220> FEATURE:
<221> NAME/KEY: VARIANT
<222> LOCATION: (53)..(53)
<223> OTHER INFORMATION: Xaa is S or I
<220> FEATURE:
<221> NAME/KEY: VARIANT
<222> LOCATION: (57)..(57)
<223> OTHER INFORMATION: Xaa is T or I
<220> FEATURE:
<221> NAME/KEY: VARIANT
<222> LOCATION: (58)..(58)
<223> OTHER INFORMATION: Xaa is T or I
<220> FEATURE:
<221> NAME/KEY: VARIANT
<222> LOCATION: (59)..(59)
<223> OTHER INFORMATION: Xaa is Y or H
<220> FEATURE:
<221> NAME/KEY: VARIANT
<222> LOCATION: (70)..(70)
<223> OTHER INFORMATION: Xaa is I or M

<400> SEQUENCE: 270

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Xaa Tyr
            20                  25                  30

Xaa Met Xaa Trp Ile Arg Gln Ala Pro Gly Lys Gly Leu Glu Trp Val
        35                  40                  45

Ser Tyr Ile Ser Xaa Ser Gly Ser Xaa Xaa Tyr Ala Asp Ser Val
    50                  55                  60

Lys Gly Arg Phe Thr Xaa Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 271
<211> LENGTH: 10
<212> TYPE: PRT
<213> ORGANISM: Homo sapiens
<220> FEATURE:
<221> NAME/KEY: VARIANT
<222> LOCATION: (6)..(6)
<223> OTHER INFORMATION: Xaa is D or S
<220> FEATURE:
<221> NAME/KEY: VARIANT
<222> LOCATION: (8)..(8)
<223> OTHER INFORMATION: Xaa is S or Y
<220> FEATURE:
<221> NAME/KEY: VARIANT
<222> LOCATION: (10)..(10)

```
<223> OTHER INFORMATION: Xaa is S or T

<400> SEQUENCE: 271

Gly Phe Thr Phe Ser Xaa Tyr Xaa Met Xaa
1               5                   10

<210> SEQ ID NO 272
<211> LENGTH: 17
<212> TYPE: PRT
<213> ORGANISM: Homo sapiens
<220> FEATURE:
<221> NAME/KEY: VARIANT
<222> LOCATION: (4)..(4)
<223> OTHER INFORMATION: Xaa is S or I
<220> FEATURE:
<221> NAME/KEY: VARIANT
<222> LOCATION: (8)..(8)
<223> OTHER INFORMATION: Xaa is T or I
<220> FEATURE:
<221> NAME/KEY: VARIANT
<222> LOCATION: (9)..(9)
<223> OTHER INFORMATION: Xaa is T or I
<220> FEATURE:
<221> NAME/KEY: VARIANT
<222> LOCATION: (10)..(10)
<223> OTHER INFORMATION: Xaa is Y or H

<400> SEQUENCE: 272

Tyr Ile Ser Xaa Ser Gly Ser Xaa Xaa Xaa Tyr Ala Asp Ser Val Lys
1               5                   10                  15
Gly

<210> SEQ ID NO 273
<211> LENGTH: 10
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is G or D
<220> FEATURE:
<221> NAME/KEY: VARIANT
<222> LOCATION: (2)..(2)
<223> OTHER INFORMATION: Xaa is I or G

<400> SEQUENCE: 273

Xaa Xaa Ala Ala Ala Gly Ala Phe Asp Ile
1               5                   10

<210> SEQ ID NO 274
<211> LENGTH: 98
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is E or Q
<220> FEATURE:
<221> NAME/KEY: VARIANT
<222> LOCATION: (5)..(5)
<223> OTHER INFORMATION: Xaa is V or E
<220> FEATURE:
<221> NAME/KEY: VARIANT
<222> LOCATION: (6)..(6)
<223> OTHER INFORMATION: Xaa is E or Q
<220> FEATURE:
<221> NAME/KEY: VARIANT
<222> LOCATION: (20)..(20)
<223> OTHER INFORMATION: Xaa is F or L
<220> FEATURE:
<221> NAME/KEY: VARIANT
<222> LOCATION: (50)..(50)
```

<223> OTHER INFORMATION: Xaa is S or F

<400> SEQUENCE: 274

Xaa Val Gln Leu Xaa Xaa Ser Gly Gly Gly Leu Val Lys Pro Gly Gly
1               5                   10                  15

Ser Leu Arg Xaa Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Xaa Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 275
<211> LENGTH: 17
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is S or F

<400> SEQUENCE: 275

Xaa Ile Ser Ser Ser Ser Ser Tyr Ile Tyr Tyr Ala Asp Ser Val Lys
1               5                   10                  15

Gly

<210> SEQ ID NO 276
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is G or D
<220> FEATURE:
<221> NAME/KEY: VARIANT
<222> LOCATION: (2)..(2)
<223> OTHER INFORMATION: Xaa is I or W

<400> SEQUENCE: 276

Xaa Xaa Val Gly Ala Thr Phe Asp Tyr
1               5

<210> SEQ ID NO 277
<211> LENGTH: 96
<212> TYPE: PRT
<213> ORGANISM: Homo sapiens
<220> FEATURE:
<221> NAME/KEY: VARIANT
<222> LOCATION: (26)..(26)
<223> OTHER INFORMATION: Xaa is T or A
<220> FEATURE:
<221> NAME/KEY: VARIANT
<222> LOCATION: (54)..(54)
<223> OTHER INFORMATION: Xaa is S or N

<400> SEQUENCE: 277

Gln Leu Val Glu Ser Gly Gly Gly Val Val Gln Pro Gly Arg Ser Leu
1               5                   10                  15

```
Arg Leu Ser Cys Ala Ala Ser Gly Phe Xaa Phe Ser Tyr Gly Met
             20                  25                  30

His Trp Val Arg Gln Ala Pro Gly Lys Gly Leu Glu Trp Val Ala Val
         35                  40                  45

Ile Ser Tyr Asp Gly Xaa Asn Lys Tyr Tyr Ala Asp Ser Val Lys Gly
 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
             85                  90                  95
```

<210> SEQ ID NO 278
<211> LENGTH: 10
<212> TYPE: PRT
<213> ORGANISM: Homo sapiens
<220> FEATURE:
<221> NAME/KEY: VARIANT
<222> LOCATION: (3)..(3)
<223> OTHER INFORMATION: Xaa is T or A

<400> SEQUENCE: 278

```
Gly Phe Xaa Phe Ser Ser Tyr Gly Met His
 1               5                  10
```

<210> SEQ ID NO 279
<211> LENGTH: 17
<212> TYPE: PRT
<213> ORGANISM: Homo sapiens
<220> FEATURE:
<221> NAME/KEY: VARIANT
<222> LOCATION: (7)..(7)
<223> OTHER INFORMATION: Xaa is S or N

<400> SEQUENCE: 279

```
Val Ile Ser Tyr Asp Gly Xaa Asn Lys Tyr Tyr Ala Asp Ser Val Lys
 1               5                  10                  15

Gly
```

<210> SEQ ID NO 280
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is I or D
<220> FEATURE:
<221> NAME/KEY: VARIANT
<222> LOCATION: (2)..(2)
<223> OTHER INFORMATION: Xaa is T or L
<220> FEATURE:
<221> NAME/KEY: VARIANT
<222> LOCATION: (3)..(3)
<223> OTHER INFORMATION: Xaa is M or V
<220> FEATURE:
<221> NAME/KEY: VARIANT
<222> LOCATION: (7)..(7)
<223> OTHER INFORMATION: Xaa is V or I
<220> FEATURE:
<221> NAME/KEY: VARIANT
<222> LOCATION: (8)..(8)
<223> OTHER INFORMATION: Xaa is I or R
<220> FEATURE:
<221> NAME/KEY: VARIANT
<222> LOCATION: (9)..(9)
<223> OTHER INFORMATION: Xaa is I or G

<400> SEQUENCE: 280

```
Xaa Xaa Xaa Val Arg Gly Xaa Xaa Xaa
1               5
```

```
<210> SEQ ID NO 281
<211> LENGTH: 97
<212> TYPE: PRT
<213> ORGANISM: Homo sapiens
<220> FEATURE:
<221> NAME/KEY: VARIANT
<222> LOCATION: (27)..(27)
<223> OTHER INFORMATION: Xaa is G or D
<220> FEATURE:
<221> NAME/KEY: VARIANT
<222> LOCATION: (31)..(31)
<223> OTHER INFORMATION: Xaa is S or N
<220> FEATURE:
<221> NAME/KEY: VARIANT
<222> LOCATION: (51)..(51)
<223> OTHER INFORMATION: Xaa is I or F

<400> SEQUENCE: 281

Gln Val Gln Leu Gln Glu Ser Gly Pro Gly Leu Val Lys Pro Ser Glu
1               5                   10                  15

Thr Leu Ser Leu Thr Cys Thr Val Ser Gly Xaa Ser Ile Ser Xaa Tyr
            20                  25                  30

Tyr Trp Ser Trp Ile Arg Gln Pro Pro Gly Lys Gly Leu Glu Trp Ile
        35                  40                  45

Gly Tyr Xaa Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

```
<210> SEQ ID NO 282
<211> LENGTH: 10
<212> TYPE: PRT
<213> ORGANISM: Homo sapiens
<220> FEATURE:
<221> NAME/KEY: VARIANT
<222> LOCATION: (2)..(2)
<223> OTHER INFORMATION: Xaa is G or D
<220> FEATURE:
<221> NAME/KEY: VARIANT
<222> LOCATION: (6)..(6)
<223> OTHER INFORMATION: Xaa is S or N

<400> SEQUENCE: 282

Gly Xaa Ser Ile Ser Xaa Tyr Tyr Trp Ser
1               5                   10
```

```
<210> SEQ ID NO 283
<211> LENGTH: 16
<212> TYPE: PRT
<213> ORGANISM: Homo sapiens
<220> FEATURE:
<221> NAME/KEY: VARIANT
<222> LOCATION: (2)..(2)
<223> OTHER INFORMATION: Xaa is I or F

<400> SEQUENCE: 283

Tyr Xaa Tyr Tyr Ser Gly Ser Thr Asn Tyr Asn Pro Ser Leu Lys Ser
1               5                   10                  15
```

```
<210> SEQ ID NO 284
```

```
<211> LENGTH: 6
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is S or D
<220> FEATURE:
<221> NAME/KEY: VARIANT
<222> LOCATION: (2)..(2)
<223> OTHER INFORMATION: Xaa is S or R

<400> SEQUENCE: 284

Xaa Xaa Gly Trp Asp Tyr
1               5

<210> SEQ ID NO 285
<211> LENGTH: 96
<212> TYPE: PRT
<213> ORGANISM: Homo sapiens
<220> FEATURE:
<221> NAME/KEY: VARIANT
<222> LOCATION: (21)..(21)
<223> OTHER INFORMATION: Xaa is K or Q
<220> FEATURE:
<221> NAME/KEY: VARIANT
<222> LOCATION: (26)..(26)
<223> OTHER INFORMATION: Xaa is S or I
<220> FEATURE:
<221> NAME/KEY: VARIANT
<222> LOCATION: (29)..(29)
<223> OTHER INFORMATION: Xaa is S or N
<220> FEATURE:
<221> NAME/KEY: VARIANT
<222> LOCATION: (48)..(48)
<223> OTHER INFORMATION: Xaa is I or V
<220> FEATURE:
<221> NAME/KEY: VARIANT
<222> LOCATION: (52)..(52)
<223> OTHER INFORMATION: Xaa is G or D
<220> FEATURE:
<221> NAME/KEY: VARIANT
<222> LOCATION: (91)..(91)
<223> OTHER INFORMATION: Xaa is M or I

<400> SEQUENCE: 285

Gln Leu Val Gln Ser Gly Ala Glu Val Lys Lys Pro Gly Glu Ser Leu
1               5                   10                  15

Lys Ile Ser Cys Xaa Gly Ser Gly Tyr Xaa Phe Thr Xaa Tyr Trp Ile
            20                  25                  30

Gly Trp Val Arg Gln Met Pro Gly Lys Gly Leu Glu Trp Met Gly Xaa
        35                  40                  45

Ile Tyr Pro Xaa Asp Ser Asp Thr Arg Tyr Ser Pro Ser Phe Gln Gly
    50                  55                  60

Gln Val Thr Ile Ser Ala Asp Lys Ser Ile Ser Thr Ala Tyr Leu Gln
65                  70                  75                  80

Trp Ser Ser Leu Lys Ala Ser Asp Thr Ala Xaa Tyr Tyr Cys Ala Arg
                85                  90                  95

<210> SEQ ID NO 286
<211> LENGTH: 10
<212> TYPE: PRT
<213> ORGANISM: Homo sapiens
<220> FEATURE:
<221> NAME/KEY: VARIANT
<222> LOCATION: (3)..(3)
<223> OTHER INFORMATION: Xaa is S or I
<220> FEATURE:
<221> NAME/KEY: VARIANT
<222> LOCATION: (6)..(6)
```

```
<223> OTHER INFORMATION: Xaa is S or N

<400> SEQUENCE: 286

Gly Tyr Xaa Phe Thr Xaa Tyr Trp Ile Gly
1               5                   10

<210> SEQ ID NO 287
<211> LENGTH: 17
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is I or V
<220> FEATURE:
<221> NAME/KEY: VARIANT
<222> LOCATION: (5)..(5)
<223> OTHER INFORMATION: Xaa is G or D

<400> SEQUENCE: 287

Xaa Ile Tyr Pro Xaa Asp Ser Asp Thr Arg Tyr Ser Pro Ser Phe Gln
1               5                   10                  15

Gly

<210> SEQ ID NO 288
<211> LENGTH: 8
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is R or K
<220> FEATURE:
<221> NAME/KEY: VARIANT
<222> LOCATION: (5)..(5)
<223> OTHER INFORMATION: Xaa is L or H

<400> SEQUENCE: 288

Xaa Trp Leu Gln Xaa Phe Asp Tyr
1               5

<210> SEQ ID NO 289
<211> LENGTH: 470
<212> TYPE: PRT
<213> ORGANISM: Homo sapiens

<400> SEQUENCE: 289

Lys Arg Phe His Asp Val Leu Gly Asn Glu Arg Pro Ser Ala Tyr Met
1               5                   10                  15

Arg Glu His Asn Gln Leu Asn Gly Trp Ser Ser Asp Glu Asn Asp Trp
                20                  25                  30

Asn Glu Lys Leu Tyr Pro Val Trp Lys Arg Gly Asp Met Arg Trp Lys
            35                  40                  45

Asn Ser Trp Lys Gly Gly Arg Val Gln Ala Val Leu Thr Ser Asp Ser
        50                  55                  60

Pro Ala Leu Val Gly Ser Asn Ile Thr Phe Ala Val Asn Leu Ile Phe
65                  70                  75                  80

Pro Arg Cys Gln Lys Glu Asp Ala Asn Gly Asn Ile Val Tyr Glu Lys
                85                  90                  95

Asn Cys Arg Asn Glu Ala Gly Leu Ser Ala Asp Pro Tyr Val Tyr Asn
                100                 105                 110

Trp Thr Ala Trp Ser Glu Asp Ser Asp Gly Glu Asn Gly Thr Gly Gln
            115                 120                 125
```

```
Ser His His Asn Val Phe Pro Asp Gly Lys Pro Phe Pro His His Pro
130                 135                 140

Gly Trp Arg Arg Trp Asn Phe Ile Tyr Val Phe His Thr Leu Gly Gln
145                 150                 155                 160

Tyr Phe Gln Lys Leu Gly Arg Cys Ser Arg Val Ser Val Asn Thr
            165                 170                 175

Ala Asn Val Thr Leu Gly Pro Gln Leu Met Glu Val Thr Val Tyr Arg
            180                 185                 190

Arg His Gly Arg Ala Tyr Val Pro Ile Ala Gln Val Lys Asp Val Tyr
            195                 200                 205

Val Val Thr Asp Gln Ile Pro Val Phe Val Thr Met Phe Gln Lys Asn
210                 215                 220

Asp Arg Asn Ser Ser Asp Glu Thr Phe Leu Lys Asp Leu Pro Ile Met
225                 230                 235                 240

Phe Asp Val Leu Ile His Asp Pro Ser His Phe Leu Asn Tyr Ser Thr
                245                 250                 255

Ile Asn Tyr Lys Trp Ser Phe Gly Asp Asn Thr Gly Leu Phe Val Ser
            260                 265                 270

Thr Asn His Thr Val Asn His Thr Tyr Val Leu Asn Gly Thr Phe Ser
            275                 280                 285

Leu Asn Leu Thr Val Lys Ala Ala Pro Gly Pro Cys Pro Pro
290                 295                 300

Pro Pro Pro Arg Pro Ser Lys Pro Thr Pro Ser Leu Ala Thr Thr
305                 310                 315                 320

Leu Lys Ser Tyr Asp Ser Asn Thr Pro Gly Pro Ala Gly Asp Asn Pro
            325                 330                 335

Leu Glu Leu Ser Arg Ile Pro Asp Glu Asn Cys Gln Ile Asn Arg Tyr
            340                 345                 350

Gly His Phe Gln Ala Thr Ile Thr Ile Val Glu Gly Ile Leu Glu Val
            355                 360                 365

Asn Ile Ile Gln Met Thr Asp Val Leu Met Pro Val Pro Trp Pro Glu
370                 375                 380

Ser Ser Leu Ile Asp Phe Val Val Thr Cys Gln Gly Ser Ile Pro Thr
385                 390                 395                 400

Glu Val Cys Thr Ile Ile Ser Asp Pro Thr Cys Glu Ile Thr Gln Asn
            405                 410                 415

Thr Val Cys Ser Pro Val Asp Val Asp Glu Met Cys Leu Leu Thr Val
            420                 425                 430

Arg Arg Thr Phe Asn Gly Ser Gly Thr Tyr Cys Val Asn Leu Thr Leu
            435                 440                 445

Gly Asp Asp Thr Ser Leu Ala Leu Thr Ser Thr Leu Ile Ser Val Pro
450                 455                 460

Asp Arg Asp Pro Ala Ser
465                 470

<210> SEQ ID NO 290
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 290
caccatggac tggcacctgg aggatc                                    26
```

```
<210> SEQ ID NO 291
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 291
caccatggac tggacctgga gacatc                                        26

<210> SEQ ID NO 292
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 292
caccatggac tggacctgga gggtc                                         25

<210> SEQ ID NO 293
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 293
caccatggac tggatttgga ggatc                                         25

<210> SEQ ID NO 294
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 294
caccatggac acactttgct cacac                                         25

<210> SEQ ID NO 295
<211> LENGTH: 26
<212> TYPE: DNA
<213> ORGANISM: Artificial
<220> FEATURE:
<223> OTHER INFORMATION: chemically synthesized primer

<400> SEQUENCE: 295
caccatggaa gttggggctg agctgg                                        26

<210> SEQ ID NO 296
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 296
caccatggag ttgtggactg agctgg                                        26

<210> SEQ ID NO 297
<211> LENGTH: 26
<212> TYPE: DNA
<213> ORGANISM: Artificial Sequence
<220> FEATURE:
<223> OTHER INFORMATION: chemically synthesized primer
```

```
<400> SEQUENCE: 297
caccatggag tttgggctgt agctgg                                    26

<210> SEQ ID NO 298
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 298
caccatggaa ctggggctcc gctgg                                     25

<210> SEQ ID NO 299
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 299
caccatggag ttggggctgt gctgg                                     25

<210> SEQ ID NO 300
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 300
caccatggag ttttggctga gctgg                                     25

<210> SEQ ID NO 301
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 301
caccatgacg gagtttgggc tgagc                                     25

<210> SEQ ID NO 302
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 302
caccatgaaa gcacctgtgg ttcttc                                    26

<210> SEQ ID NO 303
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 303
caccatgaaa catctgtggt tcttc                                     25

<210> SEQ ID NO 304
<211> LENGTH: 25
```

```
<212> TYPE: DNA
<213> ORGANISM: Artificial Sequence
<220> FEATURE:
<223> OTHER INFORMATION: chemically synthesized primer

<400> SEQUENCE: 304
caccatgggg tcaaccgcca tcctc                                              25

<210> SEQ ID NO 305
<211> LENGTH: 28
<212> TYPE: DNA
<213> ORGANISM: Artificial Sequence
<220> FEATURE:
<223> OTHER INFORMATION: chemically synthesized primer

<400> SEQUENCE: 305
caccatgtct gtctccttcc tcatcttc                                           28

<210> SEQ ID NO 306
<211> LENGTH: 21
<212> TYPE: DNA
<213> ORGANISM: Artificial Sequence
<220> FEATURE:
<223> OTHER INFORMATION: chemically synthesized primer

<400> SEQUENCE: 306
atggggtccc aggttcacct c                                                  21

<210> SEQ ID NO 307
<211> LENGTH: 22
<212> TYPE: DNA
<213> ORGANISM: Artificial Sequence
<220> FEATURE:
<223> OTHER INFORMATION: chemically synthesized primer

<400> SEQUENCE: 307
atgttgccat cacaactcat tg                                                 22

<210> SEQ ID NO 308
<211> LENGTH: 98
<212> TYPE: PRT
<213> ORGANISM: Homo sapiens

<400> SEQUENCE: 308

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 309
<211> LENGTH: 369
<212> TYPE: DNA
<213> ORGANISM: Homo sapiens
```

```
<400> SEQUENCE: 309
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccct a acagtggtgg cacaaactat     180
gcacagaagt ttcaggacag ggtcaccatg accagggaca cgtccatcag cacagcctac     240
atggagctga gcaggctgag atctgacgac acggccgtgt attactgtgc gagagatttc     300
tttggttcgg ggagtctcct ctactttgac tactggggcc agggaaccct ggtcaccgtc     360
tcctcagcc                                                             369

<210> SEQ ID NO 310
<211> LENGTH: 123
<212> TYPE: PRT
<213> ORGANISM: Homo sapiens

<400> SEQUENCE: 310

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Phe Phe Gly Ser Gly Ser Leu Leu Tyr Phe Asp Tyr Trp
            100                 105                 110

Gly Gln Gly Thr Leu Val Thr Val Ser Ser Ala
        115                 120

<210> SEQ ID NO 311
<211> LENGTH: 25
<212> TYPE: PRT
<213> ORGANISM: Homo sapiens

<400> SEQUENCE: 311

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 312
<211> LENGTH: 10
<212> TYPE: PRT
<213> ORGANISM: Homo sapiens

<400> SEQUENCE: 312

Gly Tyr Thr Phe Thr Gly Tyr Tyr Met His
1               5                   10

<210> SEQ ID NO 313
<211> LENGTH: 14
<212> TYPE: PRT
<213> ORGANISM: Homo sapiens
```

<400> SEQUENCE: 313

Trp Val Arg Gln Ala Pro Gly Gln Gly Leu Glu Trp Met Gly
1               5                   10

<210> SEQ ID NO 314
<211> LENGTH: 17
<212> TYPE: PRT
<213> ORGANISM: Homo sapiens

<400> SEQUENCE: 314

Trp Ile Asn Pro Asn Ser Gly Gly Thr Asn Tyr Ala Gln Lys Phe Gln
1               5                   10                  15
Asp

<210> SEQ ID NO 315
<211> LENGTH: 32
<212> TYPE: PRT
<213> ORGANISM: Homo sapiens

<400> SEQUENCE: 315

Arg Val Thr Met Thr Arg Asp Thr Ser Ile Ser Thr Ala Tyr Met Glu
1               5                   10                  15
Leu Ser Arg Leu Arg Ser Asp Asp Thr Ala Val Tyr Tyr Cys Ala Arg
            20                  25                  30

<210> SEQ ID NO 316
<211> LENGTH: 13
<212> TYPE: PRT
<213> ORGANISM: Homo sapiens

<400> SEQUENCE: 316

Asp Phe Phe Gly Ser Gly Ser Leu Leu Tyr Phe Asp Tyr
1               5                   10

<210> SEQ ID NO 317
<211> LENGTH: 12
<212> TYPE: PRT
<213> ORGANISM: Homo sapiens

<400> SEQUENCE: 317

Trp Gly Gln Gly Thr Leu Val Thr Val Ser Ser Ala
1               5                   10

<210> SEQ ID NO 318
<211> LENGTH: 339
<212> TYPE: DNA
<213> ORGANISM: Homo sapiens

<400> SEQUENCE: 318
gatattgtga tgacccagac tccactctct ctgtccgtca cccctggaca gccggcctcc      60
atctcctgca agtctagtca gagcctcctg catagtggtg aaagaccta tttgtattgg     120
tacctgcaga ggccaggcca gcctccacag ctcctgatct atgaagtttc caaccggttc    180
tctggagtgc cagataggtt cagtggcagc gggtcaggga cagatttcac actgaaaatc    240
agccgggtgg aggctgagga tgttggggtt tattactgca tgcaaagtat acaccttccg    300
ctcactttcg gcggagggac caaggtggag atcaaacga                           339

<210> SEQ ID NO 319
<211> LENGTH: 113
<212> TYPE: PRT
<213> ORGANISM: Homo sapiens

<400> SEQUENCE: 319

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Gly Gly Lys Thr Tyr Leu Tyr Trp Tyr Leu Gln Arg Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile His Leu Pro Leu Thr Phe Gly Gly Gly Thr Lys Val Glu Ile Lys
                100                 105                 110

Arg

<210> SEQ ID NO 320
<211> LENGTH: 23
<212> TYPE: PRT
<213> ORGANISM: Homo sapiens

<400> SEQUENCE: 320

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 321
<211> LENGTH: 16
<212> TYPE: PRT
<213> ORGANISM: Homo sapiens

<400> SEQUENCE: 321

Lys Ser Ser Gln Ser Leu Leu His Ser Gly Gly Lys Thr Tyr Leu Tyr
1               5                   10                  15

<210> SEQ ID NO 322
<211> LENGTH: 15
<212> TYPE: PRT
<213> ORGANISM: Homo sapiens

<400> SEQUENCE: 322

Trp Tyr Leu Gln Arg Pro Gly Gln Pro Pro Gln Leu Leu Ile Tyr
1               5                   10                  15

<210> SEQ ID NO 323
<211> LENGTH: 7
<212> TYPE: PRT
<213> ORGANISM: Homo sapiens

<400> SEQUENCE: 323

Glu Val Ser Asn Arg Phe Ser
1               5

<210> SEQ ID NO 324
<211> LENGTH: 32
<212> TYPE: PRT
<213> ORGANISM: Homo sapiens

```
<400> SEQUENCE: 324

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 325
<211> LENGTH: 9
<212> TYPE: PRT
<213> ORGANISM: Homo sapiens

<400> SEQUENCE: 325

Met Gln Ser Ile His Leu Pro Leu Thr
1               5

<210> SEQ ID NO 326
<211> LENGTH: 11
<212> TYPE: PRT
<213> ORGANISM: Homo sapiens

<400> SEQUENCE: 326

Phe Gly Gly Gly Thr Lys Val Glu Ile Lys Arg
1               5                   10

<210> SEQ ID NO 327
<211> LENGTH: 22
<212> TYPE: DNA
<213> ORGANISM: Artificial Sequence
<220> FEATURE:
<223> OTHER INFORMATION: chemically synthesized primer

<400> SEQUENCE: 327
gaattcagag ttaaaccttg ag                                        22

<210> SEQ ID NO 328
<211> LENGTH: 22
<212> TYPE: DNA
<213> ORGANISM: Artificial Sequence
<220> FEATURE:
<223> OTHER INFORMATION: chemically synthesized primer

<400> SEQUENCE: 328
caggaatctg atctgttacc ac                                        22

<210> SEQ ID NO 329
<211> LENGTH: 23
<212> TYPE: DNA
<213> ORGANISM: Artificial Sequence
<220> FEATURE:
<223> OTHER INFORMATION: chemically synthesized primer

<400> SEQUENCE: 329
ctgaccctac aagatgccaa gag                                       23

<210> SEQ ID NO 330
<211> LENGTH: 29
<212> TYPE: DNA
<213> ORGANISM: Artificial Sequence
<220> FEATURE:
<223> OTHER INFORMATION: chemically synthesized primer

<400> SEQUENCE: 330
atcatgcatt gcaacattta ttgatggag                                 29
```

-continued

```
<210> SEQ ID NO 331
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 331
ttggcagatt gtctgtagcc                                                    20

<210> SEQ ID NO 332
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 332
aggcattgtg catgctgctt                                                    20

<210> SEQ ID NO 333
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 333
tattgaaagt gccgagatcc                                                    20

<210> SEQ ID NO 334
<211> LENGTH: 19
<212> TYPE: DNA
<213> ORGANISM: Artificial Sequence
<220> FEATURE:
<223> OTHER INFORMATION: chemically synthesized primer

<400> SEQUENCE: 334
tgcaaggacc acagccatc                                                     19

<210> SEQ ID NO 335
<211> LENGTH: 21
<212> TYPE: DNA
<213> ORGANISM: Artificial Sequence
<220> FEATURE:
<223> OTHER INFORMATION: chemically synthesized primer

<400> SEQUENCE: 335
tcaatggaac cttcagcctt a                                                  21

<210> SEQ ID NO 336
<211> LENGTH: 19
<212> TYPE: DNA
<213> ORGANISM: Artificial Sequence
<220> FEATURE:
<223> OTHER INFORMATION: chemically synthesized primer

<400> SEQUENCE: 336
gaaggggtgg gttttgaag                                                     19

<210> SEQ ID NO 337
<211> LENGTH: 25
<212> TYPE: DNA
<213> ORGANISM: Artificial Sequence
<220> FEATURE:
<223> OTHER INFORMATION: chemically synthesized primer
```

<400> SEQUENCE: 337
ctcactgtga aagctgcagc accag					25

<210> SEQ ID NO 338
<211> LENGTH: 21
<212> TYPE: DNA
<213> ORGANISM: Artificial Sequence
<220> FEATURE:
<223> OTHER INFORMATION: chemically synthesized primer

<400> SEQUENCE: 338
tcaatggaac cttcagcctt a					21

<210> SEQ ID NO 339
<211> LENGTH: 19
<212> TYPE: DNA
<213> ORGANISM: Artificial Sequence
<220> FEATURE:
<223> OTHER INFORMATION: chemically synthesized primer

<400> SEQUENCE: 339 gaagggtgg gttttgaag					19

<210> SEQ ID NO 340
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 340
ctcactgtga aagctgcagc accag					25

<210> SEQ ID NO 341
<211> LENGTH: 30
<212> TYPE: DNA
<213> ORGANISM: Artificial Sequence
<220> FEATURE:
<223> OTHER INFORMATION: chemically synthesized

<400> SEQUENCE: 341
tgatcagtaa ggatttcacc tctgtttgta					30

<210> SEQ ID NO 342
<211> LENGTH: 30
<212> TYPE: DNA
<213> ORGANISM: Artificial Sequence
<220> FEATURE:
<223> OTHER INFORMATION: chemically synthesized

<400> SEQUENCE: 342
accttgtcat gtaccatcaa taaagtaccc					30

<210> SEQ ID NO 343
<211> LENGTH: 12
<212> TYPE: PRT
<213> ORGANISM: Homo sapiens

<400> SEQUENCE: 343

Ala Thr Thr Leu Lys Ser Tyr Asp Ser Asn Thr Pro
 1               5                  10

<210> SEQ ID NO 344
<211> LENGTH: 25
<212> TYPE: PRT

```
<213> ORGANISM: Artificial Sequence
<220> FEATURE:
<223> OTHER INFORMATION: chemically synthesized

<400> SEQUENCE: 344

Leu Ser Ala Asp Asp Ala Lys Lys Asp Ala Ala Lys Lys Asp Ala
1               5                   10                  15

Lys Lys Asp Asp Ala Lys Lys Asp Leu
                20                  25

<210> SEQ ID NO 345
<211> LENGTH: 60
<212> TYPE: DNA
<213> ORGANISM: Artificial Sequence
<220> FEATURE:
<223> OTHER INFORMATION: chemically synthesized primer

<400> SEQUENCE: 345
tctcttcctc ctgctactct ggctcccaga taccaccggt gaaatagtga tgacgcagtc     60

<210> SEQ ID NO 346
<211> LENGTH: 57
<212> TYPE: DNA
<213> ORGANISM: Artificial Sequence
<220> FEATURE:
<223> OTHER INFORMATION: chemically synthesized primer

<400> SEQUENCE: 346
ccggaattct tactatttgt catcatcgtc cttataatcg ctagctgagg agacggt        57

<210> SEQ ID NO 347
<211> LENGTH: 60
<212> TYPE: DNA
<213> ORGANISM: Artificial Sequence
<220> FEATURE:
<223> OTHER INFORMATION: chemically synthesized primer

<400> SEQUENCE: 347
acgcgtcgac ccaccatgga agccccagcg cagcttctct tcctcctgct actctggctc     60

<210> SEQ ID NO 348
<211> LENGTH: 60
<212> TYPE: DNA
<213> ORGANISM: Artificial Sequence
<220> FEATURE:
<223> OTHER INFORMATION: chemically synthesized primer

<400> SEQUENCE: 348
tctcttcctc ctgctactct ggctcccaga taccaccggt gaaatagtga tgacgcagtc     60

<210> SEQ ID NO 349
<211> LENGTH: 57
<212> TYPE: DNA
<213> ORGANISM: Artificial Sequence
<220> FEATURE:
<223> OTHER INFORMATION: chemically synthesized primer

<400> SEQUENCE: 349
ccggaattct tactatttgt catcatcgtc cttataatcg ctagctttca gctccag        57

<210> SEQ ID NO 350
<211> LENGTH: 60
<212> TYPE: DNA
<213> ORGANISM: Artificial Sequence
<220> FEATURE:
<223> OTHER INFORMATION: chemically synthesized primer
```

<400> SEQUENCE: 350

```
acgcgtcgac ccaccatgga agccccagcg cagcttctct tcctcctgct actctggctc    60
```

<210> SEQ ID NO 351
<211> LENGTH: 55
<212> TYPE: DNA
<213> ORGANISM: Artificial Sequence
<220> FEATURE:
<223> OTHER INFORMATION: chemically synthesized primer

<400> SEQUENCE: 351

```
actctggctc ccagatacca ccggagaaat agtgatgacg cagtctccag ccacc    55
```

<210> SEQ ID NO 352
<211> LENGTH: 51
<212> TYPE: DNA
<213> ORGANISM: Artificial Sequence
<220> FEATURE:
<223> OTHER INFORMATION: chemically synthesized primer

<400> SEQUENCE: 352

```
ccgctcgagc tatttgtcat catcgtcctt ataatctttc agctccagct t    51
```

<210> SEQ ID NO 353
<211> LENGTH: 74
<212> TYPE: DNA
<213> ORGANISM: Artificial Sequence
<220> FEATURE:
<223> OTHER INFORMATION: chemically synthesized primer

<400> SEQUENCE: 353

```
tcttcgcgac caccatggaa accccagcgc agcttctctt cctcctgcta ctctggctcc    60
cagataccac cgga                                                     74
```

<210> SEQ ID NO 354
<211> LENGTH: 852
<212> TYPE: DNA
<213> ORGANISM: Artificial Sequence
<220> FEATURE:
<223> OTHER INFORMATION: chemically synthesized primer

<400> SEQUENCE: 354

```
atggaagccc cagcgcagct tctcttcctc ctgctactct ggctcccaga taccaccggt    60
gaaatagtga tgacgcagtc tccagccacc ctgtctgtgt ctccagggga aagagccacc   120
ctctcctgca gggccagtca gagtgttgac aacaacttag tctggtacca gcagaaacct   180
ggccaggctc ccaggctcct catctatggt gcatccacca gggccactgg tatcccagcc   240
aggttcagtg gcagtgggtc tgggacagag ttcactctca ccatcagtag tctgcagtct   300
gaagattttg cagtttatta ctgtcagcag tataataact ggcctccgtg gacgttcggc   360
caagggacca aggtggaaat caaactttcc gcggacgatg cgaaaaagga tgctgcgaag   420
aaagatgacg ctaagaaaga cgatgctaaa aaggacctgc aggtgcagct gcaggagtcg   480
ggcccaggac tggtgaagcc ttcacagacc ctgtccctca cctgcactgt ctctggtggc   540
tccatcagca gttttaatta ctactggagc tggatccgcc accacccagg aagggcctg    600
gagtggattg gtacatctat tacagtggga gcacctact ccaacccgtc cctcaagagt    660
cgagttacca tatcagtaga cacgtctaag aaccagttct ccctgacgct gagctctgtg   720
actgccgcgg acacggccgt gtattactgt gcgagagggt ataactggaa ctactttgac   780
```

```
tactgggcc agggaaccct ggtcaccgtc tcctcagcta gcgattataa ggacgatgat    840
gacaaatagt aa                                                        852
```

<210> SEQ ID NO 355
<211> LENGTH: 282
<212> TYPE: PRT
<213> ORGANISM: Homo sapiens

<400> SEQUENCE: 355

```
Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Asp Asn Asn Leu Val Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Pro Trp Thr Phe Gly Gln Gly Thr Lys Val Glu Ile Lys
        115                 120                 125

Leu Ser Ala Asp Asp Ala Lys Lys Asp Ala Ala Lys Lys Asp Asp Ala
    130                 135                 140

Lys Lys Asp Asp Ala Lys Lys Asp Leu Gln Val Gln Leu Gln Glu Ser
145                 150                 155                 160

Gly Pro Gly Leu Val Lys Pro Ser Gln Thr Leu Ser Leu Thr Cys Thr
                165                 170                 175

Val Ser Gly Gly Ser Ile Ser Ser Phe Asn Tyr Tyr Trp Ser Trp Ile
            180                 185                 190

Arg His His Pro Gly Lys Gly Leu Glu Trp Ile Gly Tyr Ile Tyr Tyr
        195                 200                 205

Ser Gly Ser Thr Tyr Ser Asn Pro Ser Leu Lys Ser Arg Val Thr Ile
    210                 215                 220

Ser Val Asp Thr Ser Lys Asn Gln Phe Ser Leu Thr Leu Ser Ser Val
225                 230                 235                 240

Thr Ala Ala Asp Thr Ala Val Tyr Tyr Cys Ala Arg Gly Tyr Asn Trp
                245                 250                 255

Asn Tyr Phe Asp Tyr Trp Gly Gln Gly Thr Leu Val Thr Val Ser Ser
            260                 265                 270

Ala Ser Asp Tyr Lys Asp Asp Asp Lys
        275                 280
```

<210> SEQ ID NO 356
<211> LENGTH: 1617
<212> TYPE: DNA
<213> ORGANISM: Artificial Sequence
<220> FEATURE:
<223> OTHER INFORMATION: chemically synthesized

<400> SEQUENCE: 356

```
atggaagccc agcgcagct tctcttcctc ctgctactct ggctcccaga taccaccggt     60
gaaatagtga tgacgcagtc tccagccacc ctgtctgtgt ctccagggga agagccacc   120
```

```
ctctcctgca gggccagtca gagtgttgac aacaacttag tctggtacca gcagaaacct    180
ggccaggctc ccaggctcct catctatggt gcatccacca gggccactgg tatcccagcc    240
aggttcagtg gcagtgggtc tgggacagag ttcactctca ccatcagtag tctgcagtct    300
gaagattttg cagtttatta ctgtcagcag tataataact ggcctccgtg gacgttcggc    360
caagggacca aggtggaaat caaacttttcc gcggacgatg cgaaaaagga tgctgcgaag    420
aaagatgacg ctaagaaaga cgatgctaaa aaggacctgc aggtgcagct gcaggagtcg    480
ggcccaggac tggtgaagcc ttcacagacc ctgtccctca cctgcactgt ctctggtggc    540
tccatcagca gttttaatta ctactggagc tggatccgcc accacccagg aagggcctg     600 gagtggattg ggtacatcta ttacagtggg agcacctact ccaacccgtc cctcaagagt    660
cgagttacca tatcagtaga cacgtctaag aaccagttct ccctgacgct gagctctgtg    720
actgccgcgg acacggccgt gtattactgt gcgagagggt ataactggaa ctactttgac    780
tactggggcc agggaaccct ggtcaccgtc tcctcaggag gtggtggatc cgatatcaaa    840
ctgcagcagt caggggctga actggcaaga cctggggcct cagtgaagat gtcctgcaag    900
acttctggct acacctttac taggtacacg atgcactggg taaaacagag gcctggacag    960
ggtctggaat ggattggata cattaatcct agccgtggtt atactaatta caatcagaag   1020
ttcaaggaca aggccacatt gactacagac aaatcctcca gcacagccta catgcaactg   1080
agcagcctga catctgagga ctctgcagtc tattactgtg caagatatta tgatgatcat   1140
tactgccttg actactgggg ccaaggcacc actctcacag tctcctcact ttccgcggac   1200
gatgcgaaaa aggatgctgc gaagaaagat gacgctaaga aagacgatgc taaaaaggac   1260
ctggacattc agctgaccca gtctccagca atcatgtctg catctccagg ggagaaggtc   1320
accatgacct gcagagccag ttcaagtgta agttacatga ctggtacca gcagaagtca   1380 ggcacctccc ccaaaagatg gatttatgac acatccaaag tggcttctgg agtcccttat   1440
cgcttcagtg gcagtgggtc tgggacctca tactctctca caatcagcag catggaggct   1500
gaagatgctg ccacttatta ctgccaacag tggagtagta cccgctcac gttcggtgct   1560 gggaccaagc tggagctgaa agctagcgat tataaggacg atgatgacaa atagtaa     1617
```

<210> SEQ ID NO 357
<211> LENGTH: 537
<212> TYPE: PRT
<213> ORGANISM: Artificial Sequence
<220> FEATURE:
<223> OTHER INFORMATION: chemically synthesized

<400> SEQUENCE: 357

```
Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Asp Asn Asn Leu Val Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95
```

```
Ser Leu Gln Ser Glu Asp Phe Ala Val Tyr Tyr Cys Gln Gln Tyr Asn
            100                 105                 110

Asn Trp Pro Pro Trp Thr Phe Gly Gln Gly Thr Lys Val Glu Ile Lys
        115                 120                 125

Leu Ser Ala Asp Asp Ala Lys Lys Asp Ala Ala Lys Lys Asp Asp Ala
130                 135                 140

Lys Lys Asp Asp Ala Lys Lys Asp Leu Gln Val Gln Leu Gln Glu Ser
145                 150                 155                 160

Gly Pro Gly Leu Val Lys Pro Ser Gln Thr Leu Ser Leu Thr Cys Thr
                165                 170                 175

Val Ser Gly Gly Ser Ile Ser Ser Phe Asn Tyr Tyr Trp Ser Trp Ile
            180                 185                 190

Arg His His Pro Gly Lys Gly Leu Glu Trp Ile Gly Tyr Ile Tyr Tyr
        195                 200                 205

Ser Gly Ser Thr Tyr Ser Asn Pro Ser Leu Lys Ser Arg Val Thr Ile
    210                 215                 220

Ser Val Asp Thr Ser Lys Asn Gln Phe Ser Leu Thr Leu Ser Ser Val
225                 230                 235                 240

Thr Ala Ala Asp Thr Ala Val Tyr Tyr Cys Ala Arg Gly Tyr Asn Trp
                245                 250                 255

Asn Tyr Phe Asp Tyr Trp Gly Gln Gly Thr Leu Val Thr Val Ser Ser
            260                 265                 270

Gly Gly Gly Gly Ser Asp Ile Lys Leu Gln Gln Ser Gly Ala Glu Leu
        275                 280                 285

Ala Arg Pro Gly Ala Ser Val Lys Met Ser Cys Lys Thr Ser Gly Tyr
    290                 295                 300

Thr Phe Thr Arg Tyr Thr Met His Trp Val Lys Gln Arg Pro Gly Gln
305                 310                 315                 320

Gly Leu Glu Trp Ile Gly Tyr Ile Asn Pro Ser Arg Gly Tyr Thr Asn
                325                 330                 335

Tyr Asn Gln Lys Phe Lys Asp Lys Ala Thr Leu Thr Thr Asp Lys Ser
            340                 345                 350

Ser Ser Thr Ala Tyr Met Gln Leu Ser Ser Leu Thr Ser Glu Asp Ser
        355                 360                 365

Ala Val Tyr Tyr Cys Ala Arg Tyr Tyr Asp Asp His Tyr Cys Leu Asp
    370                 375                 380

Tyr Trp Gly Gln Gly Thr Thr Leu Thr Val Ser Ser Leu Ser Ala Asp
385                 390                 395                 400

Asp Ala Lys Lys Asp Ala Ala Lys Lys Asp Ala Lys Lys Asp Asp
            405                 410                 415

Ala Lys Lys Asp Leu Asp Ile Gln Leu Thr Gln Ser Pro Ala Ile Met
            420                 425                 430

Ser Ala Ser Pro Gly Glu Lys Val Thr Met Thr Cys Arg Ala Ser Ser
        435                 440                 445

Ser Val Ser Tyr Met Asn Trp Tyr Gln Gln Lys Ser Gly Thr Ser Pro
    450                 455                 460

Lys Arg Trp Ile Tyr Asp Thr Ser Lys Val Ala Ser Gly Val Pro Tyr
465                 470                 475                 480

Arg Phe Ser Gly Ser Gly Ser Gly Thr Ser Tyr Ser Leu Thr Ile Ser
            485                 490                 495

Ser Met Glu Ala Glu Asp Ala Ala Thr Tyr Tyr Cys Gln Gln Trp Ser
        500                 505                 510

Ser Asn Pro Leu Thr Phe Gly Ala Gly Thr Lys Leu Glu Leu Lys Ala
```

515                 520                 525
Ser Asp Tyr Lys Asp Asp Asp Lys
   530                 535

<210> SEQ ID NO 358
<211> LENGTH: 1677
<212> TYPE: DNA
<213> ORGANISM: Artificial Sequence
<220> FEATURE:
<223> OTHER INFORMATION: chemically synthesized

<400> SEQUENCE: 358

| | | | | | |
|---|---|---|---|---|---|
| atggaaaccc | cagcgcagct | tctcttcctc | ctgctactct | ggctcccaga | taccaccgga | 60 |
| gaaatagtga | tgacgcagtc | tccagccacc | ctgtctgtgt | ctccagggga | aagagccacc | 120 |
| ctctcctgca | gggccagtca | gagtgttgac | aacaacttag | tctggtacca | gcagaaacct | 180 |
| ggccaggctc | ccaggctcct | catctatggt | gcatccacca | gggccactgg | tatcccagcc | 240 |
| aggttcagtg | gcagtgggtc | tgggacagag | ttcactctca | ccatcagtag | tctgcagtct | 300 |
| gaagattttg | cagtttatta | ctgtcagcag | tataataact | ggcctccgtg | gacgttcggc | 360 |
| caagggacca | aggtggaaat | caaactttcc | gcggacgatg | cgaaaaagga | tgctgcgaag | 420 |
| aaagatgacg | ctaagaaaga | cgatgctaaa | aaggacctgc | aggtgcagct | gcaggagtcg | 480 |
| ggcccaggac | tggtgaagcc | ttcacagacc | ctgtccctca | cctgcactgt | ctctggtggc | 540 |
| tccatcagca | gttttaatta | ctactggagc | tggatccgcc | accccagg | aagggcctg | 600 |
| gagtggattg | gtacatcta | ttacagtggg | agcaccatct | ccaacccgtc | cctcaagagt | 660 |
| cgagttacca | tatcagtaga | cacgtctaag | aaccagttct | ccctgacgct | gagctctgtg | 720 |
| actgccgcgg | acacggccgt | gtattactgt | gcgagaggt | ataactgaa | ctactttgac | 780 |
| tactggggcc | agggaaccct | ggtcaccgtc | tcctcattat | cagcggatga | cgccaagaaa | 840 |
| gacgcagcca | aaaaggacga | tgcaaagaag | gatgacgcaa | agaaagattt | agatatcaaa | 900 |
| ctgcagcagt | caggggctga | actggcaaga | cctggggcct | cagtgaagat | gtcctgcaag | 960 |
| acttctggct | acaccttac | taggtacacg | atgcactggg | taaacagag | gcctggacag | 1020 |
| ggtctggaat | ggattggata | cattaatcct | agccgtggtt | atactaatta | caatcagaag | 1080 |
| ttcaaggaca | aggccacatt | gactacagac | aaatcctcca | gcacagccta | catgcaactg | 1140 |
| agcagcctga | catctgagga | ctctgcagtc | tattactgtg | caagatatta | tgatgatcat | 1200 |
| tactgccttg | actactgggg | ccaaggcacc | actctcacag | tctcctcact | ttccgcggac | 1260 |
| gatgcgaaaa | aggatgctgc | gaagaaagat | gacgctaaga | aagacgatgc | taaaaaggac | 1320 |
| ctggacattc | agctgaccca | gtctccagca | atcatgtctg | catctccagg | ggagaaggtc | 1380 |
| accatgacct | gcagagccag | ttcaagtgta | agttacatga | actggtacca | gcagaagtca | 1440 |
| ggcacctccc | ccaaaagatg | gatttatgac | acatccaaag | tggcttctgg | agtcccttat | 1500 |
| cgcttcagtg | gcagtgggtc | tgggacctca | tactctctca | caatcagcag | catggaggct | 1560 |
| gaagatgctg | ccacttatta | ctgccaacag | tggagtagta | acccgctcac | gttcggtgct | 1620 |
| gggaccaagc | tggagctgaa | agattataag | gacgatgatg | acaaatagct | cgagcgg | 1677 |

<210> SEQ ID NO 359
<211> LENGTH: 555
<212> TYPE: PRT
<213> ORGANISM: Artificial Sequence
<220> FEATURE:
<223> OTHER INFORMATION: chemically synthesized

```
<400> SEQUENCE: 359

Met Glu Thr Pro Ala Gln Leu Leu Phe Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Asp Asn Asn Leu Val Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Pro Trp Thr Phe Gly Gln Gly Thr Lys Val Glu Ile Lys
        115                 120                 125

Leu Ser Ala Asp Asp Ala Lys Lys Asp Ala Ala Lys Lys Asp Asp Ala
    130                 135                 140

Lys Lys Asp Asp Ala Lys Lys Asp Leu Gln Val Gln Leu Gln Glu Ser
145                 150                 155                 160

Gly Pro Gly Leu Val Lys Pro Ser Gln Thr Leu Ser Leu Thr Cys Thr
                165                 170                 175

Val Ser Gly Gly Ser Ile Ser Ser Phe Asn Tyr Tyr Trp Ser Trp Ile
            180                 185                 190

Arg His His Pro Gly Lys Gly Leu Glu Trp Ile Gly Tyr Ile Tyr Tyr
        195                 200                 205

Ser Gly Ser Thr Tyr Ser Asn Pro Ser Leu Lys Ser Arg Val Thr Ile
210                 215                 220

Ser Val Asp Thr Ser Lys Asn Gln Phe Ser Leu Thr Leu Ser Ser Val
225                 230                 235                 240

Thr Ala Ala Asp Thr Ala Val Tyr Tyr Cys Ala Arg Gly Tyr Asn Trp
                245                 250                 255

Asn Tyr Phe Asp Tyr Trp Gly Gln Gly Thr Leu Val Thr Val Ser Ser
            260                 265                 270

Leu Ser Ala Asp Asp Ala Lys Lys Asp Ala Ala Lys Lys Asp Asp Ala
        275                 280                 285

Lys Lys Asp Asp Ala Lys Lys Asp Leu Asp Ile Lys Leu Gln Gln Ser
    290                 295                 300

Gly Ala Glu Leu Ala Arg Pro Gly Ala Ser Val Lys Met Ser Cys Lys
305                 310                 315                 320

Thr Ser Gly Tyr Thr Phe Thr Arg Tyr Thr Met His Trp Val Lys Gln
                325                 330                 335

Arg Pro Gly Gln Gly Leu Glu Trp Ile Gly Tyr Ile Asn Pro Ser Arg
            340                 345                 350

Gly Tyr Thr Asn Tyr Asn Gln Lys Phe Lys Asp Lys Ala Thr Leu Thr
        355                 360                 365

Thr Asp Lys Ser Ser Ser Thr Ala Tyr Met Gln Leu Ser Ser Leu Thr
    370                 375                 380

Ser Glu Asp Ser Ala Val Tyr Tyr Cys Ala Arg Tyr Tyr Asp Asp His
385                 390                 395                 400

Tyr Cys Leu Asp Tyr Trp Gly Gln Gly Thr Thr Leu Thr Val Ser Ser
                405                 410                 415
```

```
Leu Ser Ala Asp Asp Ala Lys Lys Asp Ala Lys Lys Asp Asp Ala
            420                 425                 430

Lys Lys Asp Asp Ala Lys Lys Asp Leu Asp Ile Gln Leu Thr Gln Ser
            435                 440                 445

Pro Ala Ile Met Ser Ala Ser Pro Gly Glu Lys Val Thr Met Thr Cys
450                 455                 460

Arg Ala Ser Ser Val Ser Tyr Met Asn Trp Tyr Gln Gln Lys Ser
465                 470                 475                 480

Gly Thr Ser Pro Lys Arg Trp Ile Tyr Asp Thr Ser Lys Val Ala Ser
                485                 490                 495

Gly Val Pro Tyr Arg Phe Ser Gly Ser Gly Ser Gly Thr Ser Tyr Ser
                500                 505                 510

Leu Thr Ile Ser Ser Met Glu Ala Glu Asp Ala Ala Thr Tyr Tyr Cys
                515                 520                 525

Gln Gln Trp Ser Ser Asn Pro Leu Thr Phe Gly Ala Gly Thr Lys Leu
            530                 535                 540

Glu Leu Lys Asp Tyr Lys Asp Asp Asp Lys
545                 550                 555

<210> SEQ ID NO 360
<211> LENGTH: 100
<212> TYPE: PRT
<213> ORGANISM: Homo sapiens

<400> SEQUENCE: 360

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 361
<211> LENGTH: 98
<212> TYPE: PRT
<213> ORGANISM: Homo sapiens

<400> SEQUENCE: 361

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg

<210> SEQ ID NO 362
<211> LENGTH: 98
<212> TYPE: PRT
<213> ORGANISM: Homo sapiens

<400> SEQUENCE: 362

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
                35                  40                  45

Ser Ser Ile Ser Ser Ser Ser Ser Tyr Ile Tyr Tyr Ala Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 363
<211> LENGTH: 98
<212> TYPE: PRT
<213> ORGANISM: Homo sapiens

<400> SEQUENCE: 363

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 364
<211> LENGTH: 98
<212> TYPE: PRT
<213> ORGANISM: Homo sapiens

<400> SEQUENCE: 364

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 365
<211> LENGTH: 99
<212> TYPE: PRT
<213> ORGANISM: Homo sapiens

<400> SEQUENCE: 365

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 366
<211> LENGTH: 97
<212> TYPE: PRT
<213> ORGANISM: Homo sapiens

<400> SEQUENCE: 366

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg

<210> SEQ ID NO 367
<211> LENGTH: 98
<212> TYPE: PRT
<213> ORGANISM: Homo sapiens

<400> SEQUENCE: 367

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr

```
            20                  25                  30
Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

```
<210> SEQ ID NO 368
<211> LENGTH: 101
<212> TYPE: PRT
<213> ORGANISM: Homo sapiens

<400> SEQUENCE: 368

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100
```

```
<210> SEQ ID NO 369
<211> LENGTH: 96
<212> TYPE: PRT
<213> ORGANISM: Homo sapiens

<400> SEQUENCE: 369

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

```
<210> SEQ ID NO 370
<211> LENGTH: 95
<212> TYPE: PRT
<213> ORGANISM: Homo sapiens

<400> SEQUENCE: 370
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 371
<211> LENGTH: 100
<212> TYPE: PRT
<213> ORGANISM: Homo sapiens

<400> SEQUENCE: 371

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 372
<211> LENGTH: 95
<212> TYPE: PRT
<213> ORGANISM: Homo sapiens

<400> SEQUENCE: 372

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 373
<211> LENGTH: 100
<212> TYPE: PRT
<213> ORGANISM: Homo sapiens

<400> SEQUENCE: 373

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 374
<211> LENGTH: 95
<212> TYPE: PRT
<213> ORGANISM: Homo sapiens

<400> SEQUENCE: 374

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 375
<211> LENGTH: 17
<212> TYPE: DNA
<213> ORGANISM: Homo sapiens

<400> SEQUENCE: 375
ggtataactg gaacgac                                                17

<210> SEQ ID NO 376
<211> LENGTH: 20
<212> TYPE: DNA
<213> ORGANISM: Homo sapiens

<400> SEQUENCE: 376
ggtatagtgg gagctactac                                             20

<210> SEQ ID NO 377
<211> LENGTH: 31
<212> TYPE: DNA
<213> ORGANISM: Homo sapiens

<400> SEQUENCE: 377
gtattactat ggttcgggga gttattataa c                                31

<210> SEQ ID NO 378
<211> LENGTH: 37
<212> TYPE: DNA
<213> ORGANISM: Homo sapiens

<400> SEQUENCE: 378
gtattatgat tacgtttggg ggagttatcg ttatacc                     37

<210> SEQ ID NO 379
<211> LENGTH: 31
<212> TYPE: DNA
<213> ORGANISM: Homo sapiens

<400> SEQUENCE: 379
gtattactat gatagtagtg gttattacta c                           31

<210> SEQ ID NO 380
<211> LENGTH: 31
<212> TYPE: DNA
<213> ORGANISM: Homo sapiens

<400> SEQUENCE: 380
gtattacgat attttgactg gttattataa c                           31

<210> SEQ ID NO 381
<211> LENGTH: 16
<212> TYPE: DNA
<213> ORGANISM: Homo sapiens

<400> SEQUENCE: 381
tgactacggt gactac                                            16

<210> SEQ ID NO 382
<211> LENGTH: 20
<212> TYPE: DNA
<213> ORGANISM: Homo sapiens

<400> SEQUENCE: 382
gtagagatgg ctacaattac                                        20

<210> SEQ ID NO 383
<211> LENGTH: 21
<212> TYPE: DNA
<213> ORGANISM: Homo sapiens

<400> SEQUENCE: 383
gggtatagca gcagctggta c                                      21

<210> SEQ ID NO 384
<211> LENGTH: 21
<212> TYPE: DNA
<213> ORGANISM: Homo sapiens

<400> SEQUENCE: 384
gggtatagca gtggctggta c                                      21

<210> SEQ ID NO 385
<211> LENGTH: 15
<212> TYPE: PRT
<213> ORGANISM: Homo sapiens

<400> SEQUENCE: 385

Ala Phe Asp Ile Trp Gly Gln Gly Thr Met Val Thr Val Ser Ser

-continued

```
1               5                   10                  15
```

<210> SEQ ID NO 386
<211> LENGTH: 15
<212> TYPE: PRT
<213> ORGANISM: Homo sapiens

<400> SEQUENCE: 386

```
Tyr Phe Asp Tyr Trp Gly Gln Gly Thr Leu Val Thr Val Ser Ser
1               5                   10                  15
```

<210> SEQ ID NO 387
<211> LENGTH: 16
<212> TYPE: PRT
<213> ORGANISM: Homo sapiens

<400> SEQUENCE: 387

```
Asn Trp Phe Asp Pro Trp Gly Gln Gly Thr Leu Val Thr Val Ser Ser
1               5                   10                  15
```

<210> SEQ ID NO 388
<211> LENGTH: 20
<212> TYPE: PRT
<213> ORGANISM: Homo sapiens

<400> SEQUENCE: 388

```
Tyr Tyr Tyr Tyr Tyr Gly Met Asp Val Trp Gly Gln Gly Thr Thr Val
1               5                   10                  15

Thr Val Ser Ser
            20
```

<210> SEQ ID NO 389
<211> LENGTH: 12
<212> TYPE: PRT
<213> ORGANISM: Homo sapiens

<400> SEQUENCE: 389

```
Trp Thr Phe Gly Gln Gly Thr Lys Val Glu Ile Lys
1               5                   10
```

<210> SEQ ID NO 390
<211> LENGTH: 12
<212> TYPE: PRT
<213> ORGANISM: Homo sapiens

<400> SEQUENCE: 390

```
Tyr Thr Phe Gly Gln Gly Thr Lys Leu Glu Ile Lys
1               5                   10
```

<210> SEQ ID NO 391
<211> LENGTH: 12
<212> TYPE: PRT
<213> ORGANISM: Homo sapiens

<400> SEQUENCE: 391

```
Phe Thr Phe Gly Pro Gly Thr Lys Val Asp Ile Lys
1               5                   10
```

<210> SEQ ID NO 392
<211> LENGTH: 12
<212> TYPE: PRT
<213> ORGANISM: Homo sapiens

<400> SEQUENCE: 392

```
Leu Thr Phe Gly Gly Gly Thr Lys Val Glu Ile Lys
1               5                   10
```

<210> SEQ ID NO 393
<211> LENGTH: 12
<212> TYPE: PRT
<213> ORGANISM: Homo sapiens

<400> SEQUENCE: 393

```
Ile Thr Phe Gly Gln Gly Thr Arg Leu Glu Ile Lys
1               5                   10
```

<210> SEQ ID NO 394
<211> LENGTH: 445
<212> TYPE: PRT
<213> ORGANISM: Homo sapiens

<400> SEQUENCE: 394

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
                20                  25                  30

Asn Tyr Tyr Trp Ser Trp Ile Arg His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Gly Tyr Asn Trp Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300
```

```
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
            325                 330                 335
Thr Lys Gly Gln Pro Arg Glu Pro Gln Val Tyr Thr Leu Pro Pro Ser
        340                 345                 350
Arg Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
            405                 410                 415
Gln Gly Asn Val Phe Ser Cys Ser Val Met His Glu Ala Leu His Asn
        420                 425                 430
His Tyr Thr Gln Lys Ser Leu Ser Leu Ser Pro Gly Lys
            435                 440                 445

<210> SEQ ID NO 395
<211> LENGTH: 449
<212> TYPE: PRT
<213> ORGANISM: Homo sapiens

<400> SEQUENCE: 395

Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Phe
            20                  25                  30
Asn Tyr Tyr Trp Ser Trp Ile Arg His Pro Gly Lys Gly Leu Glu
        35                  40                  45
Trp Ile Gly Tyr Ile Tyr Tyr Ser Gly Ser Thr Tyr Ser Asn Pro Ser
    50                  55                  60
Leu Lys Ser Arg Val Thr Ile Ser Val Asp Thr Ser Lys Asn Gln Phe
65                  70                  75                  80
Ser Leu Thr Leu Ser Ser Val Thr Ala Ala Asp Thr Ala Val Tyr Tyr
                85                  90                  95
Cys Ala Arg Gly Tyr Asn Trp Asn Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
```

-continued

```
Ser Val Phe Leu Phe Pro Pro Lys Pro Lys Asp Thr Leu Met Ile Ser
            245             250                 255

Arg Thr Pro Glu Val Thr Cys Val Val Val Asp Val Ser His Glu Asp
            260             265                 270

Pro Glu Val Lys Phe Asn Trp Tyr Val Asp Gly Val Glu Val His Asn
            275             280                 285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315                     320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345                 350

Leu Pro Pro Ser Arg Glu Glu Met Thr Lys Asn Gln Val Ser Leu Thr
            355             360                 365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395                     400

Asp Ser Asp Gly Ser Phe Phe Leu Tyr Ser Lys Leu Thr Val Asp Lys
                405             410                 415

Ser Arg Trp Gln Gln Gly Asn Val Phe Ser Cys Ser Val Met His Glu
            420             425                 430

Ala Leu His Asn His Tyr Thr Gln Lys Ser Leu Ser Leu Ser Pro Gly
            435             440                 445

Lys
```

ANTIBODIES DIRECTED TO GPNMB AND USES THEREOF

RELATED APPLICATIONS

This application is a continuation of U.S. patent application Ser. No. 13/151,690, filed Jun. 2, 2011, which is a continuation of U.S. patent application Ser. No. 12/911,269, filed Oct. 25, 2010, which is a continuation of U.S. patent application Ser. No. 12/721,099, filed Mar. 10, 2010, which is a continuation of U.S. patent application Ser. No. 12/506,029, field Jul. 20, 2009, which is a continuation of U.S. patent application Ser. No. 12/290,779, filed Nov. 3, 2008, which is a continuation of U.S. patent application Ser. No. 11/792,032, which is a national stage application, filed under 35 U.S.C. §371, of International Application No. PCT/US2005/043482, filed on Nov. 30, 2005, which claims priority to U.S. Provisional Application No. 60/632,023, filed Nov. 30, 2004; and U.S. Provisional Application No. 60/733,779, filed Nov. 7, 2005; the contents of each of which are hereby incorporated by reference in their entirety.

INCORPORATION-BY-REFERENCE OF SEQUENCE LISTING

The contents of the text file named "669C10USSeqList.txt," which was created on Sep. 24, 2012 and is 167 KB in size, are hereby incorporated by reference in their entirety.

FIELD OF THE INVENTION

The present invention relates to antibodies with specificity to GPNMB, and uses of such antibodies. In particular, the present invention provides fully human monoclonal antibodies that specifically bind to GPNMB, and uses thereof. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDRs) are provided. The present invention also provides immunoconjugates comprising anti-GPNMB antibodies and methods of using such immunoconjugates. The present invention further provides bi-specific antibodies comprising an anti-GPNMB antibody component and an anti-CD3 component, and methods of using such bispecific antibodies.

BACKGROUND OF THE INVENTION

GPNMB

A putative transmembrane glycoprotein called "nmb" (Acc. No. X76534 EMBL), referred to herein as GPNMB, was identified and described by Weterman et al., (Int J Cancer 60:73-81, 1995) as differentially expressed in low-metastatic human melanoma cancer cell lines and xenografts, compared to a more aggressive melanoma cell line. GPNMB shares 33% identity with the precursor of pMe117 melanocyte-specific protein (Kwon et al., 1991, PNAS 88:9228-9232). GPNMB is 71% homologous to a dendritic cell-associated transmembrane protein, DC-HIL (Shikano et al., 2001 Biol. Chem. 276:8125-8134). GPNMB is also known as the hematopoietic growth factor inducible neurokinin-1 protein HGFIN (Bandari et al, Reg. Peptides 111:169-178) and the bone-related gene osteoactivin (Owen et al. Crit. Rev Eukaryot Gene Expr 2003, 13(2-4):205-220)

It was also reported that nmb could reduce the metastatic potential of a highly metastatic nmb-negative melanoma cell line (Weterman, 1995). GPNMB was considered a candidate glioblastoma tumor marker after public database mining and expression profiling (Loging et al., 2000, Genome Research 10:1393-1402). This gene was found overexpressed in lung tumors (US Patent Publication No. US20030064947), as well as breast, rectal and colon cancers (US Patent Publication No. US2003100720). NCBI SAGE data also shows overexpression of this gene in stomach and pancreatic carcinoma. The mouse ortholog has been shown to be highly upregulated in a neural stem cell line NSC, derived from the TSC2 knockout model for Tuberous Sclerosis Complex Syndrome (International Publication No. WO 2003/080856).

Antibodies

Antibodies, also known as immunoglobulins, are typically tetrameric glycosylated proteins composed of two light (L) chains (about 25 kDa) and two heavy (H) chains (about 50-70 kDa). The amino-terminal portion of each chain includes a variable domain of about 100 to 110 or more amino acids primarily responsible for antigen recognition. The carboxy-terminal portion of the L and H chain has one and three or four constant domains, respectively that are primarily responsible for effector function. There are two types of human L chains, classified as kappa and lambda. H chains are classified as mu, delta, gamma, alpha, or epsilon based upon the constant domain amino acid sequence, defining the antibody's isotype as IgM, IgD, IgG, IgA, and IgE, respectively. Isotypes may be further divided into subclasses e.g. $IgG_1$, $IgG_2$, $IgG_3$, $IgG_4$.

Immunoglobulins can be produced naturally in vivo by B lymphocytes. Each clone of B cells produces antibody with an antigen receptor having a unique prospective antigen binding structure. The repertoire of antigen receptors, approximately $10^7$ possibilities, exists in vivo prior to antigen stimulation. This diversity is produced by somatic recombination, i.e., the joining of different antibody gene segments. Immunoglobulin H chain, kappa L chain and lambda L chain are encoded by three separate genetic loci and each locus has multiple copies of at least 3 types of gene segments encoding variable (V), constant (C) and joining (J) regions, the heavy chain gene also includes a diversity (D) region. The selection of specific V, C and J regions (and D for the heavy chain) from amongst the various gene segments available (45 heavy chain V; 35 kappa V; 23 heavy chain D; 6 heavy chain J; 5 kappa J) generates approximately $10^{11}$ possible specificities of germ-line sequences exhibited in B cells. The joining of V, C and J regions can result in the loss or addition of residues at the junctions. The L and H chain V region of human antibodies consists of relatively conserved framework regions (FR) that form a scaffold for three hypervariable regions also known as complementary determining regions (CDR). From the amino terminus of either the heavy or light chain, the V domain is made up of FR and CDR regions in the following order: FR1-CDR1-FR2-CDR2-FR3. Joining of the V domain with a D (heavy chain only) and J domain adds CDR3-FR4. The CDRs are generally responsible for antigen binding.

The specificity of monoclonal antibodies have made them attractive agents for targeting cancer in vivo with the hopes of eradicating disease while sparing normal tissue. The approach, which initially utilized mouse monoclonal antibodies has encountered limitations to potential effectiveness such as immunogenicity; inefficient effector functions and short half-life in vivo. Technologies were developed for: chimeric antibodies which sought to utilize the antigen binding variable domains of mouse monoclonal antibodies combined with the constant regions of human antibodies (Boulianne, et al. 1984 *Nature* 312:643-646; Morrison et al, 1984 *PNAS*

USA 81:6851-6855); humanized antibodies which grafted antigen binding complementary determining regions (CDRs) from mouse antibodies to human immunoglobulin (Jones, et al, 1986 *Nature* 321: 522-525; Riechmann, et al, 1988 *Nature* 332:323-327; Verhoeyen, et al, 1988 *Science* 239:1534-1536; Vaughan, et al, 1998 *Nature Biotechnol.* 16:535-539); and phage display libraries of single chain scFvs or Fab fragments of antibodies (de Haard, et al, 1999 *J Biol. Chem.* 274: 18218-18230; Knappik, et al, 20001 *Mol. Biol.* 296:57-86; Sheets, et al, 1998 *PNAS USA* 95:6157-6162; Vaughan, et al, 1994 *Nature Biotechnol* 14:309-314, 1996; Griffiths et al *EMBO J.* 13:3245-3260). Additionally, transgenic animals having human immunoglobulin genes and nonfunctional endogenous genes have been developed for immunization and production of fully human monoclonal antibodies (Fishwild, et al, 1996 *Nature Biotechnol* 14:845-851; Mendez, et al, 1997 *Nature Genet.* 15:146-156; Nicholson, et al, 1999 J. Immunol 163, 6898-6906).

Single Chain Antibodies: Single chain Fv antibodies (scFvs) were first described in the late 1980's (Bird et al., Science 242:423-426 (1988); Huston et al., Proc. Natl. Acad. Sci. USA 85:5879-5883 (1988)). A polypeptide linker, typically ranging in length from 5 to 27 amino acid residues, is used to join the C-terminus of the variable light chain domain ($V_L$) to the N-terminus of the variable heavy chain domain ($V_H$). Alternatively, the linker joins the C-terminus of the $V_H$ to the N-terminus of the $V_L$. Both formats ($V_L$-$V_H$ and $V_H$-$V_L$) have been used successfully in the literature. The most common linker used in the literature is the $(Gly_4Ser)_3$ 15 amino acid linker, however there are several other linkers that have been utilized, including a 25 amino acid linker called 205C (Pantoliano et al., Biochemistry 30:10117-10125 (1991)). Single chain antibodies are currently in the clinic; one of the most advanced is h5G1.1 or Pexelizumab. This scFv is specific for human C5 complement and is being used in clinical trials for cardiac patients undergoing cardiopulmonary bypass surgery (Shernan et al., Ann. Thorac Surg. 77:942-949 (2004)).

Bispecific Antibodies (bi-Abs): An area of mAb research where considerable progress has been made is in the development of bispecific antibodies (biAbs). There are distinct advantages to developing therapeutic antibody molecules with dual specificity. For example, biAbs can serve as mediators to target immune effector cells such as CTLs to unwanted cells (Baeuerle et al., Curr. Opin. Mol. Ther. 5:413-419 (2003)). In another example, chemically linked bispecific antibodies directed against Fc gamma receptors CD16, CD64, and CD89, were significantly more effective in vitro than conventional IgG antibodies (Peipp and Valerius, Biochem. Soc. Trans. 30:507-511 (2002)). One of the challenges in developing biAbs as viable therapeutics has been producing large enough quantities of a stable moiety for clinical applications. Another challenge has been in determining the right combination of validated targets and the underlying biology that would lead to a therapeutic product. For recent reviews on the difficulties experienced with biAbs, see (Kontermann, Acta Pharmacol Sin 26:1-9 (2005); Peipp and Valerius, Soc. Trans. 30:507-511 (2002)).

Bispecific Single Chain Antibodies (bi-scFv): A notable type of biAb that can be made is a bi-specific single chain antibody or bi-scFv. For a review on the generation of bi-scFv's see (Kipriyanov and Le Gall, Curr Opin Drug Discov Devel 7:233-242 (2004)). Bi-scFvs are typically comprised of 4 variable domains, 2 heavy ($V_H$) and 2 light ($V_L$), which are derived from 2 different antibodies. The 4 domains are linked together with 3 short linkers, ranging in length from 5-27 amino acids. The biological activity of this type of antibody depends on several features concerning the construction of the molecule. For example, both the linker sequences between the antibody V domains and the order of the 4 antibody V domains themselves (for the 2 antibodies) can vary, as well as the expression system that is used; all of which can greatly affect the solubility and biological activity of the various resulting products (Kipriyanov et al., J. Mol. Biol. 330:99-111 (2003); Le Gall et al., Protein Eng. Des. Sel. 17:357-366 (2004); Pavlinkova et al., Clin Cancer Res. 5:2613-1619 (1999)).

Cytotoxic T Lymphocytes: Under normal circumstances, T cells are activated when the CD3/T cell receptor (CD3/TCR) complex binds to a relevant MHC molecule associated with a specific Ag peptide. Engagement of CD3/TCR with MHC results in intracellular signals necessary to trigger an immune response against a pathogen or tumor. Similar signals that cause T cell activation can also be achieved by antibodies that can bind certain structures of the CD3/TCR complex. In the literature, it has been shown that biAbs recognizing both the TCR/CD3 complex and tumor associated antigen (TAA) can trigger the activation program in CTLs in the presence of target cells (Chapoval et al., J Immunol 155:1296-1303 (1995)).

Recombinant technologies are being utilized to enable further improvements upon antibody molecules with the goal of enhancing in vivo efficacy. Such technologies provide, for example, for optimizing molecular size, affinity, pharmacokinetics, toxicity, specificity, valency, effector functions, direct and indirect arming, combination therapy, and various prodrug approaches.

It would be desirable to have an antibody suitable for in vivo targeting of GPNMB expressing pathologies and to enable therapeutic efficacy.

SUMMARY OF THE INVENTION

The current invention provides human monoclonal antibodies that specifically bind GPNMB as well as variants, derivatives and antigen binding fragments of such antibodies.

The invention provides preferred somatic recombinations of human antibody gene segments to provide specificity for GPNMB and genetically engineered anti-GPNMB antibody variants and derivatives that originate from these gene segments. In addition, the current invention provides multiple affinity matured human antibodies with binding specificity for GPNMB.

In one embodiment, the present invention provides an antibody, or binding fragment thereof, that binds to GPNMB, wherein said antibody, or binding fragment thereof, neutralizes a GPNMB-induced activity, and wherein said antibody, or binding fragment thereof, cross-reacts with a fully human anti-GPNMB antibody selected from the group consisting of Mab1.2.1, Mab1.10.1, and Mab2.22.1 or an antibody in the same antigen-binding bin as fully human anti-GPNMB antibody Mab1.2.1, Mab1.10.1, or Mab2.22.1.

In another embodiment, the present invention provides an antibody, or binding fragment thereof, that binds to GPNMB, wherein said antibody, or binding fragment thereof, neutralizes a GPNMB-induced activity, and wherein said antibody, or binding fragment thereof, cross-reacts with a fully human anti-GPNMB antibody selected from the group consisting of Mab2.3.1 and Mab1.15.1 or an antibody in the same antigen-binding bin as fully human anti-GPNMB antibody Mab2.3.1 or Mab1.15.1.

In yet another embodiment, the present invention provides an antibody, or binding fragment thereof, that binds to GPNMB, wherein said antibody, or binding fragment thereof, neutralizes a GPNMB-induced activity, and wherein said antibody, or binding fragment thereof, cross-reacts with fully human anti-GPNMB antibody Mab2.10.1 or an antibody in the same antigen-binding bin as fully human anti-GPNMB antibody Mab2.10.1.

In one embodiment, the present invention provides naked IgG1 anti-GPNMB antibodies that have cytotoxic effect to cells overexpressing GPNMB. In a specific embodiment, the present invention provides methods of treating or preventing diseases associated with overexpression of GPNMB comprising administering to a subject in need thereof a composition comprising a naked IgG1 anti-GPNMB antibody and an immunomodulator (such as, but not limited to, interferons and cytokines).

In another embodiment, the present invention provides immunoconjugates that comprise an anti-GPNMB antibody or a fragment thereof, and a cytotoxic agent. In a specific embodiment, the cytotoxic agent is auristatin E (dolastatin-10) or a derivative thereof. Methods of using such immunoconjugated are also provided.

In one embodiment, the present invention provides bispecific antibodies comprising an anti-GPNMB component and an anti-CD3 antibody component, which enable the cytotoxic killing of target tumor cells by T cells. In another embodiment, the present invention provides single chain Fv antibody conjugated to a cytotoxic agent. In a specific embodiment, the cytotoxic agent is auristatin E (dolastatin-10) or a derivative thereof. Methods of using such bispecific antibodies and conjugated single chain Fv antibodies are also provided.

Amino acid sequences for anti-GPNMB human monoclonal antibodies of the invention and nucleic acid sequences encoding them are provided.

Compositions comprising human anti-GPNMB antibodies, including therapeutic compositions comprising same, and methods of use are provided. Particularly, therapeutic immunoconjugates comprising anti-GPNMB antibodies and a cytotoxic or cytostatic agent for treating GPNMB expressing cancers and other GPNMB related disorders are provided. Dosage regimens are also provided.

Additional aspects of the disclosure will be set forth in part in the description which follows, and in part will be obvious from the description, or may be learned by practicing the invention.

DETAILED DESCRIPTION OF THE INVENTION

Figure 1:
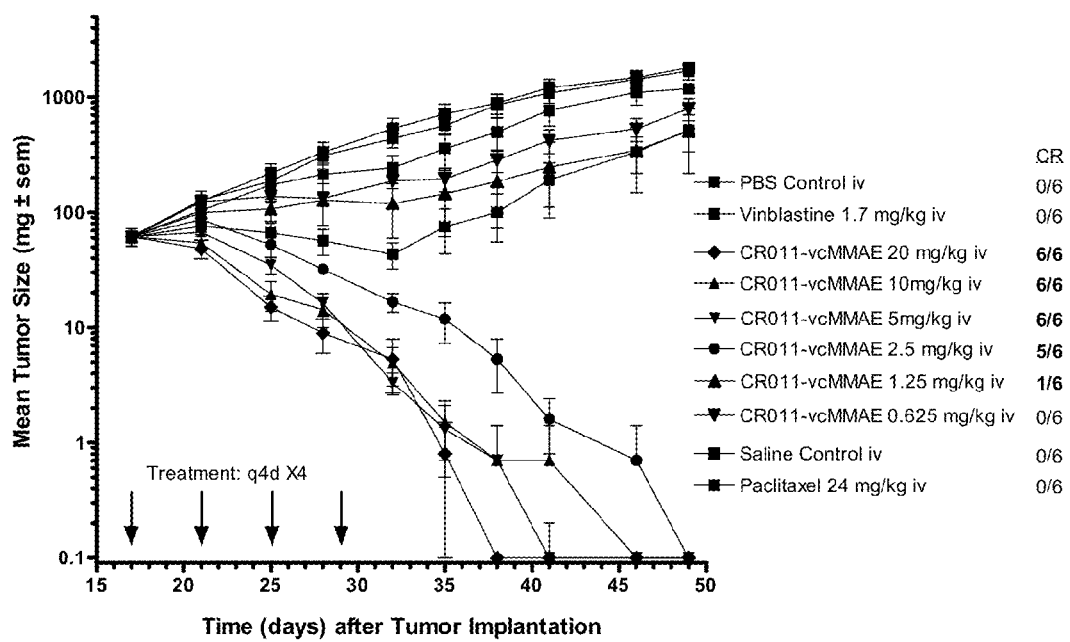
FIG. 1: Tumor growth inhibition and complete regression of SK-MEL-2 xenografts in athymic mice after treatment with 2.50 to 20 mg/kg i.v. every 4 days for 4 treatments. The responses of tumor-bearing animals to reference drugs such as vinblastine (1.7 mg/kg i.v. q4d ×4) and paclitaxel (24 mg/kg i.v. q2d ×4) are also shown. Control groups are treated with either phosphate-buffered saline (PBS) or physiological saline.

As used herein, the term "antibody" refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, engineered, and grafted antibodies. Unless otherwise modified by the term "intact," as in "intact antibodies," for the purposes of this disclosure, the term "antibody" also includes antibody fragments such as Fab, F(ab')$_2$, Fv, scFv, bi-scFv, bi-Ab, Fd, dAb, and other antibody fragments that retain antigen-binding function, i.e., the ability to bind GPNMB specifically. Typically, such fragments would comprise an antigen-binding domain.

As used herein, the terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant."

An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

As used herein, the term "repertoire" refers to a genetically diverse collection of nucleotides derived wholly or partially from sequences that encode expressed immunoglobulins. The sequences are generated by in vivo rearrangement of, e.g., V, D, and J segments for H chains and, e.g., V and J segment for L chains. Alternatively, the sequences may be generated from a cell line by in vitro stimulation, in response to which the rearrangement occurs. Alternatively, part or all of the sequences may be obtained by combining, e.g., unrearranged V segments with D and J segments, by nucleotide synthesis, randomised mutagenesis, and other methods, e.g., as disclosed in U.S. Pat. No. 5,565,332.

As used herein, the terms "specific interaction" and "specific binding" refer to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6$ $M^{-1}$, or more preferably higher than $10^8$ $M^{-1}$. If necessary, non-specific binding can be reduced without substantially affecting specific binding by varying the binding conditions. The appropriate binding conditions such as concentration of antibodies, ionic strength of the solution, temperature, time allowed for binding, concentration of a blocking agent (e.g., serum albumin, milk casein), etc., may be optimized by a skilled artisan using routine techniques.

As used herein, the term "substantially as set out" refers that the relevant CDR, $V_H$, or $V_L$ domain of the invention will be either identical to or have only insubstantial differences in the specified regions (e.g., a CDR), the sequence of which is set out. Insubstantial differences include minor amino acid changes, such as substitutions of 1 or 2 out of any 5 amino acids in the sequence of a specified region.

As used herein, the term "CR011" refers to a fully human monoclonal antibody that specifically binds to GPNMB. In some embodiments, CR011 refers to those antibodies that are identified in Tables 2A-2D of the present application. In some embodiments, CR011 refers to Mab 1.15.1 as described in the instant invention.

The terms "GPNMB" and "CG56972" are used interchangeably herein. As used herein, the terms "GPNMB" or "CG56972" refer to a transmembrane glycoprotein that has an amino acid sequence as set forth in SEQ ID NO: 289, an analog, derivative or a fragment thereof, or a fusion protein comprising GPNMB, an analog, derivative or a fragment thereof. In certain embodiments, the term "GPNMB" refers to the mature, processed form of GPNMB. In other embodiments, the term "GPNMB" refers to the extracellular domain of GPNMB.

As used herein, the term "GPNMB activity" refers to one or more activities associated with GPNMB. To "modulate" GPNMB activity is to alter the baseline results observed with, and that can be attributed to GPNMB. To "neutralize" GPNMB is to cancel one or more effects, e.g. activity observed with, and that can be attributed to GPNMB.

As used herein, the term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

As used herein, the term "inhibit" or "inhibition of" refers to reducing by a measurable amount, or to prevent entirely.

As used herein, the term "Cytotoxic effect" in reference to the effect of an agent on a cell, means killing of the cell. "Cytostatic effect" refers to an inhibition of cell proliferation. A "cytotoxic agent" refers an agent that has a cytotoxic or cytostatic effect on a cell, thereby depleting or inhibiting the growth of, respectively, cells within a cell population.

As used herein, the terms "prevent," "preventing," and "prevention" refer to the inhibition of the development or onset of a disorder associated with aberrant expression and/or activity of GPNMB (e.g., cancer) or the prevention of the recurrence, onset, or development of one or more symptoms of a disorder associated with aberrant expression and/or activity of GPNMB (e.g., cancer) in a subject resulting from the administration of a therapy or the administration of a combination of therapies.

As used herein, the term "effective amount" refers to a dosage or amount that is sufficient to reduce the activity of GPNMB to result in amelioration of symptoms in a patient or to achieve a desired biological outcome.

As used herein, the term "prophylactically effective amount" refers to the amount of a therapy which is sufficient to result in the prevention of the development, recurrence, or onset of a disorder associated with aberrant expression and/or activity of GPNMB (e.g., cancer) or one or more symptoms thereof, or to enhance or improve the prophylactic effect(s) of another therapy.

As used herein, a "protocol" includes dosing schedules and dosing regimens. The protocols herein are methods of use and include prophylactic and therapeutic protocols.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, such as a cynomolgous monkey, chimpanzee, and a human), and more preferably a human.

As used herein, the terms "therapeutic agent" and "therapeutic agents" refer to an agent that can be used in the prevention, treatment, management, or amelioration of a disorder associated with aberrant expression and/or activity of GPNMB (e.g., cancer) or one or more symptoms thereof. In certain embodiments, the term "therapeutic agent" refers to an antibody that immunospecifically binds to GPNMB. In certain other embodiments, the term "therapeutic agent" refers an agent other than an antibody that immunospecifically binds to GPNMB.

As used herein, the terms "therapies" and "therapy" can refer to any protocol(s), method(s), and/or agent(s) that can be used in the prevention, treatment, management, or amelioration of a disorder associated with aberrant expression and/or activity of GPNMB (e.g., cancer) or one or more symptoms thereof. In certain embodiments, the terms "therapies" and "therapy" refer to anti-cancer therapy, biological therapy, supportive therapy, and/or other therapies useful in treatment, management, prevention, or amelioration of cancer or one or more symptoms thereof known to one of skill in the art such as medical personnel.

As used herein, the terms "treat," "treatment," and "treating" refer to the eradication, removal, modification, or control of primary, regional, or metastatic cancer tissue, or the reduction or amelioration of the progression, severity, and/or duration of a disorder associated with aberrant expression and/or activity of GPNMB or amelioration of one or more symptoms thereof resulting from the administration of one or more therapies. In certain embodiments, such terms in the context of cancer refer to a reduction in the growth of cancerous cells, a decrease in number of cancerous cells and/or a reduction in the growth, formation and/or volume of a tumor. In other embodiments, such terms refer to the minimizing or delay of the spread of cancer resulting from the administration of one or more therapies to a subject with such a disease. Treatment can include, for example, a decrease in the severity of a sypmtopm, the number of symptoms, or frequency of relapse.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. (See e.g., Sambrook et al. *Molecular Cloning: A Laboratory Manual*, 2d ed., Cold Spring Harbor Laboratory Press, Cold Spring Harbor, N.Y. 1989). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The current invention provides germline human antibody heavy chain V, D, J combinations and light chain V, J combinations including nucleotide and amino acid sequence of the $V_H$ and $V_L$ domain FR and CDR regions with specificity for GPNMB.

Upon exposure to antigen, those B cells with antigen binding specificity based on germline sequences are activated, proliferate, and differentiate to produce immunoglobulins of different isotypes as well as undergo somatic mutation and/or affinity maturation to produce immunoglobulins of higher affinity for the antigen. The current invention provides the nucleotide and amino acid sequence of such affinity matured V domain FR and CDR regions having specificity to GPNMB.

Fab type antibody fragments containing the antigen binding portion of the antibody molecule may consist of the L chain covalently linked by a disulfide bond to a portion of the H chain which has the V domain and first constant domain. Single chain Fv antibody fragment (scFv) has the H variable domain linked to the L variable domain by a polypeptide linker. The invention provides antibody fragments such as Fab and scFv molecules having sequences derived from germline or affinity matured V domains of antibodies binding specifically to GPNMB.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments (see, e.g., Songsivilai & Lachmann, 1990 Clin. Exp. Immunol. 79: 315-321; Kostelny et al., 1992 J. Immunol. 148:1547-1553). Bispecific antibodies do not exist in the form of fragments having a single binding site (e.g., Fab, Fab', and Fv).

It will be appreciated that such bifunctional or bispecific antibodies are contemplated and encompassed by the invention. A bispecific single chain antibody with specificity to GPNMB and to the CD3 antigen on cytotoxic T lymphocytes can be used to direct these T cells to tumor cells expressing GPNMB and cause apoptosis and eradication of the tumor. Bispecific scFv constructs for this purpose are described herein. The scFv components specific for GPNMB can be derived from anti-GPNMB antibodies described herein. In some embodiments, the anti-GPNMB antibody components disclosed herein can be used to generate a biologically active scFv directed against GPNMB. The anti-CD3 scFv component of the therapeutic bispecific scFv was derived from a sequence deposited in Genbank (accession number CAE85148). Alternative antibodies known to target CD3 or other T cell antigens may similarly be effective in treating malignancies when coupled with anti-GPNMB, whether on a single-chain backbone or a full IgG.

GPNMB binding human antibodies may include H or L constant domains including L kappa or lambda constant regions, or any isotype H constant domain. In one embodiment of the invention, a human antibody with binding specificity to GPNMB contains germline sequences such as the heavy chain V regions: VH1-2 (SEQ ID NO: 308), VH2-5 (SEQ ID NO: 360), VH3-11 (SEQ ID NO: 361), VH3-21 (SEQ ID NO: 362), VH3-30 (SEQ ID NO:363), VH3-33 (SEQ ID NO: 364), VH4-31 (SEQ ID NO: 365), VH4-59 (SEQ ID NO:366) or VH5-51 (SEQ ID NO:367); the heavy chain D region: D1-20 (amino acid sequences translated by SEQ ID NO: 375), D1-26 (amino acid sequences translated by SEQ ID NO:376), D3-10 (amino acid sequences translated by SEQ ID NO:377), D3-16 (amino acid sequences translated by SEQ ID NO:378), D3-22 (amino acid sequences translated by SEQ ID NO: 379), D3-9 (amino acid sequences translated by SEQ ID NO:380), D4-17 (amino acid sequences translated by SEQ ID NO: 381), D5-24 (amino acid sequences translated by SEQ ID NO: 382), D6-13 (amino acid sequences translated by SEQ ID NO:383), or D6-19 (amino acid sequences translated by SEQ ID NO: 384); the heavy chain J region: JH3b (SEQ ID NO: 385), JH4b (SEQ ID NO:386), JH5b (SEQ ID NO: 387) or JH6b (SEQ ID NO: 388); the light chain V kappa regions A2 (SEQ ID NO:373), A3 (SEQ ID NO: 371), A20 (SEQ ID NO: 370), A27 (SEQ ID NO: 369), A30 (SEQ ID NO:374), L2 (SEQ ID NO:372) or O1 (SEQ ID NO: 368); and the J region JK1 (SEQ ID NO:389), JK2 (SEQ ID NO: 390), JK3 (SEQ ID NO: 391), JK4 (SEQ ID NO: 392) or JK5 (SEQ ID NO: 393). (generally, see *Kabat Sequences of Proteins of Immunological Interest, National Institutes of Health*, Bethesda, Md. 1987 and 1991; also see Chothia & Lesk 1987 *J. Mol. Biol.* 196:901-917; Chothia et al. 1989 *Nature* 342:878-883). In a particular embodiment of the invention human antibodies with binding specificity to GPNMB are combined germline regions as shown in Table 1.

TABLE 1

Human anti-GPNMB antibody germline region combinations.

| Ab | VH | D | JH | VL | JL |
|---|---|---|---|---|---|
| 1.10.2 | VH4-59 | D6-19 | JH4b | A3 | JK5 |
| 1.15.1 | VH4-31 | D1-20 | JH4b | L2 | JK1 |
| 1.2.2 | VH2-5 | D3-16 | JH4b | O1 | JK5 |

TABLE 1-continued

Human anti-GPNMB antibody germline region combinations.

| Ab | VH | D | JH | VL | JL |
|---|---|---|---|---|---|
| 1.7.1 | VH4-31 | D1-20 | JH4b | L2 | JK1 |
| 2.10.2 | VH3-30 | D3-10 | JH6b | A3 | JK5 |
| 2.15.1 | VH3-33 | D4-17 | JH4b | A20 | JK4 |
| 2.16.1 | VH3-11 | D6-13 | JH3b | L2 | JK3 |
| 2.17.1 | VH1-2 | D6-19 | JH5b | A2 | JK4 |
| 2.21.2 | VH3-21 | D1-26 | JH4b | A20 | JK5 |
| 2.22.1 | VH4-31 | D3-22 | JH6b | A30 | JK1 |
| 2.24.1 | VH5-51 | D5-24 | JH4b | A27 | JK1 |
| 2.3.1 | VH1-2 | D3-10 | JH4b | A2 | JK4 |
| 2.7.1 | VH3-33 | D3-10 | JH4b | A20 | JK4 |
| 2.8.1 | VH2-5 | D3-9 | JH4b | O1 | JK4 |

In an embodiment of the invention, the isolated antibody has a heavy chain variable region polypeptide comprising an amino acid sequence selected from the group consisting of SEQ ID NOs:2, 20, 38, 56, 74, 92, 110, 128, 146, 164, 182, 200, 218, 236, 253, 256, 260, 265, 270, 274, 277, 281 and 285. Such amino acid sequences can be encoded by nucleotide sequences selected from the group consisting of SEQ ID NOs: 1, 19, 37, 55, 73, 91, 109, 127, 145, 163, 181, 199, 217 and 235. In another embodiment, the invention provides an isolated antibody that specifically binds to GPNMB and has a light chain variable region polypeptide comprising an amino acid sequence selected from the group consisting of SEQ ID NOs: 11, 29, 47, 65, 83, 101, 119, 137, 155, 173, 191, 209, 227 and 245. Such amino acid sequences can be encoded by nucleotide sequences selected from the group consisting of SEQ ID NOs: 10, 28, 46, 64, 82, 100, 118, 136, 154, 172, 190, 208, 226 and 244. In yet another embodiment, the invention provides an isolated antibody that specifically binds to GPNMB and has a heavy chain polypeptide comprising an amino acid sequence selected from the group consisting of SEQ ID NOs: 2, 20, 38, 56, 74, 92, 110, 128, 146, 164, 182, 200, 218, 236, 253, 256, 260, 265, 270, 274, 277, 281 and 285 and has a light chain polypeptide comprising an amino acid sequence selected from the group consisting of SEQ ID NOs: 11, 29, 47, 65, 83, 101, 119, 137, 155, 173, 191, 209, 227 and 245. In yet another embodiment of the invention, anti-GP-NMB antibodies comprise at least one CDR of any of the H or L CDR polypeptide sequences SEQ ID NOs: 4, 6, 8, 13, 15, 17, 22, 24, 26, 31, 33, 35, 40, 42, 44, 49, 51, 53, 58, 60, 62, 67, 69, 71, 76, 78, 80, 85, 87, 89, 94, 96, 98, 103, 105, 107, 112, 114, 116, 121, 123, 125, 130, 132, 134, 139, 141, 143, 148, 150, 152, 157, 159, 161, 166, 168, 170, 175, 177, 179, 184, 186, 188, 193, 195, 197, 202, 204, 206, 211, 213, 215, 220, 222, 224, 229, 231, 233, 238, 240, 242, 247, 249, 251, 254, 257, 261, 266, 271, 278, 282, 286, 255, 258, 262, 267, 272, 275, 279, 283, 287, 259, 263, 264, 268, 269, 273, 276, 280, 284 and 288.

In particular embodiments, human anti-GPNMB antibodies are Mab1.10.2, Mab1.15.1, Mab1.2.2, Mab1.7.1, Mab2.10.2, Mab2.15.1, Mab2.16.1, Mab2.17.1, Mab2.21.2, Mab2.22.1, Mab2.24.1, Mab2.3.1, Mab2.7.1, and Mab2.8.1. These antibodies have amino acid sequences and nucleic acid sequences encoding them identified in this application as shown in Tables 2A-2D.

TABLE 2A

Antibody Nucleotide (DNA) and Amino Acid (AA) Sequences

| Gene Segment | 1.10.2 | 1.15.1 | 1.2.2 | 1.7.1 |
|---|---|---|---|---|
| H variable DNA | SEQ ID NO: 1 | SEQ ID NO: 19 | SEQ ID NO: 37 | SEQ ID NO: 55 |
| H variable AA | SEQ ID NO: 2 | SEQ ID NO: 20 | SEQ ID NO: 38 | SEQ ID NO: 56 |
| H FR1 | SEQ ID NO: 3 | SEQ ID NO: 21 | SEQ ID NO: 39 | SEQ ID NO: 57 |
| H CDR1 | SEQ ID NO: 4 | SEQ ID NO: 22 | SEQ ID NO: 40 | SEQ ID NO: 58 |
| H FR2 | SEQ ID NO: 5 | SEQ ID NO: 23 | SEQ ID NO: 41 | SEQ ID NO: 59 |
| H CDR2 | SEQ ID NO: 6 | SEQ ID NO: 24 | SEQ ID NO: 42 | SEQ ID NO: 60 |
| H FR3 | SEQ ID NO: 7 | SEQ ID NO: 25 | SEQ ID NO: 43 | SEQ ID NO: 61 |
| H CDR3 | SEQ ID NO: 8 | SEQ ID NO: 26 | SEQ ID NO: 44 | SEQ ID NO: 62 |
| H FR4 | SEQ ID NO: 9 | SEQ ID NO: 27 | SEQ ID NO: 45 | SEQ ID NO: 63 |
| L variable DNA | SEQ ID NO: 10 | SEQ ID NO: 28 | SEQ ID NO: 46 | SEQ ID NO: 64 |
| L variable AA | SEQ ID NO: 11 | SEQ ID NO: 29 | SEQ ID NO: 47 | SEQ ID NO: 65 |
| L FR1 | SEQ ID NO: 12 | SEQ ID NO: 30 | SEQ ID NO: 48 | SEQ ID NO: 66 |
| L CDR1 | SEQ ID NO: 13 | SEQ ID NO: 31 | SEQ ID NO: 49 | SEQ ID NO: 67 |
| L FR2 | SEQ ID NO: 14 | SEQ ID NO: 32 | SEQ ID NO: 50 | SEQ ID NO: 68 |
| L CDR2 | SEQ ID NO: 15 | SEQ ID NO: 33 | SEQ ID NO: 51 | SEQ ID NO: 69 |
| L FR3 | SEQ ID NO: 16 | SEQ ID NO: 34 | SEQ ID NO: 52 | SEQ ID NO: 70 |
| L CDR3 | SEQ ID NO: 17 | SEQ ID NO: 35 | SEQ ID NO: 53 | SEQ ID NO: 71 |
| L FR4 | SEQ ID NO: 18 | SEQ ID NO: 36 | SEQ ID NO: 54 | SEQ ID NO: 72 |

TABLE 2B

Antibody Nucleotide (DNA) and Amino Acid (AA) Sequences

| Gene Segment | 2.10.2 | 2.15.1 | 2.16.1 | 2.17.1 |
|---|---|---|---|---|
| H variable DNA | SEQ ID NO: 73 | SEQ ID NO: 91 | SEQ ID NO: 109 | SEQ ID NO: 127 |
| H variable AA | SEQ ID NO: 74 | SEQ ID NO: 92 | SEQ ID NO: 110 | SEQ ID NO: 128 |
| H FR1 | SEQ ID NO: 75 | SEQ ID NO: 93 | SEQ ID NO: 111 | SEQ ID NO: 129 |
| H CDR1 | SEQ ID NO: 76 | SEQ ID NO: 94 | SEQ ID NO: 112 | SEQ ID NO: 130 |
| H FR2 | SEQ ID NO: 77 | SEQ ID NO: 95 | SEQ ID NO: 113 | SEQ ID NO: 131 |
| H CDR2 | SEQ ID NO: 78 | SEQ ID NO: 96 | SEQ ID NO: 114 | SEQ ID NO: 132 |
| H FR3 | SEQ ID NO: 79 | SEQ ID NO: 97 | SEQ ID NO: 115 | SEQ ID NO: 133 |
| H CDR3 | SEQ ID NO: 80 | SEQ ID NO: 98 | SEQ ID NO: 116 | SEQ ID NO: 134 |
| H FR4 | SEQ ID NO: 81 | SEQ ID NO: 99 | SEQ ID NO: 117 | SEQ ID NO: 135 |
| L variable DNA | SEQ ID NO: 82 | SEQ ID NO: 100 | SEQ ID NO: 118 | SEQ ID NO: 136 |
| L variable AA | SEQ ID NO: 83 | SEQ ID NO: 101 | SEQ ID NO: 119 | SEQ ID NO: 137 |
| L FR1 | SEQ ID NO: 84 | SEQ ID NO: 102 | SEQ ID NO: 120 | SEQ ID NO: 138 |

TABLE 2B-continued

Antibody Nucleotide (DNA) and Amino Acid (AA) Sequences

| Gene Segment | 2.10.2 | 2.15.1 | 2.16.1 | 2.17.1 |
|---|---|---|---|---|
| L CDR1 | SEQ ID NO: 85 | SEQ ID NO: 103 | SEQ ID NO: 121 | SEQ ID NO: 139 |
| L FR2 | SEQ ID NO: 86 | SEQ ID NO: 104 | SEQ ID NO: 122 | SEQ ID NO: 140 |
| L CDR2 | SEQ ID NO: 87 | SEQ ID NO: 105 | SEQ ID NO: 123 | SEQ ID NO: 141 |
| L FR3 | SEQ ID NO: 88 | SEQ ID NO: 106 | SEQ ID NO: 124 | SEQ ID NO: 142 |
| L CDR3 | SEQ ID NO: 89 | SEQ ID NO: 107 | SEQ ID NO: 125 | SEQ ID NO: 143 |
| L FR4 | SEQ ID NO: 90 | SEQ ID NO: 108 | SEQ ID NO: 126 | SEQ ID NO: 144 |

TABLE 2C

Antibody Nucleotide (DNA) and Amino Acid (AA) Sequences

| Gene Segment | 2.21.2 | 2.22.1 | 2.24.1 | 2.3.1 |
|---|---|---|---|---|
| H variable DNA | SEQ ID NO: 145 | SEQ ID NO: 163 | SEQ ID NO: 181 | SEQ ID NO: 199 |
| H variable AA | SEQ ID NO: 146 | SEQ ID NO: 164 | SEQ ID NO: 182 | SEQ ID NO: 200 |
| H FR1 | SEQ ID NO: 147 | SEQ ID NO: 165 | SEQ ID NO: 183 | SEQ ID NO: 201 |
| H CDR1 | SEQ ID NO: 148 | SEQ ID NO: 166 | SEQ ID NO: 184 | SEQ ID NO: 202 |
| H FR2 | SEQ ID NO: 149 | SEQ ID NO: 167 | SEQ ID NO: 185 | SEQ ID NO: 203 |
| H CDR2 | SEQ ID NO: 150 | SEQ ID NO: 168 | SEQ ID NO: 186 | SEQ ID NO: 204 |
| H FR3 | SEQ ID NO: 151 | SEQ ID NO: 169 | SEQ ID NO: 187 | SEQ ID NO: 205 |
| H CDR3 | SEQ ID NO: 152 | SEQ ID NO: 170 | SEQ ID NO: 188 | SEQ ID NO: 206 |
| H FR4 | SEQ ID NO: 153 | SEQ ID NO: 171 | SEQ ID NO: 189 | SEQ ID NO: 207 |
| L variable DNA | SEQ ID NO: 154 | SEQ ID NO: 172 | SEQ ID NO: 190 | SEQ ID NO: 208 |
| L variable AA | SEQ ID NO: 155 | SEQ ID NO: 173 | SEQ ID NO: 191 | SEQ ID NO: 209 |
| L FR1 | SEQ ID NO: 156 | SEQ ID NO: 174 | SEQ ID NO: 192 | SEQ ID NO: 210 |
| L CDR1 | SEQ ID NO: 157 | SEQ ID NO: 175 | SEQ ID NO: 193 | SEQ ID NO: 211 |
| L FR2 | SEQ ID NO: 158 | SEQ ID NO: 176 | SEQ ID NO: 194 | SEQ ID NO: 212 |
| L CDR2 | SEQ ID NO: 159 | SEQ ID NO: 177 | SEQ ID NO: 195 | SEQ ID NO: 213 |
| L FR3 | SEQ ID NO: 160 | SEQ ID NO: 178 | SEQ ID NO: 196 | SEQ ID NO: 214 |
| L CDR3 | SEQ ID NO: 161 | SEQ ID NO: 179 | SEQ ID NO: 197 | SEQ ID NO: 215 |
| L FR4 | SEQ ID NO: 162 | SEQ ID NO: 180 | SEQ ID NO: 198 | SEQ ID NO: 216 |

TABLE 2D

Antibody Nucleotide (DNA) and Amino Acid (AA) Sequences

| Gene Segment | 2.7.1 | 2.8.1 |
|---|---|---|
| H variable DNA | SEQ ID NO: 217 | SEQ ID NO: 235 |
| H variable AA | SEQ ID NO: 218 | SEQ ID NO: 236 |
| H FR1 | SEQ ID NO: 219 | SEQ ID NO: 237 |
| H CDR1 | SEQ ID NO: 220 | SEQ ID NO: 238 |
| H FR2 | SEQ ID NO: 221 | SEQ ID NO: 239 |
| H CDR2 | SEQ ID NO: 222 | SEQ ID NO: 240 |
| H FR3 | SEQ ID NO: 223 | SEQ ID NO: 241 |
| H CDR3 | SEQ ID NO: 224 | SEQ ID NO: 242 |
| H FR4 | SEQ ID NO: 225 | SEQ ID NO: 243 |
| L variable DNA | SEQ ID NO: 226 | SEQ ID NO: 244 |
| L variable AA | SEQ ID NO: 227 | SEQ ID NO: 245 |
| L FR1 | SEQ ID NO: 228 | SEQ ID NO: 246 |
| L CDR1 | SEQ ID NO: 229 | SEQ ID NO: 247 |
| L FR2 | SEQ ID NO: 230 | SEQ ID NO: 248 |
| L CDR2 | SEQ ID NO: 231 | SEQ ID NO: 249 |
| L FR3 | SEQ ID NO: 232 | SEQ ID NO: 250 |
| L CDR3 | SEQ ID NO: 233 | SEQ ID NO: 251 |
| L FR4 | SEQ ID NO: 234 | SEQ ID NO: 252 |

VH4-31 Derived Anti-GPNMB Antibodies:

In a particular embodiment, GPNMB-binding human antibodies of the invention comprise germline V heavy chain region VH4-31 or are derived therefrom and have an amino acid sequence of the formula:

```
                                        (SEQ ID NO: 253)
X1SGPGLVKPSQX2LSLTCTVS GGSIS SX3X4YX5WX6

WIRX7HPGKGLEWIG YIYYSGX8TYX9NPSLKS
```

-continued
```
RVX10ISVDTSKNQFSLX11LSSVTAADTAVYYCAR
```

Where: $X_1$ is E or Q;

$X_2$ is T or N;

$X_3$ is A, F or G;

$X_4$ is N or G;

$X_5$ is Y or F;

$X_6$ is T or S;

$X_7$ is Q or H;

$X_8$ is S or N;

$X_9$ is C, S or Y;

$X_{10}$ is I or T;

$X_{11}$ is K or T;.

In specific embodiments SEQ ID NO:253 is combined with D3-22 or D1-20. Furthermore the combination of SEQ ID NO:253 with D3-22 or D1-20 is combined with JH6b or JH4b and in specific embodiments, after affinity maturation these GPNMB-binding human antibodies, for example Mab1.15.1, Mab1.7.1 and Mab2.22.1, have amino acid sequences SEQ ID NOs:20, 56 and 164 and can be encoded by nucleotide sequences SEQ ID NO:19, 55 and 163.

Furthermore, in particular embodiments H chain CDR1 sequences are the germline VH4-31 CDR or affinity matured sequences thereof, of the formula:

```
CDR1: GGSIS SX₃X₄YX₅WX₆        (SEQ ID NO: 254)

Where: X₃ is A, F or G;

X₄ is N or G;

X₅ is Y or F;

X₆ is T or S;.
```

In specific embodiments an anti-GPNMB antibody of the invention comprise a CDR1 sequence selected from the following: SEQ ID NO:22, 58, 166.

In particular embodiments H chain CDR2 sequences are the germline VH4-31 CDR or affinity matured sequences thereof of the formula:

```
CDR2: YIYYSGX₈TYX₉NPSLKS        (SEQ ID NO: 255)

Where: X₈ is S or N;

X₉ is C, S or Y;.
```

In specific embodiments an anti-GPNMB antibody of the invention comprise a CDR2 sequence selected from the following: SEQ ID NO: 24, 60, and 168.

In particular embodiments, the H chain CDR3 sequence is a D3-22, JH6b combination having SEQ ID NO:170. Alternatively, in particular embodiments the H chain CDR3 sequence is a D1-20, JH4b combination having SEQ ID NO:26 or 62.

VH1-2 Derived Anti-GPNMB Antibodies:

In a particular embodiment, GPNMB-binding human antibodies of the invention comprise germline V heavy chain region VH1-2 or are derived therefrom and include an amino acid sequence of the formula:

```
                                (SEQ ID NO: 256)
QLVQSGAEVKKPGASVKVSCKAS GYTFT GX₁YMH

WVRQX₂PGQGLEWMG WINPNSGGTX₃YX₄QKFQX₅

RVTMTRDTSISTX₆YMELSRLRSDDTAVYYCAR

Where: X₁ is Y or F;

X₂ is A or T;

X₃ is N or Y;

X₄ is A or V;

X₅ is D or G;

X₆ is A or V;.
```

In specific embodiments SEQ ID NO:256 is combined with D3-10 or D6-19. Furthermore the combination ov SEQ ID NO:256 with D3-10 or D6-19 is combined with JH4b or JH5b and in specific embodiments, after affinity maturation these GPNMB-binding human antibodies, for example Mab2.3.1 and Mab 2.17.1 have amino acid sequences: SEQ ID NO:128 and 200 and can be encoded by nucleotide sequences SEQ ID NO:127 and 199.

Furthermore, in particular embodiments H chain CDR1 sequences are the germline VH1-2 CDR or affinity matured sequences thereof, of the formula:

```
CDR1: GYTFTGX₁YMH              (SEQ ID NO: 257)

Where: X₁ is Y or F,
```

In specific embodiments an anti-GPNMB antibody of the invention comprise a CDR1 sequence selected from SEQ ID NO: 130 and 202.

In particular embodiments H chain CDR2 sequences are the germline VH1-2 CDR or affinity matured sequences thereof of the formula:

```
CDR2: WINPNSGGTX₃YX₄QKFQX₅      (SEQ ID NO: 258)

Where: X₃ is N or Y;

X₄ is A or V;

X₅ is D or G.
```

In specific embodiments an anti-GPNMB antibody of the invention comprise a CDR2 sequence selected from SEQ ID NO:132 and 204.

In particular embodiments H chain CDR3 sequences are germline D3-10, JH4b combinations or affinity matured sequences thereof, having the amino acid sequence of the formula:

```
CDR3: X₁X₂X₃GSGSX₄X₅            (SEQ ID NO: 259)

Where: X₁ is Y or D;

X₂ is Y or F;

X₃ is Y or F;

X₄ is Y or L;

X₅ is Y or L.
```

In specific embodiments an anti-GPNMB antibody of the invention comprise a CDR3 sequence selected from SEQ ID NO:134 and 206.

VH2-5 Derived Anti-GPNMB Antibodies:

In a particular embodiment, GPNMB-binding human antibodies of the invention comprise germline V heavy chain region VH2-5 or are derived therefrom and include an amino acid sequence of the formula:

```
                                (SEQ ID NO: 260)
ITLKESGPTLVX₁PTQTLTLTCTFS GFSLS X₂X₃GX₄GVG

WIRQPPGKALX₅WLX₆ LIYWNDDKX₇YSPSLX₈S

RLTITKDTSKNQVVLX₉X₁₀ TNMDPVDTATYYCAH

Where: X₁ is K or T;

X₂ is T or A;

X₃ is S or G;

X₄ is M or V;

X₅ is D or E;

X₆ is A or T;

X₇ is R or H;
```

-continued

X₈ is K or R;

X₉ is T or R;

X₁₀ is M or I;.

In specific embodiments SEQ ID NO:260 is combined with D3-9 or D3-16 and furthermore is combined with JH4b. In specific embodiments, after affinity maturation these GPNMB-binding human antibodies, for example, Mab 2.8.1 and Mab 1.2.2 have amino acid sequences SEQ ID NO: 38 and 236 and can be encoded by nucleotide sequences SEQ ID NO: 37 and 235.

Furthermore, in particular embodiments H chain CDR1 sequences are the germline VH2-5 CDR or affinity matured sequences thereof, of the formula:

```
                                    (SEQ ID NO: 261)
CDR1: GFSLS X₂X₃GX₄GVG

Where: X₂ is T or A;

X₃ is S or G;

X₄ is M or V;.
```

In specific embodiments an anti-GPNMB antibody of the invention comprise a CDR1 sequence selected from SEQ ID NO: 40 and 238.

In particular embodiments H chain CDR2 sequences are the germline VH2-5 CDR2 or affinity matured sequences thereof of the formula:

```
                                    (SEQ ID NO: 262)
CDR2: LIYWNDDKX₇YSPSLX₈S

Where: X₇ is R or H;

X₈ is K or R;.
```

In specific embodiments an anti-GPNMB antibody of the invention comprise a CDR2 sequence selected from SEQ ID NO:42 and 240.

In particular embodiments H chain CDR3 sequences are germline D3-9, JH4b combinations or affinity matured sequences thereof and include an amino acid sequence of the formula:

```
                                    (SEQ ID NO: 263)
CDR3: X₁YDILTGX₂X₃

Where: X₁ is Y or H;

X₂ is Y or F;
and

X₃ is Y or N.
```

In a specific embodiments an anti-GPNMB antibody of the invention comprises a CDR3 amino acid sequence SEQ ID NO:242.

In yet another particular embodiment H chain CDR3 sequences are germline D3-16, JH4b combinations or affinity matured sequences thereof and include an amino acid sequence of the formula:

```
                                    (SEQ ID NO: 264)
CDR3: YDYX₁WGS

Where: X₁ is V or D.
```

In a specific embodiment an anti-GPNMB antibody of the invention comprises a CDR3 amino acid sequence SEQ ID NO: 44.

VH3-33 Derived Anti-GPNMB Antibodies:

In a particular embodiment, GPNMB-binding human antibodies of the invention comprise germline V heavy chain region VH3-33 or are derived therefrom and have an amino acid sequence of the formula:

```
                                    (SEQ ID NO: 265)
QVQLX₁X₂SGGGVVQPGRSLRLSCAAS GFTFX₃X₄YGX₅H

WVRQAPGKGLEWVA VIWX₆DGX₇NKYYADSVKG

RFTISRDNSKNTLYLQMNSLRAEDX₈AVYYCAX₉

Where: X₁ is V or E;

X₂ is E or Q;

X₃ is S or N;

X₄ is S or N;

X₅ is M or I;

X₆ is Y or F;

X₇ is S or R;

X₈ is T or A;

X₉ is R or K.
```

In specific embodiments SEQ ID NO:265 is combined with D3-10 or D4-17 and furthermore with JH4b. In specific embodiments, after affinity maturation these GPNMB-binding human antibodies, for example Mab 2.7.1 and Mab2.15.1 have amino acid sequences: SEQ ID NO:92 and 218 and can be encoded by nucleotide sequences SEQ ID NO:91 and 217.

Furthermore, in particular embodiments H chain CDR1 sequences are the germline VH3-33 CDR or affinity matured sequences thereof, of the formula:

```
                                    (SEQ ID NO: 266)
CDR1: GFTFX₃X₄YGX₅H

Where: X₃ is S or N;

X₄ is S or N;

X₅ is M or I;.
```

In specific embodiments an anti-GPNMB antibody of the invention comprise a CDR1 amino acid sequence selected from SEQ ID NO:94 and 220.

In particular embodiments H chain CDR2 sequences are the germline VH3-33 CDR2 or affinity matured sequences thereof of the formula:

```
                                    (SEQ ID NO: 267)
CDR2: VIWX₆DGX₇NKYYADSVKG

Where: X₆ is Y or F;

X₇ is S or R;.
```

In specific embodiments an anti-GPNMB antibody of the invention comprise a CDR2 sequence selected from SEQ ID NO:96 and 222.

In particular embodiments H chain CDR3 sequences are D3-10, JH4b combinations or affinity matured sequences thereof and include an amino acid sequence of the formula:

CDR3: YYYGSGX$_1$ (SEQ ID NO: 268)

Where: X$_1$ is S or L.

A specific embodiment is anti-GPNMB antibody 2.7.1 having a CDR3 amino acid sequence SEQ ID NO:224.

In an alternative embodiment H chain CDR3 sequences are D4-17, JH4b combinations or affinity matured sequences thereof and include an amino acid sequence of the formula:

CDR3: DYGDX$_1$ (SEQ ID NO: 269)

Where: X$_1$ is Y or S.

A specific embodiment is anti-GPNMB antibody 2.15.1 having a CDR3 amino acid sequence SEQ ID NO: 98.

VH3-11 Derived Anti-GPNMB Antibodies:

In a particular embodiment, GPNMB-binding human antibodies of the invention comprise germline V heavy chain region VH3-11 or are derived therefrom and have an amino acid sequence of the formula:

(SEQ ID NO: 270)
QVQLVESGGGLVKPGGSLRLSCAAS GFTFS X$_1$YX$_2$MX$_3$ WIRQAPGKG

LEWVS YISX$_4$SGSX$_5$X$_6$X$_7$YADSVKG RFTX$_8$SRDNAKNSLYLQMNSLR

AEDTAVYYCAR

Where: X$_1$ is D or S;

X$_2$ is S or Y;

X$_3$ is S or T;

X$_4$ is S or I;

X$_5$ is T or I;

X$_6$ is T or I;

X$_7$ is Y or H;

X$^8$ is I or M;.

CDR1: GFTFS X$_1$YX$_2$MX$_3$ (SEQ ID NO: 271)

Where: X$_1$ is D or S;

X$_2$ is S or Y;

X$_3$ is S or T;.

In specific embodiments an anti-GPNMB antibody of the invention comprise a CDR1 amino acid sequence SEQ ID NO:112.

In particular embodiments H chain CDR2 sequences are the germline VH3-11 CDR2 or affinity matured sequences thereof of the formula:

(SEQ ID NO: 272)
CDR2: YISX$_4$SGSX$_5$X$_6$X$_7$YADSVKG

Where: X$_4$ is S or I;

X$_5$ is T or I;

X$_6$ is T or I;

X$_7$ is Y or H;.

In specific embodiments an anti-GPNMB antibody of the invention comprises a CDR2 sequence SEQ ID NO:114.

In particular embodiments H chain CDR3 sequences are D6-13, JH3b combinations or affinity matured sequences thereof and include an amino acid sequence of the formula:

CDR3: X$_1$X$_2$AAAG - - - AFDI (SEQ ID NO: 273)

Where: X$_1$ is G or D;

X$_2$ is I or G;.

A specific embodiment is anti-GPNMB antibody 2.16.1 having a CDR3 amino acid sequence SEQ ID NO:116.

VH3-21 Derived Anti-GPNMB Antibodies:

In a particular embodiment, GPNMB-binding human antibodies of the invention comprise germline V heavy chain region VH3-21 or are derived therefrom and have an amino acid sequence of the formula:

(SEQ ID NO: 274)
X$_1$VQLX$_2$X$_3$SGGGLVKPGGSLRX$_4$ SCAAS GFTFS SYSMN WVRQAPGKGLEWVS X$_5$ISS

SSSYIYYADSVKG RFTISRDNAKNSLYLQMNSLRAEDTAVYYCAR

Where: X$_1$ is E or Q;

X$_2$ is V or E;

X$_3$ is E or Q;

X$_4$ is F or L;

X$_5$ is S or F;.

In specific embodiments SEQ ID NO:270 is combined with D6-13 and furthermore with JH3b. In specific embodiments, after affinity maturation these GPNMB-binding human antibodies, for example Mab 2.16.1 have amino acid sequence SEQ ID NO:110 and can be encoded by nucleotide sequence SEQ ID NO:109.

Furthermore, in particular embodiments H chain CDR1 sequences are the germline VH3-11 CDR1 or affinity matured sequences thereof, of the formula:

In specific embodiments SEQ ID NO:274 is combined with D1-26 and furthermore with JH4b. In specific embodiments, after affinity maturation these GPNMB-binding human antibodies, for example Mab 2.21.1 have amino acid sequence SEQ ID NO:146 and can be encoded by nucleotide sequence SEQ ID NO:145.

Furthermore, in particular embodiments H chain CDR1 sequences are the germline VH3-21 CDR1, SEQ ID NO:148 or affinity matured sequences thereof.

In particular embodiments H chain CDR2 sequences are the germline VH3-21 CDR2 or affinity matured sequences thereof of the formula:

(SEQ ID NO: 275)
CDR2: X$_5$ISS SSSYIYYADSVKG

Where: X$_5$ is S or F;.

In specific embodiments an anti-GPNMB antibody of the invention comprises a CDR2 amino acid sequence SEQ ID NO:150.

In particular embodiments H chain CDR3 sequences are D1-26, JH4b combinations or affinity matured sequences thereof and include an amino acid sequence of the formula:

(SEQ ID NO: 276)
CDR3: X$_1$X$_2$VGAT-FDY

Where: X$_1$ is G or D;

X$_2$ is I or W;.

A specific embodiment is anti-GPNMB antibody 2.21.1 having a CDR3 amino acid sequence SEQ ID NO:152.

VH3-30 Derived Anti-GPNMB Antibodies:

In a particular embodiment, GPNMB-binding human antibodies of the invention comprise germline V heavy chain region VH3-30 or are derived therefrom and include an amino acid sequence of the formula:

(SEQ ID NO: 277)
QLVESGGGVVQPGRSLRLSCAAS GFX$_1$FS SYGMH

WVRQAPGKGLEWVA VISYDGX$_2$NKYYADSVKG

RFTISRDNSKNTLYLQMNSLRAEDTAVYYCAK

Where: X$_1$ is T or A;

X$_2$ is S or N;.

In specific embodiments SEQ ID NO:277 is combined with D3-10 and furthermore with JH6b. In specific embodiments, after affinity maturation these GPNMB-binding human antibodies, for example Mab 2.10.2 have amino acid sequence SEQ ID NO:74 and can be encoded by nucleotide sequence SEQ ID NO:73.

Furthermore, in particular embodiments H chain CDR1 sequences are the germline VH3-30 CDR1, or affinity matured sequences thereof having an amino acid sequence of the formula:

(SEQ ID NO: 278)
GFX$_1$FS SYGMH

Where: X$_1$ is T or A;.

In specific embodiments an anti-GPNMB antibody of the invention comprise a CDR1 sequence SEQ ID NO:76.

In particular embodiments H chain CDR2 sequences are the germline VH3-30 CDR2 or affinity matured sequences thereof of the formula:

(SEQ ID NO: 279)
CDR2: VISYDGX$_2$NKYYADSVKG

Where: X$_2$ is S or N;.

In specific embodiments an anti-GPNMB antibody of the invention comprises a CDR2 amino acid sequence SEQ ID NO:78.

In particular embodiments H chain CDR3 sequences are D3-10, JH6b combinations or affinity matured sequences thereof and include an amino acid sequence of the formula:

(SEQ ID NO: 280)
CDR3: X$_1$X$_2$X$_3$VRGX$_4$X$_5$X$_6$

Where: X$_1$ is I or D;

X$_2$ is T or L;

X$_3$ is M or V;

X$_4$ is V or I;

X$_5$ is I or R;

X$_6$ is I or G;.

A specific embodiment is anti-GPNMB antibody 2.10.2 having a CDR3 amino acid sequence SEQ ID NO:80.

VH4-59 Derived Anti-GPNMB Antibodies:

In a particular embodiment, GPNMB-binding human antibodies of the invention comprise germline V heavy chain region VH4-59 or are derived therefrom and include an amino acid sequence of the formula:

(SEQ ID NO: 281)
QVQLQESGPGLVKPSETLSLTCTVS GX$_1$SIS X$_2$YYWS

WIRQPPGKGLEWIG YX$_3$YYSGSTNYNPSLKS

RVTISVDTSKNQFSLKLSSVTAADTAVYYCAR

Where: X$_1$ is G or D;

X$_2$ is S or N;

X$_3$ is I or F;.

In specific embodiments SEQ ID NO:281 is combined with D6-19 and furthermore with JH4b. In specific embodiments, after affinity maturation these GPNMB-binding human antibodies, for example Mab 1.10.2 have amino acid sequence SEQ ID NO:2 and can be encoded by nucleotide sequence SEQ ID NO:1.

Furthermore, in particular embodiments H chain CDR1 sequences are the germline VH4-59 CDR1, or affinity matured sequences thereof having an amino acid sequence of the formula:

(SEQ ID NO: 282)
GX$_1$SIS X$_2$YYWS

Where: X$_1$ is G or D;

X$_2$ is S or N;.

In specific embodiments an anti-GPNMB antibody of the invention comprise a CDR1 sequence SEQ ID NO:4.

In particular embodiments H chain CDR2 sequences are the germline VH4-59 CDR2 or affinity matured sequences thereof of the formula:

(SEQ ID NO: 283)
CDR2: YX$_3$YYSGSTNYNPSLKS

Where: X$_3$ is I or F;.

In specific embodiments an anti-GPNMB antibody of the invention comprises a CDR2 amino acid sequence SEQ ID NO:6.

In particular embodiments H chain CDR3 sequences are D6-19, JH4b combinations or affinity matured sequences thereof and include an amino acid sequence of the formula:

(SEQ ID NO: 284)
CDR3: X₁X₂GW - - - DY

Where: X₁ is S or D;

X₂ is S or R;.

A specific embodiment is anti-GPNMB antibody 1.10.2 having a CDR3 amino acid sequence SEQ ID NO:8.

VH5-51 Derived Anti-GPNMB Antibodies:

In a particular embodiment, GPNMB-binding human antibodies of the invention comprise germline V heavy chain region VH5-51 or are derived therefrom and include an amino acid sequence of the formula:

(SEQ ID NO: 285)
QLVQSGAEVKKPGESLKISCX₁GS GYX₂FT X₃YW<u>I</u>G

WVRQMP<u>G</u>KGLEWMG X₄IYPX₅DSDTRYSPSFQG

QVTISADKSISTAYLQWSSLKASDTAX₆YYCAR

Where: X₁ is K or Q;

X₂ is S or I;

X₃ is S or N;

X₄ is I or V;

X₅ is G or D;

X₆ is M or I;.

In specific embodiments SEQ ID NO:285 is combined with D5-24 and furthermore with JH4b. In specific embodiments, after affinity maturation these GPNMB-binding human antibodies, for example Mab 2.24.1 have amino acid sequence SEQ ID NO:182 and can be encoded by nucleotide sequence SEQ ID NO:181.

Furthermore, in particular embodiments H chain CDR1 sequences are the germline VH5-51 CDR1, or affinity matured sequences thereof having an amino acid sequence of the formula:

(SEQ ID NO: 286)
GYX₂FT X₃YW<u>I</u>G

Where: X₂ is S or I;

X₃ is S or N;.

In specific embodiments an anti-GPNMB antibody of the invention comprise a CDR1 sequence SEQ ID NO:184.

In particular embodiments H chain CDR2 sequences are the germline VH5-51 CDR2 or affinity matured sequences thereof of the formula:

(SEQ ID NO: 287)
CDR2: X₄IYPX₅DSDTRYSPSFQG

Where: X₄ is I or V;

X₅ is G or D;.

In specific embodiments an anti-GPNMB antibody of the invention comprises a CDR2 amino acid sequence SEQ ID NO:186.

In particular embodiments H chain CDR3 sequences are D5-24, JH4b combinations or affinity matured sequences thereof and include an amino acid sequence of the formula:

(SEQ ID NO: 288)
CDR3: X₁WLQX2 - - - FDY

Where: X₁ is R or K;

X2 is L or H;.

A specific embodiment is anti-GPNMB antibody 2.24.1 having a CDR3 amino acid sequence SEQ ID NO:188.

The antibodies of the invention bind an epitope of GPNMB (SEQ ID NO:289), preferably within the mature sequence of GPNMB and more preferably within the extracellular domain (ECD) of GPNMB.

Antibodies of the invention bind GPNMB with an affinity of $10^{-6}$ to $10^{-11}$. Preferably with an affinity of $10^{-7}$ or greater and even more preferably $10^{-8}$ or greater. In a preferred embodiment, antibodies described herein bind to GPNMB with very high affinities (Kd), for example a human antibody that is capable of binding GPNMB with a Kd less than, but not limited to, $10^{-7}$, $10^{-8}$, $10^{-9}$, $10^{-10}$, $10^{-11}$, $10^{-12}$, $10^{-13}$ or $10^{-14}$ M, m or any range or value therein. Affinity and/or avidity measurements can be measured by KinExA® and/or BIACORE®, as described herein. In particular embodiments antibodies of the invention bind to GPNMB with Kds ranging from 50 to 150 μM.

Epitope mapping and secondary and tertiary structure analyses can be carried out to identify specific 3D structures assumed by the disclosed antibodies and their complexes with antigens (see, e.g., *Epitope Mapping Protocols*, ed. Morris, Humana Press, 1996). Such methods include, but are not limited to, X-ray crystallography (*Biochem. Exp. Biol.*, 11:7-13, 1974) and computer modeling of virtual representations of the presently disclosed antibodies (Fletterick et al. (1986) *Computer Graphics and Molecular Modeling, in Current Communications in Molecular Biology*, Cold Spring Harbor Laboratory, Cold Spring Harbor, N.Y.).

Furthermore, the specific part of the protein immunogen recognized by antibody may be determined by assaying the antibody reactivity to parts of the protein, for example an N terminal and C terminal half. The resulting reactive fragment can then be further dissected, assaying consecutively smaller parts of the immunogen with the antibody until the minimal reactive peptide is defined. Alternatively, the binding specificity, that is the epitope, of anti-GPNMB antibodies of the invention may be determined by subjecting GPNMB immunogen to SDS-PAGE either in the absence or presence of a reduction agent and analyzed by immunoblotting. Epitope mapping may also be performed using SELDI. SELDI ProteinChip® (LumiCyte) arrays used to define sites of protein-protein interaction. GPNMB protein antigen or fragments thereof may be specifically captured by antibodies covalently immobilized onto the PROTEINCHIP array surface. The bound antigens may be detected by a laser-induced desorption process and analyzed directly to determine their mass.

The epitope recognized by anti-GPNMB antibodies described herein may be determined by exposing the PROTEINCHIP Array to a combinatorial library of random peptide 12-mer displayed on Filamentous phage (New England Biolabs). Antibody-bound phage are eluted and then amplified and taken through additional binding and amplification cycles to enrich the pool in favor of binding sequences. After three or four rounds, individual binding clones are further tested for binding by phage ELISA assays performed on antibody-coated wells and characterized by specific DNA sequencing of positive clones.

Derivatives

This disclosure also provides a method for obtaining an antibody specific for GPNMB. CDRs in such antibodies are not limited to the specific sequences of H and L variable domains identified in Table 1 and may include variants of these sequences that retain the ability to specifically bind GPNMB. Such variants may be derived from the sequences listed in Table 1 by a skilled artisan using techniques well known in the art. For example, amino acid substitutions, deletions, or additions, can be made in the FRs and/or in the CDRs. While changes in the FRs are usually designed to improve stability and immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity of the antibody for its target. For example, conservative amino acid substitutions can be made within any one of the disclosed CDRs. Various alterations can be made according to the methods described in the art (*Antibody Engineering*, 2.sup.nd ed., Oxford University Press, ed. Borrebaeck, 1995). These include but are not limited to nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Substitutes for an amino acid within the sequence may be selected from other members of the class to which the amino acid belongs (see Table 3). Furthermore, any native residue in the polypeptide may also be substituted with alanine (*Acta Physiol. Scand. Suppl.* 643:55-67, 1998; *Adv. Biophys.* 35:1-24, 1998).

TABLE 3

Amino acid substitutions

| Original aa Residue | Possible Substitutions | Prefered substitution |
| --- | --- | --- |
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala Gly | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

Derivatives and analogs of antibodies of the invention can be produced by various techniques well known in the art, including recombinant and synthetic methods (Maniatis (1990) *Molecular Cloning, A Laboratory Manual*, 2.sup.nd ed., Cold Spring Harbor Laboratory, Cold Spring Harbor, N.Y., and Bodansky et al. (1995) *The Practice of Peptide Synthesis*, 2.sup.nd ed., Spring Verlag, Berlin, Germany).

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in the art (for example, *Proteins, Structures and Molecular Principles* (Creighton, Ed., W. H. Freeman and Company, New York (1984)).

In one embodiment, a method for making an H variable domain which is an amino acid sequence variant of an H variable domain of the invention comprises a step of adding, deleting, substituting, or inserting one or more amino acids in the amino acid sequence of the presently disclosed H variable domain, optionally combining the H variable domain thus provided with one or more L variable domains, and testing the H variable domain or H variable/L variable combination or combinations for specific binding to GPNMB or and, optionally, testing the ability of such antigen-binding domain to modulate GPNMB activity. The L variable domain may have an amino acid sequence that is identical or is substantially as set out according to Table 1.

An analogous method can be employed in which one or more sequence variants of a L variable domain disclosed herein are combined with one or more H variable domains.

A further aspect of the disclosure provides a method of preparing antigen-binding fragment that specifically binds with GPNMB. The method comprises: (a) providing a starting repertoire of nucleic acids encoding a H variable domain that either includes a CDR3 to be replaced or lacks a CDR3 encoding region; (b) combining the repertoire with a donor nucleic acid encoding an amino acid sequence substantially as set out herein for a H variable CDR3 such that the donor nucleic acid is inserted into the CDR3 region in the repertoire, so as to provide a product repertoire of nucleic acids encoding a H variable domain; (c) expressing the nucleic acids of the product repertoire; (d) selecting a binding fragment specific for GPNMB; and (e) recovering the specific binding fragment or nucleic acid encoding it.

Again, an analogous method may be employed in which a L variable CDR3 of the invention is combined with a repertoire of nucleic acids encoding a L variable domain, which either include a CDR3 to be replaced or lack a CDR3 encoding region. The donor nucleic acid may be selected from nucleic acids encoding an amino acid sequence substantially as set out in SEQ ID NOs: 2, 20, 38, 56, 74, 92, 110, 128, 146, 164, 182, 200, 218, 236, 253, 256, 260, 265, 270, 274, 277, 281, 285, 11, 29, 47, 65, 83, 101, 119, 137, 155, 173, 191, 209, 227 and 245. A sequence encoding a CDR of the invention (e.g., CDR3) may be introduced into a repertoire of variable domains lacking the respective CDR (e.g., CDR3), using recombinant DNA technology, for example, using methodology described by Marks et al. (*Bio/Technology* (1992) 10: 779-783). In particular, consensus primers directed at or adjacent to the 5' end of the variable domain area can be used in conjunction with consensus primers to the third framework region of human H variable genes to provide a repertoire of H variable domains lacking a CDR3. The repertoire may be combined with a CDR3 of a particular antibody. Using analogous techniques, the CDR3-derived sequences may be shuffled with repertoires of H variable or L variable domains lacking a CDR3, and the shuffled complete H variable or L variable domains combined with a cognate L variable or H variable domain to make the GPNMB specific antibodies of the invention. The repertoire may then be displayed in a suitable host system such as the phage display system such as described in WO92/01047 so that suitable antigen-binding fragments can be selected.

Analogous shuffling or combinatorial techniques may be used (e.g. Stemmer, *Nature* (1994) 370: 389-391). In further embodiments, one may generate novel H variable or L variable regions carrying one or more sequences derived from the sequences disclosed herein using random mutagenesis of one or more selected H variable and/or L variable genes, such as error-prone PCR (*Proc. Nat. Acad. Sci. U.S.A.* (1992) 89: 3576-3580). Another method that may be used is to direct mutagenesis to CDRs of H variable or L variable genes (*Proc. Nat. Acad. Sci. U.S.A.* (1994) 91: 3809-3813; *J. Mol. Biol.* (1996) 263: 551-567). Similarly, one or more, or all three CDRs may be grafted into a repertoire of H variable or L variable domains, which are then screened for an antigen-binding fragment specific for GPNMB.

A portion of an immunoglobulin variable domain will comprise at least one of the CDRs substantially as set out herein and, optionally, intervening framework regions as set out herein. The portion may include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of antibodies by recombinant DNA techniques may result in the introduction of N- or C-terminal residues encoded by linkers introduced to facilitate cloning or other manipulation steps. Other manipulation steps include the introduction of linkers to join variable domains to further protein sequences including immunoglobulin heavy chain constant regions, other variable domains (for example, in the production of diabodies), or proteinaceous labels as discussed in further detail below.

Although the embodiments illustrated in the Examples comprise a "matching" pair of H variable and L variable domains, a skilled artisan will recognize that alternative embodiments may comprise antigen-binding fragments containing only a single CDR from either L variable or H variable domain. Either one of the single chain specific binding domains can be used to screen for complementary domains capable of forming a two-domain specific antigen-binding fragment capable of, for example, binding to GPNMB. The screening may be accomplished by phage display screening methods using the so-called hierarchical dual combinatorial approach disclosed in WO92/01047, in which an individual colony containing either an H or L chain clone is used to infect a complete library of clones encoding the other chain (L or H) and the resulting two-chain specific binding domain is selected in accordance with phage display techniques as described.

Anti-GPNMB antibodies described herein can be linked to another functional molecule, e.g., another peptide or protein (albumin, another antibody, etc.), toxin, radioisotope, cytotoxic or cytostatic agents. For example, the antibodies can be linked by chemical cross-linking or by recombinant methods. The antibodies may also be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their circulating half-life. Exemplary polymers and methods to attach them are also shown in U.S. Pat. Nos. 4,766,106; 4,179,337; 4,495,285, and 4,609,546.

The disclosed antibodies may also be altered to have a glycosylation pattern that differs from the native pattern. For example, one or more carbohydrate moieties can be deleted and/or one or more glycosylation sites added to the original antibody. Addition of glycosylation sites to the presently disclosed antibodies may be accomplished by altering the amino acid sequence to contain glycosylation site consensus sequences known in the art. Another means of increasing the number of carbohydrate moieties on the antibodies is by chemical or enzymatic coupling of glycosides to the amino acid residues of the antibody (WO 87/05330; *CRC Crit. Rev. Biochem.*, 22: 259-306, 1981). Removal of any carbohydrate moieties from the antibodies may be accomplished chemically or enzymatically (*Arch. Biochem. Biophys.*, 259: 52,1987; *Anal. Biochem.*, 118: 131, 1981; *Meth. Enzymol.*, 138: 350, 1987). The antibodies may also be tagged with a detectable, or functional, label. Detectable labels include radiolabels such as $^{131}I$ or $^{99}Tc$, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

The valency of the antibodies may be custom designed to affect affinity and avidity, retention time at binding sites (see e.g. *Am H. Pathol*, 2002 160:1597-1608; *J. Med. Chem.* 2002 45:2250-2259; *Br. J. Cancer* 2002 86:1401-1410; *Biomol. Eng.* 2001 18:95-108; *Int J. Cancer* 2002 100:367-374).

Multiple specificity (bifunctional) binding reagents may be designed based upon the GPNMB specific sequences of the invention (*Biomol. Eng.*2001 18:31-40). For example, a bispecific or bifunctional antibody is an artificial hybrid antibody having two different heavy/light chain pairs and two different binding sites. Bispecific antibodies can be produced by a variety of methods including fusion of hybridomas or linking of Fab' fragments (*Clin. Exp. Immunol.* 1990, 79: 315-321; *J. Immunol.* 199, 2148:1547-1553). Such bispecific antibodies can be generated comprising a specificity to GPNMB and a second specificity to a second molecule using techniques that are well known (*Immunol Methods* 1994, 4:72-81; Wright and Harris, supra.; Traunecker et al. 1992 *Int. J. Cancer* (Suppl.) 7:51-52). Bispecific antibodies prepared in this manner selectively kill cells expressing GPNMB.

Antibodies, in which CDR sequences differ only insubstantially from those set out in SEQ ID NOs: 4, 6, 8, 13, 15, 17, 22, 24, 26, 31, 33, 35, 40, 42, 44, 49, 51, 53, 58, 60, 62, 67, 69, 71, 76, 78, 80, 85, 87, 89, 94, 96, 98, 103, 105, 107, 112, 114, 116, 121, 123, 125, 130, 132, 134, 139, 141, 143, 148, 150, 152, 157, 159, 161, 166, 168, 170, 175, 177, 179, 184, 186, 188, 193, 195, 197, 202, 204, 206, 211, 213, 215, 220, 222, 224, 229, 231, 233, 238, 240, 242, 247, 249 and 251. And formulas: 254, 257, 261, 266, 271, 278, 282, 286, 255, 258, 262, 267, 272, 275, 279, 283, 287, 259, 263, 264, 268, 269, 273, 276, 280, 284, 288, are encompassed within the scope of this invention. Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody. Changes to FRs include, but are not limited to engineering certain framework residues that are important for antigen contact or for stabilizing the binding site, e.g., changing the class or subclass of the constant region, changing specific amino acid residues which might alter the effector function such as Fc receptor binding (U.S. Pat. Nos. 5,624,821; 5,648,260; Lund et al. (1991) *J. Immun.* 147: 2657-2662; Morgan et al. (1995) *Immunology* 86: 319-324), or changing the species from which the constant region is derived.

One of skill in the art will appreciate that the derivatives and modifications described above are not all-exhaustive, and that many other modifications would be obvious to a skilled artisan in light of the teachings of the present disclosure.

Nucleic Acids, Cloning and Expression Systems

The present disclosure further provides isolated nucleic acids encoding the disclosed antibodies. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The nucleic acids provided herein comprise a coding sequence for a CDR, a H variable domain, and/or a L variable domain disclosed herein.

The present disclosure also provides constructs in the form of plasmids, vectors, phagemids, transcription or expression cassettes which comprise at least one nucleic acid encoding a CDR, a H variable domain, and/or a L variable domain disclosed here.

The disclosure further provides a host cell which comprises one or more constructs as above.

Also provided are nucleic acids encoding any CDR(CDR1, CDR2, CDR3 from either the H or L variable domain), H variable or L variable domain, as well as methods of making of the encoded products. The method comprises expressing the encoded product from the encoding nucleic acid. Expression may be achieved by culturing under appropriate conditions recombinant host cells containing the nucleic acid. Following production by expression, a H variable or L variable domain, or specific binding member may be isolated and/or purified using any suitable technique, then used as appropriate.

Antigen-binding fragments, H variable and/or L variable domains and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art including cells suitable for producing antibodies (*Gene Expression Systems*, Academic Press, eds. Fernandez et al., 1999). Briefly, suitable host cells include bacteria, plant cells, mammalian cells, and yeast and baculovirus systems. Mammalian cell lines available in the art for expression of a heterologous polypeptide include Chinese hamster ovary (CHO) cells, HeLa cells, baby hamster kidney cells, NS0 mouse myeloma cells, and many others. A common bacterial host is *E. coli*. Any protein expression system compatible with the invention may be used to produce the disclosed antibodies. Suitable expression systems also include transgenic animals (*Gene Expression Systems*, Academic Press, eds. Fernandez et al., 1999).

Suitable vectors can be chosen or constructed, so that they contain appropriate regulatory sequences, including promoter sequences, terminator sequences, polyadenylation sequences, enhancer sequences, marker genes and other sequences as appropriate. Vectors may be plasmids or viral, e.g., phage, or phagemid, as appropriate (see Sambrook et al., *Molecular Cloning: A Laboratory Manual,* 2.sup.nd ed., Cold Spring Harbor Laboratory Press, 1989). Many known techniques and protocols for manipulation of nucleic acid, for example, in preparation of nucleic acid constructs, mutagenesis, sequencing, introduction of DNA into cells and gene expression, and analysis of proteins, are known in the art (*Current Protocols in Molecular Biology,* 2.sup.nd Edition, eds. Ausubel et al., John Wiley & Sons, 1992).

The invention also provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

Immunoconjugates

In another aspect, the antibodies of the invention can be used as a targeting agent for delivery of another therapeutic or a cytotoxic agent to a cell expressing GPNMB. The method includes administering an anti-GPNMB antibody coupled to a therapeutic or a cytotoxic agent or under conditions that allow binding of the antibody to GPNMB.

Anti-GPNMB antibodies are conjugated to a therapeutic agent, such as a cytotoxic compound, such that the resulting immunoconjugate exerts a cytotoxic or cytostatic effect on a GPNMB expressing cell. Particularly suitable moieties for conjugation to antibodies are chemotherapeutic agents, pro-drug converting enzymes or toxins. For example, an anti-GPNMB antibody can be conjugated to a cytotoxic agent such as a chemotherapeutic agent (see infra) or a toxin (e.g. abrin, ricin A, pseudomonas exotoxin, or diphtheria toxin). Alternatively, anti-GPNMB antibody may be conjugated to a pro-drug converting enzyme. The pro-drug converting enzyme can be recombinantly fused to the antibody or derivative thereof or chemically conjugated thereto using known methods. Examplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Any agent that exerts a therapeutic effect on GPNMB expressing cells can be used as an agent for conjugation to an anti-GPNMB antibody of the invention. Useful classes of cytotoxic agents include, for example, antitubulin agents, auristatins, DNA minor groove binders, NDA replication inhibitiors, alkylating agents (e.g., platinum complexes such as cis-plantin, mono(platinum), bis(platinum) and tri-nuclear platinum complexes and carboplatin), anthracyclines, antiboiotics, antifolates, antimetabilites, chemotherapy sensitizers, duocarmycins, etoposides, fluorinated purimidines, ionophores, lexitropsins, nitrosoureas, platinols, pre-forming compounds, purine antimetabolites, puromcins, radiation sensitizers, steroids, taxanes, topoisomerase inhibitors, vinca alkaloids, or the like.

The therapeutic agent can be a cytotoxic agent. Suitable cytotoxic agents include, for example, dolastatins (e.g. auristatin E, AFP, MMAF, MMAE), DNA minor groove binders (e.g., enediynes and lexitropsins), cuocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In a specific embodiment, the cytotoxic or cytostatic agent is auristatin E (dolastatin-10) or a derivative thereof (e.g. an ester formed between auristatin E and a keto acid). Other typical auristatin derivatives include AFP, MMAR, and MMAE. The synthesis and structure of auristatin E and its derivates are described in U.S. patent Application Publication No. 20030083263; PCT/US03/24209; PCT/US02/13435; and U.S. Pat. Nos. 6,323,315; 6,239,104; 6,034065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In a specific embodiment anti-GPNMB antibody 1.15.1 was coupled to monomethylauristatin E via intracellular protease-sensitive valine-citrulline peptide linker (vcMMAE). Methods for making the immunoconjugate can be found in Doronina S. O. et al, 2003 Nature Biotechnology 21(7):778-794.

Techniques for conjugating therapeutic agents to proteins, and in particular, antibodies are known in the art (see, e.g. Amon et al., 1985 in Monoclonal Antibodies and Cancer Therapy, Reisfeld et al. eds., Alan R. Liss, Inc., 1985; Hellstrom et al., 1987 in Controlled Drug Delivery, Robinson et al. eds., Marcel Dekker, Inc., $2^{nd}$ ed. 1987; Thorpe 1985, in Monoclonal Antibodies '84: Biological and Clinical Applications, Pinchera et al. eds., EDITOR, 1985; Monoclonal Antibodies for Cancer Detection and Therapy, Baldwin et al. eds., Academic Press 1985; and Thorpe et al., 1982, Immunol. Rev. 62:119-58).

In certain embodiments of the invention, anti-GPNMB antibodies binding to GPNMB expressing cells, are internalized and accumulate in the cell. Thereby anti-GPNMB antibody immunoconjugates accumulate in GPNMB expressing cells. Typically when the anti-GPNMB antibody immunoconjugate is internalized, the agent is preferentially active. Alternatively, anti GPNMB immunoconjugates are not internalized and the drug is effective to deplete or inhibit GPNMB expressing cells by binding to the cell membrane. The therapeutic agent can be conjugated in a manner that reduces its activity unless it is cleaved off the antibody (e.g. by hydrolysis or by a cleaving agent). In this case, the agent can be attached to the antibody or derivative thereof with a cleavable linker that is sensitive to cleavage in the intracellular environment of the target but is not substantially sensitive to the extracellular environment, such that the conjugate is cleaved from the antibody or derivative thereof when it is internalized by the GPNMB expressing cell (e.g. in the endosomal or, for example by virtue of pH sensitivity or protease sensitivity, in the lysosomal environament or in a caveolea).

A therapeutic agent of the immunoconjugate can be charged relative to the plasma membrane (e.g. polarized or net charge relative to the plasma membrane), thereby further minimizing the ability of the agent to cross the plasma membrane once internalized by a cell.

The anti-GPNMB antibody immunoconjugate can comprise a linker region between the therapeutic agent and the antibody. The linker can be cleavable under intracellular conditions, such that cleavage of the linker releases the therapeutic agent from the antibody in the intracellular environment. The linker can be, e.g. a peptidyl linker that is cleaved by an intracellular peptidase or protease enzyme, including but not limited to a lysosomal or endosomal protease. Often the peptidyl linker is at least two amino acids long or at least three amino acids long. Cleaving agnets can include cathepsins and D and plasmin, all of which are known to hydrolyze dipeptide drug derivative s resulting in the release of active drug inside target cells (see Dubowchik and Walker, 1999 Pharm. Therapuetics 83:67-123). Other linkers are described e.g. in U.S. Pat. No. 6,214,345.

Linkers can be pH-sensitive can often be hydrolizable under acidic conditions such as is found in the lysosome (see e.g. U.S. Pat. Nos. 5,122,368; 5,824,805; 5,622,929; Dubowchik and Walker, 1999 Pharm. Therapeutics 83:67-123; Neville et al., 1989 BIol. Chem. 264:14653-14661). Such linkers are relatively stable under neutral pH conditions, such as those in the blood, but are unstable at below pH 5.5 or 5.0, the pH of the lysosome. Linkers can be cleavable under reducing conditions (e.g. a disulfide linker) (see e.g., Thorpe et al., 1987 Cancer Res. 47:5924-5931; Wawrzynczak et al., In Immunnoconjugates: Antibody Conjugates in Radioimmagery and Therapy of Cancer, C. W. Vogel ed, Oxford U. Press, 1987; U.S. Pat. No. 4,880,935). The linker can be a malonate linker (Johnson et al., 1995, Anticancer Res. 15:1387-93), a maleimidobenzoly linker (lau et al., 1995, Bioorg-Med-Chem. 3(10):1299-1304) or a 3'-N-amide analog (Lau et al., 1995, Bioorg-Med-Chem. 3(10):1305-1312).

Prophylactic and Therapeutic Uses of the Present Invention

The antibodies of the invention can act as either agonists or antagonists of GPNMB, depending on the methods of their use. The antibodies can be used to prevent, diagnose, or treat medical disorders in a subject, especially in humans. Antibodies of the invention can also be used for isolating GPNMB or GPNMB-expressing cells. Furthermore, the antibodies can be used to treat a subject at risk of or susceptible to a disorder or having a disorder associated with aberrant GPNMB expression or function. Antibodies of the invention can be used to detect GPNMB in such subjects.

The present invention provides methods for treating and/or preventing a disease or disorder associated with overexpression of GPNMB and/or cell hyperproliferative disorders, particularly cancer, in a subject comprising administering an effective amount of a composition that can target cells expressing GPNMB, and inhibiting the GPNMB expression or function, and/or having therapeutic or prophylactic effects on the hyperproliferative cell disease. In one embodiment, the method of the invention comprises administering to a subject a composition comprising an immunoconjugate that comprises an antibody of the invention and a cytotoxic agent against the hyperproliferative cell disease. In another embodiment, the method of the invention comprises administering to a subject in need thereof a composition comprising a naked IgG1 antibody of the invention and one or more immunomodulators. In yet another embodiment, the method of the invention comprises administering to a subject in need thereof a composition comprising a single chain Fv antibody (anti-GPNMB) conjugated to a cytotoxic agent, or a composition comprising a bispecific antibody that have a single chain anti-GPNMB antibody component and a anti-CD3 antibody component. In a preferred embodiment, the hyperproliferative cell disease is cancer. More preferably, the cancer is melanoma, or a cancer of the CNS system, such as astrocytoma, glioblastoma, medulloblastoma, or neoplastic meningitis.

The present invention provides therapies comprising administering one of more antibodies of the invention and compositions comprising said antibodies to a subject, preferably a human subject, for preventing and/or treating a disorder characterized by or associated with aberrant expression and/or activity of GPNMB or a symptom thereof. In one embodiment, the invention provides a method of preventing or treating a disorder characterized by or associated with aberrant expression and/or activity of GPNMB or a symptom thereof, said method comprising administering to a subject in need thereof an effective amount of one or more antibodies of the invention. In certain embodiments, an effective amount of one or more immunoconjugates comprising one or more antibodies of the invention is administered to a subject in need thereof to prevent or treat a disorder characterized by or associated with aberrant expression and/or activity of GPNMB or a symptom thereof.

The invention also provides methods of preventing or treating a disorder characterized by or associated with aberrant expression and/or activity of GPNMB or a symptom thereof, said methods comprising administering to a subject in need thereof one or more of the antibodies of the invention and one or more therapies (e.g., one or more prophylactic or therapeutic agents) other than antibodies of the invention. The prophylactic or therapeutic agents of the combination therapies of the invention can be administered sequentially or concurrently. In a specific embodiment, the combination therapies of the invention comprise an effective amount of one or more antibodies of the invention and an effective amount of at least one other therapy (e.g., prophylactic or therapeutic agent) which has a different mechanism of action than said antibodies. In certain embodiments, the combination therapies of the present invention improve the prophylactic or therapeutic effect of one or more antibodies of the invention by functioning together with the antibodies to have an additive or synergistic effect. In certain embodiments, the combination therapies of the present invention reduce the side effects associated with the therapies (e.g., prophylactic or therapeutic agents).

The prophylactic or therapeutic agents of the combination therapies can be administered to a subject, preferably a human subject, in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In a specific embodiment, a pharmaceutical composition comprising one or more antibodies of the invention described herein is administered to a subject, preferably a human, to prevent and/or treat a disorder characterized by or associated with aberrant expression and/or activity of GPNMB or a symptom thereof. In accordance with the invention, pharmaceutical compositions of the invention may also comprise one or more therapies (e.g., prophylactic or therapeutic agents), other than antibodies of the invention.

The antibodies of the invention may also be used to detect the presence of GPNMB in biological samples (in diagnostic methods or use as an efficacy marker). The amount of GPNMB detected may be correlated with the expression level of GPNMB, which, in turn, is correlated with the disease, tumor type, tumor burden or stage using methods known in the art (see for example recommendations of the AAPS Ligand Binding Assay Bioanalytical Focus Group (LBABFG) *Pharm Res.* 2003 November; 20(11):1885-900). Detection methods that employ antibodies are well known in the art and include, for example, ELISA, radioimmunoassay, immunoblot, Western blot, IHC, immunofluorescence, immunoprecipitation. The antibodies may be provided in a diagnostic kit that incorporates one or more of these techniques to detect GPNMB. Such a kit may contain other components, packaging, instructions, or other material to aid the detection of the protein. In a specific embodiment, the antibodies of the invention are conjugated to a radioactive isotope, and are injected to a subject to detect cells that overexpressing GPNMB.

Where the antibodies are intended for diagnostic purposes, it may be desirable to modify them, for example, with a ligand group (such as biotin) or a detectable marker group (such as a fluorescent group, a radioisotope or an enzyme). If desired, the antibodies of the invention may be labeled using conventional techniques. Suitable detectable labels include, for example, fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. For detection, suitable binding partners include, but are not limited to, biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Antibodies of the invention can be used in screening methods to identify inhibitors of GPNMB effective as therapeutics. In such a screening assay, a first binding mixture is formed by combining GPNMB and an antibody of the invention; and the amount of binding in the first binding mixture ($M_0$) is measured. A second binding mixture is also formed by combining GPNMB, the antibody, and the compound or agent to be screened, and the amount of binding in the second binding mixture ($M_1$) is measured. A compound to be tested may be another anti-GPNMB antibody. The amounts of binding in the first and second binding mixtures are then compared, for example, by calculating the $M_1/M_0$ ratio. The compound or agent is considered to be capable of modulating a GPNMB-associated responses if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention. Compounds found to reduce the GPNMB-antibody binding by at least about 10% (i.e., $M_1/M_{0<0.9}$), preferably greater than about 30% may thus be identified and then, if desired, secondarily screened for the capacity to ameliorate a disorder in other assays or animal models as described below. The strength of the binding between GPNMB and an antibody can be measured using, for example, an enzyme-linked immunoadsorption assay (ELISA), radio-immunoassay (RIA), surface plasmon resonance-based technology (e.g., Biacore), all of which are techniques well known in the art.

The compound may then be tested in vitro as described in the Examples, infra.

Dosage and Frequency of Administration

The amount of a prophylactic or therapeutic agent or a composition of the invention which will be effective in the prevention and/or treatment of a disorder associated with or characterized by aberrant expression and/or activity of GPNMB can be determined by standard clinical methods. For example, the dosage of the composition which will be effective in the treatment and/or prevention of cancer can be determined by administering the composition to an animal model. In addition, in vitro assays may optionally be employed to help identify optimal dosage ranges. Preliminary doses as, for example, determined according to animal tests, and the scaling of dosages for human administration is performed according to art-accepted practices. Toxicity and therapeutic efficacy can be determined by standard pharmaceutical procedures in cell cultures or experimental animals. The data obtained from the cell culture assays or animal studies can be used in formulating a range of dosage for use in humans. Therapeutically effective dosages achieved in one animal model can be converted for use in another animal, including humans, using conversion factors known in the art (see, e.g., Freireich et al. (1966) *Cancer Chemother. Reports,* 50(4): 219-244).

Selection of the preferred effective dose can be determined (e.g., via clinical trials) by a skilled artisan based upon the consideration of several factors which will be known to one of ordinary skill in the art. Such factors include the disease to be treated or prevented, the symptoms involved, the patient's body mass, gender, immune status and other factors known by the skilled artisan to reflect the accuracy of administered pharmaceutical compositions. Suitable regimens can be selected by one skilled in the art by considering such factors and by following, for example, dosages reported in literature and recommended in the Physician's Desk Reference (59th ed., 2005).

The precise dose to be employed in the formulation will also depend on the route of administration, and the seriousness of the cancer, and should be decided according to the judgment of the practitioner and each patient's circumstances. Effective doses may be extrapolated from dose-response curves derived from in vitro or animal model test systems.

For other cancer therapeutic agents administered to a patient, the typical doses of various cancer therapeutics are known in the art. Given the invention, certain preferred embodiments will encompass the administration of lower dosages in combination treatment regimens than dosages recommended for the administration of single agents.

In a specific embodiment, the dosage of an antibody or an immunoconjugate comprising an antibody of the invention administered to prevent and/or treat a disorder associated with or characterized by aberrant expression and/or activity of GPNMB (e.g., cancer) in a patient is 30 mg/kg or less, 25 mg/kg or less, 20 mg/kg or less, 15 mg/kg or less, preferably 12 mg/kg or less, 11 mg/kg or less, 10 mg/kg or less, 9 mg/kg or less, 8 mg/kg or less, 7 mg/kg or less, 6 mg/kg or less, 5 mg/kg or less, 4 mg/kg or less, 3 mg/kg or less, 2 mg/kg or less, or 1 mg/kg or less of a patient's body weight. In another embodiment, the dosage of an antibody or an immunoconjugate of the invention administered to prevent and/or treat a disorder associated with or characterized by aberrant expression and/or activity of GPNMB (e.g., cancer) in a patient is a unit dose of about 0.01 mg/kg to about 20 mg/kg, about 0.1 mg/kg to about 10 mg/kg, about 0.1 mg/kg to about 8 mg/kg, about 0.1 mg/kg to about 7 mg/kg, about 0.1 mg/kg to about 6 mg/kg, about 0.1 mg/kg to about 5 mg/kg, about 0.1 mg/kg to about 4 mg/kg, preferably, about 0.1 mg/kg to about 3 mg/kg, about 0.2 mg/kg to 3 mg/kg, about 0.3 mg/kg to about 3 mg/kg, about 0.4 mg/kg to about 3 mg/kg, about 0.6 mg/kg to about 3 mg/kg, about 0.8 mg/kg to about 3 mg/kg, about 0.1 mg/kg to 2 mg/kg, about 0.1 mg/kg to 1 mg/kg. In certain embodiments, the dosage of an antibody or an immunoconjugate comprising an antibody of the invention administered to prevent and/or treat a disorder associated with or characterized by aberrant expression and/or activity of GPNMB (e.g., cancer) in a patient is a unit dose of about 0.1 mg/kg, about 0.2 mg/kg, about 0.4 mg/kg, about 0.6 mg/kg, about 0.8 mg/kg, about 1.1 mg/kg, or about 1 mg/kg.

In certain embodiments, a subject is administered one or more doses of an effective amount of one or more antibodies or immunoconjugates of the invention to prevent and/or treat a disorder associated with or characterized by aberrant expression and/or activity of GPNMB, wherein the dose of an effective amount of said antibodies, immunoconjugates, compositions, or combination therapies reduces and/or inhibits proliferation of cancerous cells by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80 to 85%, at least 85% to 90%, at least 90% to 95%, or at least 95% to 98% relative to a control such as PBS in an in vitro and/or in vivo assay well-known in the art.

In other embodiments, a subject is administered one or more doses of an effective amount of one or more antibodies or immunoconjugates of the invention to prevent and/or treat a disorder associated with or characterized by aberrant expression and/or activity of GPNMB, wherein the dose of an effective amount achieves a serum titer of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the antibodies of the invention. In yet other embodiments, a subject is administered a dose of an effective amount of one or more antibodies or immunoconjugates of the invention to achieve a serum titer of at least 0.1 µg/mL, at least 0.5 µg/mL, at least 1 µg/mL, at least, 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the antibodies and a subsequent dose of an effective amount of one or more antibodies or immunoconjugates of the invention is administered to maintain a serum titer of at least 0.1 µg/mL, at least 0.5 µg/mL, at least 1 µg/mL, at least, 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL. In accordance with these embodiments, a subject may be administered 1, 2, 3, 4, 5, 6, 7, 8, 9, 10, 11, 12 or more subsequent doses.

In a specific embodiment, the invention provides methods of preventing and/or treating a disorder associated with or characterized by aberrant expression and/or activity of GPNMB, said method comprising administering to a subject in need thereof a unit dose of at least 0.01 mg/kg, at least 0.1 mg/kg, at least 0.2 mg/kg, at least 0.4 mg/kg, at least 0.6 mg/kg, at least 0.8 mg/kg, at least 1 mg/kg, or at least 1.1 mg/kg of one or more antibodies or immunoconjugates of the invention. In another embodiment, the invention provides methods of preventing and/or treating a disorder associated with or characterized by aberrant expression and/or activity of GPNMB, said method comprising administering to a subject in need thereof a unit dose of at least 0.01 mg/kg, at least 0.1 mg/kg, at least 0.2 mg/kg, at least 0.4 mg/kg, at least 0.6 mg/kg, at least 0.8 mg/kg, at least 1 mg/kg, or at least 1.1 mg/kg of one or more antibodies or immunoconjugates of the invention once every 7 days, preferably, once every 10 days, once every 12 days, once every 14 days, once every 16 days, once every 18 days, once every three weeks, or once a month. In a preferred embodiment, an immunoconjuage of the instant invention is administered at a unit dose of about 0.1 mg/kg, about 0.2 mg/kg, about 0.4 mg/kg, about 0.6 mg/kg, about 0.8 mg/kg, about 1.1 mg/kg, or about 1 mg/kg once every 10 to 20 days with 2 to 4 cycles.

The present invention provides methods of preventing and/or treating a disorder associated with or characterized by aberrant expression and/or activity of GPNMB, said method comprising: (a) administering to a subject in need thereof one or more doses of a prophylactically or therapeutically effective amount of one or more antibodies or immunoconjugates of the invention; and (b) monitoring the plasma level/concentration of the said administered antibody or antibodies in said subject after administration of a certain number of doses of the said antibody or antibodies. Moreover, preferably, said certain number of doses is 1, 2, 3, 4, 5, 6, 7, or 8 doses of a prophylactically or therapeutically effective amount one or more antibodies or immunoconjugates of the invention.

In a specific embodiment, the invention provides a method of preventing and/or treating a disorder associated with or characterized by aberrant expression and/or activity of GPNMB, said method comprising: (a) administering to a subject in need thereof a dose of at least 0.1 mg/kg (preferably at least at least 0.2 mg/kg, at least 0.4 mg/kg, at least 0.6 mg/kg, at least 0.8 mg/kg, at least 1 mg/kg, or at least 1.1 mg/kg) of one or more antibodies or immunoconjugates of the invention; and (b) administering one or more subsequent doses to said subject when the plasma level of the antibody or antibodies administered in said subject is less than 0.1 µg/mL, preferably less than 0.25 µg/mL, less than 0.5 µg/mL, less than 0.75 µg/mL, or less than 1 µg/mL. In another embodiment, the invention provides a method of preventing and/or treating a disorder associated with or characterized by aberrant expression and/or activity of GPNMB, said method comprising: (a) administering to a subject in need thereof one or more doses of at least at least 0.1 mg/kg (preferably at least at least 0.2 mg/kg, at least 0.4 mg/kg, at least 0.6 mg/kg, at least 0.8 mg/kg, at least 1 mg/kg, or at least 1.1 mg/kg) of one or more antibodies of the invention; (b) monitoring the plasma level of the administered antibody or antibodies of the invention in said subject after the administration of a certain number of doses; and (c) administering a subsequent dose of the antibody or antibodies of the invention when the plasma level of the administered antibody or antibodies in said subject is less than 0.1 µg/mL, preferably less than 0.25 µg/mL, less than 0.5 µg/mL, less than 0.75 µg/mL, or less than 1 µg/mL. Preferably, said certain number of doses is 1, 2, 3, 4, 5, 6, 7, or 8 doses of an effective amount of one or more antibodies or immunoconjugates of the invention.

Therapies (e.g., prophylactic or therapeutic agents), other than antibodies or immunoconjugates of the invention, which have been or are currently being used to prevent and/or treat a disorder associated with or characterized by aberrant expression and/or activity of GPNMB can be administered in combination with one or more antibodies or immunoconjugates of the invention according to the methods of the invention to treat and/or prevent a disorder associated with or characterized by aberrant expression and/or activity of GPNMB. Preferably, the dosages of prophylactic or therapeutic agents used in combination therapies of the invention are lower than those which have been or are currently being used to prevent and/or treat a disorder associated with or characterized by aberrant expression and/or activity of GPNMB.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patient visit.

In certain embodiments, one or more antibodies of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

Pharmaceutical Compositions and Methods of Administration

The disclosure provides compositions comprising anti-GPNMB antibodies. Such compositions may be suitable for pharmaceutical use and administration to patients. The compositions typically comprise one or more antibodies of the present invention and a pharmaceutically acceptable excipient. The phrase "pharmaceutically acceptable excipient" includes any and all solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intraperitoneal, intramuscular, intracavity, subcutaneous or transdermal. It may also be possible to obtain compositions which may be topically or orally administered, or which may be capable of transmission across mucous membranes.

Solutions or suspensions used for intradermal or subcutaneous application typically include one or more of the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars; polyalcohols such as mannitol, sorbitol, and sodium chloride in the composition. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and/or by the use of surfactants. Prolonged absorption of the injectable compositions can be brought about by including in the composition an agent which delays absorption, for example, aluminum monostearate, and gelatin.

Oral compositions generally include an inert diluent or an edible carrier. They can be enclosed in gelatin capsules or compressed into tablets. For oral administration, the antibodies can be combined with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, detergents, bile salts, and fusidic acid derivatives. Transmucosal administration may be accomplished, for example, through the use of lozenges, nasal sprays, inhalers, or suppositories. For example, in case of antibodies that comprise the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated into ointments, salves, gels, or creams as generally known in the art. For administration by inhalation, the antibodies may be delivered in the form of an aerosol spray from pressured container or dispenser, which contains a suitable propellant, e.g., a gas such as carbon dioxide, or a nebulizer.

In certain embodiments, the presently disclosed antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antibodies can also be used as pharmaceutically acceptable carriers. These can be prepared according to methods known to those skilled in the art, for example, as described in U.S. Pat. No. 4,522,811.

It may be advantageous to formulate oral or parenteral compositions in a dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of the composition of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

For any composition used in the present invention, the therapeutically effective dose can be estimated initially from cell culture assays. Examples of suitable bioassays include DNA replication assays, clonogenic assays and other assays as, for example, described in the Examples. The data obtained from the cell culture assays and animal studies can be used in formulating a range of dosage for use in humans. A dose may be formulated in animal models to achieve a circulating plasma concentration range that includes the $IC_{50}$ (i.e., the concentration of the antibody which achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending upon the dosage form employed and the route of administration utilized.

Antibodies can be modified to become immunotoxins utilizing techniques that are well known in the art (Vitetta 1993, *Immunol Today* 14:252; U.S. Pat. No. 5,194,594). Cyotoxic immunoconjugates are known in the art and have been used as therapeutic agents. Such immunoconjugates may for example, use maytansinoids (U.S. Pat. No. 6,441,163), tubulin polymerization inhibitor, auristatin (Mohammad et al, 1999 *Int. J. Oncol* 15(2):367-72; Doronina et al, 2003 *Nature Biotechnology* 21(7): 778-784), dolastatin derivatives (Ogawa et al, 2001 *Toxicol Lett.* 121(2):97-106) 21(3)778-

784), Mylotarg® (Wyeth Laboratories, Philidelphia, Pa.); maytansinoids (DM1), taxane or mertansine (ImmunoGen Inc.).

Immunoradiopharmaceuticals utilizing anti-GPNMB antibodies may be prepared utilizing techniques that are well known in the art (Junghans et al. in *Cancer Chemotherapy and Biotherapy* 655-686 (2d edition, Chafner and Longo, eds., Lippincott Raven (1996); U.S. Pat. Nos. 4,681,581, 4,735,210, 5,101,827, 5,102,990 (RE 35,500), 5,648,471, and 5,697,902). Each of the immunotoxins and radiolabeled antibody molecules selectively kill cells expressing GPNMB. Radiolabels are known in the art and have been used for diagnostic or therapeutic radioimmuno conjugates. Examples of radiolabels include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$, $^{177}Lu$, $^{105}Rh$, Rhenium-186 Rhenium-188 Samarium-153, Copper-64, Scandium-47). For example, radionuclides which have been used in radioimmunoconjugate guided clinical diagnosis include, but are not limited to: $^{131}I$, $^{125}I$, $^{123}I$, $^{99}Tc$, $^{67}Ga$, as well as $^{111}In$. Antibodies have also been labeled with a variety of radionuclides for potential use in targeted immunotherapy (see Peirersz et al., 1987). These radionuclides include, for example, $^{188}Re$ and $^{186}Re$ as well as $^{90}Y$, and to a lesser extent $^{199}Au$ and $^{67}Cu$. I-(131) (see for example U.S. Pat. No. 5,460,785). Radiotherapeutic chelators and chelator conjugates are known in the art (U.S. Pat. Nos. 4,831,175, 5,099,069, 5,246,692, 5,286,850, and 5,124,471).

EXAMPLES

The following examples, including the experiments conducted and results achieved are provided for illustrative purposes only and are not to be construed as limiting upon the present invention.

Example 1

Immunogen

Recombinant human GPNMB (SEQ ID NO:289), specifically the extra-cellular domain (ECD) was prepared for use as the immunogen. Generally, cDNA encoding the ECD of GPNMB with a C-terminus V5-HIS tag was transfected into HEK 293 cells, expressed and purified using cation exchange chromatography with a POROS HS 50 (Applied Biosystems, Foster City, Calif.). Sample was eluted with 1M NaCl at a pH of 5.5, followed by metal affinity chromatography (Pharmacia metal chelate 5 mL). The sample was eluted against a linear gradient from 10-500 mM imidazole over 10 CV (column volumn) Dialysis occurred using 20 mM Tris/50 mM NaCl at pH 7.4 (2 L×2). The sample was then filtered through a 0.22 µm filter.

Example 2

Immunization

A preferred method for generating fully human antibodies uses XenoMouse® strains of mice which have been engineered to contain 245 kb and 190 kb-sized germline configuration fragments of the human heavy chain locus and kappa light chain locus (Green et al. 1994 *Nature Genetics* 7:13-21; Mendez et al. 1997 *Nature Genetics* 15:146-156; Green and Jakobovits, 19981 *Exp. Med.* 188:483-495; U.S. Pat. Nos. 6,162,963, 6,150,584, 6,114,598, 6,075,181, and 5,939,598.) In an alternative approach, the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal (Taylor et al., 1992, Chen et al., 1993, Tuaillon et al., 1993, Choi et al., 1993, Lonberg et al., 1994), Taylor et al., (1994), and Tuaillon et al., (1995), Fishwild et al., (1996); U.S. Pat. Nos. 5,545,807, 5,545,806, 5,625,825, 5,625,126, 5,633,425, 5,661,016, 5,770,429, 5,789,650, 5,814,318, 5,877,397, 5,874,299, 6,255,458, 5,591,669, 6,023,010, 5,612,205, 5,721,367, 5,789,215, 5,643,763, 5,981,175). It is understood that the λκ XenoMouse® may be used to generate anti-GPNMB antibodies utilizing lambda V regions. Such antibodies are within the scope of the invention.

Immunization

GPNMB-V5His immunogen (as prepared in Example 1) was used as an antigen. Monoclonal antibodies against GPNMB were developed by sequentially immunizing XenoMouse® mice (XenoMouse® XMG2 strain), Abgenix, Inc. Fremont, Calif. XenoMouse® animals were immunized via footpad route for all injections. The total volume of each injection was 50 µl per mouse, 25 µl per footpad.

For cohort 1 (10 XMG2 mice), the initial immunization was with 10 µg of GPNMB-V5His admixed 1:1 (v/v) with 100 µg alum gel ("Adju-Phos": aluminum phosphate gel adjuvant, Superfos BIOSECTOR™ a/s, distributed by E. M. Sergent Pulp and Chemical Co., Clifton, N.J., cat. # 1452-250) per mouse. The subsequent five boosts were made with 5 µg of GPNMB-V5H is admixed 1:1 (v/v) with 100 µg alum gel in pyrogen-free D-PBS. The seventh boost consisted of 5 µg of GPNMB-V5His admixed 1:1 (v/v) with TITERMAX GOLD® (Sigma; cat. # T2684). The eighth injection consisted of 5 µg of GPNMB-V5His admixed 1:1 v/v with 100 µg alum gel. A final boost was made with 5 µg GPNMB-V5His in pyrogen-free DPBS, without adjuvant. The XenoMouse® mice were immunized on days 0, 3, 6, 10, 14, 17, 23, and 27 for this protocol and fusions were performed on day 31. The bleed was made through Retro-Orbital Bleed procedure on day 21 after the sixth boost.

For cohort 2 (10 XMG2 mice), the initial immunization was with 10 µg of GPNMB-V5His admixed 1:1 (v/v) with 100 µg alum gel per mouse. The subsequent two boosts were made with 5 µg of GPNMB-V5His admixed 1:1 (v/v) with 100 µg alum gel in pyrogen-free D-PBS. The fourth boost consisted of 5 µg of GPNMB-V5His admixed 1:1 (v/v) with TITERMAX GOLD® (Sigma; cat. # T2684). The following fifth to seventh injection consisted of 5 µg of GPNMB-V5His admixed 1:1 v/v with 100 µg alum gel. The eighth injection and final boost was made with 5 µg GPNMB-V5His in pyrogen-free DPBS, without adjuvant. The XenoMouse® mice were immunized on days 0, 3, 7, 11, 14, 17, 22, 25 and 74. for this protocol and fusions were performed on day 78. The bleeds was made through Retro-Orbital Bleed procedure on day 21 after the sixth boost.

The footpad injection was performed by the following protocol using only the ventral surface of both hind limb paws. A solution was injected beneath the skin without piercing the muscle tissue by using an insulin ½ mL syringe with attached 28 or 30 gauge×½" needle. The mouse to be injected was grasped by the loose fur along its neck and back so that it was immobilized and was turned over so the ventral side was accessible. The hind limb of the mouse was grasped and the needle was inserted (bevel side up) at the ankle, threading just under the skin until the needle tip reached the paw. The needle was inserted along the outside length of the hind foot carefully, to avoid the vein located towards the inner side of the foot. Once the tip of the needle reached the paw, the solution was injected slowly until resistance was felt or the designated volume had been dispensed. The needle was then withdrawn and the second hind foot injected in the same manner.

The following Table 4 provides the immunization schedule for the 2 groups of mice.

TABLE 4

Immunization Schedule of GPNMB Antigen: GPNMB-soluble at 043 mg/mL

| Target | Group No. | Mode of Immunization | No. of mice | Antigen | 1st injection | 2nd boost |
|---|---|---|---|---|---|---|
| GPNMB | 1 | Footpad | 10 | GPNMB-soluble | 10 ug/mouse Alum Gel Day 0 | 5 ug/mouse Alum Gel Day 3 |

| Target | 3rd boost | 4th boost | 5th boost | 6th boost | Bleed | 7th boost | 8th boost | Fusion |
|---|---|---|---|---|---|---|---|---|
| GPNMB | 5 ug/mouse Alum Gel Day 6 | 5 ug/mouse Alum Gel Day 10 | 5 ug/mouse Alum Gel Day 14 | 5 ug/mouse Alum Gel Day 17 | Day 21 | 5 ug/mouse Titermax Gold Day 23 | 10 ug/mouse D-PBS Day 27 | Day 31 |

| Target | group# | Mode of Immunization | # mice | Antigen | 1st injection | 2nd boost |
|---|---|---|---|---|---|---|
| GPNMB | 2 | Footpad | 10 | GPNMB-soluble | 10 ug/mouse Alum Gel Day 0 | 5 ug/mouse Alum Gel Day 3 |

| Target | 3rd boost | 4th boost | 5th boost | 6th boost | Bleed | 7th boost | 8th boost | 9th boost | Fusion |
|---|---|---|---|---|---|---|---|---|---|
| GPNMB | 5 ug/mouse Alum Gel Day 7 | 5 ug/mouse Titermax Gold Day 11 | 5 ug/mouse Alum Gel Day 14 | 5 ug/mouse Alum Gel Day 17 | Day 21 | 5 ug/mouse Alum Gel Day 22 | 10 ug/mouse D-PBS Day 25 | 10 ug/mouse D-PBS Day 100 | Day 104 |

Selection of Animals for Harvest by Titer

Anti-GPNMB antibody titers in the serum from immunized XenoMouse® mice were determined by ELISA. Briefly, three sets of ELISAs were set up. GPNMB (+NMB) at 1 μg/mL, GPNMB(−NMB) at 1 μg/mL, and NMB at 1 μg/mL were coated onto Costar Labcoat Universal Binding Polystyrene 96-well plates (Corning, Acton, Mass.) overnight at 4° C. in Antigen Coating Buffer (0.1 M Carbonate Buffer, pH 9.6 NaHCO$_3$ (MW 84) 8.4 g/L). The next day, the plates were washed three times with washing buffer (0.05% Tween 20 in 1×PBS) using a Biotek plate washer. The plates were then blocked with 200 ul/well blocking buffer (0.5% BSA, 0.1% Tween 20, 0.01% Thimerosal in 1×PBS) and incubated at room temperature for 1 h. After the one-hour blocking, the plates were washed three times with washing buffer using a Biotek plate washer. Sera from either GPNMB immunized XenoMouse® mice or naïve XenoMouse® animals were titrated in 0.5% BSA/PBS buffer at 1:3 dilutions in duplicate from a 1:100 initial dilution. The last well was left blank. These plates were incubated at room temperature for 2 h, and the plates were then washed three times with washing buffer using a Biotek plate washer. A goat anti-human IgG Fc-specific horseradish peroxidase (HRP, Pierce, Rockford, Ill.) conjugated antibody was added at a final concentration of 1 μg/mL and incubated for 1 hour at room temperature. The plates were washed three times with washing buffer using a Biotek plate washer. After washing, the plates were developed with the addition of TMB chromogenic substrate (BioFx BSTP-0100-01) for 10-20 min or until negative control wells start to show color. Then the ELISA was stopped by the addition of Stop Solution (650 nM Stop reagent for TMB (BioFx BSTP-0100-01), reconstituted with 100 mL H$_2$O per bottle). The specific titer of each XenoMouse® animal was determined from the optical density at 650 nm and is shown in Tables 2 and 3 below. The titer value is the reciprocal of the greatest dilution of sera with an OD reading two-fold that of background. Therefore, the higher the number, the greater was the humoral immune response to GPNMB. The results are provided in Table 5.

TABLE 5

XENOMOUSE ® Anti-GPNMB Serum titers

Group 1 mice, fusion on Day 21 after 6 inj.

| Mouse ID | Reactivity to GPNMB Titers via hIgG | Reactivity to GPNMB (+GPNMB) Titers via hIgG | Reactivity to GPNMB Titers via hIgG |
|---|---|---|---|
| 1-1 | 20,000 | 5,000 | 225 |
| 1-2 | 5,000 | 800 | 200 |
| 1-3 | 35,000 | 7,500 | 225 |
| 1-4 | 75,000 | 22,000 | 225 |
| 1-5 | 8,000 | 2,000 | 325 |
| 1-6 | 6,000 | 800 | 1800 |
| 1-7 | 22,000 | 7,500 | 225 |
| 1-8 | 6,000 | 2,000 | 200 |
| 1-9 | 7,000 | 2,000 | 75 |
| 1-10 | 22,000 | 7,500 | 200 |
| 1-NC1 | <100 | <100 | <100 |
| 1-NC2 | <100 | <100 | <100 |

Group 2 mice, bled on Day 21 after 6 inj.

| Mouse ID | Reactivity to GPNMB (−GPNMB) Titers via hIgG | Reactivity to GPNMB (+GPNMB) Titers via hIgG | Reactivity to GPNMB Titers via hIgG |
|---|---|---|---|
| 2-1 | 100,000 | 2,600 | 50 |
| 2-2 | 8,000 | 2,600 | 50 |
| 2-3 | 15,000 | 4,000 | 50 |
| 2-4 | 7,000 | 2,200 | 75 |
| 2-5 | 22,000 | 6,500 | 250 |
| 2-6 | 60,000 | 22,000 | 60 |
| 2-7 | 19,000 | 7,000 | 50 |
| 2-8 | 5,000 | 1,200 | 50 |
| 2-9 | 16,000 | 3,500 | 110 |
| 2-10 | 12,000 | 5,000 | 110 |
| 2-NC1 | <100 | <100 | <100 |
| 2-NC2 | <100 | <100 | <100 |

Pooled anti-GPNMB sera from immunized animals was also evaluated by FACS for reactivity to UACC-62, SF539, SKMELS, U87MG, and LOX1MVI cell lines. Pooled sera were tested at 1:10, 1:100 and 1:500 compared to Anti-IL13 serum (control) and prebleeds diluted at 1:10, 1:100 (control).

Example 3

Antibodies

Hybridoma cell lines were generated from immunized mice demonstrated to have anti-GPNMB titers using standard techniques (see Mendez et al, 1997, Nat. Genet. 15:146-156).

Immunized mice were sacrificed by cervical dislocation, and the lymph nodes were harvested and pooled from each cohort. The lymphoid cells were dissociated by grinding in DMEM to release the cells from the tissues, and the cells were suspended in DMEM. The cells were counted, and 0.9 mL DMEM per 100 million lymphocytes was added to the cell pellet to resuspend the cells gently but completely. Using 100 µl of CD90+ magnetic beads per 100 million cells, the cells were labeled by incubating the cells with the magnetic beads at 4° C. for 15 minutes. The magnetically-labeled cell suspension containing up to $10^8$ positive cells (or up to $2 \times 10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3X63Ag8.653 cells purchased from ATCC, cat.# CRL 1580 (Kearney et al, J. Immunol. 123, 1979, 1548-1550) at a ratio of 1:1. The cell mixture was gently pelleted by centrifugation at 800 g. After complete removal of the supernatant, the cells were treated with 2-4 mL of Pronase solution (CalBiochem, cat. # S3702; 0.5 mg/mL in PBS) for no more than 2 minutes. Then 3-5 mL of FBS was added to stop the enzyme activity and the suspension was adjusted to 40 mL total volume using electro cell fusion solution, ECFS (0.3 M Sucrose, Sigma, Cat# S7903, 0.1 mM Magnesium Acetate, Sigma, Cat# M2545, 0.1 mM Calcium Acetate, Sigma, Cat# C4705). The supernatant was removed after centrifugation and the cells were resuspended in 40 mL ECFS. This wash step was repeated and the cells again were resuspended in ECFS to a concentration of $2 \times 10^6$ cells/mL.

Electro-cell fusion was performed using a fusion generator, model ECM2001, Genetronic, Inc., San Diego, Calif. The fusion chamber size used was 2.0 mL, using the Abgenix, Inc. optimum instrument settings to do ECF.

After ECF, the cell suspensions were carefully removed from the fusion chamber under sterile conditions and transferred into a sterile tube containing the same volume of Hybridoma Culture Medium (DMEM (JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim)). The cells were incubated for 15-30 minutes at 37° C., and then centrifuged at 400 g (1000 rpm [but in what rotor? Otherwise, leave out the rpm]) for five minutes. The cells were gently resuspended in a small volume of Hybridoma Selection Medium (Hybridoma Culture Medium supplemented with 0.5×HA (Sigma, cat. # A9666)), and the volume was adjusted appropriately with more Hybridoma Selection Medium, based on a final plating of $5 \times 10^6$ B cells total per 96-well plate and 200 µL per well. The cells were mixed gently and pipetted into 96-well plates and allowed to grow. On day 7 or 10, one-half the medium was removed, and the cells were re-fed with Hybridoma Selection Medium.

After 14 days of culture, hybridoma supernatants were screened for GPNMB specific monoclonal antibodies. In the Primary screen, the ELISA plates (Fisher, Cat. No. 12-565-136) were coated with 50 µL/well of GPNMB (1 µg/mL) in Coating Buffer (0.1 M Carbonate Buffer, pH 9.6, NaHCO$_3$ 8.4 g/L), then incubated at 4° C. overnight. After incubation, the plates were washed with Washing Buffer (0.05% Tween 20 in PBS) three times. 200 µL/well Blocking Buffer (0.5% BSA, 0.1% Tween 20, 0.01% Thimerosal in 1×PBS) were added and the plates were incubated at room temperature for 1 h. After incubation, the plates were washed with Washing Buffer three times. Aliquots (50 µL/well) of hybridoma supernatants and positive and negative controls were added, and the plates were incubated at room temperature for 2 h. The positive control used throughout was serum from the relevant GPNMB immunized XenoMouse® mouse and the negative control was serum from the KLH-immunized relevant strain of XenoMouse® mouse. After incubation, the plates were washed three times with Washing Buffer. 100 µL/well of detection antibody goat anti-huIgGfc-HRP (Caltag, Cat. No. H10507, using concentration was 1:2000 dilution) was added and the plates were incubated at room temperature for 1 hour. After incubation, the plates were washed three times with Washing Buffer. 100 µl/well of TMB (BioFX Lab. Cat. No. TMSK-0100-01) was added, and the plates were allowed to develop for about 10 minutes (until negative control wells barely started to show color). 50 µl/well stop solution (TMB Stop Solution (BioFX Lab. Cat. No. STPR-0100-01) was then added and the plates were read on an ELISA plate reader at a wavelength of 450 nm.

The old culture supernatants from the positive hybridoma cells growth wells based on primary screen were removed completely and the IL-1b positive hybridoma cells were suspended with fresh hybridoma culture medium and were transferred to 24-well plates. After 2 days in culture, these supernatants were ready for a secondary confirmation screen. In the secondary confirmation screen, the positives in the first screening were screened in GPNMB binding ELISA described as above, and two sets of detective system for the secondary confirmation ELISA, one set for hIgG detection, one set for human Ig kappa light chain detection (goat anti-hIg kappa-HRP, Southern Biotechnology, Cat. No. 2060-05) in order to demonstrate fully human composition for both heavy and light chains. The two sets of ELISA procedures were identical to the descriptions above except the three different detection antibodies were used separately. All positive hits from the secondary confirmation ELISA assay were counter screened for binding to immunogen by ELISA in order to exclude those that cross-react with IL-1a. The ELISA plates (Fisher, Cat. No. 12-565-136) were coated with 50 µL/well of irrelevant VSHis-fusion protein, 1 ug/mL in Coating Buffer (0.1 M Carbonate Buffer, pH 9.6, NaHCO$_3$ 8.4 g/L), then incubated at 4° C. overnight. The remaining procedures were identical to the descriptions above. There are 33 fully human GPNMB specific monoclonal antibodies that were generated.

Hybridoma supernatants were screened for binding to GPNMB by ELISA as described above in Example 2. Results are shown in Table 6.

TABLE 6

Hybridoma anti-GPNMB activity.

|  | 3 µg/mL Avg OD | 1 µg/mL Avg OD | 333 ng/mL Avg OD | 111 ng/mL Avg OD | 37 ng/mL Avg OD | 12.3 ng/mL Avg OD |
| --- | --- | --- | --- | --- | --- | --- |
| 1.2.2 | 0.763 | 0.499 | 0.356 | 0.199 | 0.094 | 0.049 |
| 1.7.3 | 1.003 | 0.871 | 0.760 | 0.451 | 0.239 | 0.094 |
| 1.15.1 | 1.159 | 1.051 | 0.902 | 0.701 | 0.381 | 0.168 |

TABLE 6-continued

Hybridoma anti-GPNMB activity.

| | 3 µg/mL Avg OD | 1 µg/mL Avg OD | 333 ng/mL Avg OD | 111 ng/mL Avg OD | 37 ng/mL Avg OD | 12.3 ng/mL Avg OD |
|---|---|---|---|---|---|---|
| 1.16.2 | 0.036 | 0.015 | 0.010 | 0.008 | 0.008 | 0.007 |
| 2-3 | 1.282 | 1.204 | 0.963 | 0.713 | 0.359 | 0.179 |
| 2-6 | 1.254 | 1.295 | 1.092 | 0.875 | 0.443 | 0.183 |
| 2-7 | 0.827 | 0.719 | 0.680 | 0.494 | 0.308 | 0.156 |
| 2-8 | 0.921 | 0.635 | 0.229 | 0.109 | 0.056 | 0.028 |
| 2-10 | 1.095 | 1.066 | 0.849 | 0.583 | 0.272 | 0.132 |
| 2-15 | 0.601 | 0.568 | 0.578 | 0.395 | 0.246 | 0.127 |
| 2-16 | 0.359 | 0.173 | 0.068 | 0.032 | 0.017 | 0.011 |
| 2-17 | 0.053 | 0.019 | 0.010 | 0.009 | 0.008 | 0.011 |
| 2-22 | 0.714 | 0.707 | 0.538 | 0.355 | 0.171 | 0.068 |
| 2-24 | 0.060 | 0.042 | 0.028 | 0.023 | 0.016 | 0.017 |
| Isotype control | 0.009 | 0.008 | 0.009 | 0.009 | 0.009 | 0.011 |
| Irrelevant Antibody | 0.009 | 0.008 | 0.012 | 0.013 | | |
| Secondary Ab control | 0.011 | | | | | |
| Anti-V5 Ab control | 3.066 | | | | | |

Certain Hybridoma cell supernatants (29) were analyzed for binding to GPNMB by BiaCore® 2000 biosensor equipped with a research-grade CMS sensor chip. A 1:25 dilution of cell supernatant was passed over a protein A surface for 5 min followed by washing the surface for 10 mins. Subsequently, GPNMB was injected for 90 sec. over the surface at a concentration of 880 nM followed by dissociation. Double-referenced binding data were obtained by subtracting the signal from a control flow cell and subtracting the baseline drift of a buffer injected just prior to the antigen injection. GPNMB binding ddata for each mAb was normalized for the amount of mAb captured on each surface. Normalized, drift corrected responses were also measured. The sensorgrams were fit to a simple 1:1 kinetic model. The results are shown in Table 7. Sixteen of the cell supernatants contained mAb that significantly bound to GPNMB and three Mabs, 15.1, 15.2, and 15.3 showed strong binding to GPNMB.

TABLE 7

| Sample | Kd (nM) | ka (M−1 s−1) | kd (s−1) | Expression Level |
|---|---|---|---|---|
| 15.1 | 52 | 16524 | 8.55E−04 | medium |
| 15.3 | 59 | 13417 | 7.97E−04 | medium |
| 15.2 | 61 | 12635 | 7.70E−04 | high |
| 2.2 | 96 | 9257 | 8.90E−04 | medium |
| 10.2 | 118 | 3955 | 4.66E−04 | low |
| 7.3 | 121 | 9648 | 1.17E−03 | medium |
| 7.1 | 122 | 11842 | 1.44E−03 | medium |
| 7.2 | 141 | 9356 | 1.32E−03 | high |
| 10.3 | 147 | 3626 | 5.32E−04 | low |
| 10.1 | 209 | 4235 | 8.85E−04 | low |
| 8.2 | 242 | 7555 | 1.83E−03 | medium |
| 8.3 | 264 | 6551 | 1.73E−03 | low |
| 8.1 | 329 | 6830 | 2.25E−03 | medium |
| 12.3 | 407 | 1549 | 6.31E−04 | medium |
| 12.2 | 435 | 1280 | 5.57E−04 | medium |
| 12.1 | 630 | 1587 | 1.00E−03 | low |
| 1.1 | >1000 | <1500 | nd | high |
| 1.2 | >1000 | <1500 | nd | high |
| 1.3 | >1000 | <1500 | nd | medium |
| 2.1 | >1000 | <1500 | nd | medium |
| 5.1 | >1000 | <1500 | nd | medium |
| 5.2 | >1000 | <1500 | nd | medium |
| 5.3 | >1000 | <1500 | nd | medium |
| 9.1 | >1000 | <1500 | nd | medium |
| 9.2 | >1000 | <1500 | nd | low |
| 9.3 | >1000 | <1500 | nd | low |
| 11.1 | >1000 | <1500 | nd | low |
| 11.2 | >1000 | <1500 | nd | low |
| 11.3 | >1000 | <1500 | nd | low |

Example 4

Binding of Antibodies

Certain antibodies, described herein were binned in accordance with the protocol described in U.S. Patent Application Publication No. 20030157730. MxhIgG conjugated beads are prepared for coupling to primary antibody. The volume of supernatant needed is calculated using the following formula: (n+10)×50 µL (where n=total number of samples on plate). Where the concentration is known, 0.5 µg/mL is used. Bead stock is gently vortexed, then diluted in supernatant to a concentration of 2500 of each bead per well or 0.5×10⁵/mL and incubated on a shaker in the dark at RT overnight, or 2 hours if at a known concentration of 0.5µ/mL. Following aspiration, 50 µL of each bead is added to each well of filter plate, then washed once by adding 100 µL/well wash buffer and aspirating. Antigen and controls are added to filter plate 50 µL/well then covered and allowed to incubate in the dark for 1 hour on shaker. Following a wash step, a secondary unknown antibody is added at 50 µL/well using the same dilution (or concentration if known) as is used for the primary antibody. The plates are then incubated in the dark for 2 hours at RT on shaker followed by a wash step. Next, 50 µL/well biotinylated mxhIgG diluted 1:500 is added and allowed to incubate in the dark for 1 hour on shaker at RT. Following a wash step, 50 µL/well Streptavidin-PE is added at 1:1000 and allowed to incubate in the dark for 15 minutes on shaker at RT. Following a wash step, each well is resuspended in 80 µL blocking buffer and read using Luminex Results show that the monoclonal antibodies belong to distinct bins. Competitive binding by antibodies from different bins supports antibody specificity for similar or adjacent epitopes. Non competitive binding supports antibody specificity for unique epitopes.

Three bins were created to further test the binding of six anti-GPNMB antibodies. Bin 1 included GPNMB antibodies (1.2.1), (1.10.1), and (2.22.1). Bin 2 included GPNMB antibodies (2.3.1) and (1.15.1), and Bin 3 included GPNMB antibody (2.10.1). The results of the binning assays are provided below in Tables 8 and 9.

Tissue sections were blocked in blocking buffer (5% BSA (Sigma), 1% goat serum (Jackson Immunolabs, West Grove, Pa.) in PBS) for 1 hour. Primary and secondary antibodies were precomplexed in 5% BSA and 1% goat serum in PBS for 1 hour at 37° C. at a molar ratio of approximately 10:1 of anti-GPNMB or control IgG to secondary biotinylated goat

TABLE 8

|      | BB  | 1.1 | 1.2 | 1.3 | 1.5 | 1.7 | 1.8 | 1.9 | 1.11 | 1.12 | 1.13 | 1.15 | xV5 |
|------|-----|-----|-----|-----|-----|-----|-----|-----|------|------|------|------|-----|
| BB   | 0   | 16  | 58  | 24  | 6   | 25  | 14  | 9   | 8    | 9    | 7    | 15   | 32  |
| 1.1  | −16 | 0   | 57  | 16  | −29 | 34  | 9   | −35 | −9   | −7   | −24  | 35   | 28  |
| 1.2  | −42 | −16 | 0   | −60 | −89 | −49 | −81 | −75 | −73  | −65  | −81  | −43  | 45  |
| 1.3  | −11 | −33 | 8   | 0   | −75 | −40 | −49 | 171 | −29  | −33  | −67  | −73  | −15 |
| 1.5  | 25  | 35  | 64  | 60  | 0   | 20  | 10  | 24  | 17   | 27   | 12   | −8   | 61  |
| 1.7  | −1  | 76  | 65  | 20  | −8  | 0   | −8  | 4   | 4    | 6    | −3   | −3   | 95  |
| 1.8  | −7  | 29  | 45  | 35  | −3  | −7  | 0   | 4   | −1   | 0    | −6   | 3    | 52  |
| 1.9  | −5  | 18  | 47  | −7  | −10 | 3   | 4   | 0   | 4    | 5    | −5   | −1   | 17  |
| 1.11 | 18  | 40  | 60  | 29  | −11 | 1   | 15  | 16  | 0    | 8    | 5    | −23  | 48  |
| 1.12 | −10 | 26  | 43  | 27  | −5  | 3   | −12 | −4  | −12  | 0    | −9   | −13  | 57  |
| 1.13 | 1   | 30  | 40  | 27  | 2   | 9   | 2   | 10  | 11   | 17   | 0    | −13  | 59  |
| 1.15 | −19 | 91  | 79  | 71  | 15  | 21  | 8   | 12  | 10   | 15   | 13   | 0    | 89  |
| xV5  | 41  | 134 | 239 | 46  | 5   | 443 | 230 | −1  | 70   | 257  | 24   | 535  | 0   |

|   | I   | II  | III | IV         | V   | VI                 | VII | VIII | IX  |
|---|-----|-----|-----|------------|-----|--------------------|-----|------|-----|
|   | 1.1 | 1.2 | 1.3 | 1.5<br>1.13| 1.7 | 1.8<br>1.11<br>1.12| 1.9 | 1.15 | xV5 |

TABLE 9

|      | 1.1 | 1.2 | 1.3 | 1.5  | 1.7 | 1.8 | 1.9 | 1.11 | 1.12 | 1.13 | 1.15 | xV5 | BB  |
|------|-----|-----|-----|------|-----|-----|-----|------|------|------|------|-----|-----|
| 1.1  | 0   | 72  | 39  | −36  | 49  | 8   | −14 | −3   | 18   | −14  | 35   | 28  | −2  |
| 1.2  | 10  | 0   | −60 | −103 | −46 | −64 | −76 | −71  | −69  | −83  | −74  | 44  | −46 |
| 1.3  | −49 | −9  | 0   | −111 | −88 | −78 | 281 | −66  | −57  | −93  | −115 | −89 | −33 |
| 1.5  | 61  | 106 | 77  | 0    | 13  | 28  | 17  | 20   | 40   | 2    | −3   | 87  | 19  |
| 1.7  | 94  | 77  | 51  | −25  | 0   | −9  | −3  | 12   | 4    | −4   | −17  | 96  | 17  |
| 1.8  | 42  | 71  | 74  | −24  | 2   | 0   | −9  | 1    | −1   | −12  | −5   | 61  | 4   |
| 1.9  | 14  | 74  | 28  | −24  | 6   | 4   | 0   | 3    | 5    | −13  | 8    | 16  | −17 |
| 1.11 | 59  | 66  | 77  | −20  | 3   | −5  | 13  | 0    | 11   | −9   | −5   | 92  | 21  |
| 1.12 | 84  | 67  | 61  | −36  | −12 | −8  | −6  | −4   | 0    | −16  | −34  | 95  | 12  |
| 1.13 | 74  | 93  | 49  | −12  | 22  | 12  | 23  | 21   | 19   | 0    | 20   | 98  | 55  |
| 1.15 | 127 | 90  | 51  | −9   | 17  | 12  | 19  | 19   | 21   | 5    | 0    | 125 | 59  |
| xV5  | 189 | 330 | 22  | 14   | 611 | 376 | −17 | 113  | 445  | 44   | 750  | 0   | 100 |
| BB   | 25  | 73  | 65  | 3    | 34  | 23  | 14  | 19   | 22   | 13   | 39   | 44  | 0   |

|               | I   | II  | III | IV  | V                         | VI  | VII  | VIII |
|---------------|-----|-----|-----|-----|---------------------------|-----|------|------|
| Cut-off = 100 | 1.1 | 1.2 | 1.3 | 1.5 | 1.7<br>1.8<br>1.11<br>1.12<br>1.13 | 1.9 | 1.15 | xV5  |

|              | I   | II  | III | IV          | V   | VI                 | VII | VIII | IX  |
|--------------|-----|-----|-----|-------------|-----|--------------------|-----|------|-----|
| Cut-off = 90 | 1.1 | 1.2 | 1.3 | 1.5<br>1.13 | 1.7 | 1.8<br>1.11<br>1.12| 1.9 | 1.15 | xV5 |

Example 5

GPNMB Immunohistochemistry (IHC) Analysis

Anti-GPNMB monoclonal antibodies were evaluated for reactivity with frozen and fixed tissue specimens. Tissue sections (5 μm) were cut from formalin fixed and paraffin embedded tissue samples and were rehydrated through incubations in xylene and a graded ethanol series terminating in PBS. Endogenous peroxidase activity was quenched in a 3% solution of hydrogen peroxide in methanol.

anti-human IgG (Jackson Immunolabs). Complexes were blocked with a 1:2000 dilution of human serum and incubated again for 1 hour at 37° C. Tissue sections were incubated with anti-GPNMB antibody or isotype control antibody complexes diluted in blocking buffer for 1 hour. Sections were washed in 3 changes of PBS for 5 to 10 minutes each and incubated with a 1:200 dilution of streptavidin conjugated horseradish peroxidase (Jackson Immunolabs) in blocking buffer for 30 minutes and then washed as before. Antibody was detected using DAB reagent (Vector labs). Sections were counterstained in hematoxylin (Fisher Scientific) and dehydrated through alcohol and xylene and coverslipped with permount (Fisher Scientific).

Anti-GPNMB Mabs 2.22.1 and 2.22.2 were used to stain normal and tumor human tissue microarrays (IMPATH, Los Angeles, Calif.). Positive staining was seen in lung, ovarian, renal, esophagus, and head & neck carcinomas, squamous cell carcinoma, melanomas and normal skin specimens. Melanoma and lung carcinomas showed the highest staining intensities with subcellular staining located in the membrane and cytoplasm. Anti-GPNMB Mab 2.10.2 also stained primary melanoma.

Anti-GPNMB antibody staining of melanoma tissue microarray showed a large proportion of melanoma cases to be positively stained as shown in Tables 10 and 11.

TABLE 10 anti-GPNMB Mab Melanoma Staining Intensity

| Staining Intensity* | # of Samples | % |
|---|---|---|
| 0 | 10 | 17 |
| 1 | 1 | 2 |
| 1-2 | 2 | 3 |
| 1-3 | 11 | 19 |
| 2 | 9 | 15 |
| 2-3 | 17 | 29 |
| 3 | 9 | 15 |
| Total | n = 59 | 100 |

On a scale of 0 (no staining) to 3 (strong staining)

TABLE 11 anti-GPNMB Mab Staining Frequency

| % Tumor Reactivity* | # Samples | % |
|---|---|---|
| 0-24 | 18 | 31 |
| 25-49 | 6 | 10 |
| 50-74 | 7 | 12 |
| 75-100 | 28 | 47 |
|  | n = 59 | 100% |

*% tumor cells exhibiting positive staining

Anti-GPNMB antibody stained 10 of 14 lung squamous cell carcinoma (SCC) samples in a general oncology tissue microarray and 24 of 60 in a SCC specific array were positive.

Example 6

FACS analysis of Anti-GPNMB Antibody Binding to Melanoma Cell Lines

The specificity of anti-GPNMB antibodies to cell membrane-bound GPNMB protein expressed by melanoma cancer cell line, UACC-62 was analyzed by FACS analysis. A renal cancer cell line, TK10, which does not express GPNMB antigen was used as a negative control. Isotype matched antibody pK16.3 was used as a negative control. Cells were washed twice with PBS (Ca and Mg free), incubated with Versene at 37° C. until cells detached, counted and aliquoted at 1 million cells per assay tube. Cells were then washed twice and resuspended in ice-cold FACS buffer (0.01M HEPES, 0.15M NaCl, 0.1% NaN$_3$ and 4% FBS). Primary antibody at 1 µg/mL was added to the cells. Cells were incubated on ice for 30 min, washed 2-3 times and resuspended in 1 mL of ice-cold FACS buffer. R-PE-conjugated goat anti-human antibody (Jackson ImmunoResearch Laboratory) at 1:100 dilution was added and cells were incubated on ice for 30 min. After washing 3 times with 1 mL of ice-cold FACS buffer, cells were fixed with 0.5-1 mL of 1% formaldehyde in PBS and analyzed by flow cytometry.

Results expressed as Geo Mean Ratios are summarized in Table 12 and show UACC-62 cells but not TK10 cells highly express CR011 protein on the cell surface which was detected by 2.10.2; 2.22.1 and 1.15.1 antibodies.

TABLE 12

Geo Mean Ratio of anti-GPNMB Staining (relative to pK16)

| Antibody | UACC-62 Cells | TK10 Cells |
|---|---|---|
| CR011.2.10.2 | 2.60 | 1.10 |
| CR011.2.22.1 | 4.46 | 1.10 |
| CR011.1.2.2 | 1.24 | 0.98 |
| CR011.1.15.1 | 7.89 | 0.96 |
| CR011.2.6.2 | 1.90 | 1.70 |

To examine the relative GPNMB antigen expression among melanoma cell lines, MAb 1.15.1 antibody was used to survey a panel of 15 melanoma cell lines by FACS analysis. As shown in Table 13, 80% (12/15) of cell lines showed GPNMB antigen expression. Cell line SK-MeI-2 demonstrated the highest Geo Mean ratio among the cell lines tested.

TABLE 13

Geo Mean Ratio of anti GPNMB Staining of Melanoma Cell Lines

| Cell Line | Geo Mean Ratio (relative to isotype) |
|---|---|
| SK-Mel 2 | 16.5 |
| M14 | 16.1 |
| MEWO | 14.1 |
| WM-266-4 | 13.6 |
| HEMNLP | 10.2 |
| G361 | 8 |
| HT144 | 7.4 |
| UACC-257 | 7 |
| RPMI-7951 | 6 |
| SK-Mel 5 | 5.7 |
| UACC-62 | 5.5 |
| A2058 | 4.1 |
| SK-Mel 24 | 1.9 |
| WM115 | 1.3 |
| LOXIMVI | 1 |

Example 7

FACS Analysis of Anti-GPNMB MAb Binding to Lymphoma and Leukemia

To determine the relative expression of GPNMB on the surface of hematopoietic malignant cells, cell lines derived from various lymphomas and leukemias were incubated with anti-GPNMB antibody and analyzed by FACS. Lymphoma or leukemia derived cells were washed twice with ice-cold FACS buffer and resuspended at 1 million cells per assay tube. MAb 1.15.1 antibody at 1 µg/mL was added to cells and cells were incubated on ice for 30 min. Cells were then washed 2-3 times and resuspended in 1 mL of ice-cold FACS buffer. R-PE-conjugated goat anti-human antibody at 1:100 dilution was added and cells were incubated on ice for 30 min. Cells were washed 3 times with 1 mL of ice-cold FACS buffer, fixed with 0.5-1 mL of 1% formaldehyde in PBS and analyzed by Flow Cytometry. Approximately half of the cell lines examined, which were derived from both myeloid and lymphoid lineages, showed GPNMB cell surface expression (Table 14). Cell line U937 demonstrated the highest Geo Mean ratio among the cell lines tested.

TABLE 14

Geo Mean Ratio of anti-GPNMB Staining of Lymphoma and Leukemia Cells

| Cell line | Geo Mean Ratio |
|---|---|
| U937 (histiocytic lymphoma, monocytic) | 17.3 |
| Jurkat (acute T-cell leukemia) | 14.7 |
| SR (anaplastic large T cell lymphoma, ALCL) | 7.1 |
| KG-1 (acute myelogenous leukemia) | 6.9 |
| MOLT-4 (acute T cell lymphoblastic leukemia) | 6.2 |
| THP-1 (acute monocytic leukemia) | 6.1 |
| MV4-11 (myelomonocytic leukemia) | 1.9 |
| AML-193 (acute monocytic leukemia) | 1.8 |
| HUT-78 (T cell lymphoma) | 1.5 |
| CCRF-CEM (acute T cell lymphoblastic leukemia) | 10.9 |
| Karpas 299 (ALCL) | 10.7 |
| SU-DHL-1 (ALCL) | 4.8 |
| SU-DHL-4 (B cell lymphoma) | 1.8 |
| ML-2 (acute myelomonocytic leukemia) | 2.1 |
| HH (cutaneous T-cell leukemia) | 1 |
| SUP-M2 (ALCL) | 4.8 |
| PL-21 (acute myeloid leukemia) | 12 |
| DEL (ALCL) | 7.9 |
| SIG-M5 (acute monocytic leukemia) | 2.9 |
| K562 (Chronic myelogenous leukemia) | 2.8 |
| KG1a (acute myelogenous leukemia) | 2.7 |
| HL-60 (acute promyelocytic leukemia) | 2.3 |
| WSU-NH2 (B cell lymphoma) | 1 |
| EOL-1 (acute myeloid leukemia) | 1 |
| HUT-102 (T cell lymphoma) | 1 |

Example 8

Detection of GPNMB protein by IP and Western Blot Analysis

Cells were washed twice with PBS (Ca and Mg free), incubated with Versene at 37° C. until cells detached, counted, collected and lysed in lysis buffer (0.15M NaCl, 0.02M Tris HCl, 10% glycerol, 1% NP-40, 0.01M EDTA and protease inhibitors containing pancreas extract, pronase, thermolysin, chymotrypsin and papain (Roche, Germany) for 30 min on ice. Supernatants were collected and protein concentrations were determined by BCA protein assay kit (Pierce, USA). Primary antibody was added to the cell lysates and incubated on ice for 3 hr followed by addition of Protein-G agarose (Amersham, USA) for 2 hr Immunoprecipitated proteins were washed, boiled in sample buffer and resolved by 4-20% gels. For immunoblotting, proteins were transferred to PVDF membranes (Invitrogen, USA) and probed with anti-GPNMB antibody (0.5 μg/mL) followed by HRP-conjugated goat anti-human antibody (Jackson ImmunoResearch Laboratory) at 1:4000 dilution. The immunocomplexes were detected with ECL Western blotting detection reagents (Amersham, USA).

Western blot analysis showed anti-GPNMB antibodies immunoprecipitated GPNMB protein expressed in cell lysates of UACC-62, SK-Mel5 and SK-Mel2 cell lines. The results are in concurrence with the cell surface expression determined by FACS analysis.

Example 9

Anti GPNMB Antibody Mediated Indirect Cell Killing

UACC-62, a GPNMB antigen expressing cell line, and TK10, a non-expressing cell line were plated onto flat bottom 96-well tissue culture plates (Becton Dickinson, Franklin Lakes, N.J., USA) at a density of 3000 cells per well. Once the cells reached ~25% confluency, 100 ng/well of secondary antibody-toxin conjugate (goat anti-human IgG-saporin; Advanced Targeting Systems, San Diego, USA, HUM-ZAP; cat. # IT-22) was added. Anti-GPNMB MAbs 2.10.2, 2.22.1, 1.15.1 or isotype control mAb (pK16.3) were added to each well at a final concentration of 10 or 50 ng/mL. An anti-EGFR monoclonal antibody (MS-269-PABX, NeoMarkers, Fremont, Calif., USA) was used as a positive primary antibody control. Chemotherapy reagent 5-FU at 600 uM was used as a positive reagent control. On day 5, the cells were trypsinized, transferred to 6-well tissue culture plates and incubated at 37° C. Plates were examined daily and between 8-10 days, all plates were Giemsa stained and colonies were counted.

Figure 2:
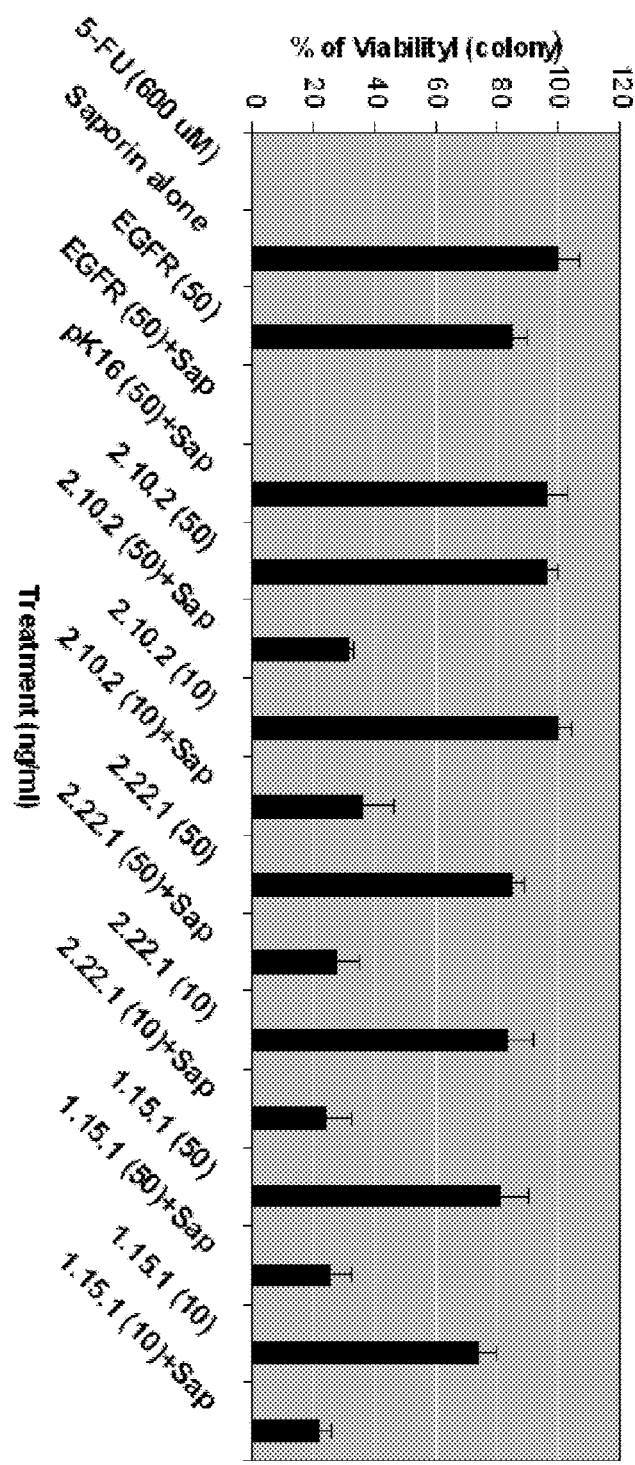
FIG. 2: Indirect immunotoxin killing of UACC-62 melanoma cells by anti-GPNMB antibodies
Figure 3:
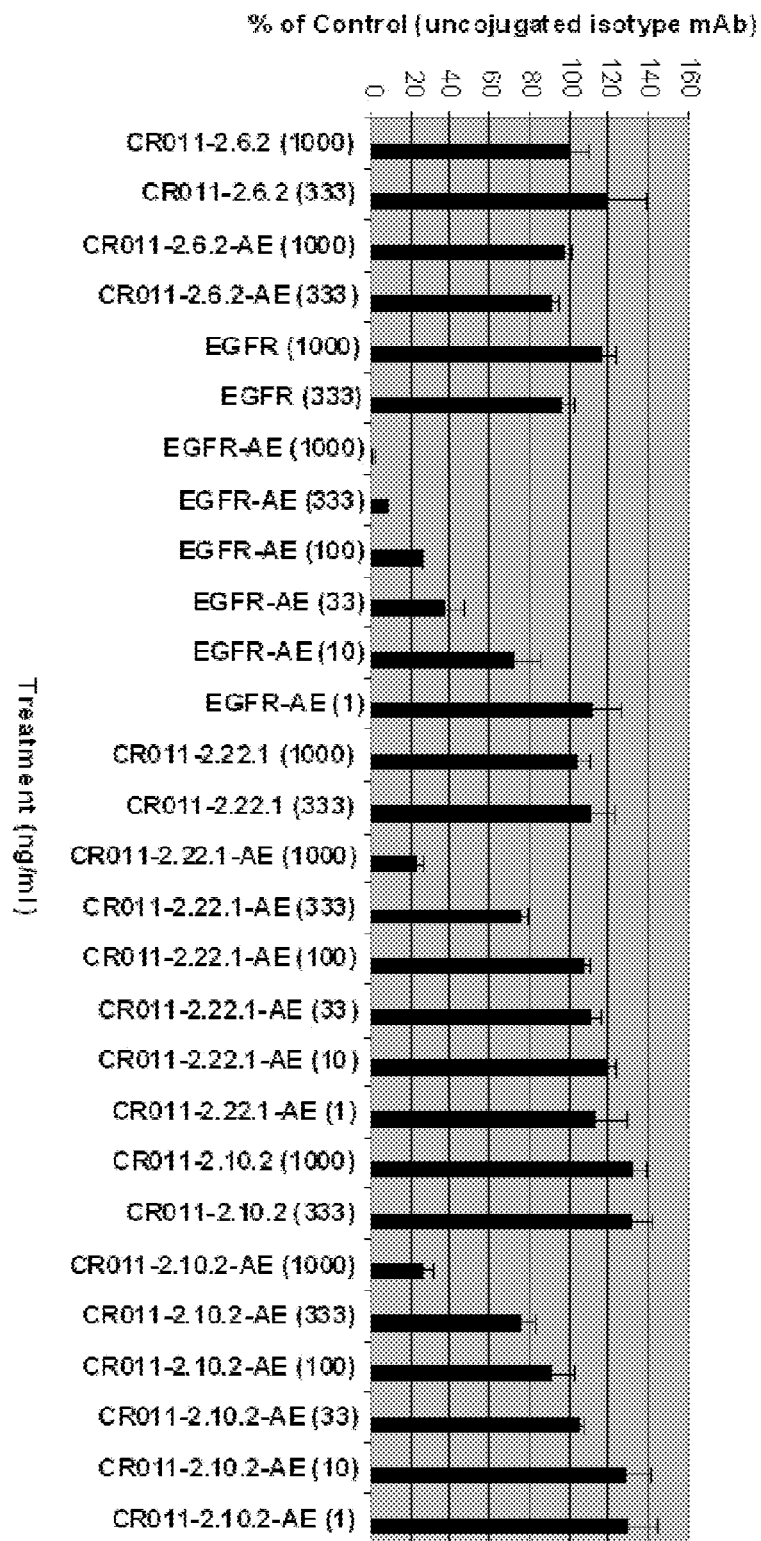
FIG. 3: Inhibition of colony formation of UACC-62 cells incubated with Auristatin E (AE) conjugated anti-GPNMB antibodies.

The percent viability of GPNMB positive UACC-62 after treatment is shown in FIG. 2. Chemotherapy reagent 5-FU induced a complete killing whereas addition of saporin toxin-conjugated secondary antibody alone or in combination with isotype control pK16.3 antibody had no effect on cell growth for both cell lines. Both UACC-62 and TK10 cell lines express EGFR protein and addition of EGFR specific antibody at 50 ng/mL and secondary antibody toxin conjugate resulted in a complete killing of UACC-62 and TK10 cells. At the same dose, all three GPNMB specific antibodies, 2.10.2, 2.22.1 and 1.15.1 induced over 70% killing of UACC-62 cells. Anti-GPNMB antibodies 2.10.2 and 2.22.1 induced less than 5% and 1.15.1 less than 24% cell death in GPNMB negative TK10 cells.

Example 10

Cell killing by Auristatin-E (AE) Conjugated Anti-GPNMB Antibodies

UACC-62 and TK10 cells were plated onto flat bottom 96-well tissue culture plates (Becton Dickinson, Franklin Lakes, N.J., USA). On day 2 or cells reach ~25% confluency, various concentrations (1 to 1000 ng/mL) of unconjugated and Auristatin E-conjugated antibodies (Seattle Genetics, Bothell, Wash., USA), including isotype control, EGFR (NeoMarkers MS-269-PABX, Fremont, Calif., USA), 2.22.1 or 2.10.2, were added to cells. MAb 2.3.1 was chosen for the isotype control in this study because it does not bind to GPNMB expressing cells as demonstrated by FACS analysis. A monoclonal antibody generated against the EGF receptor was used to demonstrate specific killing mediated by AE-conjugated antibody. On day 5, the cells were trypsinized, transferred to 6-well tissue culture plates and incubated at 37° C. Plates were examined daily. On days 8-10, all plates were Giemsa stained and colonies on the plates were counted.

Figure 4:
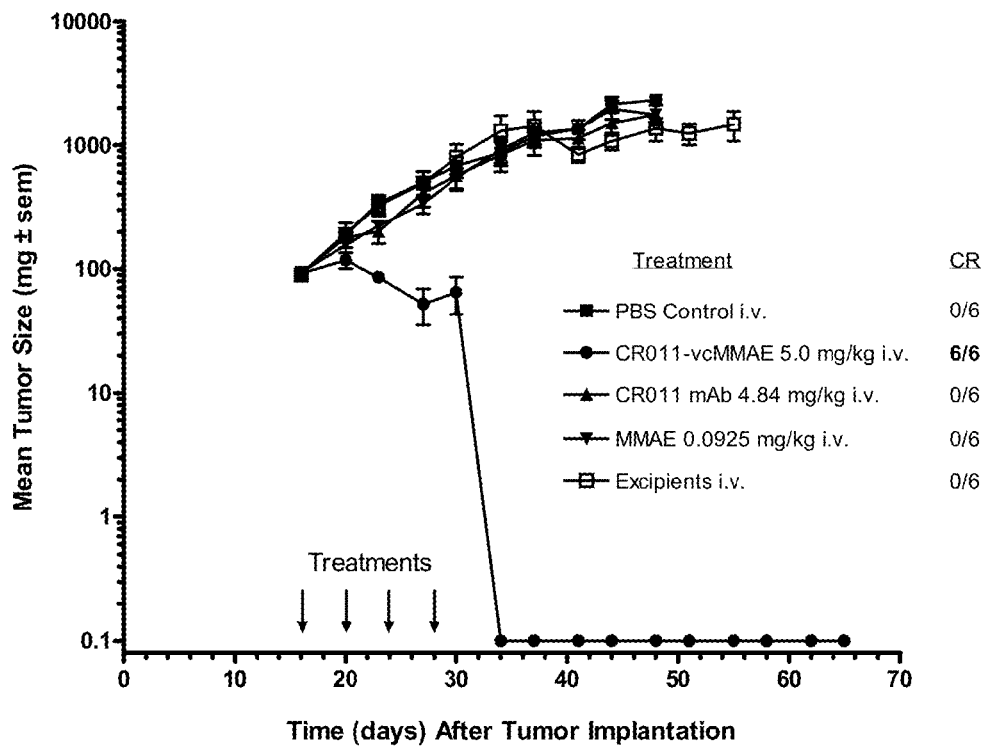
FIG. 4: Tumor growth inhibition and complete regression of SK-MEL-2 xenografts in athymic mice after treatment with CR011-vcMMAE 5.0 mg/kg i.v. every 4 days for 4 treatments. The lack of responses of tumor-bearing animals to unconjugated CR011 or to free monomethylauristatin E demonstrate that the intact immunoconjugate is essential for anti-tumor effects.
Figure 5:
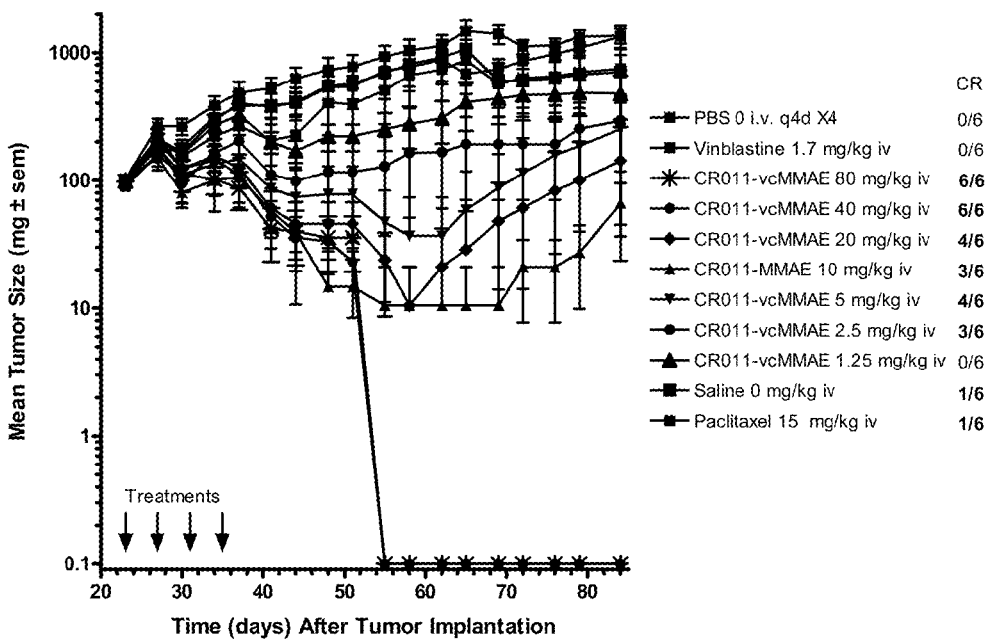
FIG. 5: Tumor size reduction and complete regression of SK-MEL-2 xenografts in athymic mice after treatment with 1.25 to 20 mg/kg i.v. every 4 days for 4 treatments. The responses of tumor-bearing animals to reference drugs such as Vinblastine (1.7 mg/kg i.v. q4d ×4) and paclitaxel (24 mg/kg i.v. q2d ×4) are also shown. Control groups are treated with either phosphate-buffered saline (PBS) or physiological saline.

The percent viability in GPNMB positive UACC-62 cells and negative TK10 cells is presented in FIGS. 4 and 5, respectively. The results indicate that unconjugated and AE-conjugated 2.6.2 immunoconjugate had no effect on growth of both UACC-62 and TK10 cells. However, both UACC-62 and TK10 cell lines were susceptible to AE-EGFR immunoconjugate mediated cell killing in a dose-dependent fashion with over 95% cell death at 1000 ng/mL. At the same dose, both 2.22.1-AE and 2.10.2-AE immunoconjugates induced approximately 75% cell death of UACC-62 cells when compared to the isotype control. The cell killing response was dose dependent. GPNMB negative TK10 cell survival was not affected by 2.22.1-AE nor 2.10.2-AE immunoconjugates at the same dose range. These results demonstrate the specific and cytotoxic effects of AE conjugated anti-GPNMB antibodies on antigen expressing cells.

Example 11

Melanoma Cells Susceptible to MAb1.15.1-AE Immunoconjugate Killing

Melanoma cell lines were plated onto flat bottom 96-well tissue culture plates (Becton Dickinson, Franklin Lakes, N.J., USA). On day 2 or when cells reach ~25% confluency, various concentrations of unconjugated and Auristatin E-conjugated 1.15.1 were added to cells. MAb 2.6.2-AE was also used as a conjugated isotype control in this study. On day 5, the cells were trypsinized, transferred to 6-well tissue culture plates and incubated at 37° C. Plates were examined daily. On days 8-10, all plates were Giemsa stained and colonies on the plates were counted.

The $IC_{50}$ of 1.15.1-AE mediated killing on GPNMB positive and negative cells are presented in Table 15. Unconjugated 1.15.1 and AE-conjugated 2.6.2 had no effect on growth of all the melanoma cell lines tested. However, cell lines SK-Mel2, WM-266-4, G361, UACC-257, UACC-62, RPMI-7951 and SK-Mel5 were susceptible to 1.15.1-AE mediated killing in a dose-dependent fashion. SK-Mel2 demonstrated the lowest $IC_{50}$ in this study (Table 15). These results show the specific and cytotoxic effects of AE conjugated 1.15.1 on most of GPNMB expressing melanoma cells.

TABLE 15

Geo Mean Ratios and $IC_{50}$ Values of
1.15.1-AE Killing of Melanoma Cells

| Melanoma Cell Line | Geo Mean Ratio (relative to isotype) | Clonogenic Assay with 1.15.1-AE IC50 in ng/mL (pM) |
|---|---|---|
| SK-Mel 2 | 16.5 | 111 (750) |
| M14 | 16.1 | Inconclusive |
| MEWO | 14.1 | Inconclusive |
| WM-266-4 | 13.6 | 345 (2300) |
| HEMNLP | 10.2 | Inconclusive |
| G361 | 8 | 1053 (6500) |
| HT144 | 7.4 | Inconclusive |
| UACC-257 | 7 | 825 (5500) |
| RPMI-7951 | 6 | 972 (6000) |
| SK-Mel 5 | 5.7 | 237 (1600) |
| UACC-62 | 5.5 | 697 (4300) |
| A2058 | 4.1 | No effect |
| SK-Mel 24 | 1.9 | No data |
| WM115 | 1.3 | No data |
| LOXIMVI | 1 | No effect |

Example 12

MAb 1.15.1-AE Killing of Lymphoma and Leukemia Cell Lines

Lymphoma or leukemia cell lines were mixed with methylcellulose base media (R&D Systems, USA) and in various concentrations of unconjugated and Auristatin E-conjugated 1.15.1 antibody before plating onto 6-well tissue culture plates (Becton Dickinson, Franklin Lakes, N.J., USA). MAb 2.6.2-AE was also included as a conjugated isotype control in this study because it does not bind to GPNMB expressing cells. Plates were incubated at 37° C. and examined daily. On days 14-18, colonies on the plates were counted.

The $IC_{50}$ of 1.15.1-AE induced cell killing on antigen expressing cells is presented in Table 16. Unconjugated 1.15.1 and AE-conjugated 2.6.2 immunoconjugate had no effect on growth of all antigen positive hematopoietic cell lines. However, as presented in Table 16, cell lines U937, SR and THP-1 derived from either myeloid or lymphoid lineage were susceptible to 1.15.1-AE mediated killing in a dose-dependent manner with $IC_{50}$ values ranging from 207 ng/mL (1.4 nM) to 340 ng/mL (2.4 nM). These results show the specific and cytotoxic effects of 1.15.1-AE immunoconjugate on GPNMB antigen expressing hematopoietic malignant cell lines.

TABLE 16

Geo Mean Ratios and $IC_{50}$ Values of 1.15.1-
AE Killing of Lymphoma and Leukemia Cells

| Cell line | Geo Mean Ratio | Clonogenic Assay with 1.15.1-AE IC50 in ng/mL (pM) |
|---|---|---|
| U937 (histiocytic lymphoma, monocytic) | 17.3 | 340 (2400) |
| Jurkat (acute T-cell leukemia) | 14.7 | No effect (repeating) |
| SR (anaplastic large T cell lymphoma, ALCL) | 7.1 | 296 (2000) |
| KG-1 (acute myelogenous leukemia) | 6.9 | No growth |
| MOLT-4 (acute T cell lymphoblastic leukemia) | 6.2 | No effect (repeating) |
| THP-1 (acute monocytic leukemia) | 6.1 | 207 (1400) |
| MV4-11 (myelomonocytic leukemia) | 1.9 | ND |
| AML-193 (acute monocytic leukemia) | 1.8 | ND |
| HUT-78 (T cell lymphoma) | 1.5 | ND |
| CCRF-CEM (acute T cell lymphoblastic leukemia) | 10.9 | No growth |
| Karpas 299 (ALCL) | 10.7 | Inconclusive |
| SU-DHL-1 (ALCL) | 4.8 | No effect |
| SU-DHL-4 (B cell lymphoma) | 1.8 | ND |
| ML-2 (acute myelomonocytic leukemia) | 2.1 | ND |
| HH (cutaneous T-cell leukemia) | 1 | ND |
| SUP-M2 (ALCL) | 4.8 | No growth |
| PL-21 (acute myeloid leukemia) | 12 | No effect |
| DEL (ALCL) | 7.9 | No effect |
| SIG-M5 (acute monocytic leukemia) | 2.9 | ND |
| K562 (Chronic myelogenous leukemia) | 2.8 | ND |
| KG1a (acute myelogenous leukemia) | 2.7 | ND |
| HL-60 (acute promyelocytic leukemia) | 2.3 | ND |
| WSU-NH2 (B cell lymphoma) | 1 | ND |
| EOL-1 (acute myeloid leukemia) | 1 | ND |
| HUT-102 (T cell lymphoma) | 1 | ND |

* ND: Not done

Example 13

CR011-vcMMAE Inhibits the Growth of Human SK-MEL-2 Melanoma Xenografts Leading to Complete Regression of Established Melanoma Tumors in Athymic Mice (Study N-386)

Study N-386 was performed to assess the potency and therapeutic efficacy of the antibody-drug conjugate, CR011-vcMMAE, against the established human SK-MEL-2 melanoma xenograft in athymic mice.

Materials and Methods:

Test Animals: Five- to 6-week old athymic mice (CD-1 nu/nu females), used for human tumor xenografts, were obtained from Harlan Laboratories (Indianapolis, Ind.). Animals were housed in specific pathogen-free conditions, according to the guidelines of the Association for Assessment and Accreditation of Laboratory Animal Care International (AAALAC International). Test animals were provided pelleted food and water ad libitum and kept in a room with conditioned ventilation (HVAC), temperature (22°±2° C.), relative humidity (55%±15%), and photoperiod (12 hr). All studies were carried out with approved institutional animal care and use protocols.

Human Melanoma Xenograft Models. The tumor inhibitory activity of the CR011-MMAE immunoconjugate was measured in an anti-tumor xenograft model using athymic mice, according to published methods (see Geran et al., Cancer Chemother. Rep. 3:1-104 (1972)). Briefly, test animals were implanted subcutaneously by trocar with small fragments of a human melanoma (60-125 mg) excised from athymic mouse tumor donors. When tumors became established (10-20 days), the animals were pair-matched into groups (n=6 mice/group), and treatment was administered by intravenous injection (tail vein).

The SK-MEL-2 human melanoma (ATCC #HTB-68) was derived from a metastatic site (skin of thigh) of a 60 year old Caucasian male with malignant melanoma, and the SK-MEL-5 human melanoma (ATCC #HTB-70) was derived from a metastatic site (axillary lymph node) of a 24 year old Caucasian female with malignant melanoma (see Fogh et al., J. Natl. Cancer Inst. 59: 221-226 (1977)). Both cell lines were obtained from the American Type Culture Collection.

The effects of treatment were monitored by repetitive tumor measurements across 2 diameters with Vernier calipers; tumor size (in mg) was calculated using a standard formula, $(W^2 \times L)/2$, assuming a specific gravity of 1.0. Tumor size and body weights were assessed twice weekly. Mice were examined daily, however, and moribund animals were humanely euthanized if clinical indications of excessive pain or distress were noted (i.e., prostration, hunched posture, paralysis/paresis, distended abdomen, ulcerations, abscesses, seizures, and/or hemorrhages). Animals with tumors exceeding 2,000 mg were removed from the study and euthanized humanely.

Xenograft studies in the athymic mouse have been shown to effectively demonstrate anti-tumor effects for a variety of agents which have been shown subsequently to have activity against clinical cancer (Johnson et al., *Br J Cancer* 84:1424-1431 (2001)).

Results:

Anti-Tumor Effects In Vivo vs. SK-MEL-2 Melanoma. Based on the potency and cytotoxicity of CR011-vcMMAE against GPNMB-expressing cells in vitro, the anti-tumor effects were examined in vivo.

The effects of intravenous CR011-vcMMAE treatment on the growth of subcutaneous human SK-MEL-2 melanoma are shown in FIG. 1. After SK-MEL-2 tumor fragments were implanted and tumors became established (day 17, 61 mg), treatment commenced with intravenous administration of: CR011-vcMMAE (0.625-20 mg/kg i.v., every 4 days for a total of 4 treatments (i.e., q4d ×4); saline and phosphate-buffered saline controls (i.v., q4d ×4); and two known anti-tumor reference agents, vinblastine sulfate (i.v., 1.7 mg/kg, q4d ×4) and paclitaxel (i.v., 24 mg/kg, q2d ×4). The reference agents were administered at the maximum tolerated dose (MTD) determined in prior studies.

Tumors in animals treated with saline or PBS grew progressively until the tumor mass reached 2,000 mg at which time the animals were removed from the study and euthanized humanely. SK-MEL-2 tumors have a high "take" rate in immunocompromised hosts (97%) and a low rate of spontaneous regression (3%) (Dykes et al., Development of human tumor xenograft models for in vivo evaluation of new antitumor drugs, in Immunodeficient mice in Oncology, vol. 42 (Fiebig H H and Berger DPe eds) pp 1-22, Contrib. Oncol. Basel, Karger (1992)).

Vinblastine produced a very slight, but not significant, anti-tumor effect ($P \leq 0.20$); in this and other tumor models (e.g., SK-MEL-5) vinblastine produces noticeable tumor growth inhibition, but which is only occasionally significant. Paclitaxel, however, showed significant tumor growth inhibition and tumor stasis (i.e., 100% growth inhibition) for approximately 2 weeks after treatment commenced ($P \leq 0.0077$).

The anti-tumor effects of CR011-vcMMAE administered i.v. to SK-MEL-2-bearing mice were remarkable. At 20, 10, 5 or 2.5 mg/kg tumors rapidly diminished in size for the majority of the test animals; significant treatment effects were noted as early as 4 days after treatment commenced ($P \leq 0.014$). Tumors that regressed completely did not re-grow during the observation period (>200 days).

The animals in this study showed no abnormal treatment effects on gross examination. Twice weekly body weight determinations showed no observable or statistically significant effects of treatment with CR011-vcMMAE on body weight or weight gain.

Conclusions:

CR011-vcMMAE produces substantial, dose-dependent and reproducible anti-tumor effects that begin as tumor growth inhibition but soon lead to complete regression of established human melanoma xenografts; the regressions are long-lived and re-growth of tumors after successful therapy has not been observed.

Example 14

Sequencing of Antibodies and their Corresponding DNA

Sequences of human GPNMB mAbs-derived heavy and kappa chain transcripts from hybridomas were obtained by direct sequencing of PCR products generated from poly(A+) RNA. PCR products were also cloned into pCRII using a TA cloning kit (Invitrogen) and both strands were sequenced using Prism dye-terminator sequencing kits and an ABI 377 sequencing instrument. Each PCR reaction used a mixture of 5' sense primers which are provided in Table 17 below.

TABLE 17

| Primers Used | |
|---|---|
| VH cacc ATG GAC TGG(C) ACC TGG AGG ATC | SEQ ID NO: 290 |
| VH cacc ATG GAC TGG ACC TGG AGA(C) ATC | SEQ ID NO: 291 |
| VH cacc ATG GAC TGG ACC TGG AGG GTC | SEQ ID NO: 292 |
| VH cacc ATG GAC TGG ATT TGG AGG ATC | SEQ ID NO: 293 |
| VH cacc ATG GAC ACA CTT TGC TC(A)C AC | SEQ ID NO: 294 |

TABLE 17-continued

| Primers Used | |
|---|---|
| VH cacc ATG GAA(G) TTG GGG CTG AGC TGG | SEQ ID NO: 295 |
| VH cacc ATG GAG TTG(T) GGA CTG AGC TGG | SEQ ID NO: 296 |
| VH cacc ATG GAG TTT GGG CTG(T) AGC TGG | SEQ ID NO: 297 |
| VH cacc ATG GAA CTG GGG CTC CGC TGG | SEQ ID NO: 298 |
| VH cacc ATG GAG TTG GGG CTG TGC TGG | SEQ ID NO: 299 |
| VH cacc ATG GAG TTT TGG CTG AGC TGG | SEQ ID NO: 300 |
| VH cacc ATG ACG GAG TTT GGG CTG AGC | SEQ ID NO: 301 |
| VH cacc ATG AAA(G) CAC CTG TGG TTC TTC | SEQ ID NO: 302 |
| VH cacc ATG AAA CAT CTG TGG TTC TTC | SEQ ID NO: 303 |
| VH cacc ATG GGG TCA ACC GCC ATC CTC | SEQ ID NO: 304 |
| VH cacc ATG TCT GTC TCC TTC CTC ATC TTC | SEQ ID NO: 305 |
| VK ATG GGG TCC CAG GTT CAC CTC | SEQ ID NO: 306 |
| VK ATG TTG CCA TCA CAA CTC ATT G | SEQ ID NO: 307 |

All sequences were analyzed by alignments to the "V BASE sequence directory" (Tomlinson et al., MRC Centre for Protein Engineering, Cambridge, UK) using MACVECTOR® and GENEWORKS™ software programs.

Example 15

Structural Analysis of Anti-GPNMB Antibodies

The variable heavy chains and the variable light chains for the antibodies shown in Table 17 were sequenced to determine their DNA and protein sequences.

```
Antibody -1.10.2
Heavy chain variable region
Nucleotide sequence
                                                          (SEQ ID NO: 1)
5'AGGTGCAGCTGCAGGAGTCGGGCCCAGGACTGGTGAAGCCTTCGGAGACCCTGTCCCTCACCTGCACTGTCT

CTGGTGACTCCATCAGTAATTACTACTGGAGCTGGATCCGGCAGCCCCCAGGGAAGGGACTGGAGTGGATTGGG

TATTTCTATTACAGTGGGAGCACCAACTACAACCCCTCCCTCAAGAGTCGAGTCACCATATCAGTAGACACGTC

CAAGAACCAGTTCTCCCTGAAACTGAGCTCTGTGACCGCTGCGGACACGGCCGTGTATTACTGTGCGAGAGATA

GGGGCTGGGCTGACTACTGGGGCCAGGGAACCCTGGTCACCGTCTCCTCAGCC 3'

Amino acid sequence
                                                          (SEQ ID NO: 2)
5'QVQLQESGPGLVKPSETLSLTCTVS GDSISNYYWS WIRQPPGKGLEWIG YFYYSGSTNYNPSLKS

RVTISVDTSKNQFSLKLSSVTAADTAVYYCAR DRGWADY WGQGTLVTVSSA 3'
```

TABLE 18

| 1.10.2 Heavy chain V region domains. | | | |
|---|---|---|---|
| REGION | SEQUENCE | AA RESIDUES* | SEQ ID NO: |
| FR1 | QVQLQESGPGLVKPSETESLTCTVS | 1-25 | SEQ ID NO: 3 |
| CDR1 | GDSISNYYWS | 26-35 | SEQ ID NO: 4 |

TABLE 18-continued

1.10.2 Heavy chain V region domains.

| REGION | SEQUENCE | AA RESIDUES* | SEQ ID NO: |
|---|---|---|---|
| FR2 | WIRQPPGKGLEWIG | 36-49 | SEQ ID NO: 5 |
| CDR2 | YFYYSGSTNYNPSLKS | 50-65 | SEQ ID NO: 6 |
| FR3 | RVTISVDTSKNQFSLKLSSVTAADTAVYYCAR | 66-97 | SEQ ID NO: 7 |
| CDR3 | DRGWADY | 98-104 | SEQ ID NO: 8 |
| FR4 | WGQGTLVTVSSA | 105-116 | SEQ ID NO: 9 |

*AA Residues of SEQ ID NO: 2

Light chain variable region
Nucleotide sequence
(SEQ ID NO: 10)
5'GAAATTGTGTTGACGCAGTCTCCAGGCACCCTGTCTTTGTCTCCAGGGGAAAGGGCCACCCTCT
CCTGCAGAACCAGTCAGAGTATTAGCAGCAGCTATTTAGCCTGGTACCAGCAGAAACCTGGCCA
GGTTCCCAGGCTCCTCATCTATGGTGCTTCCAGCAGGGCCACTGGCATCCCAGACAGGTTCAGTG
GCAGTGGGTCTGGGACAGACTTCACTCTCACCATCAGCAGACTGGAGCCTGAAGATTTTGCAGTG
TATTATTGTCAGCAGTATGGTAGCTCGATCACCTTCGGCCAAGGGACACGACTGGAGATTAAACG
A 3'

Amino acid sequence
(SEQ ID NO: 11)
5'EIVLTQSPGTLSLSPGERATLSC RTSQSISSSYLA WYQQKPGQVPRLLIY GASSRAT
GIPDRFSGSGSGTDFTLTISRLEPEDFAVYYC QQYGSSIT FGQGTRLEIKR 3'

TABLE 19

1.10.2 Light chain V region domains.

| REGION | SEQUENCE | AA RESIDUES* | SEQ ID |
|---|---|---|---|
| FRI | EIVLTQSPGTLSLSPGERATLSC | 1-23 | SEQ ID NO: 12 |
| CDR1 | RTSQSISSSYLA | 24-35 | SEQ ID NO: 13 |
| FR2 | WYQQKPGQVPRLLIY | 36-50 | SEQ ID NO: 14 |
| CDR2 | GASSRAT | 51-57 | SEQ ID NO: 15 |
| FR3 | GIPDRFSGSGSGTDFTLTISRLEPEDFAVYYC | 58-89 | SEQ ID NO: 16 |
| CDR3 | QQYGSSIT | 90-97 | SEQ ID NO: 17 |
| FR4 | FGQGTRLEIKR | 98-108 | SEQ ID NO: 18 |

*AA Residues of SEQ ID NO: 11

Antibody -1.15.1
Heavy chain variable region
Nucleotide sequence
(SEQ ID NO: 19)
5'CAGGTGCAGCTGCAGGAGTCGGGCCCAGGACTGGTGAAGCCTTCACAGACCCTGTCCCTCACCTGCACTGTC
TCTGGTGGCTCCATCAGCAGTTTTAATTACTACTGGAGCTGGATCCGCCACCACCCAGGGAAGGGCCT
GGAGTGGATTGGGTACATCTATTACAGTGGGAGCACCTACTCCAACCCGTCCCTCAAGAGTCGAGTTACC
ATATCAGTAGACACGTCTAAGAACCAGTTCTCCCTGACGCTGAGCTCTGTGACTGCCGCGGACACGGCCG -continued

TGTATTACTGTGCGAGAGGGTATAACTGGAACTACTTTGACTACTGGGGCCAGGGAACCCTGGTCACCGT

CTCCTCAGCC 3'

Amino acid sequence
(SEQ ID NO: 20)
5'QVQLQESGPGLVKPSQTLSLTCTVSGGSISSFNYYWSWIRHHPGKGLEWIGYIYYSGSTYSNPSLKSRVTIS

VDTSKNQFSLTLSSVTAADTAVYYCARGYNWNYFDYWGQGTLVTVSSA 3'

TABLE 20

1.15.1 Heavy chain V region domains.

| REGION | SEQUENCE | AA RESIDUES* | SEQ ID |
|---|---|---|---|
| FR1 | QVQLQESGPGLVKPSQTLSLTCTVSGGSIS | 1-30 | SEQ ID NO: 21 |
| CDR1 | SFNYYWS | 31-37 | SEQ ID NO: 22 |
| FR2 | WIRHHPGKGLEWIG | 38-51 | SEQ ID NO: 23 |
| CDR2 | YIYYSGSTYSNPSLKS | 52-67 | SEQ ID NO: 24 |
| FR3 | RVTISVDTSKNQFSLTLSSVTAADTAVYYCAR | 68-99 | SEQ ID NO: 25 |
| CDR3 | GYNWNYFDY | 100-108 | SEQ ID NO: 26 |
| FR4 | WGQGTLVTVSSA | 109-120 | SEQ ID NO: 27 |

*AA Residues of SEQ ID NO: 20

Light chain variable region
Nucleotide sequence
(SEQ ID NO: 28)
5'GAAATAGTGATGACGCAGTCTCCAGCCACCCTGTCTGTGTCTCCAGGGGAAAGAGCCACCCTCTCCTGCAGG

GCCAGTCAGAGTGTTGACAACAACTTAGTCTGGTACCAGCAGAAACCTGGCCAGGCTCCCAGGCTCCT

CATCTATGGTGCATCCACCAGGGCCACTGGTATCCCAGCCAGGTTCAGTGGCAGTGGGTCTGGGACAGAG

TTCACTCTCACCATCAGTAGTCTGCAGTCTGAAGATTTTGCAGTTTATTACTGTCAGCAGTATAATAACT

GGCCTCCGTGGACGTTCGGCCAAGGGACCAAGGTGGAAATCAAACGA 3'

Amino acid sequence
(SEQ ID NO: 29)
5'EIVMTQSPATLSVSPGERATLSCRASQSVDNNLVWYQQKPGQAPRLLIYGASTRATGIPARFSGSGSGTEFT

LTISSLQSEDFAVYYCQQYNNWPPWTFGQGTKVEIKR 3'

TABLE 21

1.15.1 Light chain V region domains.

| REGION | SEQUENCE | AA RESIDUES* | SEQ ID |
|---|---|---|---|
| FR1 | EIVMTQSPATLSVSPGERATLSC | 1-23 | SEQ ID NO: 30 |
| CDR1 | RASQSVDNNLV | 24-34 | SEQ ID NO: 31 |
| FR2 | WYQQKPGQAPRLLIY | 35-49 | SEQ ID NO: 32 |
| CDR2 | GASTRAT | 50-56 | SEQ ID NO: 33 |
| FR3 | GIPARFSGSGSGTEFTLTISSLQSEDFAVYYC | 57-88 | SEQ ID NO: 34 |
| CDR3 | QQYNNWPPWT | 89-98 | SEQ ID NO: 35 |
| FR4 | FGQGTKVEIKR | 99-109 | SEQ ID NO: 36 |

*AA Residues of SEQ ID NO: 29

Antibody -1.2.2
Heavy chain variable region
Nucleotide sequence
(SEQ ID NO: 37)
5' ATCACCTTGAAGGAGTCTGGTCCTACGCTGGTGAAACCCACACAGACCCTCACGCTGACC

TGCACCTTCTCTGGGTTCTCACTCAGCGCTGGTGGAGTGGGTGTGGGCTGGATCCGTCAG

CCCCCAGGAAAGGCCCTGGAGTGGCTTGCACTCATTTATTGGAATGATGATAAGCGCTAC

AGCCCATCTCTGAGGAGCAGGCTCACCATCACCAAGGACACCTCCAAAAACCAGGTGGTC

CTTACAATTACCAACATGGACCCTGTGGACACAGCCACATATTATTGTGCACACAGTCAC

TATGATTACGATTGGGGGAGTTACTTTGACTACTGGGGCCAGGGAACCCTGGTCACCGTC

TCCTCAGCC 3'

Amino acid sequence
(SEQ ID NO: 38)
5' ITLKESGPTLVKPTQTLTLTCTFS GFSLSAGGVGVG WIRQPPGKALEWLA LIYWNDDKRY

SPSLRS RLTITKDTSKNQVVLTITNMDPVDTATYYCAH SHYDYDWGSYFDY WGQGTLVTVSSA 3'

TABLE 22

1.2.2 Heavy chain V region domains.

| REGION | SEQUENCE | AA RESIDUES* | SEQ ID |
|---|---|---|---|
| FRI | ITLKESGPTLVKPTQTLTLTCTFS | 1-24 | SEQ ID NO: 39 |
| CDR1 | GFSLSAGGVGVG | 25-36 | SEQ ID NO: 40 |
| FR2 | WIRQPPGKALEWLA | 37-50 | SEQ ID NO: 41 |
| CDR2 | LIYWNDDKRYSPSLRS | 51-66 | SEQ ID NO: 42 |
| FR3 | RLTITKDTSKNQVVLTITNMDPVDTATYYCAH | 67-98 | SEQ ID NO: 43 |
| CDR3 | SHYDYDWGSYFDY | 99-111 | SEQ ID NO: 44 |
| FR4 | WGQGTLVTVSSA | 112-123 | SEQ ID NO: 45 |

*AA Residues of SEQ ID NO: 38

Light chain variable region
Nucleotide sequence
(SEQ ID NO: 46)
5' GATATTGTGATGACCCAGACTCCACTCTCCCTGCCCGTCACCCCTGGAGAGCCGGCCTCC

ATCTCCTGCAGGTCTAGTCAGAGCCTCTTGGATAGTGATGATGGAAACACCTATTTGGAC

TGGTACCTGCAGAAGCCAGGACAGTCTCCACAGCTCCTGATCTATACGCTTTCCTATCGG

GCCTCTGGAGTCCCAGACAGGTTCAGTGGCAGTGGGTCAGGCACTGATTTCACACTGAAC

ATCAGCAGGGTGGAGGCTGAGGATGTTGGAGTTTATTACTGCATGCAACGTATAGAGTTT

CCTATCACCTTCGGCCAAGGGACACGACTGGAGATTAAACGA 3'

Amino acid sequence
(SEQ ID NO: 47)
5' DIVMTQTPLSLPVTPGEPASISC RSSQSLLDSDDGNTYLD WYLQKPGQSPQLLIY TLSYRAS

GVPDRFSGSGSGTDFTLNISRVEAEDVGVYYC MQRIEFPIT FGQGTRLEIKR 3'

TABLE 23

1.2.2 Light chain V region domains.

| REGION | SEQUENCE | AA RESIDUES* | SEQ ID |
|---|---|---|---|
| FRI | DIVMTQTPLSLPVTPGEPASISC | 1-23 | SEQ ID NO: 48 |
| CDR1 | RSSQSLLDSDDGNTYLD | 24-40 | SEQ ID NO: 49 |

TABLE 23-continued 1.2.2 Light chain V region domains.

| REGION | SEQUENCE | AA RESIDUES* | SEQ ID |
|---|---|---|---|
| FR2 | WYLQKPGQSPQLLIY | 41-55 | SEQ ID NO: 50 |
| CDR2 | TLSYRAS | 56-62 | SEQ ID NO: 51 |
| FR3 | GVPDRFSGSGSGTDFTLNISRVEAEDVGVYYC | 63-94 | SEQ ID NO: 52 |
| CDR3 | MQRIEFPIT | 95-103 | SEQ ID NO: 53 |
| FR4 | FGQGTRLEIKR | 104-114 | SEQ ID NO: 54 |

*AA Residues of SEQ ID NO: 47

Antibody -1.7.1
Heavy chain variable region
Nucleotide sequence
(SEQ ID NO: 55)
5' CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGCTAATTACTACTGGACCTGGATCCGC

CAGCACCCAGGGAAGGGCCTGGAGTGGATTGGGTACATCTATTACAGTGGGAGCACCTAC

TGCAACCCGTCCCTCAAGAGTCGAGTTATCATATCAGTAGACACGTCTAAGAACCAGTTC

TCCCTGAAGCTGAGCTCTGTGACTGCCGCGGACACGGCCGTGTATTACTGTGCGAGAGGG

TATAACTGGAACTACTTTGACTACTGGGGCCAGGGAACCCTGGTCACCGTCTCCTCAGCC 3'

Amino acid sequence
(SEQ ID NO: 56)
5' QVQLQESGPGLVKPSQTLSLTCTVS GGSISSANYYWT WIRQHPGKGLEWIG YIYYSGSTY

CNPSLKS RVIISVDTSKNQFSLKLSSVTAADTAVYYCAR GYNWNYFDY WGQGTLVTVSSA 3'

TABLE 24

1.7.1 Heavy chain V region domains.

| REGION | SEQUENCE | AA RESIDUES* | SEQ ID |
|---|---|---|---|
| FRI | QVQLQESGPGLVKPSQTESETCTV | 1-25 | SEQ ID NO: 57 |
| CDR1 | GGSISSANYYWT | 26-37 | SEQ ID NO: 58 |
| FR2 | WIRQHPGKGLEWIG | 38-51 | SEQ ID NO: 59 |
| CDR2 | YIYYSGSTYCNPSLKS | 52-67 | SEQ ID NO: 60 |
| FR3 | RVIISVDTSKNQFSLKLSSVTAADTAVYYCAR | 68-99 | SEQ ID NO: 61 |
| CDR3 | GYNWNYFDY | 100-108 | SEQ ID NO: 62 |
| FR4 | WGQGTLVTVSSA | 109-120 | SEQ ID NO: 63 |

*AA Residues of SEQ ID NO: 56

Light chain variable region
Nucleotide sequence
(SEQ ID NO: 64)
5'GATATAGTGATGACGCAGTCTCCAGCCACCCTGTCTGTGTCTCCAGGGGAAAGAGCCACCCTCTCCTGCAGG

GCCAGTCAGAGTGTTAGCAGCAACTTAGCCTGGTACCAGGAGAGACCTGGCCAGGCTCCCAGACTCCTCATCTA

TGGTGCATCCACCAGGGCCACTGGTATCCCAGCCAGGTTCAGTGGCAGTGGGTCTGGGACAGAGTTCACTCTCA

CCATCAGCAGCCTGCAGTCTGAAGATTTTGCAGTTTATTACTGTCAGCAGTATAATAAGTGGCCTCCGTGGACG

TTCGGCCAAGGGACCAAGGTGGAAATCGAACGAACT 3'

-continued

Amino acid sequence
(SEQ ID NO: 65)
5' DIVMTQSPATLSVSPGERATLSC RASQSVSSNLA WYQERPGQAPRLLIY GASTRAT

GIPARFSGSGSGTEFTLTISSLQSEDFAVYYC QQYNKWPPWT FGQGTKVEIER 3'

TABLE 25

1.7.1 Light chain V region domains.

| REGION | SEQUENCE | AA RESIDUES* | SEQ ID |
|---|---|---|---|
| FR1 | DIVMTQSPATLSVSPGERATLSC | 1-23 | SEQ ID NO: 66 |
| CDR1 | RASQSVSSNLA | 24-34 | SEQ ID NO: 67 |
| FR2 | WYQERPGQAPRLLIY | 35-49 | SEQ ID NO: 68 |
| CDR2 | GASTRAT | 50-56 | SEQ ID NO: 69 |
| FR3 | GIPARFSGSGSGTEFTLTISSLQSEDFAVYYC | 57-88 | SEQ ID NO: 70 |
| CDR3 | QQYNKWPPWT | 89-98 | SEQ ID NO: 71 |
| FR4 | FGQGTKVEIER | 99-109 | SEQ ID NO: 72 |

*AA Residues of SEQ ID NO: 65

Antibody -2.10.2
Heavy chain variable region
Nucleotide sequence
(SEQ ID NO: 73)
5' CAGCTGGTGGAGTCTGGGGGAGGCGTGGTCCAGCCTGGGAGGTCCCTGAGACTCTCCTGT

GCAGCCTCTGGATTCGCCTTCAGTAGCTATGGCATGCACTGGGTCCGCCAGGCTCCAGGC

AAGGGGCTGGAGTGGGTGGCAGTTATATCATATGATGGAAATAATAAATACTATGCAGAC

TCCGTGAAGGGCCGATTCACCATCTCCAGAGACAATTCCAAGAACACGCTGTATCTGCAA

ATGAACAGCCTGAGAGCTGAGGACACGGCTGTGTATTACTGTGCGAGAGATCTAGTGGTT

CGGGGAATTAGGGGGTACTACTACTACTTCGGTATGGACGTCTGGGGCCAAGGGACCACG

GTCACCGTCTCCTCAGCC 3'

Amino acid sequence
(SEQ ID NO: 74)
5' QLVESGGGVVQPGRSLRLSCAAS GFAFSSYGMH WVRQAPGKGLEWVA VISYDGNNKYYAD

SVKG RFTISRDNSKNTLYLQMNSLRAEDTAVYYCAR DLVVRGIRGYYYYFGMDV WGQGTT

VTVSSA 3'

TABLE 26

2.10.2 Heavy chain V region domains.

| REGION | SEQUENCE | AA RESIDUES* | SEQ ID |
|---|---|---|---|
| FR1 | QLVESGGGVVQPGRSLRLSCAAS | 1-23 | SEQ ID NO: 75 |
| CDR1 | GFAFSSYGMH | 24-33 | SEQ ID NO: 76 |
| FR2 | WVRQAPGKGLEWVA | 34-47 | SEQ ID NO: 77 |
| CDR2 | VISYDGNNKYYADSVKG | 48-64 | SEQ ID NO: 78 |
| FR3 | RFTISRDNSKNTLYLQMNSLRAEDTAVYYCAR | 65-96 | SEQ ID NO: 79 |
| CDR3 | DLVVRGIRGYYYYFGMDV | 97-114 | SEQ ID NO: 80 |
| FR4 | WGQGTTVTVSSA | 115-126 | SEQ ID NO: 81 |

*AA Residues of SEQ ID NO: 74

Light chain variable region
Nucleotide sequence
(SEQ ID NO: 82)
5' GATATTGTGATGACTCAGTCTCCACTCTCCCTGCCCGTCACCCCTGGAGAGCCGGCCTCC

ATCTCCTGCAGGTCTAGTCAGAGCCTCCTGCATAGTAATGGATACAACTATTTGGATTGG

TACCTGCAGAAGCCAGGGCAGTCTCCACAGCTCCTGATCTATTTGGGTTCTAATCGGGCC

TCCGGGGTCCCTGACAGGTTCAGTGGCAGTGGATCAGGCACAGATTTTACACTGAAAATC

AGCAGAGTGGAGGCTGAGGATGTTGGGGTTTATTACTGCATGCAAGGTCTACAAACTCCG

ATCACCTTCGGCCAAGGGACACGACTGGAGATTAAACGA 3'

Amino acid sequence
(SEQ ID NO: 83)
5' DIVMTQSPLSLPVTPGEPASISC RSSQSLLHSNGYNYLD WYLQKPGQSPQLLIY LGSNRAS

GVPDRFSGSGSGTDFTLKISRVEAEDVGVYYC MQGLQTPIT FGQGTRLEIKR 3'

TABLE 27

2.10.2 Light chain V region domains.

| REGION | SEQUENCE | AA RESIDUES* | SEQ ID |
| --- | --- | --- | --- |
| FRI | DIVMTQSPLSLPVTPGEPASISC | 1-23 | SEQ ID NO: 84 |
| CDR1 | RSSQSLLHSNGYNYLD | 24-39 | SEQ ID NO: 85 |
| FR2 | WYLQKPGQSPQLLIY | 40-54 | SEQ ID NO: 86 |
| CDR2 | LGSNRAS | 55-61 | SEQ ID NO: 87 |
| FR3 | GVPDRFSGSGSGTDFTLKISRVEAEDVGVYYC | 62-93 | SEQ ID NO: 88 |
| CDR3 | MQGLQTPIT | 94-102 | SEQ ID NO: 89 |
| FR4 | FGQGTRLEIKR | 103-113 | SEQ ID NO: 90 |

*AA Residues of SEQ ID NO: 83

Antibody -2.15.1
Heavy chain variable region
Nucleotide sequence
(SEQ ID NO: 91)
5' CAGGTGCAGCTGGTGGAGTCTGGGGGAGGCGTGGTCCAGCCTGGGAGGTCCCTGAGACTC

TCCTGTGCAGCGTCTGGATTCACCTTCAGTAACTATGGCATTCACTGGGTCCGCCAGGCT

CCAGGCAAGGGGCTGGAGTGGGTGGCAGTTATATGGTTTGATGGACGTAATAAATACTAT

GCAGACTCCGTGAAGGGCCGATTCACCATCTCCAGAGACAATTCCAAGAACACGCTGTAT

CTGCAAATGAACAGCCTGAGAGCCGAGGACGCGGCTGTGTATTACTGTGCGAGAGATCCC

TTTGACTATGGTGACTCCTTCTTTGACTACTGGGGCCAGGGCACCCTGGTCACCGTCTCC

TCAGCC 3'

Amino acid sequence
(SEQ ID NO: 92)
5' QVQLVESGGGVVQPGRSLRLSCAAS GFTFSNYGIH WVRQAPGKGLEWVA VIWFDGRNKYY

ADSVKG RFTISRDNSKNTLYLQMNSLRAEDAAVYYCAR DPFDYGDSFFDY WGQGTLVTVSSA 3'

TABLE 28

2.15.1 Heavy chain V region domains.

| REGION | SEQUENCE | AA RESIDUES* | SEQ ID |
| --- | --- | --- | --- |
| FRI | QVQLVESGGGVVQPGRSLRLSCAAS | 1-25 | SEQ ID NO: 93 |
| CDR1 | GFTFSNYGIH | 26-35 | SEQ ID NO: 94 |

TABLE 28-continued

2.15.1 Heavy chain V region domains.

| REGION | SEQUENCE | AA RESIDUES* | SEQ ID |
|---|---|---|---|
| FR2 | WVRQAPGKGLEWVA | 36-49 | SEQ ID NO: 95 |
| CDR2 | VIWFDGRNKYYADSVKG | 50-66 | SEQ ID NO: 96 |
| FR3 | RFTISRDNSKNTLYLQMNSLRAEDAAVYYCAR | 67-98 | SEQ ID NO: 97 |
| CDR3 | DPFDYGDSFFDY | 99-110 | SEQ ID NO: 98 |
| FR4 | WGQGTLVTVSSA | 111-122 | SEQ ID NO: 99 |

*AA Residues of SEQ ID NO: 92

Light chain variable region
Nucleotide sequence
(SEQ ID NO: 100)
5' CTGACTCAGTCTCCATCCTCCCTGTCTGCATCTGTAAGAGACAGAGTCACCATCACTTGC

CGGGCGAGTCAGGACATTAGCAATTATTTAGCCTGGTATCAGCAGAAACCAGGGAAAGTT

CCTAATCTCCTGATCTATGCTGCATCCACTTTGCAATCAGGGGTCCCATCTCGGTTCAGT

GGCAGTGGATCTGGGACAGATTTCACTCTCACCATCAGCAGCCTGCAGCCTGAAGATGTT

GCAACTTATTACTGTCAAAAGTATAACAGTGCCCCGCTCACTTTCGGCGGAGGGACCAAG

GTGGAGATCAAACGA 3'

Amino acid sequence
(SEQ ID NO: 101)
5' LTQSPSSLSASVRDRVTITC RASQDISNYLA WYQQKPGKVPNLLIY AASTLQS GVPSRFS

GSGSGTDFTLTISSLQPEDVATYYC QKYNSAPLT FGGGTKVEIKR 3'

TABLE 29

2.15.1 Light chain V region domains.

| REGION | SEQUENCE | AA RESIDUES* | SEQ ID |
|---|---|---|---|
| FRI | LTQSPSSLSASVRDRVTITC | 1-20 | SEQ ID NO: 102 |
| CDR1 | RASQDISNYLA | 21-31 | SEQ ID NO: 103 |
| FR2 | WYQQKPGKVPNLLIY | 32-46 | SEQ ID NO: 104 |
| CDR2 | AASTLQ | 47-52 | SEQ ID NO: 105 |
| FR3 | GVPSRFSGSGSGTDFTLTISSLQPEDVATYYC | 53-84 | SEQ ID NO: 106 |
| CDR3 | QKYNSAPLT | 85-93 | SEQ ID NO: 107 |
| FR4 | FGGGTKVEIKR | 94-104 | SEQ ID NO: 108 |

*AA Residues of SEQ ID NO: 101

Antibody -2.16.1
Heavy chain variable region
Nucleotide sequence
(SEQ ID NO: 109)
5' CAGGTGCAGCTGGTGGAGTCTGGGGGAGGCTTGGTCAAGCCTGGAGGGTCCCTGAGACTC

TCCTGTGCAGCCTCTGGATTCACCTTCAGTGACTACTACATGACCTGGATCCGCCAGGCT

CCAGGGAAGGGGCTGGAGTGGGTTTCATACATTAGTATTAGTGGTAGTATCACACACTAC

GCAGACTCAGTGAAGGGCCGATTCACCATGTCCAGGGACAACGCCAAGAACTCACTGTAT

CTGCAAATGAACAGCCTGAGAGCCGAGGACACGGCCGTGTATTACTGTGCGAGAGACGGA

-continued

```
GCAGCAGCTGGTACGGATGCTTTTGATATCTGGGGCCACGGGACAAAGGTCACCGTCTCT

TCAGCC 3'
```

Amino acid sequence
(SEQ ID NO: 110)
```
5' QVQLVESGGGLVKPGGSLRLSCAAS GFTFSDYYMT WIRQAPGKGLEWVS YISISGSITHY

ADSVKG RFTMSRDNAKNSLYLQMNSLRAEDTAVYYCAR DGAAAGTDAFDI WGHGTKVTVSSA 3'
```

TABLE 30

2.16.1 Heavy chain V region domains.

| REGION | SEQUENCE | AA RESIDUES* | SEQ ID |
|---|---|---|---|
| FR1 | QVQLVESGGGLVKPGGSLRLSCAAS | 1-25 | SEQ ID NO: 111 |
| CDR1 | GFTFSDYYMT | 26-35 | SEQ ID NO: 112 |
| FR2 | WIRQAPGKGLEWVS | 36-49 | SEQ ID NO: 113 |
| CDR2 | YISISGSITHYADSVKG | 50-66 | SEQ ID NO: 114 |
| FR3 | RFTMSRDNAKNSLYLQMNSLRAEDTAVYYCAR | 67-98 | SEQ ID NO: 115 |
| CDR3 | DGAAAGTDAFDI | 99-110 | SEQ ID NO: 116 |
| FR4 | WGHGTKVTVSSA | 111-122 | SEQ ID NO: 117 |

*AA Residues of SEQ ID NO: 110

Light chain variable region
Nucleotide sequence
(SEQ ID NO: 118)
```
5'GAGATAGTGATGACGCAGTCTCCAGCCACCCTATCTGTGTCTCCAGGGGACAGAGCCACCCTCTCCTGCAGG

GCCAGTCAGAATGTTAGCAGCAACTTGGCCTGGTACCAGCAGAAACCTGGCCAGGCTCCCAGGCTCCTCATCTT

TGGTGCATCCACCAGGGCCACTGGTATCCCAGCCAGGTTCAGTGGCAGTGGGTCTGGGACAGAGTTCACTCTCA

CCATCAGCAGCCTACAGTCTGAAGATTTTGCAGTTTATTACTGTCAGCAGTATCATTACTGGCCCACTTTCGGC

CCTGGGACCAAAGTGGATATCAAACGA 3'
```
Amino acid sequence
(SEQ ID NO: 119)
```
5'EIVMTQSPATLSVSPGDRATLSC RASQNVSSNLA WYQQKPGQAPRLLIF GASTRAT

GIPARFSGSGSGTEFTLTISSLQSEDFAVYYC QQYHYWPT FGPGTKVDIKR 3'
```

TABLE 31

2.16.1 Light chain V region domains.

| REGION | SEQUENCE | AA RESIDUES* | SEQ ID |
|---|---|---|---|
| FR1 | EIVMTQSPATLSVSPGDRATLSC | 1-23 | SEQ ID NO: 120 |
| CDR1 | RASQNVSSNLA | 24-34 | SEQ ID NO: 121 |
| FR2 | WYQQKPGQAPRLLIF | 35-49 | SEQ ID NO: 122 |
| CDR2 | GASTRAT | 50-56 | SEQ ID NO: 123 |
| FR3 | GIPARFSGSGSGTEFTLTISSLQSEDFAVYYC | 57-88 | SEQ ID NO: 124 |
| CDR3 | QQYHYWPT | 89-96 | SEQ ID NO: 125 |
| FR4 | FGPGTKVDIKR | 97-107 | SEQ ID NO: 126 |

*AA Residues of SEQ ID NO: 119

Antibody -2.17.1
Heavy chain variable region
Nucleotide sequence
(SEQ ID NO: 127)

5' CAGCTGGTGCAGTCTGGGGCTGAGGTGAAGAAGCCTGGGGCCTCAGTGAAGGTCTCCTGC

AAGGCTTCTGGATACACCTTCACCGGCTTCTATATGCACTGGGTGCGACAGACCCCTGGA

CAAGGGCTTGAGTGGATGGGATGGATCAACCCTAACAGTGGTGGCACATATTATGTACAG

AAGTTTCAGGGCAGGGTCACCATGACCAGGGACACGTCCATCAGCACAGTCTACATGGAG

CTGAGCAGGTTGAGATCTGACGACACGGCCGTATATTACTGTGCGAGAGATGGGTATAGC

AGTGGAGAGGACTGGTTCGACCCCTGGGGCCAGGGAACCCTGGTCACCGTCTCCTCAGCC 3'

Amino acid sequence
(SEQ ID NO: 128)

5' QLVQSGAEVKKPGASVKVSCKAS GYTFTGFYMH WVRQTPGQGLEWMG WINPNSGGTYYVQ

KFQG RVTMTRDTSISTVYMELSRLRSDDTAVYYCAR DGYSSGEDWFDP WGQGTLVTVSSA 3'

TABLE 32

2.17.1 Heavy chain V region domains.

| REGION | SEQUENCE | AA RESIDUES* | SEQ ID |
|---|---|---|---|
| FR1 | QLVQSGAEVKKPGASVKVSCKAS | 1-23 | SEQ ID NO: 129 |
| CDR1 | GYTFTGFYMH | 24-33 | SEQ ID NO: 130 |
| FR2 | WVRQTPGQGLEWMG | 34-47 | SEQ ID NO: 131 |
| CDR2 | WINPNSGGTYYVQKFQG | 48-64 | SEQ ID NO: 132 |
| FR3 | RVTMTRDTSISTVYMELSRLRSDDTAVYYCAR | 65-96 | SEQ ID NO: 133 |
| CDR3 | DGYSSGEDWFDP | 97-108 | SEQ ID NO: 134 |
| FR4 | WGQGTLVTVSSA | 109-120 | SEQ ID NO: 135 |

*AA Residues of SEQ ID NO: 128

Light chain variable region
Nucleotide sequence
(SEQ ID NO: 136)

5'GATATTGTGATGACCCAGACTCCACTCTCTCTGTCCGTCACCCCTGGACAGCCGGCCTCCATCTCCTGCAAG

TCTAGTCAGAGCCTCCTGCATAGTGGTGGAAAGACCTATTTGTATTGGTACCTGCAGAGGCCAGGCCAGCCTCC

ACAGCTCCTGATCTATGAAGTTTCCAACCGGTTCTCTGGAGTGCCAGATAGGTTCAGTGGCAGCGGGTCAGGGA

CAGATTTCACACTGAAAATCAGCCGGGTGGAGGCTGAGGATGTTGGGGTTTATTACTGCATGCAAAGTATACAC

CTTCCGCTCACTTTCGGCGGAGGGACCAAGGTGGAGATCAAACGA 3'

Amino acid sequence
(SEQ ID NO: 137)

5'DIVMTQTPLSLSVTPGQPASISC KSSQSLLHSGGKTYLY WYLQRPGQPPQLLIY EVSNRFS

GVPDRFSGSGSGTDFTLKISRVEAEDVGVYYC MQSIHLPLT FGGGTKVEIKR 3'

TABLE 33

2.17.1 Light chain V region domains.

| REGION | SEQUENCE | AA RESIDUES* | SEQ ID |
|---|---|---|---|
| FR1 | DIVMTQTPLSLSVTPGQPASISC | 1-23 | SEQ ID NO: 138 |
| CDR1 | KSSQSLLHSGGKTYLY | 24-39 | SEQ ID NO: 139 |
| FR2 | WYLQRPGQPPQLLIY | 40-54 | SEQ ID NO: 140 |

TABLE 33-continued 2.17.1 Light chain V region domains.

| REGION | SEQUENCE | AA RESIDUES* | SEQ ID |
|---|---|---|---|
| CDR2 | EVSNRFS | 55-61 | SEQ ID NO: 141 |
| FR3 | GVPDRFSGSGSGTDFTLKISRVEAEDVGVYYC | 62-93 | SEQ ID NO: 142 |
| CDR3 | MQSIHLPLT | 94-102 | SEQ ID NO: 143 |
| FR4 | FGGGTKVEIKR | 103-113 | SEQ ID NO: 144 |

*AA Residues of SEQ ID NO: 137

```
Antibody -2.21.1
Heavy chain variable region
Nucleotide sequence
                                                          (SEQ ID NO: 145)
5' CAGGTGCAGCTGGAGCAGTCGGGGGGAGGCCTGGTCAAGCCTGGGGGGTCCCTGAGATTC

TCCTGTGCAGCCTCTGGATTCACCTTCAGTAGCTATAGCATGAACTGGGTCCGCCAGGCT

CCAGGGAAGGGGCTGGAGTGGGTCTCATTCATTAGTAGTAGTAGTAGTTACATATACTAC

GCAGACTCAGTGAAGGGCCGATTCACCATCTCCAGAGACAACGCCAAGAACTCACTGTAT

CTGCAAATGAACAGCCTGAGAGCCGAGGACACGGCTGTGTATTACTGTGCGAGAGAGGAC

TGGGTGGGAGCTACCTTTGACTACTGGGGCCAGGGAACCCTGGTCACCGTCTCCTCAGCC 3'

Amino acid sequence
                                                          (SEQ ID NO: 146)
5' QVQLEQSGGGLVKPGGSLRFSCAAS GFTFSSYSMN WVRQAPGKGLEWVS FISSSSSYIYY

ADSVKG RFTISRDNAKNSLYLQMNSLRAEDTAVYYCAR EDWVGATFDY WGQGTLVTVSSA 3'
```

TABLE 34

2.21.1 Heavy chain V region domains.

| REGION | SEQUENCE | AA RESIDUES* | SEQ ID |
|---|---|---|---|
| FR1 | QVQLEQSGGGLVKPGGSLRFSCAAS | 1-25 | SEQ ID NO: 147 |
| CDR1 | GFTFSSYSMN | 26-35 | SEQ ID NO: 148 |
| FR2 | WVRQAPGKGLEWVS | 36-49 | SEQ ID NO: 149 |
| CDR2 | FISSSSSYIYYADSVKG | 50-66 | SEQ ID NO: 150 |
| FR3 | RFTISRDNAKNSLYLQMNSLRAEDTAVYYCAR | 67-98 | SEQ ID NO: 151 |
| CDR3 | EDWVGATFDY | 99-108 | SEQ ID NO: 152 |
| FR4 | WGQGTLVTVSSA | 109-120 | SEQ ID NO: 153 |

*AA Residues of SEQ ID NO: 146

```
Light chain variable region
Nucleotide sequence
                                                          (SEQ ID NO: 154)
5' GACATTCAGCTGACCCAGTCTCCATCCTCCCTGTCTGCATCTGTAGGAGACAGAGTCACC

ATCACTTGTCGGGCGAGTCAGGGCATTAGGAATTATTTAGCCTGGTATCAGCAGAAACCA

GGGAAAGTTCCTAAGCTCCTGATCTATGCTGCTTCCGCTTTGAAATTAGGGGTCCCATCT

CGGTTCAGTGGCAGTGGATCTGGGACAGATTTCACTCTCACCATCAGCAGCCTGCAGCCT

GAAGATGTTGCAACTTATTACTGTCAAAAGTATAACAGTGCCCCGATCACCTTCGGCCAA

GGGACACGACTGGACATTAAACGA 3'
```

-continued

Amino acid sequence
(SEQ ID NO: 155)
5' DIQLTQSPSSLSASVGDRVTITC RASQGIRNYLA WYQQKPGKVPKLLIY AASALKL GVPS

RFSGSGSGTDFTLTISSLQPEDVATYYC QKYNSAPIT FGQGTRLDIKR 3'

TABLE 35

2.21.1 Light chain V region domains.

| REGION | SEQUENCE | AA RESIDUES* | SEQ ID |
|---|---|---|---|
| FR1 | DIQLTQSPSSLSASVGDRVTITC | 1-23 | SEQ ID NO: 156 |
| CDR1 | RASQGIRNYLA | 24-34 | SEQ ID NO: 157 |
| FR2 | WYQQKPGKVPKLLIY | 35-49 | SEQ ID NO: 158 |
| CDR2 | AASALKL | 50-56 | SEQ ID NO: 159 |
| FR3 | GVPSRFSGSGSGTDFTLTISSLQPEDVATYYC | 57-88 | SEQ ID NO: 160 |
| CDR3 | QKYNSAPIT | 89-97 | SEQ ID NO: 161 |
| FR4 | FGQGTRLDIKR | 98-108 | SEQ ID NO: 162 |

*AA Residues of SEQ ID NO: 155

Antibody -2.22.1
Heavy chain variable region
Nucleotide sequence
(SEQ ID NO: 163)
5' CAGGTGCAGCTGGAGCAGTCGGGCCCAGGACTGGTGAAGCCTTCACAGAACCTGTCCCTC

ACCTGCACTGTCTCTGGTGGCTCCATCAGCAGTGGTGGTTATTTCTGGAGCTGGATCCGC

CAGCACCCAGGGAAGGGCCTGGAGTGGATTGGGTACATCTATTACAGTGGGAACACCTAC

TACAACCCGTCCCTCAAGAGTCGAGTTACCATATCAGTTGACACGTCTAAGAACCAGTTC

TCCCTGAAACTGAGCTCTGTGACTGCCGCGGACACGGCCGTGTATTACTGTGCGAGAGAC

TATTACTATGATACTAGTGGTTTTTCCTACCGTTACGACTGGTACTACGGTATGGACGTC

TGGGGCCAAGGGACCACGGTCACCGTCTCCTCAGCC 3'

Amino acid sequence
(SEQ ID NO: 164)
5' QVQLEQSGPGLVKPSQNLSLTCTVS GGSISSGGYFWS WIRQHPGKGLEWIG YIYYSGNTY

YNPSLKS RVTISVDTSKNQFSLKLSSVTAADTAVYYCAR DYYYDTSGFSYRYDWYYGMDV

WGQGTTVTVSSA 3'

TABLE 36

2.22.1 Heavy chain V region domains.

| REGION | SEQUENCE | AA RESIDUES* | SEQ ID |
|---|---|---|---|
| FR1 | QVQLEQSGPGLVKPSQNLSLTCTVS | 1-25 | SEQ ID NO: 165 |
| CDR1 | GGSISSGGYFWS | 26-37 | SEQ ID NO: 166 |
| FR2 | WIRQHPGKGLEWIG | 38-51 | SEQ ID NO: 167 |
| CDR2 | YIYYSGNTYYNPSLKS | 52-67 | SEQ ID NO: 168 |
| FR3 | RVTISVDTSKNQFSLKLSSVTAADTAVYYCAR | 68-99 | SEQ ID NO: 169 |
| CDR3 | DYYYDTSGFSYRYDWYYGMDV | 100-120 | SEQ ID NO: 170 |
| FR4 | WGQGTTVTVSSA | 121-132 | SEQ ID NO: 171 |

*AA Residues of SEQ ID NO: 164

Light chain variable region
Nucleotide sequence
(SEQ ID NO: 172)
5' GACATCCAGCTGACCCAGTCTCCATCCTCCCTGTCTGCATCTGTAGGAGACAGAGTCACC

ATCACTTGCCGGGCAAGTCAGGGCATTAGAAATGATTTAGGCTGGTATCAGCAGAAACCA

GGGAAAGCCCCTAAGCGCCTGATCTATGCTGCATCCAGTTTGCAAAATGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAACATAATACTTACCCGGCGTTCGGCCAAGGG

ACCAAGGTGGAAATCAAACGA 3'

Amino acid sequence
(SEQ ID NO: 173)
5' DIQLTQSPSSLSASVGDRVTITC RASQGIRNDLG WYQQKPGKAPKRLIY AASSLQN GVPS

RFSGSGSGTEFTLTISSLQPEDFATYYC LQHNTYPA FGQGTKVEIKR 3'

TABLE 37

2.22.1 Light chain V region domains.

| REGION | SEQUENCE | AA RESIDUES* | SEQ ID |
|---|---|---|---|
| FRI | DIQLTQSPSSLSASVGDRVTITC | 1-23 | SEQ ID NO: 174 |
| CDR1 | RASQGIRNDLG | 24-34 | SEQ ID NO: 175 |
| FR2 | WYQQKPGKAPKRLIY | 35-49 | SEQ ID NO: 176 |
| CDR2 | AASSLQN | 50-56 | SEQ ID NO: 177 |
| FR3 | GVPSRFSGSGSGTEFTLTISSLQPEDFATYYC | 57-88 | SEQ ID NO: 178 |
| CDR3 | LQHNTYPA | 89-97 | SEQ ID NO: 179 |
| FR4 | FGQGTKVEIKR | 98-108 | SEQ ID NO: 180 |

*AA Residues of SEQ ID NO: 173

Antibody - 2.24.1
Heavy chain variable region
Nucleotide sequence
(SEQ ID NO: 181)
5' CAGCTGGTGCAGTCTGGAGCAGAAGTGAAAAAGCCCGGGGAGTCTCTGAAGATCTCCTGT

CAGGGTTCTGGATACATCTTTACCAACTACTGGATCGGCTGGGTGCGCCAGATGCCCGGG

AAAGGCCTGGAGTGGATGGGGGTCATCTATCCTGATGACTCTGATACCAGATACAGCCCG

TCCTTCCAAGGCCAGGTCACCATCTCAGCCGACAAGTCCATCAGCACCGCCTACCTGCAG

TGGAGCAGCCTGAAGGCCTCGGACACCGCCATATATTACTGTGCGAGACAAAAATGGCTA

CAACACCCCTTTGACTACTGGGGCCAGGGAACCCTGGTCACCGTCTCCTCAGCC 3'

Amino acid sequence
(SEQ ID NO: 182)
5' QLVQSGAEVKKPGESLKISCQGS GYIFTNYWIG WVRQMPGKGLEWMG VIYPDDSDTRYSP

SFQG QVTISADKSISTAYLQWSSLKASDTAIYYCAR QKWLQHPFDY WGQGTLVTVSSA 3'

TABLE 38

2.24.1 Heavy chain V region domains.

| REGION | SEQUENCE | AA RESIDUES* | SEQ ID |
|---|---|---|---|
| FRI | QLVQSGAEVKKPGESLKISCQGS | 1-23 | SEQ ID NO: 183 |
| CDR1 | GYIFTNYWIG | 24-33 | SEQ ID NO: 184 |

TABLE 38-continued 2.24.1 Heavy chain V region domains.

| REGION | SEQUENCE | AA RESIDUES* | SEQ ID |
|---|---|---|---|
| FR2 | WVRQMPGKGLEWMG | 34-47 | SEQ ID NO: 185 |
| CDR2 | VIYPDDSDTRYSPSFQG | 48-64 | SEQ ID NO: 186 |
| FR3 | QVTISADKSISTAYLQWSSLKASDTAIYYCAR | 65-96 | SEQ ID NO: 187 |
| CDR3 | QKWLQHPFDY | 97-106 | SEQ ID NO: 188 |
| FR4 | WGQGTLVTVSSA | 107-118 | SEQ ID NO: 189 |

*AA Residues of SEQ ID NO: 182

Light chain variable region
Nucleotide sequence
(SEQ ID NO: 190)
5' GAAATTGTGTTGACGCAGTCACCAGGCACCCTGTCTTTGTCTCCAGGGGAAAGAGTCACC

CTCTCATGCAGGGCCAGTCAGAGTGTTAGCAGCAGATACTTAGCCTGGTACCAGCAGAAA

CCTGGCCAGGCTCCCAGGCTCCTCATCTATGGTGCATCCAGCAGGGCCACTGGCATCCCA

GACAGGTTCAGTGGCAGTGGGTCTGGGACAGACTTCACTCTCACCATCAGCAGACTGGAG

CCTGAAGATTTTGCAGTTTATTACTGTCAGCAGTATGGTAGCTCACCTCGGACGTTCGGC

CAAGGGACCAAGGTGGAAATCAAACGA 3'

Amino acid sequence
(SEQ ID NO: 191)
5' EIVLTQSPGTLSLSPGERVTLSC RASQSVSSRYLA WYQQKPGQAPRLLIY GASSRAT GIP

DRFSGSGSGTDFTLTISRLEPEDFAVYYC QQYGSSPRT FGQGTKVEIKR 3'

TABLE 39

2.24.1 Light chain V region domains.

| REGION | SEQUENCE | AA RESIDUES* | SEQ ID |
|---|---|---|---|
| FR1 | EIVLTQSPGTLSLSPGERVTLSC | 1-23 | SEQ ID NO: 192 |
| CDR1 | RASQSVSSRYLA | 24-35 | SEQ ID NO: 193 |
| FR2 | WYQQKPGQAPRLLIY | 36-50 | SEQ ID NO: 194 |
| CDR2 | GASSRAT | 51-57 | SEQ ID NO: 195 |
| FR3 | GIPDRFSGSGSGTDFTLTISRLEPEDFAVYY | 58-88 | SEQ ID NO: 196 |
| CDR3 | QQYGSSPRT | 89-97 | SEQ ID NO: 197 |
| FR4 | FGQGTKVEIKR | 98-109 | SEQ ID NO: 198 |

*AA Residues of SEQ ID NO: 191

Antibody -2.3.1
Heavy chain variable region
Nucleotide sequence
(SEQ ID NO: 199)
5'CAGGTGCAGCTGGTGCAGTCTGGGGCTGAGGTGAAGAAGCCTGGGGCCTCAGTGAAGGTCTCC

TGCAAGGCTTCTGGATACACCTTCACCGGCTACTATATGCACTGGGTGCGACAGGCCCCTGGACA

AGGGCTTGAGTGGATGGGATGGATCAACCCTAACAGTGGTGGCACAAACTATGCACAGAAGTTT

CAGGACAGGGTCACCATGACCAGGGACACGTCCATCAGCACAGCCTACATGGAGCTGAGCAGGC

-continued
TGAGATCTGACGACACGGCCGTGTATTACTGTGCGAGAGATTTCTTTGGTTCGGGGAGTCTCCTC

TACTTTGACTACTGGGGCCAGGGAACCCTGGTCACCGTCTCCTCAGCC 3'

Amino acid sequence
(SEQ ID NO: 200)
5'QVQLVQSGAEVKKPGASVKVSCKASGYTFTGYYMHWVRQAPGQGLEWMGWINPNSGGTNYAQKFQD

RVTMTRDTSISTAYMELSRLRSDDTAVYYCARDFFGSGSLLYFDYWGQGTLVTVSSA 3'

TABLE 40

2.3.1 Heavy chain V region domains.

| REGION | SEQUENCE | AA RESIDUES* | SEQ ID |
|---|---|---|---|
| FR1 | QVQLVQSGAEVKKPGASVKVSCKAS | 1-25 | SEQ ID NO: 201 |
| CDR1 | GYTFTGYYMH | 26-35 | SEQ ID NO: 202 |
| FR2 | WVRQAPGQGLEWMG | 36-49 | SEQ ID NO: 203 |
| CDR2 | WINPNSGGTNYAQKFQD | 50-66 | SEQ ID NO: 204 |
| FR3 | RVTMTRDTSISTAYMELSRLRSDDTAVYYCAR | 67-98 | SEQ ID NO: 205 |
| CDR3 | DFFGSGSLLYFDY | 99-111 | SEQ ID NO: 206 |
| FR4 | WGQGTLVTVSSA | 112-123 | SEQ ID NO: 207 |

*AA Residues of SEQ ID NO: 200

Light chain variable region
Nucleotide sequence
(SEQ ID NO: 208)
5'GATATTGTGATGACCCAGACTCCACTCTCTCTGTCCGTCACCCCTGGACAGCCGGCCTCCATCTCCTGCAAG

TCTAGTCAGAGCCTCCTGCATAGTGGTGGAAAGACCTATTTGTATTGGTACCTGCAGAGGCCAGGCCAGCCTCC

ACAGCTCCTGATCTATGAAGTTTCCAACCGGTTCTCTGGAGTGCCAGATAGGTTCAGTGGCAGCGGGTCAGGGA

CAGATTTCACACTGAAAATCAGCCGGGTGGAGGCTGAGGATGTTGGGGTTTATTACTGCATGCAAAGTATACAC

CTTCCGCTCACTTTCGGCGGAGGGACCAAGGTGGAGATCAAACGA 3'
Amino acid sequence
(SEQ ID NO: 209)
5'DIVMTQTPLSLSVTPGQPASISC KSSQSLLHSGGKTYLY WYLQRPGQPPQLLIY EVSNRFS

GVPDRFSGSGSGTDFTLKISRVEAEDVGVYYC MQSIHLPLT FGGGTKVEIKR 3'

TABLE 41

2.3.1 Light chain V region domains.

| REGION | SEQUENCE | AA RESIDUES* | SEQ ID |
|---|---|---|---|
| FR1 | DIVMTQTPLSLSVTPGQPASISC | 1-23 | SEQ ID NO: 210 |
| CDR1 | KSSQSLLHSGGKTYLY | 24-39 | SEQ ID NO: 211 |
| FR2 | WYLQRPGQPPQLLIY | 40-54 | SEQ ID NO: 212 |
| CDR2 | EVSNRFS | 55-61 | SEQ ID NO: 213 |
| FR3 | GVPDRFSGSGSGTDFTLKISRVEAEDVGVYYC | 62-93 | SEQ ID NO: 214 |

TABLE 41-continued 2.3.1 Light chain V region domains.

| REGION | SEQUENCE | AA RESIDUES* | SEQ ID |
|---|---|---|---|
| CDR3 | MQSIHLPLT | 94-102 | SEQ ID NO: 215 |
| FR4 | FGGGTKVEIKR | 103-113 | SEQ ID NO: 216 |

*AA Residues of SEQ ID NO: 209

Antibody -2.6.1
Heavy chain variable region
Nucleotide sequence
(SEQ ID NO: 309)

5'CAGGTGCAGCTGGTGCAGTCTGGGGCTGAGGTGAAGAAGCCTGGGGCCTCAGTGAAGGTCTCC

TGCAAGGCTTCTGGATACACCTTCACCGGCTACTATATGCACTGGGTGCGACAGGCCCCTGGACA

AGGGCTTGAGTGGATGGGATGGATCAACCCTAACAGTGGTGGCACAAACTATGCACAGAAGTTT

CAGGACAGGGTCACCATGACCAGGGACACGTCCATCAGCACAGCCTACATGGAGCTGAGCAGGC

TGAGATCTGACGACACGGCCGTGTATTACTGTGCGAGAGATTTCTTTGGTTCGGGGAGTCTCCTC

TACTTTGACTACTGGGGCCAGGGAACCCTGGTCACCGTCTCCTCAGCC 3'

Amino acid sequence
(SEQ ID NO: 310)
5'QVQLVQSGAEVKKPGASVKVSCKAS GYTFTGYYMH WVRQAPGQGLEWMG WINPNSGGTNYAQKFQD

RVTMTRDTSISTAYMELSRLRSDDTAVYYCAR DFFGSGSLLYFDY WGQGTLVTVSSA 3'

TABLE 42

2.6.1 Heavy chain V region domains.

| REGION | SEQUENCE | AA RESIDUES* | SEQ ID |
|---|---|---|---|
| FR1 | QVQLVQSGAEVKKPGASVKVSCKAS | 1-25 | 311 |
| CDR1 | GYTFTGYYMH | 26-35 | 312 |
| FR2 | WVRQAPGQGLEWMG | 36-49 | 313 |
| CDR2 | WINPNSGGTNYAQKFQD | 50-66 | 314 |

TABLE 42-continued 2.6.1 Heavy chain V region domains.

| REGION | SEQUENCE | AA RESIDUES* | SEQ ID |
|---|---|---|---|
| FR3 | RVTMTRDTSISTAYMELSRLRSDDTAVYYCAR | 67-98 | 315 |
| CDR3 | DFFGSGSLLYFDY | 99-112 | 316 |
| FR4 | WGQGTLVTVSSA | 113-124 | 317 |

*AA Residues of SEQ ID NO: 310

Light chain variable region
Nucleotide sequence
(SEQ ID NO: 318)

5'GATATTGTGATGACCCAGACTCCACTCTCTCTGTCCGTCACCCCTGGACAGCCGGCCTCCATCTCCTGCAAG

TCTAGTCAGAGCCTCCTGCATAGTGGTGGAAAGACCTATTTGTATTGGTACCTGCAGAGGCCAGGCCAGCCTCC

ACAGCTCCTGATCTATGAAGTTTCCAACCGGTTCTCTGGAGTGCCAGATAGGTTCAGTGGCAGCGGGTCAGGGA

CAGATTTCACACTGAAAATCAGCCGGGTGGAGGCTGAGGATGTTGGGGTTTATTACTGCATGCAAAGTATACAC

CTTCCGCTCACTTTCGGCGGAGGGACCAAGGTGGAGATCAAACGA 3'

Amino acid sequence
(SEQ ID NO: 319)
5'DIVMTQTPLSLSVTPGQPASISC KSSQSLLHSGGKTYLY WYLQRPGQPPQLLIY EVSNRFS

GVPDRFSGSGSGTDFTLKISRVEAEDVGVYYC MQSIHLPLT FGGGTKVEIKR 3'

TABLE 43

2.6.1 Light chain V region domains.

| REGION | SEQUENCE | AA RESIDUES* | SEQ ID |
|---|---|---|---|
| FR1 | DIVMTQTPLSLSVTPGQPASISC | 1-23 | 320 |
| CDR1 | KSSQSLLHSGGKTYLY | 24-39 | 321 |
| FR2 | WYLQRPGQPPQLLIY | 40-54 | 322 |
| CDR2 | EVSNRFS | 55-61 | 323 |
| FR3 | GVPDRFSGSGSGTDFTLKISRVEAEDVGVYYC | 62-93 | 324 |
| CDR3 | MQSIHLPLT | 94-102 | 325 |
| FR4 | FGGGTKVEIKR | 103-113 | 326 |

*AA Residues of SEQ ID NO: 319

Antibody -2.7.1
Heavy chain variable region
Nucleotide sequence (SEQ ID NO: 217)
5' CAGGTGCAGCTGGAGCAGTCGGGGGGAGGCGTGGTCCAGCCTGGGAGGTCCCTGAGACTC
TCCTGTGCAGCGTCTGGATTCACCTTCAATAACTATGGCATGCACTGGGTCCGCCAGGCT
CCAGGCAAGGGGCTGGAGTGGGTGGCAGTTATATGGTATGATGGAAGTAATAAATACTAT
GCAGACTCCGTGAAGGGCCGATTCACCATCTCCAGAGACAATTCCAAGAACACGCTGTAT
CTGCAAATGAACAGCCTGAGAGCCGAGGACACGGCTGTGTATTACTGTGCGAAAGATGAG
GAATACTACTATGTTTCGGGGCTTGACTACTGGGGCCAGGGAACCCTGGTCACCGTCTCC
TCAGCC 3'

Amino acid sequence (SEQ ID NO: 218)
5' QVQLEQSGGGVVQPGRSLRLSCAAS GFTFNNYGMH WVRQAPGKGLEWVA VIWYDGSNKYY
ADSVKG RFTISRDNSKNTLYLQMNSLRAEDTAVYYCAK DEEYYYVSGLDY WGQGTLVTVSSA 3'

TABLE 44

2.7.1 Heavy chain V region domains.

| REGION | SEQUENCE | AA RESIDUES* | SEQ ID |
|---|---|---|---|
| FR1 | QVQLEQSGGGVVQPGRSLRLSCAAS | 1-25 | SEQ ID NO: 219 |
| CDR1 | GFTFNNYGMH | 26-35 | SEQ ID NO: 220 |
| FR2 | WVRQAPGKGLEWVA | 36-49 | SEQ ID NO: 221 |
| CDR2 | VIWYDGSNKYYADSVKG | 50-66 | SEQ ID NO: 222 |
| FR3 | RFTISRDNSKNTLYLQMNSLRAEDTAVYYCAK | 67-98 | SEQ ID NO: 223 |
| CDR3 | DEEYYYVSGLDY | 99-110 | SEQ ID NO: 224 |
| FR4 | WGQGTLVTVSSA | 111-122 | SEQ ID NO: 225 |

*AA Residues of SEQ ID NO: 218

Light chain variable region
Nucleotide sequence (SEQ ID NO: 226)
5' CTGACTCAGTCTCCATCCTCCCTGTCTGCATCTGTAAGAGACAGAGTCACCATCACTTGC
CGGGCGAGTCAGGACATTAGCAATTATTTAGCCTGGTATCAGCAGAAACCAGGGAAAGTT
CCTAATCTCCTGATCTATGCTGCATCCACTTTGCAATCAGGGGTCCCATCTCGGTTCAGT
GGCAGTGGATCTGGGACAGATTTCACTCTCACCATCAGCAGCCTGCAGCCTGAAGATGTT -continued

```
GCAACTTATTACTGTCAAAAGTATAACAGTGCCCCGCTCACTTTCGGCGGAGGGACCAAG

GTGGAGATCAAACGA 3'
```

Amino acid sequence (SEQ ID NO: 227)

```
5' LTQSPSSLSASVRDRVTITC RASQDISNYLA WYQQKPGKVPNLLIY AASTLQS GVPSRFS

GSGSGTDFTLTISSLQPEDVATYYC QKYNSAPLT FGGGTKVEIKR 3'
```

TABLE 45

2.7.1 Light chain V region domains.

| REGION | SEQUENCE | AA RESIDUES* | SEQ ID |
|---|---|---|---|
| FRI | LTQSPSSLSASVRDRVTITC | 1-20 | SEQ ID NO: 228 |
| CDR1 | RASQDISNYLA | 21-31 | SEQ ID NO: 229 |
| FR2 | WYQQKPGKVPNLLIY | 32-46 | SEQ ID NO: 230 |
| CDR2 | AASTLQ | 47-52 | SEQ ID NO: 231 |
| FR3 | GVPSRFSGSGSGTDFTLTISSLQPEDVATYYC | 53-84 | SEQ ID NO: 232 |
| CDR3 | QKYNSAPLT | 85-93 | SEQ ID NO: 233 |
| FR4 | FGGGTKVEIKR | 94-104 | SEQ ID NO: 234 |

*AA Residues of SEQ ID NO: 227

Antibody - 2.8.1
Heavy chain variable region
Nucleotide sequence (SEQ ID NO: 235)

```
5' CAGATCACCTTGAAGGAGTCTGGTCCTACGCTGGTGACACCCACACAGACCCTCACGCTG

ACCTGCACCTTCTCTGGGTTCTCACTCAGCACTGGTGGAATGGGTGTGGGCTGGATCCGT

CAGCCCCCAGGAAAGGCCCTGGACTGGCTTACACTCATTTATTGGAATGATGATAAGCAC

TACAGCCCATCTCTGAAGAGCAGGCTTACCATCACCAAGGACACCTCCAAAAACCAGGTG

GTCCTTAGAATGACCAACATGGACCCTGTGGACACAGCCACTTATTACTGTGCACACCTG

CATTACGATATTTTGACTGGTTTTAACTTTGACTACTGGGGCCAGGGAACCCTGGTCACC

GTCTCCTCAGCC 3'
```

Amino acid sequence (SEQ ID NO: 236)

```
5' QITLKESGPTLVTPTQTLTLTCTFS GFSLSTGGMGVG WIRQPPGKALDWLT LIYWNDDKH

YSPSLKS RLTITKDTSKNQVVLRMTNMDPVDTATYYCAH LHYDILTGFNFDY WGQGTLVTVSSA 3'
```

TABLE 46

2.8.1 Heavy chain V region domains.

| REGION | SEQUENCE | AA RESIDUES* | SEQ ID |
|---|---|---|---|
| FRI | QITLKESGPTLVTPTQTLTLTCTFS | 1-25 | SEQ ID NO: 237 |
| CDR1 | GFSLSTGGMGVG | 26-37 | SEQ ID NO: 238 |
| FR2 | WIRQPPGKALDWLT | 38-51 | SEQ ID NO: 239 |
| CDR2 | LIYWNDDKHYSPSLKS | 52-67 | SEQ ID NO: 240 |
| FR3 | RLTITKDTSKNQVVLRMTNMDPVDTATYYCAH | 68-99 | SEQ ID NO: 241 |

TABLE 46-continued

2.8.1 Heavy chain V region domains.

| REGION | SEQUENCE | AA RESIDUES* | SEQ ID |
|---|---|---|---|
| CDR3 | LHYDILTGFNFDY | 100-112 | SEQ ID NO: 242 |
| FR4 | WGQGTLVTVSSA | 113-124 | SEQ ID NO: 243 |

*AA Residues of SEQ ID NO: 236

Light chain variable region
Nucleotide sequence
(SEQ ID NO: 244)
5'GATATTGTGATGACCCAGACTCCACTCTCCCTGCCCGTCACCCCTGGAGAGCCGGCCTCCATCTCCTGCAGG

TCTAGTCAGAGCCTCTTGGATAGTGATGATGGAAACACCTATTTGGACTGGTACCTGCAGAAGCCAGGGCAGTC

TCCACAGCTCCTGATCTATACGCTTTCCTATCGGGCCTCTGGAGTCCCAGACAGGTTCAGTGGCAGTGGGTCAG

GCACTGATTTCACACTGAAAATCAGCAGGGTGGAGGCTGAGGATGTTGGAGTTTATTACTGCATGCAACGTATA

GAGTTTCCGCTCACTTTCGGCGGAGGGACCAAGGTGGAGATCAAACGA 3'

Amino acid sequence
(SEQ ID NO: 245)
5'DIVMTQTPLSLPVTPGEPASISC RSSQSLLDSDDGNTYLD WYLQKPGQSPQLLIY TLSYRAS

GVPDRFSGSGSGTDFTLKISRVEAEDVGVYYC MQRIEFPLT FGGGTKVEIKR 3'

TABLE 47

2.8.1 Light chain V region domains.

| REGION | SEQUENCE | AA RESIDUES* | SEQ ID |
|---|---|---|---|
| FRI | DIVMTQTPLSLPVTPGEPASISC | 1-23 | SEQ ID NO: 246 |
| CDR1 | RSSQSLLDSDDGNTYLD | 24-40 | SEQ ID NO: 247 |
| FR2 | WYLQKPGQSPQLLIY | 41-55 | SEQ ID NO: 248 |
| CDR2 | TLSYRAS | 56-62 | SEQ ID NO: 249 |
| FR3 | GVPDRFSGSGSGTDFTLKISRVEAEDVGVYYC | 63-94 | SEQ ID NO: 250 |
| CDR3 | MQRIEFPLT | 95-103 | SEQ ID NO: 251 |
| FR4 | FGGGTKVEIKR | 103-114 | SEQ ID NO: 252 |

*AA Residues of SEQ ID NO: 245

Example 16

Use of anti-GPNMB Antibodies as a Diagnostic Agent

Detection of GPNMB antigen in a sample:

The following is a protocol for an Enzyme-Linked Immunosorbent Assay (ELISA) for the detection of GPNMB antigen in a sample. In the assay, wells of a microtiter plate, such as a 96-well microtiter plate or a 384-well microtiter plate, are adsorbed for several hours with a first fully human monoclonal antibody directed against GPNMB. The immobilized antibody serves as a capture antibody for any of the GPNMB that may be present in a test sample. The wells are rinsed and treated with a blocking agent such as milk protein or albumin to prevent nonspecific adsorption of the analyte.

Subsequently the wells are treated with a test sample suspected of containing the GPNMB antigen, or with a solution containing a standard amount of GPNMB antigen. Such a sample may be, for example, a serum sample from a subject suspected of having levels of circulating GPNMB considered to be diagnostic of a pathology.

After rinsing away the test sample or standard, the wells are treated with a second fully human monoclonal anti-GPNMB antibody that is labeled by conjugation with biotin. The labeled anti-GPNMB antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the GPNMB antigen in a test sample.

Determination of GPNMB Antigen Concentration in Patients:

A sandwich ELISA can also be used to quantify GPNMB levels in human serum. The 2 fully human monoclonal anti- GPNMB antibodies used in the sandwich ELISA, recognize different epitopes on the GPNMB molecule. The ELISA is performed as follows: 50 μl of capture anti-GPNMB antibody in coating buffer (0.1 M NaHCO$_3$, pH 9.6) at a concentration of 2 μg/mL is coated on ELISA plates (Fisher). After incubation at 4° C. overnight, the plates are treated with 200 μl of blocking buffer (0.5% BSA, 0.1% Tween 20, 0.01% Thimerosal in PBS) for 1 hr at 25° C. The plates are washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 μl/well of biotinylated detection anti-GPNMB antibody for 1 hr at 25° C. After washing, the plates are incubated with HRP-Streptavidin for 15 min, washed as before, and then treated with 100 μl/well of o-phenylenediamine in H$_2$O$_2$ (Sigma developing solution) for color generation. The reaction is stopped with 50 μl/well of H$_2$SO$_4$ (2M) and analyzed using an ELISA plate reader at 492 nm. Concentration of GPNMB antigen in serum samples is calculated by comparison to dilutions of purified GPNMB antigen using a four parameter curve fitting program.

Staging of Cancer in a Patient:

It will be appreciated that based on the results set forth and discussed in the above diagnostic examples, it is possible to stage a cancer in a subject based on expression levels of the GPNMB antigen. For a given type of cancer (e.g., melanoma), samples of blood are taken from subjects diagnosed as being at various stages in the progression of the disease, and/or at various points in the therapeutic treatment of the cancer. The concentration of the GPNMB antigen present in the blood samples is determined using a method that specifically determines the amount of the antigen that is present. Such a method includes an ELISA method, such as the method described in the previous diagnostic examples. Using a population of samples that provides statistically significant results for each stage of progression or therapy, a range of concentrations of the antigen that may be considered characteristic of each stage is designated.

In order to stage the progression of the cancer in a subject under study, or to characterize the response of the subject to a course of therapy, a sample of blood is taken from the subject and the concentration of the GPNMB antigen present in the sample is determined The concentration so obtained is used to identify in which range of concentrations the value falls. The range so identified correlates with a stage of progression or a stage of therapy identified in the various populations of diagnosed subjects, thereby providing a stage in the subject under study.

Example 17

Diagnosing Cancer with Antibodies Against GPNMB

A subject suspected of having an ovarian cancer tumor is identified and a tissue sample from the suspected tumor is removed for testing. The removed tissue is then contacted with anti-GPNMB antibodies having a colorimetric label. A determination is made of whether the anti-GPNMB antibodies bind specifically to the removed tissue. Binding is indicative of cancerous tissue while the absence of binding is indicative of non-cancerous tissue. The patient's conditition is diagnosed accordingly to facilitate subsequent testing, counseling, and/or treatment.

Example 18

Treating Cancer with Antibodies Against GPNMB

Targeting GPNMB on tumor cells is useful to treat a subject at risk for or afflicted with cancer. Such a subject would benefit from treatment with an anti-GPNMB antibody of the present invention. Typically, antibodies are administered in an outpatient setting by weekly administration at about 0.1-1.0 mg/kg dose by slow intravenous (IV) infusion. The appropriate therapeutically effective dose of an antibody is selected by a treating clinician and would range approximately from 1 μg/kg to 20 mg/kg, from 1 μg/kg to 10 mg/kg, from 1 μg/kg to 1 mg/kg, from 10 μg/kg to 1 mg/kg, from 10 μg/kg to 100 μg/kg, from 100 μg/kg to 1 mg/kg, and from 500 μg/kg to 5 mg/kg.

The antibodies are also used to prevent and/or to reduce severity and/or symptoms of disease associated with GPNMB-related disorders.

To test the clinical efficacy of antibodies in humans, individuals with cancer, particularly, but not limited to ovarian, lung or colon carcinoma are identified and randomized into treatment groups. Treatment groups include a group not receiving antibody treatment and groups treated with different doses of anti-GPNMB antibody. Individuals are followed prospectively and individuals receiving antibody treatment exhibit an improvement in their condition.

Example 19

The Specificity of the Anti-tumor Effects of CR011-vcMMAE (CR011-ONC-1)

The study was performed to determine the anti-tumor effects of the constituent components of the antibody-drug conjugate and its formulation and to relate these effects to the anti-tumor effects of the intact immunoconjugate.

Results:

Mice were implanted by trocar with fragments of SK-ME-2 melanoma and, after the tumors became established, treatment with CR011-vcMMAE and various components was tested to demonstrate the specificity of anti-tumor effects of this agent. Control groups, dosed with either the phosphate-buffered saline (vehicle) or the excipients of the immunoconjugate preparation (3% DMSO, sucrose, phosphate medium) steadily increased in tumor size to a maximum of 2,000 mg, at which time they were removed from the study. No apparent or statistically significant anti-tumor effects were observed. However, CR011-vcMMAE treatment (at 5 mg/kg/treatment, q4d x4) produced measurable inhibition after the first 2 doses. Tumor growth inhibition continued until no discernible tumor was detected in all 6 of the test animals (FIG. 4). In preliminary studies, tumor regression was complete and was not followed by regrowth of the tumor despite lengthy observation periods (up to 200 days).

Conclusions:

The regressions produced by the immunoconjugate were not due to the individual components of the immunoconjugate nor to components of the formulation of that immunoconjugate. This is demonstrated by the lack of tumor growth inhibition after treatment with CR011 antibody alone (group 3) or free monomethylauristatin E (group 4), where the doses applied were identical to that contained in the intact immunoconjugate. Furthermore, the lack of anti-tumor effects noted with free MMAE suggests that anti-tumor effects from MMAE as a result of slow release from the antibody-drug conjugate may not explain the anti-tumor effects of the immunoconjugate. Release of MMAE from antibody-MMAE conjugates has been shown to be a very slow process in vivo ($T_{1/2}\beta$=6.0 days in the case of the anti-CD30 antibody-Auristatin E immunoconjugate (Sanderson et al., Clin. Cancer Res. 11: 843-852 (2005)) and would provide for plasma or serum concentrations that would be considerably lower than the "bolus" doses used in this study, which were ineffective at slowing the growth of the human melanoma xenografts.

Example 20

CR011-vcMMAE Inhibits the Growth of Human SK-MEL-5 Melanoma Xenografts Leading to Complete Regression of Established Melanoma Tumors in Athymic Mice (CR011-ONC-3)

This study was performed to assess the potency and therapeutic efficacy of the antibody-drug conjugate, CR011-vcMMAE, against a second model of established human melanoma, the SK-MEL-5 xenograft.

Results:

Though unrelated in origin, the SK-MEL-5 expresses GPNMB on the surface of the cell membrane and is killed by CR011-vcMMAE in vitro. In this study, the anti-tumor effects of the CR011 immunoconjugate were examined, along with the vehicles PBS and saline, and the reference agents vinblastine and paclitaxel. In a manner similar to the SK-MEL-2 tumor, vinblastine produced a noticeable, but not significant tumor growth inhibition (P≤0.21) when compared to saline and PBS control groups (FIG. 5). Soon after the commencement of treatment with paclitaxel, however, significant tumor growth inhibition was observed (P≤0.039) at day 3 after treatment began, and this anti-tumor effect continued, producing 100% growth inhibition (stasis). The responses of SK-MEL-5-bearing test animals to vinblastine and paclitaxel were short-lived. After cessation of treatment at the maximally tolerated doses, tumors resumed rapid, progressive growth. One long-term, tumor-free survivor occurred in the paclitaxel group and one spontaneous regression occurred in the group treated with saline.

Substantial tumor growth inhibition, as well as tumor growth delay and complete regressions occurred in SK-MEL-5 tumor-bearing animals after treatment with CR011-vcMMAE, and these effects were dose-related. At 10 mg/kg/treatment, significant anti-tumor effects were noted as early as 7 days (the equivalent of 2 treatments) after treatments began, when compared to saline (P≤0.0096), and as early as 10 days after treatment began when compared to PBS-treated controls (P=0.039). In a dose-related manner, CR011-vcMMAE produced tumor growth delay leading to complete regressions of established SK-MEL-5 melanoma xenografts (see tabular insert to FIG. 5 for proportions of animals with complete regressions). Complete regressions occurred at CR011-vcMMAE doses of 2.5 mg/kg/treatment, but not at 1.25 mg/kg/treatment.

As in previous studies, no indication of toxicity by the immunconjugate occurred in treated animals as evidenced by mortality of effects on body weight or weight gain.

Conclusions:

CR011-vcMMAE exerts substantial, dose-dependent anti-tumor effects against established xenografts of the SK-MEL-5 human melanoma. After just one or two treatments significant tumor growth inhibition is noted and which leads to long-term tumor-free survivors. Complete regressions occurred at doses of >2.5 mg/kg i.v., q4d ×4.

Example 21

Pharmacokinetics of CR011-vcMMAE (CR011-PK-1A)

The purpose of this study was to determine the stability of CR011-vcMMAE in vivo after intravenous injection, the anticipated route of clinical administration.

Materials & Methods.

The CR011 antibody component of CR011-vcMMAE was measured by a sandwich style enzyme-linked immunosorbent assay (ELISA) where serum was added to the wells of microtiter plates coated with the cognate antigen (GPNMB, CG56972-03) for the CR011 antibody, and the amount of human antibody were detected with an anti-globulin conjugated to the signal generator (horseradish peroxidase).

Figure 6:
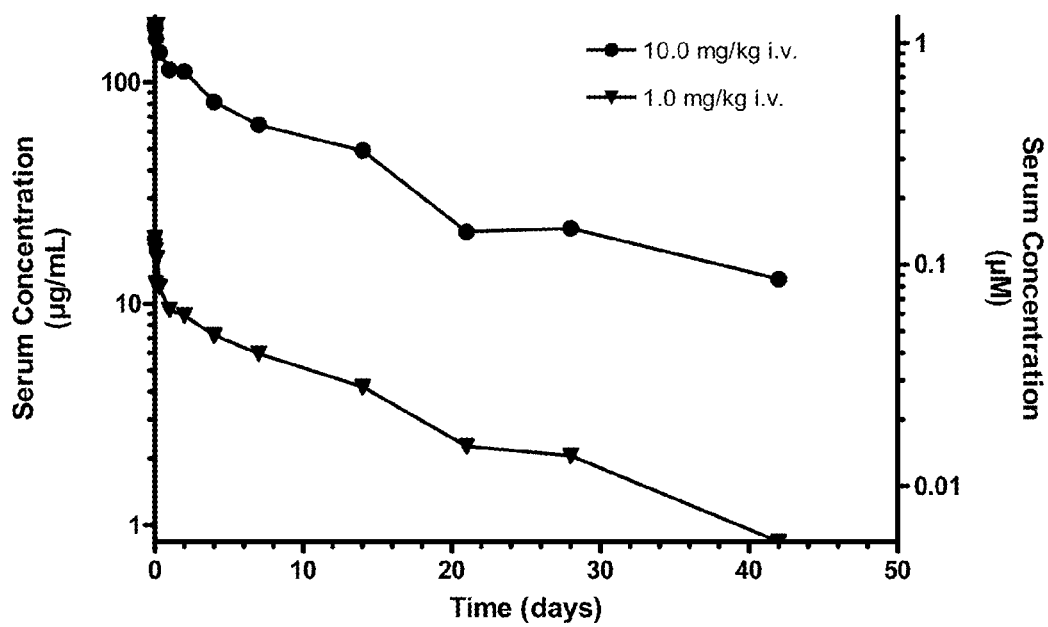
FIG. 6: The serum concentration-time profile of the antibody of CR011-vcMMAE after intravenous administration of 1 and 10 mg/kg in athymic mice. Detection was achieved with a sandwich ELISA assay, which employed the CR011 antigen (CG56972, GPNMB) and a horseradish peroxidase-conjugated anti-human globulin. Results shown are the serum concentrations expressed as μg/mL (left x-axis) and micromolarmolar concentration (right X-axis).

Results:

Pharmacokinetics. The persistence of compound availability for antibody component of CR011-vcMMAE was examined in a pharmacokinetic study in athymic mice (study CR011-PK-1, FIG. 6). The serum concentration-time profile for the antibody-drug conjugate was determined in athymic mice after intravenous administration of CR011-vcMMAE and the results are presented in FIG. 6. Athymic mice receiving 1 or 10 mg/kg intravenously showed dose-proportional serum concentrations over the entire span of sampling times (42 days). The concentration-time pattern was bi-phasic. The initial phase ($\alpha$), however, was minor as it contributed <2% of the total AUC. Nevertheless, the compound disappeared very slowly from the peripheral blood ($T_{1/2}\beta$=10.3 days) with serum concentrations of 1 μg/mL and 10 μg/mL remaining in the blood for 6 weeks after dosing.

Estimates for the pharmacokinetic parameters for CR011-vcMMAE are presented in Table 48. One parameter is noteworthy. The volume of distribution at steady state (Vss) is very low, approaching the theoretical minimum; this suggests that the com-pound does not distribute outside the extravascular space. The distribution pattern, as well as the β-elimination phase for CR011-vcMMAE are in good agreement with values obtained for antibodies in general (see Reviews by Mahmood and Green, Clin. Pharmacokinet 44: 331-347 (2005); or Lobo et al. J. Pharm. Sci. 93: 2645-2668 (2004)) and agree with values obtained for an antibody-Auristatin E immunoconjugate with comparable drug loading (Hamblett et al., Clin. Cancer Res. 10: 7063-7070 (2004)).

TABLE 48

PK Parameters for CR011-vcMMAE after Intravenous Administration.

| Parameter | Units | 1 mg/kg | 10 mg/kg |
|---|---|---|---|
| A | μg/mL | 8.97 | 74.6 |
| B | μg/mL | 9.82 | 113 |
| Alpha | 1/h | 0.179 | 0.0812 |
| Beta | 1/h | 0.00269 | 0.00281 |
| AUC | h*μg/mL | 3712 | 41210 |
| Alpha-Half Life | h | 3.88 | 8.531 |
| Beta- Half Life | h | 258 | 247 |
| Volume | mL/kg | 53.2 | 53.2 |
| Cmax | μg/mL | 18.8 | 188 |
| Cl | mL/h/kg | 0.269 | 0.243 |
| MRT | h | 368 | 348 |
| Vss | mL/kg | 99.0 | 84.5 |

Abbreviations: A: Pre-exponential constant for alpha phase; Alpha: Exponential rate constant for alpha phase; AUC Total area under the curve from 0 to infinity; B: Pre-exponential constant for beta phase; Beta: Exponential rate constant for beta phase; Cl: Total or systemic clearance; $C_{max}$: Maximum observed concentration; MRT: Mean residence time; Volume: Volume of central compartment; Vss: Steady-state volume of distribution.

Estimates for pharmacokinetic parameters are presented in Table 48. One parameter is noteworthy. The volume of distribution steady state (Vss) is, approaching the theoretical minimum. These data suggest that the compound did not received 32, 8, and 2 mg/kg cumulative dose, respectively) received the same cumulative doses, the first set receiving the "bolus dose" is different from the other 4 sets. The $C_{max}$ for each group in the "bolus" set was likely four-fold higher that the $C_{max}$ for the other 4 sets (see section on pharmacokinetics for dose-linearity after i.v. administration), since 4 sets of groups received 4 treatments, whereas the first set received only one "bolus" treatment (see column 7, Table 49 below).

TABLE 49

Protocol for the Dosing Interval Study (CR011-PHM-2).

| Group | Treatment | ROA | Dose (mg/kg) | Regimen | Dosing Interval (days) | No. Treatments (n) | Cum. Dose (mg/kg) |
|---|---|---|---|---|---|---|---|
| 1 | Phosphate Buffered Saline | | | Bolus | 0 | 1 | N.A. |
| 2 | CR011-AE | i.v. | 32 | Bolus | 0 | 1 | 32 |
| 3 | CR011-AE | i.v. | 8 | Bolus | 0 | 1 | 8 |
| 4 | CR011-AE | i.v. | 2 | Bolus | 0 | 1 | 2 |
| 5 | CR011-AE | i.v. | 8 | qd x4 | 1 | 4 | 32 |
| 6 | CR011-AE | i.v. | 2 | qd x4 | 1 | 4 | 8 |
| 7 | CR011-AE | i.v. | 0.5 | qd x4 | 1 | 4 | 2 |
| 8 | CR011-AE | i.v. | 8 | q4d x4 | 4 | 4 | 32 |
| 9 | CR011-AE | i.v. | 2 | q4d x4 | 4 | 4 | 8 |
| 10 | CR011-AE | i.v. | 0.5 | q4d x4 | 4 | 4 | 2 |
| 11 | CR011-AE | i.v. | 8 | q8d x4 | 8 | 4 | 32 |
| 12 | CR011-AE | i.v. | 2 | q8d x4 | 8 | 4 | 8 |
| 13 | CR011-AE | i.v. | 0.5 | q8d x4 | 8 | 4 | 2 |
| 14 | CR011-AE | i.v. | 8 | q16d x4 | 16 | 4 | 32 |
| 15 | CR011-AE | i.v. | 2 | q16d x4 | 16 | 4 | 8 |
| 16 | CR011-AE | i.v. | 0.5 | q16d x4 | 16 | 4 | 2 |
| 17 | Excipients | i.v. | N.A. | q16d x4 | 16 | 4 | N.A. | distribute outside the extravascular space. Taken together, these data are in good agreement with data on other immunoconjugates bearing the –vcMMAE cytotoxic moiety (see Hamblett et al., Clin. Cancer Res. 10: 7063-7070 (2004)).

Conclusions:

The CR011-vcMMAE antibody-drug conjugate has a serum-concentration profile which favors continuous exposure sufficient for disruption and eradication of melanoma xenografts. The immunoconjugate after i.v. administration has a sufficiently long half-life to ensure exposure of tumor cells for extended periods ($T_{1/2}\beta$=10.3 days), and may not require frequent dosing. The durability of CR011-vcMMAE in vivo (e.g., athymic mice) is comparable to other Auristatin E immunoconjugates.

Example 22

The Schedule Dependency of the Anti-Tumor Effects of CR011-vcMMAE (CR011-ONC-1)

The purpose of this study was to determine the extent to which the curative anti-tumor effects of the CR011 antibody-drug conjugate are dependent on the dosing regimen and, if possible, to determine the optimum dosing interval for this xenograft model.

Materials and Methods:

The protocol for this study is presented in Table 49. To test the hypothesis that curative anti-tumor effects are influenced by the dosing schedule, the anti-tumor effects of CR011-vcMMAE were measured at 5 different dosing intervals (i.e., 0, 1, 4, 8, and 16 days between treatments) and for each dosing interval 3 dosage levels were employed (i.e., cumulative doses of 2, 8, and 32 mg/kg); for each group, n=6 athymic mice.

Figure 7:
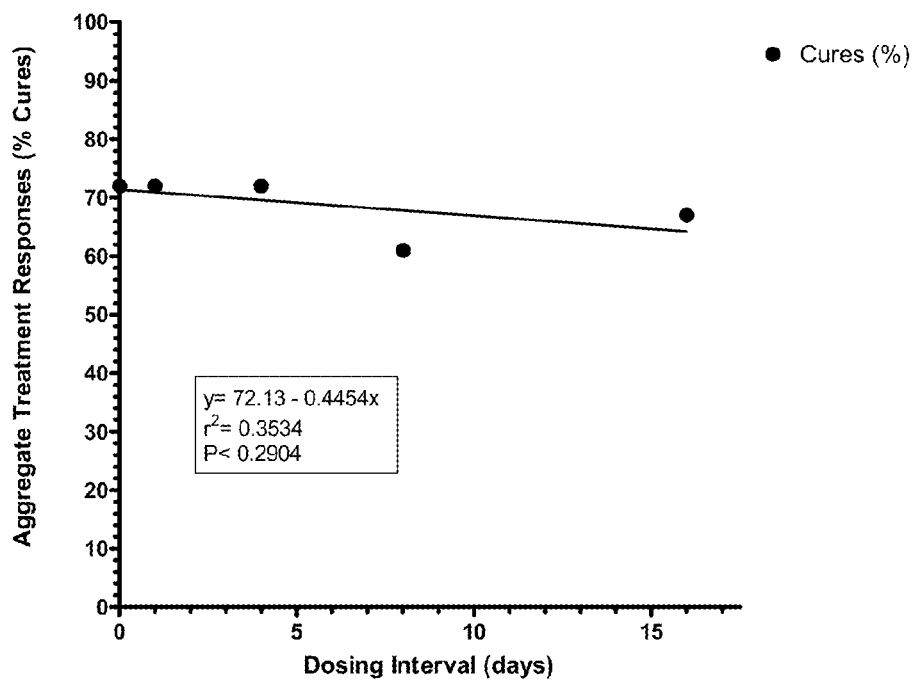
FIG. 7: Aggregate responses, expressed as percent cures, were recorded for test animals treated with 5 different, graduated dosing intervals (i.e., 0, 1, 4, 8, and 16 days between treatments). The slope of the line is not significantly different from 0 ($p<0.2904$).

Nota bene: Please note that, although all 5 sets of groups in this experiment (e.g., groups 5, 6, and 7 represent one set and Results:

For this study, the frequency of complete regressions with long-term tumor-free survivors was determined after 5 different dosing intervals were examined empirically (i.e., 0, 1, 4, 8, and 16 days between treatments). The aggregate responses for each set of groups, where a set is defined as 3 groups of graduated dosage levels but one dosage interval (groups 5, 6, and 7 represent 1 set, all of which were treated with a dosing interval of 1 day) are shown in FIG. 7. The aggregate responses for test animals responding to CR011-vcMMAE appear to suggest that bolus dosing and intervals of 1 day and 4 days provide a very slight advantage to the proportion of cures, compared to longer intervals, such as 8 days and 16 days between doses. However, this effect was not significant (P<0.2904). The data therefore suggest that the anti-tumor effects of CR011-vcMMAE in the SK-MEL-2 model are not schedule-dependent. This conclusion is strengthened by the fact that test animals in the bolus set (groups 2, 3, and 4), which were exposed to plasma concentrations approximately four-fold higher than any of the other groups, did not show any greater percentages of cured subjects.

The original design of this study was expanded to include an examination of the effects of various dosage levels. For each set, one group of animals received a cumulative dose of 8 mg/kg, which, from previous studies employing a dosing interval of 4 days, provided consistent therapeutic effects leading to long-term tumor-free animals. In addition, cumulative doses of 2 mg/kg and 32 mg/kg were employed.

Figure 8:
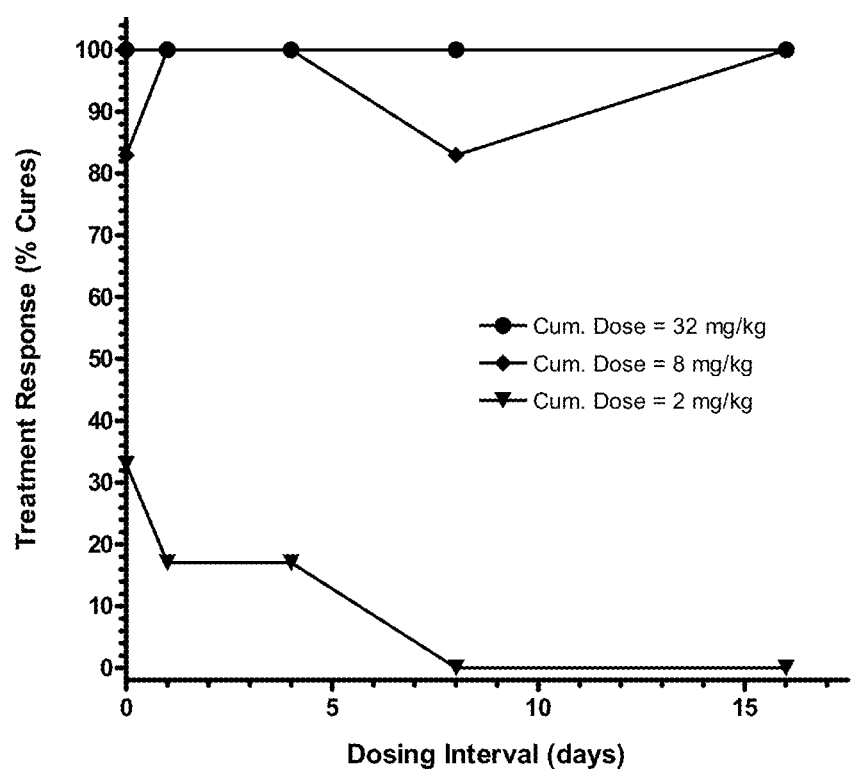
FIG. 8: The proportions of complete regressors as a function of dosing interval and stratified by cumulative dose. For each group, n=6 mice/group. Athymic mice bearing established SK-MEL-2 tumor implants (day 14, 80 mg) were treated i.v. with CR011-vcMMAE and the incidence of complete regressions is recorded.

The effects of dosage levels, in conjunction with various dosing intervals, are presented in FIG. 8. Athymic mice receiving a cumulative dose of 32 mg/kg showed complete regressions in 100% of each group, regardless of dosing interval; that is, a cumulative dose of 32 mg/kg is schedule-independent and represents a dose which is well above that sufficient for complete regressions in 100% of the test animals (5 groups of 6 animals/group=30 test animals). Animals receiving 8 mg/kg cumulative dose did not demonstrate schedule dependency and showed nearly the same proportions of complete regressions (i.e., 28/30=93%); Test animals receiving 2 mg/kg (cumulative dose), which was recognized in preliminary studies to be below the threshold for cures (using a standardized regimen of q4d ×4) appeared to be schedule dependent, though this was not significant, and produced a much lower proportion of complete regressors (i.e., 13%).
Conclusions:

The data from the dosing interval study suggests that the responses of SK-MEL-2 melanoma xenografts are not dependent on the schedule of administration of CR011-vcMMAE. While no advantage could be shown for bolus dosing or regimens with low dosing intervals, there is the suggestion that, below a certain threshold cumulative dose, there may be some advantage to combining multiple treatments into a single bolus dose.

Example 23

GPNMB Transcript Expression in Human Melanoma

GPNMB was recently shown to be expressed in glioblastoma and to mediate the in vitro and in vivo invasiveness of glioblastoma-derived tumor cells (see,e.g., Loging et al., Genome Res. 10:1393-1402 (2000); and Rich et al., J. Biol. Chem. 278:15951-15975 (2003)). To confirm and extend these findings to additional cancer types, we examined the expression of GPNMB transcripts in human cancer cell lines and tissues.
Material and Methods:

Total RNA was isolated using the RNeasy kit with a DNase digestion step (Qiagen Inc., Valencia Calif.). RT-PCR was performed using the OneStep RT-PCR kit (Qiagen) as follows. RT: 50° C. for 45 min and 95° C. for 15 min for 1 cycle. PCR: 1 min at 95° C., 1 min at 50° C. and 2 min at 72° C. for 30 cycles with final extension for 10 min at 72° C. Products were separated on a 2% agarose/0.33% low melting point agarose gel and visualized by ethidium bromide staining. The integrity of each RNA sample was verified via RT-PCR with primers designed to amplify GAPDH. Specific primers (5'-3') used were:

```
GPNMB:
                                          (SEQ ID NO: 327)
Forward-GAATTCAGAGTTAAACCTTGAG (SEQ ID NO: 328)
Reverse-CAGGAATCTGATCTGTTACCAC MART-1:
                                          (SEQ ID NO: 329)
Forward-CTGACCCTACAAGATGCCAAGAG (SEQ ID NO: 330)
Reverse-ATCATGCATTGCAACATTTATTGATGGAG Tyrosinase:
                                          (SEQ ID NO: 331)
Forward-TTGGCAGATTGTCTGTAGCC (SEQ ID NO: 332)
Reverse-AGGCATTGTGCATGCTGCTT pMEL-17:
                                          (SEQ ID NO: 333)
Forward-TATTGAAAGTGCCGAGATCC (SEQ ID NO: 334)
Reverse-TGCAAGGACCACAGCCATC
```

RTQ-PCR analysis was performed with an ABI Prism 7700 Sequence Detection System using TaqMan reagents (PE Applied Biosystems, Foster City, Calif.). Equal quantities of normalized RNA's were used as a template in PCR reactions for 40 cycles with GPNMB-specific primers to obtain threshold cycle ($C_T$) values. The following primers (5'-3') were used:

```
                                          (SEQ ID NO: 335)
Forward-TCAATGGAACCTTCAGCCTTA (SEQ ID NO: 336)
Reverse-GAAGGGGTGGGTTTTGAAG (SEQ ID NO: 337)
Probe-TET-CTCACTGTGAAAGCTGCAGCACCAG -TAMRA
```

Result:

Our transcript expression analysis indicated that GPNMB was strongly expressed in a high percentage of human metastatic melanoma samples. Using RTQ-PCR, GPNMB was found to be highly expressed (CT<27.0) in 5/7 melanoma cell lines and 5/5 melanoma clinical specimens examined (Table 50). In contrast, GPNMB was not expressed in a renal carcinoma cell line, TK-10, that was used as a negative control in our experiments.

TABLE 50

GPNMB transcript expression in human melanoma cell lines and clinical specimens

| | Sample Details | Expression* |
|---|---|---|
| Cell lines | | |
| UACC-62 | Met. Melanoma | 21.2 |
| M14 | Met. Melanoma, amelanotic | 22.2 |
| SK-Mel-5 | Met. Melanoma, axillary node | 22.9 |
| SK-Mel-28 | Met. Melanoma, skin | 24.1 |
| WM-266-4 | Met. Melanoma, skin | 24.5 |
| A-375 | Met. Melanoma, skin | 29.0 |
| LOXIMVI | Met. Melanoma, amelanotic | 30.9 |
| TK-10 | Renal cell carcinoma | 40.0 |
| Clinical specimens | | |
| #1 | Met. Melanoma | 26.6 |
| #2 | Melanoma | 26.4 |
| #3 | Melanoma | 26.9 |
| #4 | Met. Melanoma | 24.1 |
| #5 | Met. Melanoma | 25.3 |

*Threshold cycle ($C_T$) values from RTQ-PCR analysis.
Met: Metastatic.

To extend these results, we investigated the expression of GPNMB in a panel of 17 melanoma cell lines via semi-quantitative RT-PCR (Table 51). The results show that GPNMB transcript is highly expressed in 15/17 melanoma cell lines, weakly expressed in 1/17 melanoma cell line (A-375), and not detectable in 1/17 melanoma cell line (LOX-IMVI) nor in the control TK-10.

TABLE 51

RT-PCR analysis

| | | Expression* | | | |
|---|---|---|---|---|---|
| Cell line | Annotation | GPNMB | MART-1 | Tyrosinase | pMel-17 |
| M14 | Met. Melanoma, amelanotic | +++ | +++ | +++ | +++ |

TABLE 51-continued

RT-PCR analysis

| | | Expression* | | | |
|---|---|---|---|---|---|
| Cell line | Annotation | GPNMB | MART-1 | Tyrosinase | pMel-17 |
| SK-Mel-5 | Met. Melanoma, axillary node | +++ | +++ | +++ | +++ |
| SK-Mel-28 | Met. Melanoma, skin | +++ | +++ | +++ | +++ |
| WM-266-4 | Met. Melanoma, skin | +++ | +++ | +++ | +++ |
| SK-Mel-2 | Met. Melanoma, skin | +++ | +++ | +++ | +++ |
| UACC-257 | Met. Melanoma | +++ | +++ | +++ | +++ |
| A2058 | Met. Melanoma, lymph node | +++ | +++ | +++ | +++ |
| G361 | Met. Melanoma, skin | +++ | +++ | +++ | +++ |
| HT-144 | Met. Melanoma, skin | +++ | +++ | +++ | +++ |
| MEWO | Met. Melanoma, lymph node | +++ | +++ | +++ | +++ |
| SK-Mel-3 | Met. Melanoma. Lymph node | +++ | +++ | +++ | +++ |
| MALME-3M | Met. Melanoma | +++ | +++ | +++ | +++ |
| UACC-62 | Met. Melanoma | +++ | +++ | +++ | − |
| SK-Mel-24 | Met. Melanoma, lymph node | +++ | − | +++ | − |
| RPMI-7951 | Met. Melanoma, lymph node | +++ | − | + | − |
| A-375 | Met. Melanoma, skin | + | − | − | − |
| LOXIMVI | Met. Melanoma, amelanotic | − | − | − | − |
| TK-10 | Renal cell carcinoma | − | − | − | − |

*RT-PCR analysis: Strongly (+++), weakly (+) or not detectable (−).
Met: Metastatic.

Furthermore, comparing the expression of GPNMB transcript to known melanoma/melanocyte-associated gene transcripts (MART-1, tyrosinase and pMEL-17) in the melanoma cell lines (Table 51) demonstrated strong expression of MART-1, tyrosinase and pMEL-17 in 13/17, 14/17 and 12/17 melanoma cell lines, respectively. Notably, 12/17 samples co-expressed high levels of GPNMB and all three melanoma/melanocyte-associated genes. Both LOXIMVI and TK-10 cell lines, which had undetectable GPNMB expression, also lacked expression of the three melanoma/melanocyte-associated genes examined Example 24

Growth-inhibitory Activity of CR011-vcMMAE is Dependent on GPNMB Expression

Material and Methods:

Flow Cytometry: Quantitative analysis of GPNMB expression on the cell surface of cell lines was determined by flow cytometry. Approximately $1 \times 10^6$ cells were harvested, washed and incubated with a saturating amount (10 µg/mL) of either CR011 or isotype-matched control antibody in staining buffer containing PBS (pH 7.4), 4% FBS and 0.1% $NaN_3$ for 30 min on ice, followed by washing and staining with R-Phycoerythrin (PE)-conjugated goat-anti-human antibody (Jackson ImmunoResearch Laboratories, Inc, West Grove, Pa.) at 1:100 for 30 min on ice. Cells were fixed in 1% paraformaldehyde/PBS and examined on a Becton Dickinson FACS-Calibur flow cytometer. Data analysis was performed with Becton Dickinson Cell Quest software version 3.3 and the geometric mean fluorescence intensity ratio (GMR) was determined for each cell type.

Internalization of cell surface bound antibodies was assessed by a modified flow cytometry procedure. In brief, cell suspensions were labeled with 10 µg/mL unconjugated or MMAE-conjugated CR011 for 30 min on ice. After washing cells, incubation was shifted to 37° C. for 1 hr to allow internalization of bound antibodies. Cells that remained on ice (total surface bound) or that were incubated at 37° C. (internalized) were stained with PE-conjugated goat-anti-human antibody at 1:100 for 30 min to detect CR011 retained on the cell surface. Labeled cells were analyzed by flow cytometry as described above. The percentage of antibody internalized was determined using the GMRs and the following formula:

Percent internalized=Total surface bound (4° C.)−
Total surface bound (37° C.)/Total surface bound
(4° C.)×100

Immunoprecipitation and Immunoblot Analysis: Cells were harvested and lysed on ice for 30 min in lysis buffer containing 1% NP-40, 0.15 M NaCl, 0.02 M Tris-HCl, 10% glycerol, 0.01 M EDTA and complete protease inhibitor mixture (Roche Molecular Biochemicals, Indianapolis, Ind.). Supernatants were collected and the protein concentration was determined with the BCA Protein Assay Kit (Pierce, Rockford, Ill.). For immunoprecipitation, 2 µg of primary antibody was added into 0.5-1 mg of total cell lysates and incubated at 4° C. for 3 hrs, followed by incubation with protein-A-agarose (Amersham Biosciences, Upsala, Sweden) on ice for 2 hrs. The agarose beads were washed in ice-cold TBST (PBS with 0.1% Tween-20) Immunoprecipitates were recovered from supernatants after boiling in Laemmli sample buffer and centrifugation.

For immunoblot analysis, total cell lysates (50 µg) or immunoprecipitates were resolved under reducing condition on 4-20% Tris-glycine gels (Invitrogen) and electrophoretically transferred to 0.45-µm PVDF membranes (Invitrogen). Membranes were blocked with 3% BSA (Sigma, St. Louis, Mo.) in TBST for 3 hrs and probed with rabbit anti-GPNMB polyclonal antibody (1:1000) for 3 hrs. Peroxidase-conjugated goat anti-rabbit IgG (H+L) secondary antibody (Jackson ImmunoResearch Labs) was added and incubated for 30 min. The membranes were washed in TBST and subjected to enhanced chemiluminescence (Amersham) following the manufacturer's protocol.

Clonogenic Assays: The growth-inhibitory activity of CR011-vcMMAE was determined by clonogenic assay. Cells were plated in 96-well plates and allowed to recover overnight. Unconjugated CR011, free MMAE, CR011-vcMMAE or isotype-matched vcMMAE conjugated antibody at various concentrations was added to sub-confluent cell cultures and incubated for 4 days at 37° C. The cells were then transferred into 6-well plates and allowed to form colonies. Colonies were stained with Giemsa stain (Sigma) and counted. The surviving cell fractions were calculated based upon the ratio of the treated sample and the untreated control. The results were expressed as a percentage of control using GraphPad Prism Version 4 software. The IC50 was defined as the concentration resulting in a 50% reduction of colony formation compared to untreated control cultures.

Figure 9:
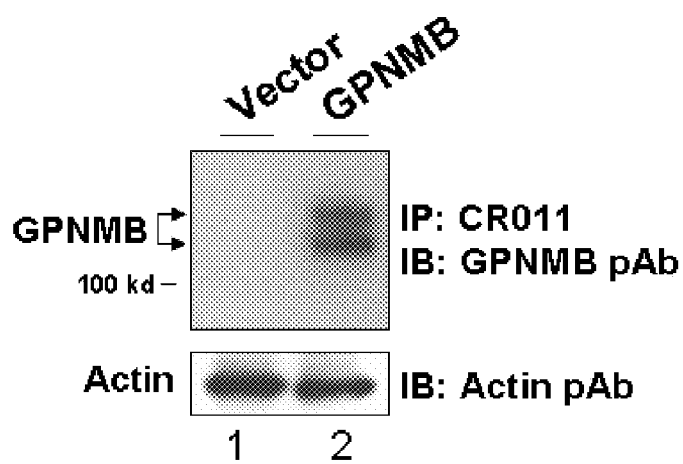
FIG. 9: Effects of ectopic expression of GPNMB or sensitivity to CR011-vcMMAE. HEK293 cells are transfected with empty vector (vector) or GPNMB-containing plasmid (GPNMB) as described in Materials and Methods. A. Cell lysates are prepared from the transfected HEK293 cells and the expression of GPNMB (upper panel) or actin (lower panel) is determined by immunoblotting. Lane 1: Empty vector transfectants. Lane 2: GPNMB transfectants. B. Flow cytometry analysis of GPNMB expression on empty vector or GPNMB transfected cells. C. CR011-vcMMAE in vitro growth inhibition of transfected cells. Cells are treated with various concentrations of CR011-vcMMAE (diamonds: vector or circles: GPNMB) or IgG2-vcMMAE (triangles: vector or squares: GPNMB) for 96 hours. After a clonogenic assay, the surviving fraction is normalized to the untreated control and expressed as a percentage of the control using GraphPad Prism graphing software. Each treatment is performed in triplicate. A representative graph from two independent experiments is shown.
Figure 9:
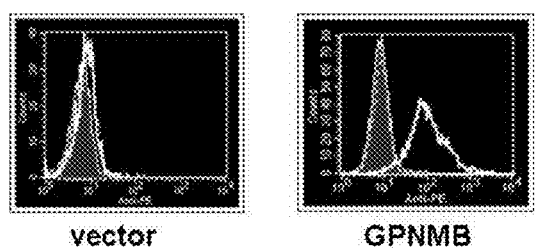
Figure 9:
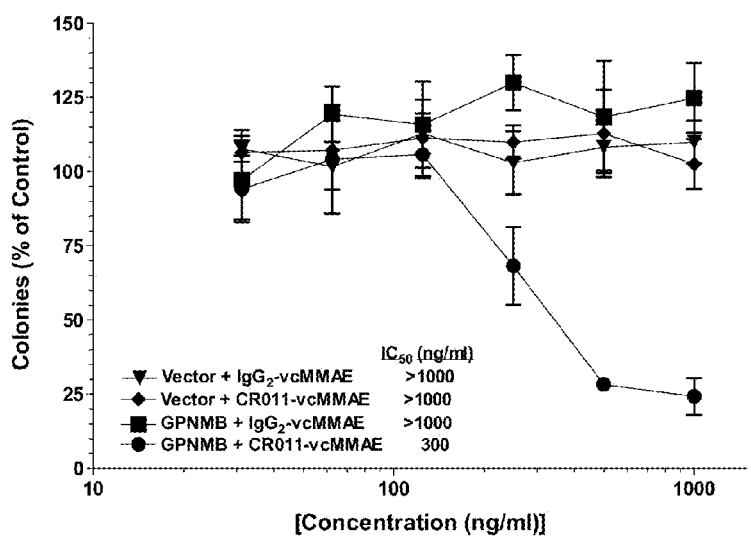

Results:

To demonstrate that CR011-vcMMAE growth-inhibitory activity is dependent on GPNMB expression, full-length GPNMB protein was ectopically expressed in HEK293 cells Immunoblot (FIG. 9A) and FACS (FIG. 9B) analyses confirmed that GPNMB was expressed in GPNMB/plasmid transfected cells. Treatment of cells with CR011-vcMMAE, followed by clonogenic assay, demonstrated that GPNMB-expressing HEK293 cells were more sensitive to CR011-vcMMAE-mediated growth-inhibition than were control cells devoid of GPNMB expression (FIG. 9C).

Figure 10:
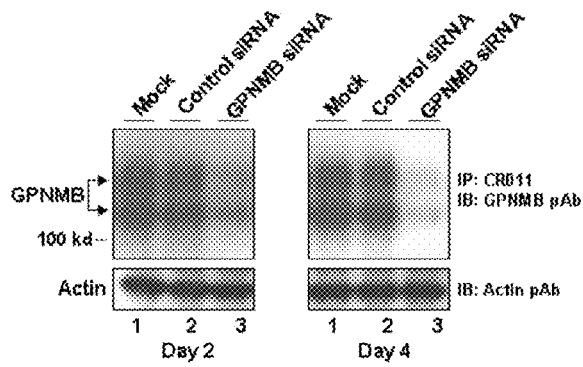
FIG. 10: Effect of GPNMB siRNA on endogenous GPNMB expression and sensitivity to CR011-vcMMAE. SK-Mel-2 cells are transfected with 50 nM of control siRNA or siRNA targeting GPNMB. A. Cell lysates are prepared from the transfected SK-Mel-2 cells 2 and 4 days post-transfection and the expression of GPNMB (upper panel) or actin (lower panel) is determined by immunoblotting. Lane 1: Mock (oligofectamine) transfection. Lane 2: Control siRNA transfection. Lane 3: GPNMB siRNA transfection. B. Flow cytometry analysis of GPNMB expression 2 and 4 days after transfection. SK-Mel-2 cells are transfected with mock, control siRNA or GPNMB siRNA as indicted in the Materials and Methods. C. CR011-vcMMAE in vitro growth inhibition of mock (diamonds), control siRNA (circles) or GPNMB siRNA (triangles) transfected SK-Mel-2 cells is determined by a clonogenic assay as described in Materials and Methods. The surviving fraction is normalized to the untreated control and expressed as a percentage of control using GraphPad Prism graphing software. Each treatment is performed in triplicate. A representative experiment from two independent studies is shown.
Figure 10:
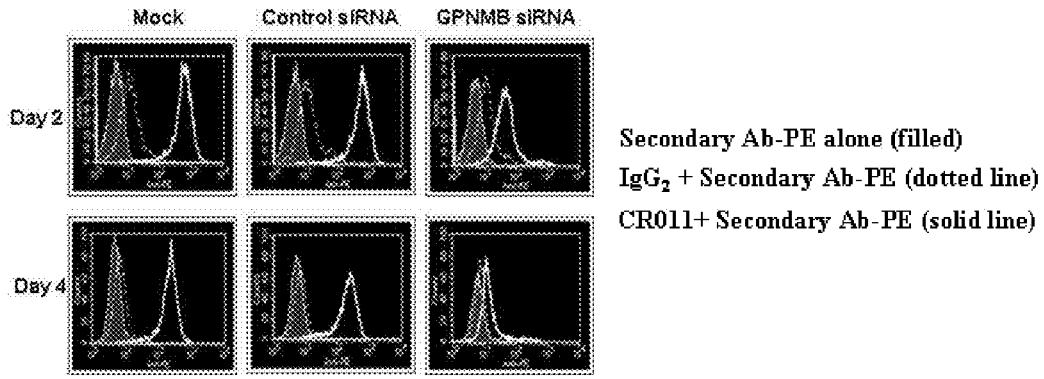
Figure 10:
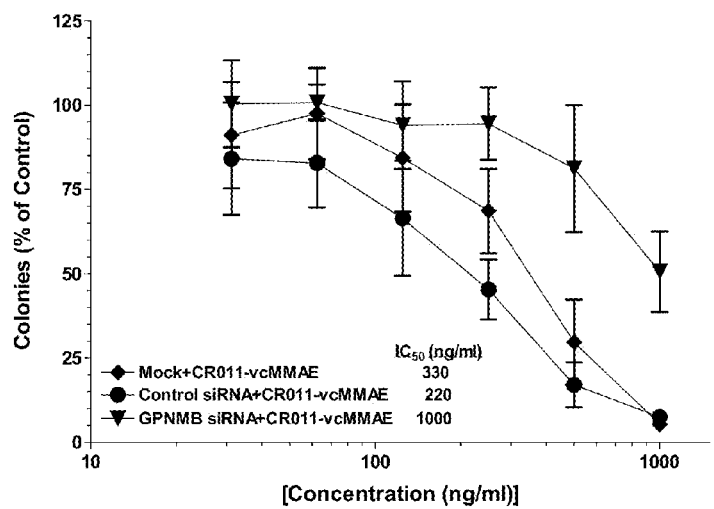

To further verify our findings, GPNMB-expressing SK-Mel-2 cells were transfected with siRNA to specifically inhibit endogenous GPNMB expression. Immunoblot and FACS analyses performed 2 and 4 days after transfection demonstrated that total GPNMB (FIG. 10A) and surface GPNMB (FIG. 10B) protein levels were significantly reduced in SK-MeI-2 cells after the transfection when compared to the control transfectants. The amount of GPNMB expression was reduced for at least 7 days after transfection. Treatment of these cells with CR011-vcMMAE demonstrated that SK-MeI-2 cells were less sensitive to the growth-inhibitory activity of CR011-vcMMAE following siRNA-mediated GPNMB knockdown (FIG. 10C). Taken together, these data indicate that the growth-inhibitory activity of CR011-vcMMAE required cell surface GPNMB expression.

Example 25

Cell Cycle Arrest and Induction of Apoptosis by CR011-vcMMAE

To evaluate CR011-vcMMAE's mechanism of growth inhibition, cell cycle analysis was performed.

Material and Methods:

The cell cycle effects of CR011-vcMMAE were evaluated after treating cells in complete growth medium for 24 or 48 hr. Briefly, cells were pulsed at the indicated times with 30 µM of bromodeoxyuridine (BrdU, Sigma) for 30 min, harvested, fixed and permeabilized in methanol. Nascent DNA synthesis was detected by anti-bromodeoxyuridine-FITC (BD Biosciences, San Jose, Calif.) staining. Total DNA content was detected using propidium iodide (PI, Sigma). For apoptosis analysis, cells were treated as above and labeled with Annexin V-FITC followed by propidium iodide exclusion using the Annexin V-FITC Apoptosis Detection kit I (BD PharMingen, San Diego, Calif.) according to the manufacturer's protocols. Flow cytometry (as described in the previous Example) was used to assay both cell cycle and apoptosis studies.

Results:

GPNMB-positive SK-Mel-2 cells or negative TK-10 control cells were treated with CR011-vcMMAE for various lengths of time, followed by bromodeoxyuridine for 30 minutes to detect nascent DNA synthesis and finally, propidium iodide to detect total DNA content. DNA synthesis and cell cycle progression were determined by flow cytometry (Table 52).

TABLE 52

Cell cycle analysis of CR011-vcMMAE treated cells

| Treatment (ng/mL) | % $G_1$ | % S-phase | % $G_2$/M | % Sub-$G_1$ |
|---|---|---|---|---|
| SK-Mel-2 24 hour | | | | |
| Untreated | 55.2 | 30.0 | 9.9 | 0.5 |
| CR011 (1000) | 63.6 | 25.2 | 6.4 | 0.5 |
| IgG$_2$-vcMMAE (1000) | 65.9 | 21.8 | 5.8 | 0.8 |
| CR011-vcMMAE (100) | 56.0 | 26.9 | 12.4 | 0.2 |
| CR011-vcMMAE (1000) | 43.7 | 20.0 | 28.5 | 1.1 |

TABLE 52-continued

Cell cycle analysis of CR011-vcMMAE treated cells

| Treatment (ng/mL) | % $G_1$ | % S-phase | % $G_2$/M | % Sub-$G_1$ |
|---|---|---|---|---|
| TK-10 24 hour | | | | |
| Untreated | 39.7 | 43.7 | 7.0 | 0.5 |
| CR011 (1000) | 42.0 | 39.8 | 6.3 | 0.3 |
| IgG$_2$-vcMMAE (1000) | 42.8 | 40.2 | 5.9 | 0.3 |
| CR011-vcMMAE (100) | 51.1 | 35.1 | 4.5 | 0.7 |
| CR011-vcMMAE (1000) | 52.6 | 34.2 | 3.9 | 0.8 |

Cell cycle analysis was carried out by flow cytometry and the percentages of cells in each phase of cell cycle were determined by CellQuest Software (Becton Dickinson).

Exposure of GPNMB-positive cells to 1000 ng/mL CR011-vcMMAE, but not to isotype control IgG2-vcMMAE for 24 hrs, resulted in a decreased percentage (10%) of cells in G1 and S-phase and an increased percentage (18.6%) of cells in G2/M when compared to untreated cells. In contrast, CR011-vcMMAE did not affect the cycling of GPNMB-negative cells. At 48 hr after the treatment, CR011-vcMMAE further reduced the percentage (11%) of cells in G1 and S-phase and increased the percentage (24%) of cells in G2/M.

The increase in the sub-G1 population following CR011-vcMMAE treatment suggested the onset of apoptosis. To investigate this possibility, analysis of apoptosis using Annexin-V surface binding and loss of propidium iodide (PI) exclusion was performed. Our results demonstrated that 1000 ng/mL of CR011-vcMMAE induced apoptosis specifically in GPNMB-expressing cells as indicated by an 11% increase in mono-stained (Annexin-V+/PI–) cells following 48 hr of CR011-vcMMAE treatment (Table 53).

TABLE 53

Induction of apoptosis in human melanoma cells by CR011-vcMMAE

| Treatment (ng/mL) | % AnnV$^-$/ PI$^+$ UL | % AnnV$^+$/ PI$^+$ UR | % AnnV$^-$/ PI$^-$ LL | % AnnV$^+$/ PI$^-$ LR |
|---|---|---|---|---|
| SK-Mel-2 48 hour | | | | |
| Untreated | 1.23 | 1.23 | 94.37 | 3.16 |
| CR011 (1000) | 0.36 | 0.45 | 94.45 | 4.74 |
| IgG$_2$-vcMMAE (1000) | 0.17 | 0.51 | 95.93 | 3.39 |
| CR011-vcMMAE (100) | 0.30 | 0.40 | 89.93 | 9.37 |
| CR011-vcMMAE (1000) | 2.08 | 2.02 | 82.08 | 13.83 |
| TK-10 48 hour | | | | |
| Untreated | 0.54 | 0.66 | 96.92 | 1.87 |
| CR011 (1000) | 0.83 | 0.34 | 98.27 | 0.55 |
| IgG$_2$-vcMMAE (1000) | 0.62 | 0.95 | 97.09 | 1.33 |
| CR011-vcMMAE (100) | 0.71 | 0.57 | 97.72 | 1.00 |
| CR011-vcMMAE (1000) | 0.86 | 0.83 | 97.75 | 0.56 |

Apoptosis analysis was carried out by flow cytometry and the percentages of cells in quadrants UL (upper left), UR (upper right), LL (lower left) and LR (lower right) were determined by CellQuest Software (Becton Dickinson). AnnV: Annexin V-FITC and PI: Propidium iodide.

In addition, an increase in dual-stained (Annexin-V+/PI+) cells following CR011-vcMMAE treatment indicated that the CR011 immunoconjugate enhanced cell death. Together, these results suggest that CR011-vcMMAE selectively induced G2/M cell cycle arrest followed by apoptotic cell death.

Example 26

CR011: A naked Fully Human IgG1 for Use in Melanoma Therapy Exploiting the Mechanism of Antibody-dependent Cellular Cytotoxicity (ADCC)

Fully human monoclonal antibodies (mAb)-IgG2 to CG56972/GPNMB, an antigen predominantly found on the surface of melanoma and brain tumor cells, were generated. The naked CR011IgG2 mAb (mAb 1.15) had no effect on CG56972 expressing cells either in vitro or in vivo. Thus we examined whether isotype switching from an IgG2 to an IgG1 might enable the mAb to kill human melanoma cells through ADCC effector functions.

Briefly, to switch CR011 from an IgG2 to IgG1 antibody, double stranded DNA encoding constant region of IgG1 (allotype Gm(f)) was synthesized, and IgG2 constant region was replaced with IgG1 constant region using overlapped PCR approach. The sequences are described below:

```
CR011 mAb 1.15.1 mature heavy chain (IgG2):
                                      (SEQ ID NO: 394)
QVQLQESGPGLVKPSQTLSLTCTVSGGSISSFNYYWSWIRHHPGKGLEWI

GYIYYSGSTYSNPSLKSRVTISVDTSKNQFSLTLSSVTAADTAVYYCARG

YNWNYFDYWGQGTLVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGK

CR011 mAb 1.15.1 mature heavy chain (IgG1):
                                      (SEQ ID NO: 395)
QVQLQESGPGLVKPSQTLSLTCTVSGGSISSFNYYWSWIRHHPGKGLEWI

GYIYYSGSTYSNPSLKSRVTISVDTSKNQFSLTLSSVTAADTAVYYCARG

YNWNYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Figure 11:
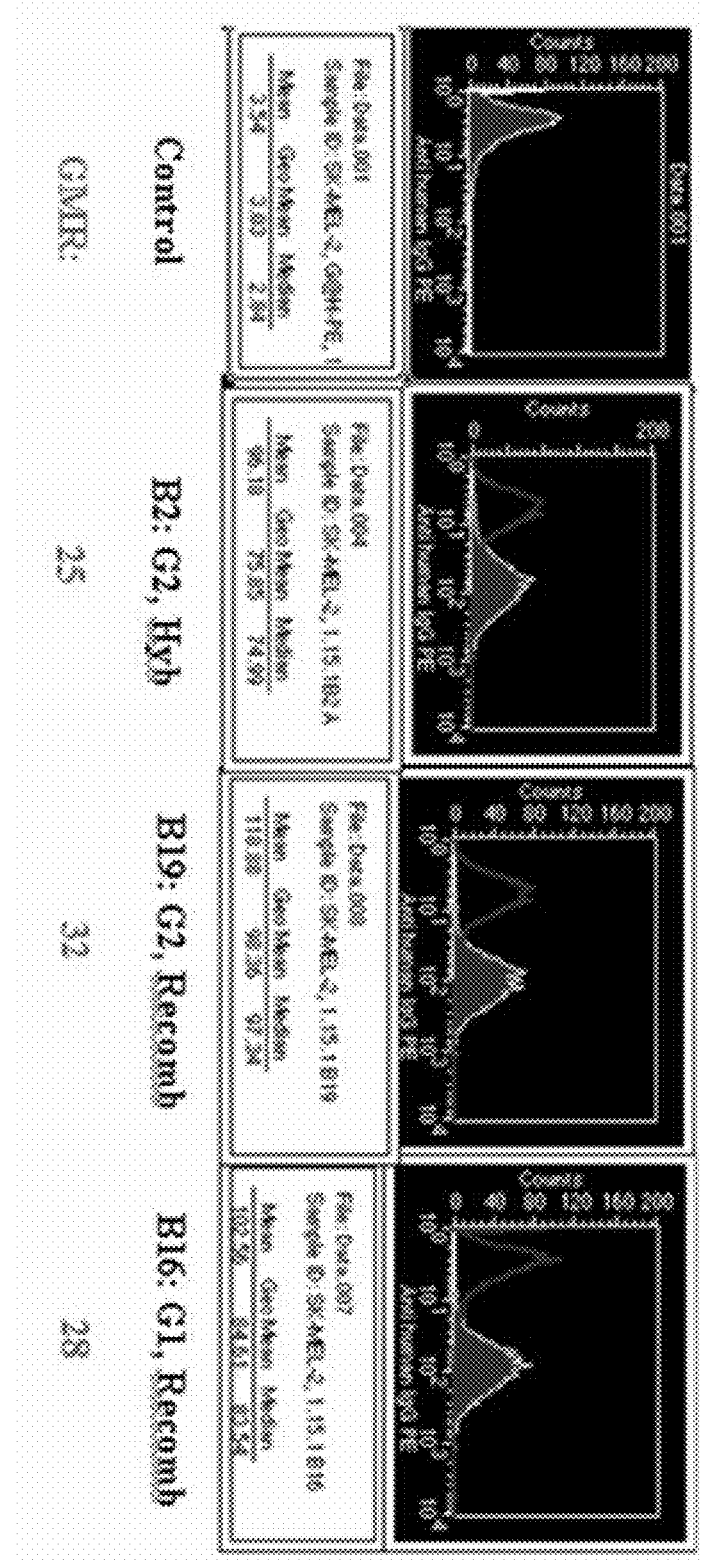
FIG. 11: FACS analysis of SK-MEL-2 with isotype control, hybridoma IgG2 (B2), recombinant IgG2 (B19) and recombinant IgG1 (B16) to CG56972/GPNMB relative to IgG2 (B2, B19) or IgG1 (Control, B16) controls.

We first analyzed the binding properties of the IgG1 and IgG2 fully human monoclonal antibodies on SK-MEL-2 melanoma cells that have been shown to express CG56972 on the cell surface and bind CR011 IgG2. As shown in FIG. 11, both the IgG1 and IgG2 mAbs caused comparable FACS shifts on SK-MEL-2 cells compared to isotype control mAbs (FIG. 11) indicating that both isotypes bind to CG56972/GPNMB with comparable saturation densities and affinities.

We next examined whether the CR011IgG1 mAb could induce ADCC in SK-MEL-2 cells in culture in the presence of human PBMC. Human PBMC were isolated from whole blood using a Ficoll-Plaque. Briefly, in a 50 mL tube, 15 mL of PBS was added to 20 mL of whole blood which was underlayed with 10 mL Ficoll-Plaque and the tube was centrifuged at 2000 RPM. Mononuclear cells were collected from the interface and washed 3 times with PBS. The ADCC assay was carried out in a 96 well plate using a fluorescence assay for cytolysis from Perkin-Elmer (DELFIA EuTDA Cytotoxic assay). The procedure is based on loading target cells with a fluorescence enhancing ligand (BATDA, bis (acetoxymethyl) terpyridine—dicarboxylate). The hydrophic ligand penetrates the membrane quickly. Within the cell the esterbonds are hydrolyzed to form a hydrophilic ligand (TDA, terpyridine—dicarboxylic acid) which can no longer pass through the membrane. After cytolysis the ligand is released and introduced to the Europium solution. The europium and the ligand form a highly fluorescent and stable chelate (EuTDA). Fluorescence intensity are recorded using excitation and emission wavelengths as $\lambda ex=340$ nm and $\lambda em=613$ nm, respectively.

Figure 12:
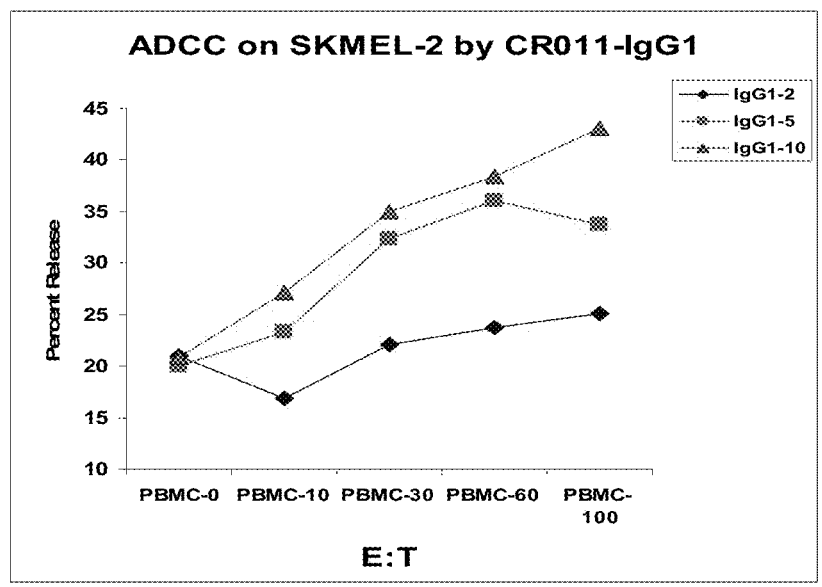
FIG. 12: (A) PBMC and mAb (IgG1) mediated ADCC of SK-MEL-2 cells. ADCC effector functions are measured as described above at 2, 5 and 10 µg/200 µl using target:effector ratios of 10, 30, 60 and 100 as indicated. (B) PBMC and mAb (IgG2) do not cause ADCC to SK-MEL-2 cells. ADCC effector functions are measured as described above at 0, 2, 5 and 10 µg/200 µl using target: effector ratios of 10, 30, 60 and 100 as indicated.
Figure 12:
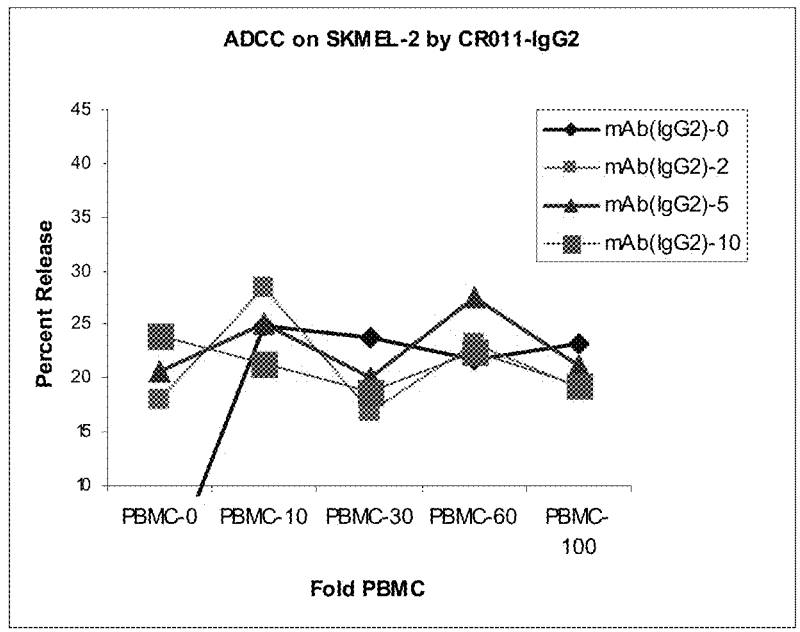

Antibody-dependent cell-mediated cytotoxicity on SK-MEL-2 cells was assayed in the presence of PBMC and CR011 monoclonal antibody using effector: target ratios of 10, 30, 60 and 100 and various concentrations of IgG1 or IgG2 mAb against CG56972/GPNMB (2, 5, 10 μg/200 μl). Our data showed that between 30 to 100 fold PBMC, IgG1 mAb caused cytolysis of SK-MEL-2 cells in a dose dependent manner (FIG. 12A) whereas IgG2 mAb did not show any cytolysis (FIG. 12B). Therefore, we conclude that CR011 IgG1 mAb to CG56972/GPNMB can kill CG56972/GPNMB expressing melanoma cells in vitro and potentially human melanoma in vivo through ADCC effector functions. CR011 IgG1 mAb can also be useful in combination with immune effector cytokines that could provide some clinical benefit in metastatic melanoma such as high dose IL-2, interferon-gamma or TNF-alpha. CR011 can also be used to treat melanoma in combination with vaccine immunotherapy, immunomodulators such as MDX-010, radiation therapy and/or chemotherapy.

Example 27

Treatment of Astrocytoma, Glioblastoma, Medulloblastoma and Other Tumors of the CNS Astrocytoma/glioblastoma is a highly drug-refractory neoplasm representing significant unmet medical needs. We identified CG56972 as a human gene (also known as GPNMB) that is highly expressed in these human cancer tissues and cancer cell lines. CG56972 is a type I transmembrane protein potentially involved in vesicular trafficking with a very restricted expression pattern in human brain. We generated fully human monoclonal antibodies against the CG56972 extracellular domain (amino acids 23-480). Our lead monoclonal antibody, designated CR011-vcMMAE was biochemically characterized and tested for therapeutic activity against cell lines derived from human brain tumors of astrocytoma, glioblastoma, medulloblastoma or neuroectodermal origin.

Transcript expression analysis demonstrated highly elevated CG56972 mRNA in brain tumors derived from astrocytoma, glioblastomas, medulloblastoma and tumors of neuroectodermal origin with restricted low expression in normal brain. CR011 bound by FACS analysis surface CG56972 on brain cancer cell lines. CR011 mAbs western blotted the predicted 100 and 120 kDa gene products. Clonogenic assays demonstrated that CR011-vcMMAE mAbs inhibited the growth of brain cancer cell lines.

Material and Methods:

Cell Lines and Culture Conditions: All human cell lines, SK-MEL-2, XF-498, SNB-78, U-118-MG, SF-539, H79MG, D392-MG, D534-MG, SK-N-SH, U-251, SF-295, D450-MG, U87MG, SF-268, T98G, and SW-1783 were obtained from the American Type Culture Collection (Manassas, Va.) or were purchased from the NCI (Bethesda, Md.). Cells were maintained in DMEM or RPMI (Invitrogen, Carlsbad, Calif.) containing 10% FBS (Gemini Bio-Products, Woodland, Calif.) and penicillin-streptomycin.

Real-Time Quantitative PCR(RTQ-PCR): Total RNA was isolated using the RNeasy kit with a DNase digestion step (Qiagen Inc., Valencia). RNA samples were derived from normal human tissues obtained commercially (Clontech, Palo Alto, Calif.; Invitrogen, Carlsbad, Calif.) or cell lines grown according to specifications. RNAs were harvested and PCR was performed as previously described (Shimkets R A et. al. Nat. Biotechnol., 1999. 17-8: 798-803) using TaqMan® reagents (PE Applied Biosystems, Foster City, Calif.). RNAs were normalized utilizing human β-actin and glyceraldehyde-3-phosphate dehydrogenase (GAPDH) TaqMan® probes according to the manufacturer's instructions. Equal quantities of normalized RNA were used as templates in PCR reactions with CG56972-specific reagents to obtain threshold cycle (CT) values. For graphic representation, CT numbers were converted to relative expression, relative to the sample exhibiting the highest level of expression. RTQ-PCR analysis was performed with an ABI Prism 7700 Sequence Detection System using TaqMan reagents (PE Applied Biosystems, Foster City, Calif.). The following primers (5'-3') were used:

```
                                         (SEQ ID NO: 338)
Forward-TCAATGGAACCTTCAGCCTTA (SEQ ID NO: 339)
Reverse-GAAGGGGTGGGTTTTGAAG (SEQ ID NO: 340)
Probe-TET-CTCACTGTGAAAGCTGCAGCACCAG -TAMRA
```

CuraChip™: Tissues were lysed in Trizol. Biotin-labeled cDNA was made by using 15 mg of total RNA with poly(T) primers. Gene expression was evaluated by hybridization to the proprietary CuraChip microarray (CuraGen, New Haven, Conn.) of 11,000 oligonucleotide probes. Slides were hybridized for 15 h at 30° C. with constant rotation, washed for 30 min at room temperature (RT), incubated in streptavidin solution (4° C., 30 min), washed three times for 15 min at RT, incubated in Cy3-conjugated detection buffer (4° C., 30 min), and washed three times for 15 min at RT. Slides were scanned (GMS 418 Scanner, Genetic Microsystems, Woburn, Mass.) and analyzed by using IMAGENE software (BioDiscovery, Marina Del Rey, Calif.). Data was subjected to 90th percentile normalization, and expression of the CG56972 gene was analyzed in comparison to that of the housekeeping gene GAPDH. The oligonucleotide sequence used to detect CG56972 is 5'-TGATCAGTAAGGATTTCACCTCT-GTTTGTA (SEQ ID NO: 341). The oligonucleotide sequence used to detect GAPDH is 5'-ACCTTGTCATG-TACCATCAATAAAGTACCC (SEQ ID NO: 342), corresponding to by 1243-1272 of the GAPDH transcript (accession no. NM 002046).

Flow Cytometry: Quantitative analysis of CG56972 expression on the surface of cell lines was determined by flow cytometry (FACS). Approximately $1\times10^6$ cells were harvested, washed and incubated with a saturating amount (10 µg/mL) of either CR011 or isotype-matched control antibody in staining buffer containing PBS (pH 7.4), 4% FBS and 0.1% $NaN_3$ for 30 min on ice, followed by washing and staining with R-Phycoerythrin (PE)-conjugated goat-anti-human antibody (Jackson ImmunoResearch Laboratories, Inc, West Grove, Pa.) at 1:100 for 30 min on ice. Cells were fixed in 1% paraformaldehyde/PBS and examined on a Becton Dickinson FACSCalibur flow cytometer. Data analysis was performed with Becton Dickinson Cell Quest software version 3.3 and the geometric mean fluorescence intensity ratio (GMR) was determined for each cell type.

Immunoblot Analysis: SK-MEL-2, XF-498, SNB-78, U-118-MG, SF-539, H79MG, D392-MG, D534-MG, SK-N-SH, U-251, SF-295, D450-MG, U87MG, SF-268, T98G, and SW-1783 cells were harvested and lysed on ice for 30 min in lysis buffer containing 1% NP-40, 0.15 M NaCl, 0.02 M Tris-HCl, 10% glycerol, 0.01 M EDTA and complete protease inhibitor mixture (Roche Molecular Biochemicals, Indianapolis, Ind.). Supernatants were collected and the protein concentration was determined with the BCA Protein Assay Kit (Pierce, Rockford, Ill.). For immunoblot analysis, 40 ul of total cell lysate from one well of confluent cells harvested from a 6 well Falcon tissue culture dish were boiled in Laemmli sample buffer, centrifuged and resolved under reducing condition on 4-20% Tris-glycine gels (Invitrogen). Gels were electrophoretically transferred to 0.45-µm PVDF membranes (Invitrogen). Membranes were blocked with 3% BSA (Sigma, St. Louis, Mo.) in TBST for 3 hrs and probed with goat anti-GPNMB polyclonal IgG (R & D Systems; 1 µg/mL, total 10 µg)) for 3 hrs. Peroxidase-conjugated anti-goat secondary antibody (Jackson ImmunoResearch Labs) was added and incubated for 30 min. The membranes were washed in TBST and subjected to enhanced chemiluminescence (Amersham) following the manufacturer's protocol.

Clonogenic Assays: The growth-inhibitory activity of CR011-vcMMAE was determined by clonogenic assay. Cells were plated in 96-well plates and allowed to recover overnight. CR011-vcMMAE or isotype-matched monoclonal antibody at various concentrations was added to sub-confluent cell cultures and incubated for 4 days at 37° C. The cells were then transferred into 6-well plates and allowed to form colonies. Colonies were stained with Giemsa stain (Sigma) and counted. The surviving cell fractions were calculated based upon the ratio of the treated sample and the untreated control. The results were expressed as a percentage of control using GraphPad Prism Version 4 software. The IC50 was defined as the concentration resulting in a 50% reduction of colony formation compared to untreated control cultures.

Results:

1. CG56972 Transcript Expression in Human Astrocytoma, Glioblastoma, Medulloblastoma and Tumors of Neuroectodermal Origin.

Figure 13:
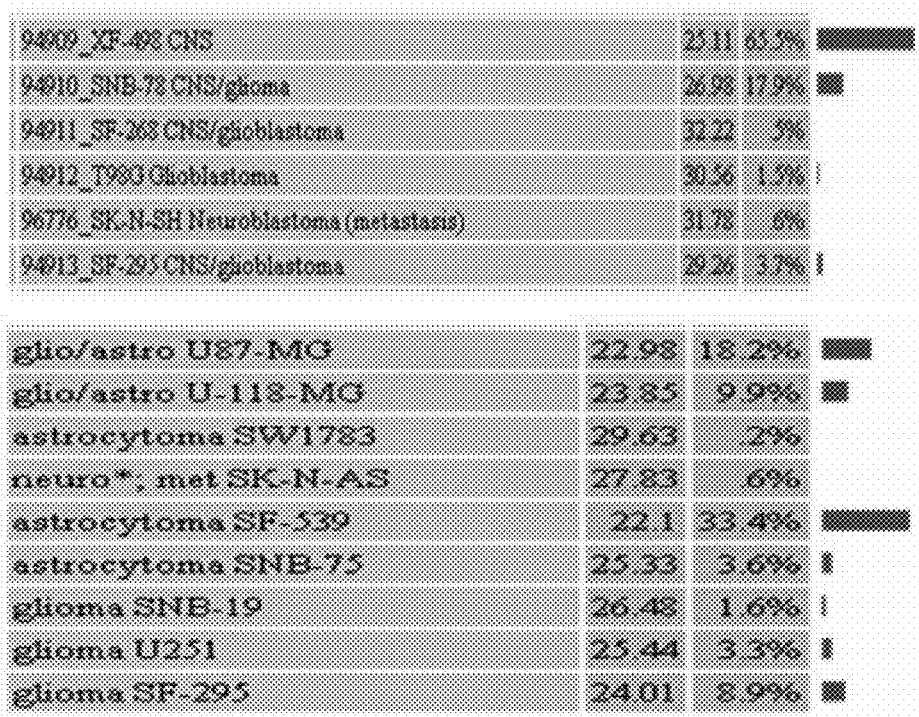
FIG. 13: Expression of CG56972 in human cancer cell lines and tissues. RTQ PCR analysis of (A) human brain cancer cell lines or (B) human brain cancer glioma and medulloblastoma biopsies. (C) Microarray analysis of CG56972 expression in human brain cancer and oligodendroglioma tissues. Tissues or cell lines are harvested, mRNA prepared and RTQ PCR or CuraChip analysis performed as described in Materials and Methods.
Figure 13:
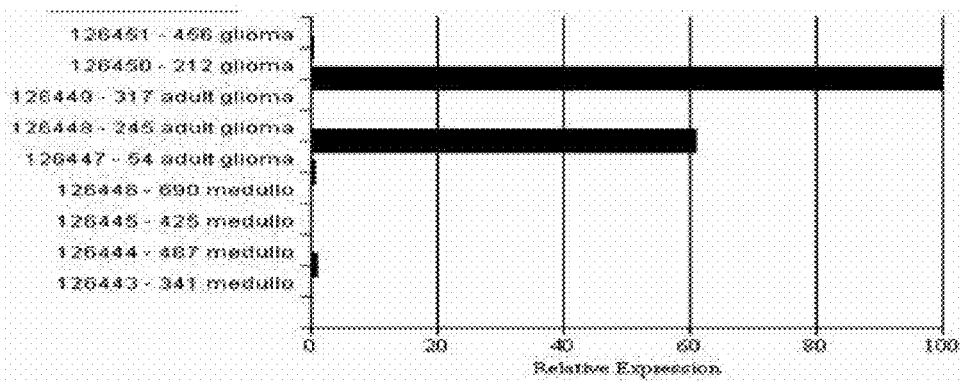
Figure 13:
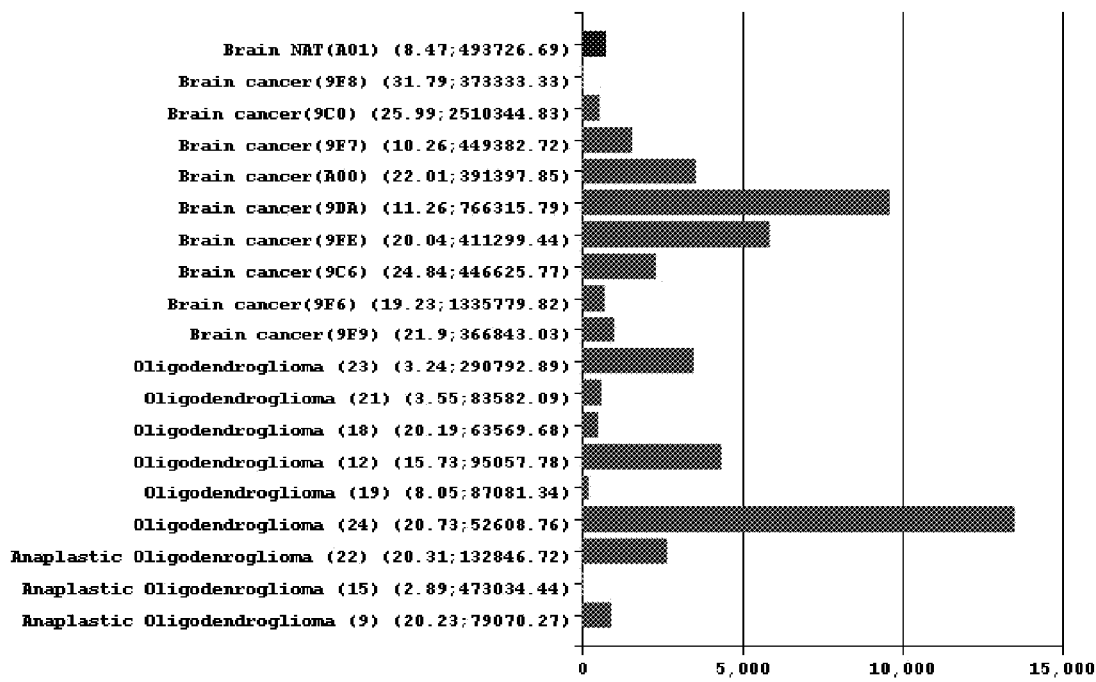

We examined the expression of CG56972 transcripts in human cancer cell lines and tissues (FIGS. 13 A & B). Our transcript expression analysis indicated that CG56972 was strongly expressed in all (15/15) human brain cancer cell lines tested (FIG. 13A) Using RTQ-PCR, CG56972 was found to be expressed in cells of mixed glioblastoma/astrocytoma orgin, glioblastoma/gliomas, astrocytomas and metastatic neuroblastomas. The majority of brain or CNS tumor cell lines showed high level expression with CTs<27. Of note, CG56972 was found to be highly expressed (CT<27.0) in XF-498, U-118-MG, SNB-78, and SF-539 cells. As shown in FIG. 13B, CG56972 was also expressed at high levels in 4/5 glioma human biopsies and 1/4 medulloblastoma human biopsies. Using microarray analysis from an in house chip containing a large panel of human genes (FIG. 13C), CG56972 was found to be highly expressed in 5/9 brain cancers of astrocytoma or glioblastoma origin as well as 4/9 oligodendrogliomas. Our analysis of these tumor expression profiles showed that CG56972 message was detected to a much lesser degree in normal brain tissues. These data are also consistent with our immunohistochemical data that demonstrated the lack of CR011 staining in normal human brain including neurons and glial cells. Taken together, these data demonstrate that the CG56972 transcript is expressed at highly elevated quantities in brain cancer and oligodendroglioma cell lines and specimens isolated from human tumors.

2. Generation of Fully Human CR011 Monoclonal Antibodies to CG56972/GPNMB

The CG56972 protein is predicted to be a type I transmembrane glycoprotein. The highly elevated expression of CG56972 transcripts and the potential cell surface localization of this protein in human cancer samples encouraged us to generate monoclonal antibodies (mAbs) as a potential cancer therapeutic. Therefore, we cloned the human CG56972 extracellular domain (ECD; aa 23-480). Sequencing of the cloned cDNA revealed the presence of an in-frame 36-nt insertion, likely due to alternative splicing at the exon 6/7 boundary, which added an additional 12-aa (ATTLKSYDSNTP) (SEQ ID NO: 343) after residue 339 of the published GPNMB protein sequence. We verified the authenticity of 36-nt insertion via RT-PCR. The cDNA was next expressed in human HEK293 cells. The resultant protein was harvested, purified from the conditioned media and used as an immunogen to generate fully human mAbs against CG56972-ECD. Following immunization of XenoMouse®, mAbs that specifically recognized the CG56972-ECD protein via ELISA were generated. Our lead mAb, designated 1.15 or CR011 against purified CG56972-ECD, exhibiting a Kd of 52 nM against purified CG56972-ECD protein, was selected for in depth characterization and will be the focus of the remainder of this example.

Figure 14:
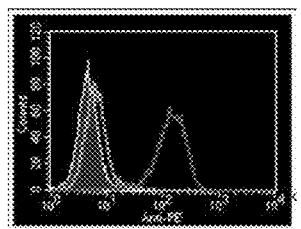
FIG. 14: FACS analysis of cell surface binding of CR011 mAb to CG56972. SK-MEL-2, XF-498, U-118-MG, SNB-78, SF-539 and SF-268 cells are labeled with a saturating concentration (10 ng/mL) of CR011 mAb or control IgG2. Bound mAb is detected by flow cytometry with PE-conjugated goat-anti-human secondary antibody as described in Materials and Methods. GM: Geometric mean. The SF-268 cell line is CG56972 transcript negative and used as a negative control.
Figure 14:
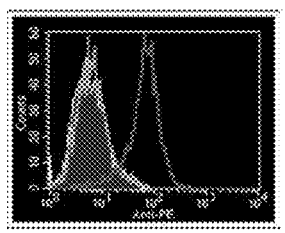
Figure 14:
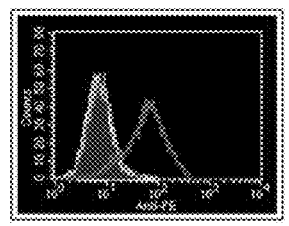
Figure 14:
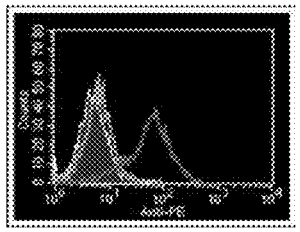
Figure 14:
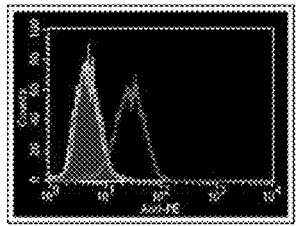
Figure 14:
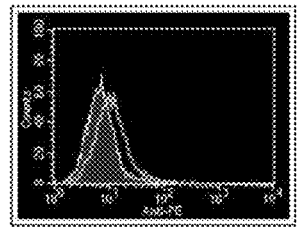

3. CR011 mAb 1.15 Detection of CG56972 Protein Expression in Human Brain Cancers We further used CR011 monoclonal antibodies to examine the surface expression of CG56972 protein on a variety of brain cancer cell lines by flow cytometry (FIG. 14 & Table 54). FACS analysis demonstrated that the brain cancer cell lines XF-498, U-118-MG, SNB-78 and SF-539; all positive for CG56972 transcript expression exhibited surface staining with CR011 monoclonal antibodies of at least 1.5-fold above isotype control mAb background (FIG. 14). The cell line SF-268, that was the most weakly positive (CT>32) for the CG56972 transcript expression (FIG. 13C & Table 54) showed minimal surface staining as expected of around 1.5-fold above control mAb background. Our SK-MEL-2 melanoma cell line that is our positive control for CG56972 expression showed strong cell surface staining.

Figure 15:
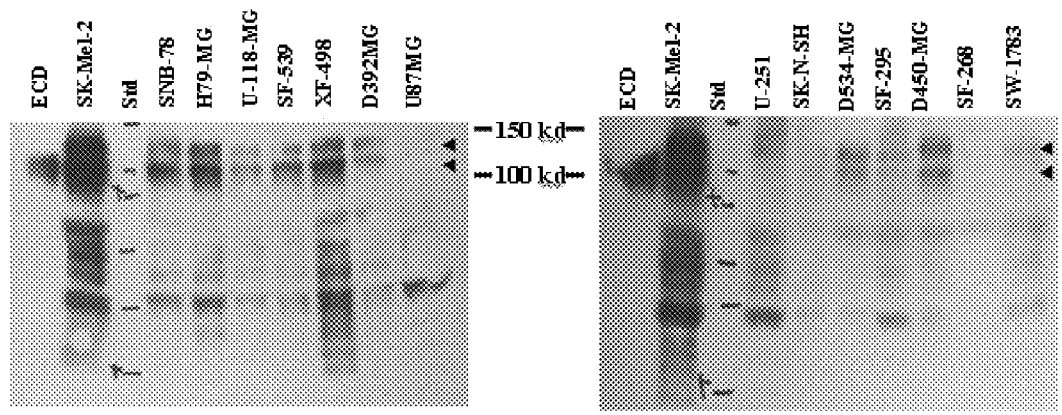
FIG. 15: Immunoblot analysis of CG5672 expression in human brain cancer cell lines. Cell lysates are resolved on Tris-glycine gels and transferred to membranes. Immunoblot analysis is carried out with a polyclonal antibody to CG56972 followed by enhanced chemiluminescence detection as described in Materials and Methods. Arrowheads indicate the relative mobility of the p100 and 120 CG56972 species. The SF-268 cell line is CG56972 transcript negative and used as a negative control.

To investigate CG56972 protein expression in our panel of brain cancer cell lines, total cell lysates were harvest, resolved by SDS-PAGE, transferred to membrane filters and subjected to immunoblot analysis with a CG56972 polyclonal antibody. As shown in FIG. 15, the CG56972 polyclonal antibody detected two protein species that are differential glycosylation products of CG56972 of approximately 100 and 120 kDa from various brain cancer cell lines that have been shown to express CG56972 transcripts (FIG. 13A). CG56972 protein was highly expressed in XF-498, SNB-78 and H79-MG and SF-539 cells. Both p100 and p120 species were detected to a lesser extent in U-118-MG, U251, D534-MG and D450-MG. Little or no CG56972 protein was detected in weakly expressing CG56972 transcript cell line, SF-268. An isotype-matched control IgG2 antibody did not immunoprecipitate CG56972 from any of the cell lines examined All of these data are consistent with the cell surface expression of the CG56972 protein of the predicted molecule weights in brain cancer.

4. In Vitro Growth-inhibition of Astrocytoma/glioblastoma Cell Lines with CR011-vcMMAE.

CG56972 possesses a very restricted human tissue expression pattern. In preliminary studies, CR011 did not inhibit the growth of CG56972-expressing cancer cell lines when used directly (data not shown). Since CG56972 is a cell surface molecule on brain cancers and melanoma, and since CR011 was internalized following incubation with CG56972-expressing cells, we evaluated whether CR011 would inhibit the growth of cancer cells when combined with a protein synthesis inhibitor (saporin)-conjugated secondary antibody. Our results indicated that CR011 could specifically inhibit the growth of CG56972-expressing cancer cells (data not shown). Thus, we conjugated CR011 directly to the cytotoxic drug monomethyl aurostatin E (MMAE) through a highly stable, but intracellular protease cleavable valine-citrulline (vc) linker. The resulting antibody-drug conjugate was named CR011-vcMMAE.

Figure 16:
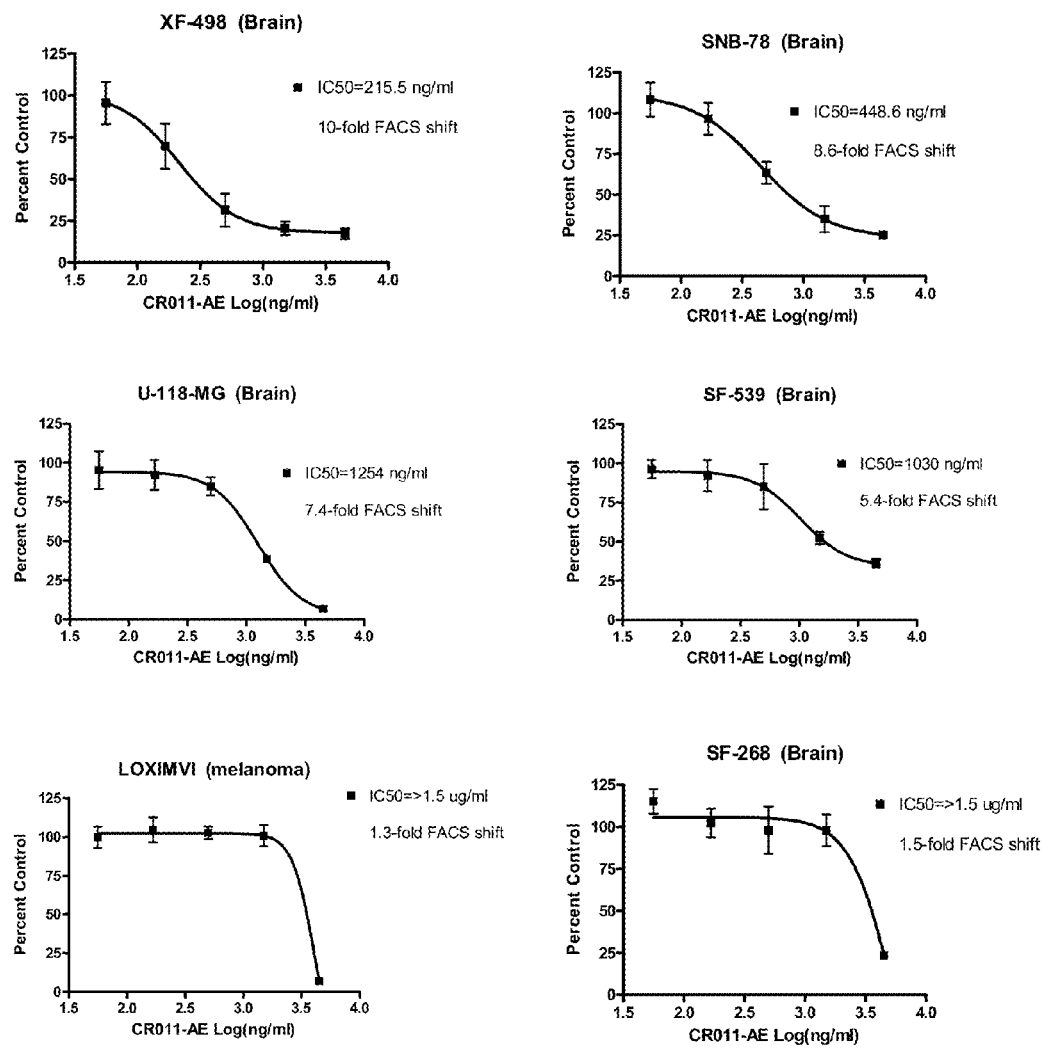
FIG. 16: CR011-vcMMAE in vitro growth inhibition of astocytoma/glioblastoma cell growth. XF-498, SNB-78, U-118-MG, SF-539, LOXIMVI and SF-268 cells are incubated with the indicated concentration of CR011-vcMMAE. Cells are also incubated with control PK16.3 mAb (data shown in Table I) as described in the Materials and Methods. Cell growth was determined by clonogenic assay. The surviving colonies are counted and plotted using GraphPad Prism graphing software. The experiment is performed in triplicate wells and repeated twice. vA representative experiment is shown. IC50s for cell killing is presented in ng/mL concentrations. The LOXIMVI and SF-268 cell lines are CG56972 transcript negative and used as negative controls.

To investigate whether CR011-vcMMAE specifically inhibited the growth of brain cancer cells, clonogenic assays were performed to assess cell viability after CR011-vcMMAE treatment. As shown in FIG. 16 and Table 54, our results indicated that CG56972-expressing cells were sensitive to growth-inhibition induced by CR011-vvMMAE, but not cells that poorly expressed this antigen (see SF-268 and LOX-IMVI) at concentrations of vcMMAE less than 3 µg/mL. Strikingly, CR011-vcMMAE possessed IC50s of approximately 215, 450, 1250, and 1050 ng/mL on XF-498, SNB-78, U-118-MG and SF-539 cells (FIG. 16 and Table 54). In these experiments, IC50s correlated with cell surface density as measured by FACS analysis. In contrast, conjugated control human IgG2 antibody-vcMMAE failed to inhibit the growth of any of the cell lines examined at concentrations up to 3 µg/mL (Table 54) with IC50s exceeding 1.5 or 4.5 µg/mL (Table 54).

TABLE 54

Summary of RTQ PCR, FACS and in vitro growth inhibition of human cancer cell lines with CR011-mAbs

| Cell Line | Description | CT Values | CR011 Fold Shift | CR011-AE IC50 (ng/ml) | IgG2-AE IC50 (ng/ml) |
|---|---|---|---|---|---|
| SK-MEL-2 | melanoma | ND | 13.1, 21.4, 17.8 | 303 | >1500 |
| XF-498 | glioblastoma | +++ | 10, 9.5 | 216 | >1500 |
| SNB-78 | astrocytoma | +++ | 8.6 | 449 | >1500 |
| U-118-MG | glioblastoma/astrocytoma | +++ | 7.4 | 1254 | >1500 |
| SF-539 | glioblastoma | + | 5.4 | 1030 | >4500 |
| H79MG | glioblastoma/astrocytoma | ND | 4.7, 3.9 | ND | ND |
| D392-MG | glioblastoma | ND | 3.1 | ND | ND |
| D534-MG | glioblastoma | ND | 2.3 | ND | ND |
| SK-N-SH | neuroblastoma | + | 2 | ND | ND |
| U-251 | glioblastoma | +++ | 1.9 | ND | ND |
| SF-295 | glioblastoma | ++ | 1.8 | ND | ND |
| D450-MG | glioblastoma | ND | 1.6 | ND | ND |
| U87MG | glioblastoma/astrocytoma | ++ | 1.5 | ND | ND |
| SF-268 | glioblastoma/astrocytoma | + | 1.5 | >1500 | >4500 |
| T98G | glioblastoma | + | 1.3 | ND | ND |
| SW 1783 | astrocytoma | + | 1.1 | ND | ND |

<sup>a</sup>CR011vcMMAE (mAb 1.15): CT values were determined by RTQ PCR as described in Materials and Methods. Geometric Mean ratios (GMR) were determined by flow cytometric analysis. Antibody-Drug Cytotoxicity (ADC) or cell killing was determined by clonogenic assay as described.
<sup>b</sup>IC$_{50}$ value is the mean and SD of a representative clonogenic assay with each experiment performed in triplicate wells.
ND: Not done.

Conclusion:

These data indicate that CR011-vcMMAE can be a highly potent and selective agent for the treatment of astrocytoma/glioblastoma and their metastasis as well as brain tumors of medulloblastoma and neuroectodermal origin. CR011-vcM-MAE can also be useful for the treatment of melanoma metastasis to brain and other brain neoplasms such as neoplastic meningitis.

Example 28

Engineered Antibodies Derived from CR011

Figure 17:
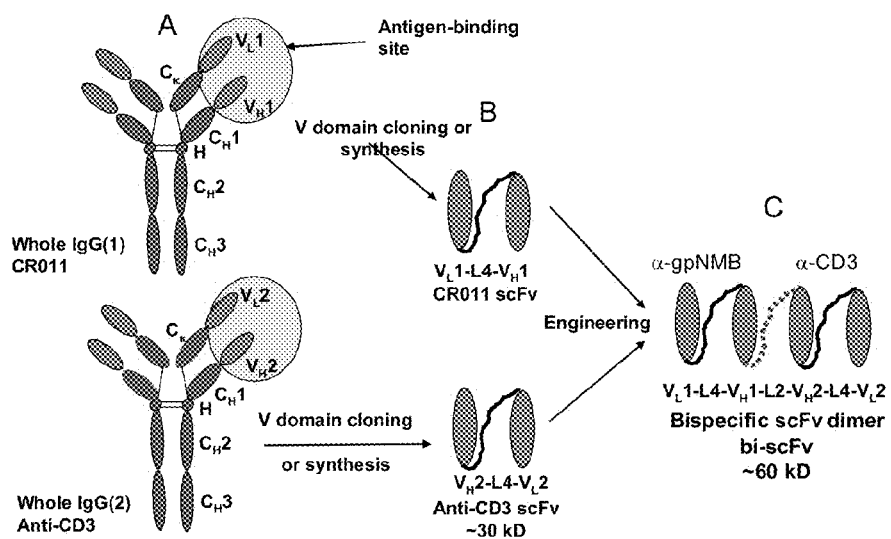
FIG. 17: Development of CR011Engineered Antibodies. Four antibody variable (V) domains (shown in C for the bi-scFv) are derived from the light and heavy chain variable domains ($V_L$ and $V_H$) making up the antigen binding sites of CR011 and anti-CD3 whole IgGs. The middle linker joining the 2 individual scFv components together (shown in dashed line) may play a key role in determining the resulting activity of each of the scFv components, including the effective cytolytic activity provided by the cytotoxic T cells engaged by the anti-CD3 scFv component of the bi-scFv.

The CR011 bi-scFv's (see FIG. 17) of this work were designed to bind to a CD3 epitope of the T cell receptor on cytotoxic human T lymphocytes and, at the same time, to target diseased cells expressing GPNMB, with the net result of facilitating the lysis or destruction of the diseased cells.

The $V_L$ and $V_H$ domains of mAb CR011, clone 1.15 were used in the construction of 3 CR011 based engineered antibodies:
(1) CR011 single chain antibody (CR011 scFv)
(2) CR011 x anti-CD3 bispecific single chain antibody (bi-scFv), Linker set L4-L2-L4
(3) CR011 x anti-CD3 bispecific single chain antibody (bi-scFv), Linker set L4-L4-L4

The components of the CR011 scFv protein were: Signal Peptide-$V_L$ (CR011)-Linker 4-$V_H$ (CR011)-Flag Tag. The components of the CR011 x anti-CD3 bi-scFv (Linker set L4-L2-L4) protein were: Signal Peptide-$V_L$ (CR011)-Linker 4-$V_H$ (CR011)-Linker 2-$V_H$ (anti-CD3)-Linker 4-$V_L$ (anti-CD3)-Flag Tag. The components of the CR011 x anti-CD3 bi-scFv (Linker set L4-L4-L4) protein were: Signal Peptide-$V_L$ (CR011)-Linker 4-$V_H$ (CR011)-Linker 4-$V_H$ (anti-CD3)-Linker 4-$V_L$ (anti-CD3)-Flag Tag.

The various DNA components outlined above were used to generate the three CR011 engineered antibody products. The DNA components were synthesized by Blue Heron and cloned into commercially available plasmid vectors by methods familiar to those skilled in the art. These plasmids were then used in PCRs to combine the components, indicated in the 3 examples above, to generate engineered antibody inserts for expression vectors. In the host expression system examples practicing this invention described below, we have used CHOK1 mammalian cells for the CR011 expression vectors, but expression is not limited to these cells; it will be recognized by those skilled in the art that the CR011 engineered antibodies of this invention can be expressed using other vectors, systems and cells, including but not limited to: pET vectors, inducible and constitutive promoters, and hosts may include E. coli, Bacillus species, yeast, including Pichia pastoris or insect cells. Other expression hosts can also include various plant species and transgenic animals such as goats.

SP (Signal Peptide): We incorporated a signal peptide in our constructs in order to express products that will be secreted. The signal peptide which was utilized for expression from CHO cells was derived from an immunoglobulin light chain leader peptide (Jirik et al., 1986), or from the CR002 antibody (CuraGen).

Order of the bi-scFv Components: The order of the antibody variable domains was fixed in both bi-scFv constructs as follows: $V_L1$-L-$V_H1$-L-$V_H2$-L-$V_L2$. Each of the 4 V domains was linked by a linker segment, L. $V_L1$ and $V_H1$ represent the immunoglobulin light and heavy chain variable domains respectively of CR011, and $V_H2$ and $V_L2$ represent the immunoglobulin heavy and light chain variable domains respectively of an anti-CD3 antibody that was used for both bi-scFv constructs. Other orders of the V domains can also be used for the 2 scFv components, as recognized by those skilled in the art, and the products evaluated for biological activity.

Tag: We used the 8 amino acid Flag tag at the C-terminus of the CR011 engineered antibodies to facilitate detection and purification of the products (Hickman et al., 2000).

Anti-CD3 scFv: The sequences of the $V_L$ and $V_H$ components of the anti-CD3 antibody used to generate the bi-scFv constructs may be found in the NCBI database under accession number CAE85148 (Lutterbuese et al.)

Linkers Used in Constructs: The sequence of L2, a short 5 amino acid linker that links the 2 monomer scFv components together in CR011 x anti-CD3 bi-scFv (L4-L2-L4 linker set) is G$_4$S (Mack et al., 1995). L4 is a 25 amino acid linker based on the 205C linker (Denzin et al., 1991): LSADD-AKKDAAKKDDAKKDDAKKDL (SEQ ID NO: 344) and is used in both of the CR011 bi-scFv species to link the CR011 $V_L$ and $V_H$ and the anti-CD3 $V_H$ and $V_L$. In the case of the CR011 x anti-CD3 bi-scFv (L4-L4-L4 linker set), L4 is also used to link the 2 monomer scFv components together. For the CR011 scFv, the L4 linker was used to link the two variable domains together.

1. DNA Plasmid Constructs for Expression of CR011 scFv and CR011X Anti-CD3 bi-scFv Species CR011 scFv Flag Tag: The PCR amplification product for generating the expression construct for CR011 scFv was generated from a synthetic DNA template (Blue Heron) using the F1/R1 primers followed by nested PCR with the F1 nested/R1 primer pair (Table 55) and Pfu Turbo DNA polymerase (Stratagene, cat 600322), as per the manufacturer's directions. A Sal I/EcoR I PCR fragment coding for the CR011 scFv cassette was cloned into the corresponding restriction sites of the pCTN vector (CuraGen Corporation, mammalian expression vector) using the Fast-Link DNA Ligation kit (Epicentre, cat#LK11025).

TABLE 55

| Name | Sequence |
|---|---|
| F1 Primer | 5'-TCTCTTCCTCCTGCTACTCTGGCTCCCAGATACCACCGGTGAAATAGTGATGACGCAGTC (SEQ ID NO: 345) |
| R1 Primer | 5'-CCGGAATTCTTACTATTTGTCATCATCGTCCTTATAATCGCTAGCTGAGGAGACGGT (SEQ ID NO: 346) |
| F1 Nested Primer | 5'-ACGCGTCGACCCACCATGGAAGCCCCAGCGCAGCTTCTCTTCCTCCTGCTACTCTGGCTC (SEQ ID NO: 347) |

TABLE 55-continued

| Name | Sequence |
|---|---|
| F2 Primer | 5'-TCTCTTCCTCCTGCTACTCTGGCTCCCAGATACCACCGGTGAAATAGTGATGACGCAGTC (SEQ ID NO: 348) |
| R2 Primer | 5'-CCGGAATTCTTACTATTTGTCATCATCGTCCTTATAATCGCTAGCTTTCAGCTCCAG (SEQ ID NO: 349) |
| F2 Nested Primer | 5'-ACGCGTCGACCCACCATGGAAGCCCCAGCGCAGCTTCTCTTCCTCCTGCTACTCTGGCTC (SEQ ID NO: 350) |
| F3 Primer | 5'-ACTCTGGCTCCCAGATACCACCGGAGAAATAGTGATGACGCAGTCTCCAGCCACC (SEQ ID NO: 351) |
| R3 Primer | 5'- CCGCTCGAGCTATTTGTCATCATCGTCCTTATAATCTTTCAGCTCCAGCTT (SEQ ID NO: 352) |
| F3 Nested Primer | 5'-TCTTCGCGACCACCATGGAAACCCCAGCGCAGCTTCTCTTCCTCCTGCTACTCTGGCTCCCAGATACCACCGGA (SEQ ID NO: 353) |

CR011 x Anti-CD3 bi-scFv (L4-L2-L4) Linker Set Flag Tag: The PCR amplification product for the CR011 x anti-CD3 bi-scFv having the (L4-L2-L4) linker set, was generated from a synthetic DNA template (Blue Heron) using the F2/R2 primers followed by nested PCR with the F2 nested/R2 primer pair (see Table 55 for sequences of oligonucleotides) and Pfu Turbo DNA polymerase (Stratagene, cat 600322), as per the manufacturer's directions. The Sal I/EcoR I PCR fragment having the coding sequence for the CR011 x anti-CD3 (L4-L2-L4) bi-scFv was cloned into the corresponding sites of the pCTN vector using Fast-Link DNA Ligation kit (Epicentre, cat#LK11025).

CR011 x Anti-CD3 bi-scFv (L4-L4-L4) Linker Set Flag Tag: The PCR amplification product for the CR011 x anti-CD3 bi-scFv having the (L4-L4-L4) linker set, was generated from a synthetic DNA template (Blue Heron) using the F3/R3 primers followed by nested PCR with the F3 nested/R3 primer pair (Table 55) and Pfu Turbo DNA polymerase (Stratagene, cat 600322), as per the manufacturer's directions. The Nru I/Xho I PCR fragment having the coding sequence for the CR011 x anti-CD3 (L4-L4-L4) bi-scFv was cloned into the corresponding sites of the pEE14.4FL2 expression vector (Lonza Biologics plc, 228 Bath Road, Slough, Berkshire SL1 4Dx, UK) using the Fast-Link DNA Ligation kit (Epicentre, cat#LK11025).

The DNA sequences of the above 3 expression construct inserts were verified by sequencing both strands of the relevant DNA products.

2. Protein Production of the CR011Engineered Antibodies in CHOK1 Cells

Adherent Chinese Hamster Ovary (CHOK1) cells (ATCC catalog# CCL-61) were grown in DMEM media (Invitrogen, cat 10564-011) supplemented with 10% fetal bovine serum (Gemini, cat 100106), GS supplement (JRH Biosciences, cat 58672-100M) and 50 mg/L gentamicin (Invitrogen, cat# 15750078).

CHOK1 cells were transfected with FuGENE 6 reagent (Roche, cat 1815075) according to the manufacturer's directions. Expression and secretion was verified by Western blotting performed ca. 48 hours after the transfections. Selection of stable secreted CR011 scFv and CR011 x anti-CD3 bi-scFv (L4-L2-L4 linker set) lines were performed in selection media A (Table 56), while selection of a stable secreted CR011 x anti-CD3 bi-scFv (L4-L4-L4 linker set) line was performed in selection media B (Table 57).

TABLE 56

| CHOK1 (Adherent) Selection Media A | Vendor | Item No. | Description |
|---|---|---|---|
| DMEM-glutamine free | JRH Biosciences | 51435-1000M | Glutamine-Free Media for GS System(TM) (DMEM/High Modified) |
| 10% dialyzed FBS (heat inactivated 56° C. for 30 minutes) | JRH Biosciences | 12117-500M | Fetal Bovine Serum, Dialyzed (500 mL) |
| 1X GS Supplement | JRH Biosciences | 58672-100M | GS Supplement (50X) |
| 50 mg/L gentamicin | Invitrogen | 15750078 | Gentamicin Reagent Solution (50 mg/mL), liquid |
| 1 mg/mL G418 | Invitrogen | 10131027 | Geneticin (G418) |

TABLE 57

| CHOK1 (Adherent) Selection Media B | Vendor | Item No. | Description |
|---|---|---|---|
| DMEM-glutamine free | JRH Biosciences | 51435-1000M | Glutamine-Free Media for GS System(TM) (DMEM/High Modified) |
| 10% dialyzed FBS (heat inactivated 56° C. for 30 minutes) | JRH Biosciences | 12117-500M | Fetal Bovine Serum, Dialyzed (500 mL) |
| 1X GS Supplement | JRH Biosciences | 58672-100M | GS Supplement (50X) |
| 50 mg/L gentamicin | Invitrogen | 15750078 | Gentamicin Reagent Solution (50 mg/mL), liquid |
| 25 µM MSX | Sigma | M5379 | L-Methionine sulfoximine (MSX) |

In each case, 8 out of 96 CR011 scFv and CR011 x anti-CD3 (L4-L2-L4 linker set) bi-scFv CHOK1 clones that were secreting products were expanded and archived. The best stable clones secreting products in each case were adapted to suspension culture in shake flasks with selection media C (Table 58) at 37° C. and 5% $CO_2$. Protein production for CR011scFv and CR011xCD3 (L4-L2-L4 linker set) bi-scFv was carried out in 4 L of selection media D (Table 59) at 30° C. and 5% $CO_2$.

TABLE 58

| CHOK1 Large Scale (Suspension) Selection Media C | Vendor | Item number | Description |
|---|---|---|---|
| Ex-Cell 302 | JRH Biosciences | 14324-1000M | Ex-Cell 302 CHO Serum-free medium without L-glutamine (1000 mL) |
| 5% FBS | JRH Biosciences | 12117-500M | Fetal Bovine Serum, Dialyzed (500 mL) |
| GS Supplement | JRH Biosciences | 58672-100M | GS Supplement (50X) |
| HT Supplement | Invitrogen | 11067030 | HT Supplement (100X) |
| 1 mg/mL G418 | Invitrogen | 10131027 | Geneticin (G418) |

TABLE 59

| CHOK1 Large Scale (Suspension) Selection Media D | Vendor | Item number | Description |
|---|---|---|---|
| Ex-Cell 302 + Ex-Cell CD CHO (1:1) | JRH Biosciences | 14324-1000M | Ex-Cell 302 CHO Serum-free medium without L-glutamine (1000 mL) |
| | JRH Biosciences | 14360-1000M | CD CHO Medium (1000 mL) |
| 5% FBS | JRH Biosciences | 12117-500M | Fetal Bovine Serum, Dialyzed (500 mL) |
| GS Supplement | JRH Biosciences | 58672-100M | GS Supplement (50X) |
| HT Supplement | Invitrogen | 11067030 | HT Supplement (100X) |
| 1 mg/mL G418 | Invitrogen | 10131027 | Geneticin (G418) |

Only one out of two hundred CR011 x anti-CD3 (L4-L4-L4 linker set) bi-scFv CHOK1 clones was found to produce a secreted product; this clone was expanded and archived. Protein production for the CR011 x anti-CD3 (L4-L4-L4 linker set) clone was carried out using a cell factory apparatus (Nunc, cat 164327), in selection media B (Table 57), 1 mM sodium butyrate (Sigma, cat#B5887) at 37° C. and 10% $CO_2$.

3. Protein Purification of the CR011 Engineered Antibodies

Protein purification for the CR011 scFv Flag and CR011 x anti-CD3 (L4-L2-L4 linker set) bi-scFv Flag was accomplished in three chromatography steps, including affinity, ion exchange and size exclusion chromatographies. For the purification of CR011 x anti-CD3 (L4-L4-L4 linker set) bi-scFv Flag protein, affinity and size exclusion chromatographies were used.

Affinity chromatography was performed using anti-FLAG M2 affinity gel (Sigma, cat# A2220-25 mL) as per the manufacturer's instructions on a BioCAD 700E instrument (Applied Biosystems). Ion exchange chromatography was performed on a MonoQ 5/50 GL column (Amersham, cat 17-5166-01) using 20 mM Tris-HCl pH7.5 as equilibration buffer and a gradient elution with 0-1 M NaCl. Size exclusion chromatography was performed using a Superdex 75/10/300 GL column (Amersham, cat 17-5174-01) following the manufacturer's protocols on BioCAD 700E (Applied Biosystems) liquid chromatography instrument.

The approximate yields from 1 L conditioned CHOK1 media were:

(1) CR011 scFv: 1.0 mg
(2) CR011 x anti-CD3 (L4-L2-L4 linker set) bi-scFv: 0.5 mg
(3) CR011 x anti-CD3 (L4-L4-L4 linker set) bi-scFv: 1.5 mg The N-terminal amino acid sequence of the purified proteins was determined by Edman degradation, using methods known to those skilled in the art. The sequence of the first five amino acids was: E I V M T in each case (the mature N-terminus of the CR011$V_L$ protein), indicating that accurate processing by signal peptidase had occurred to give a soluble, secreted product of the predicted sequence and size.

The DNA and amino acid sequences of the 3 CR011 engineered products are given below.

SEQ ID for CR011 scFv-($V_L$-L4-$V_H$) Flag. The Signal peptide of Human kappa light chain was used as described in Kabat et al. 45 CLL-CL). There was a FLAG tag included at the C-terminus. The Kozak sequence CCACC was included in the 5' PCR primer.

(SEQ ID NO: 354)

```
ATGGAAGCCCCAGCGCAGCTTCTCTTCCTCCTGCTACTCTGGCTCCCAGATACCACCGGTGAAAT

AGTGATGACGCAGTCTCCAGCCACCCTGTCTGTGTCTCCAGGGGAAAGAGCCACCCTCTCCTGCA

GGGCCAGTCAGAGTGTTGACAACAACTTAGTCTGGTACCAGCAGAAACCTGGCCAGGCTCCCAG

GCTCCTCATCTATGGTGCATCCACCAGGGCCACTGGTATCCCAGCCAGGTTCAGTGGCAGTGGGT

CTGGGACAGAGTTCACTCTCACCATCAGTAGTCTGCAGTCTGAAGATTTTGCAGTTTATTACTGTC

AGCAGTATAATAACTGGCCTCCGTGGACGTTCGGCCAAGGGACCAAGGTGGAAATCAAACTTTC

CGCGGACGATGCGAAAAAGGATGCTGCGAAGAAAGATGACGCTAAGAAAGACGATGCTAAAAA

GGACCTGCAGGTGCAGCTGCAGGAGTCGGGCCCAGGACTGGTGAAGCCTTCACAGACCCTGTCC

CTCACCTGCACTGTCTCTGGTGGCTCCATCAGCAGTTTTAATTACTACTGGAGCTGGATCCGCCAC

CACCCAGGGAAGGGCCTGGAGTGGATTGGGTACATCTATTACAGTGGGAGCACCTACTCCAACC

CGTCCCTCAAGAGTCGAGTTACCATATCAGTAGACACGTCTAAGAACCAGTTCTCCCTGACGCTG

AGCTCTGTGACTGCCGCGGACACGGCCGTGTATTACTGTGCGAGAGGGTATAACTGGAACTACTT
```

```
-continued
TGACTACTGGGGCCAGGGAACCCTGGTCACCGTCTCCTCAGCTAGCGATTATAAGGACGATGAT

GACAAATAGTAA
```

(SEQ ID NO: 355)
```
MEAPAQLLFLLLLWLPDTTGEIVMTQSPATLSVSPGERATLSCRASQSVDNNLVWYQQKPGQAPRLL

IYGASTRATGIPARFSGSGSGTEFTLTISSLQSEDFAVYYCQQYNNWPPWTFGQGTKVEIKLSADDAK

KDAAKKDDAKKDDAKKDLQVQLQESGPGLVKPSQTLSLTCTVSGGSISSFNYYWSWIRHHPGKGLE

WIGYIYYSGSTYSNPSLKSRVTISVDTSKNQFSLTLSSVTAADTAVYYCARGYNWNYFDYWGQGTLV

TVSSASDYKDDDDK
```

SEQ ID for CR011 x anti-CD3 (L4-L2-L4 linker set) bi-scFv—The Signal peptide of Human kappa light chain was used as described in Kabat et al. 45 CLL-CL). There was a FLAG tag included at the C-terminus.

(SEQ ID NO: 356)
```
ATGGAAGCCCCAGCGCAGCTTCTCTTCCTCCTGCTACTCTGGCTCCCAGATACCACCGGTGAAAT

AGTGATGACGCAGTCTCCAGCCACCCTGTCTGTGTCTCCAGGGGAAAGAGCCACCCTCTCCTGCA

GGGCCAGTCAGAGTGTTGACAACAACTTAGTCTGGTACCAGCAGAAACCTGGCCAGGCTCCCAG

GCTCCTCATCTATGGTGCATCCACCAGGGCCACTGGTATCCCAGCCAGGTTCAGTGGCAGTGGGT

CTGGGACAGAGTTCACTCTCACCATCAGTAGTCTGCAGTCTGAAGATTTTGCAGTTTATTACTGTC

AGCAGTATAATAACTGGCCTCCGTGGACGTTCGGCCAAGGGACCAAGGTGGAAATCAAACTTTC

CGCGGACGATGCGAAAAAGGATGCTGCGAAGAAAGATGACGCTAAGAAAGACGATGCTAAAAA

GGACCTGCAGGTGCAGCTGCAGGAGTCGGGCCCAGGACTGGTGAAGCCTTCACAGACCCTGTCC

CTCACCTGCACTGTCTCTGGTGGCTCCATCAGCAGTTTTAATTACTACTGGAGCTGGATCCGCCAC

CACCCAGGGAAGGGCCTGGAGTGGATTGGGTACATCTATTACAGTGGGAGCACCTACTCCAACC

CGTCCCTCAAGAGTCGAGTTACCATATCAGTAGACACGTCAAGAACCAGTTCTCCCTGACGCTG

AGCTCTGTGACTGCCGCGGACACGGCCGTGTATTACTGTGCGAGAGGGTATAACTGGAACTACTT

TGACTACTGGGGCCAGGGAACCCTGGTCACCGTCTCCTCAGGAGGTGGTGGATCCGATATCAAA

CTGCAGCAGTCAGGGGCTGAACTGGCAAGACCTGGGGCCTCAGTGAAGATGTCCTGCAAGACTT

CTGGCTACACCTTTACTAGGTACACGATGCACTGGGTAAAACAGAGGCCTGGACAGGGTCTGGA

ATGGATTGGATACATTAATCCTAGCCGTGGTTATACTAATTACAATCAGAAGTTCAAGGACAAGG

CCACATTGACTACAGACAAATCCTCCAGCACAGCCTACATGCAACTGAGCAGCCTGACATCTGA

GGACTCTGCAGTCTATTACTGTGCAAGATATTATGATGATCATTACTGCCTTGACTACTGGGGCC

AAGGCACCACTCTCACAGTCTCCTCACTTTCCGCGGACGATGCGAAAAAGGATGCTGCGAAGAA

AGATGACGCTAAGAAAGACGATGCTAAAAAGGACCTGGACATTCAGCTGACCCAGTCTCCAGCA

ATCATGTCTGCATCTCCAGGGGAGAAGGTCACCATGACCTGCAGAGCCAGTTCAAGTGTAAGTT

ACATGAACTGGTACCAGCAGAAGTCAGGCACCTCCCCCAAAAGATGGATTTATGACACATCCAA

AGTGGCTTCTGGAGTCCCTTATCGCTTCAGTGGCAGTGGGTCTGGGACCTCATACTCTCTCACAA

TCAGCAGCATGGAGGCTGAAGATGCTGCCACTTATTACTGCCAACAGTGGAGTAGTAACCCGCT

CACGTTCGGTGCTGGGACCAAGCTGGAGCTGAAAGCTAGCGATTATAAGGACGATGATGACAAA

TAGTAA
```

(SEQ ID NO: 357)
```
MEAPAQLLFLLLLWLPDTTGEIVMTQSPATLSVSPGERATESCRASQSVDNNLVWYQQKPGQAPRLL

IYGASTRATGIPARFSGSGSGTEFTLTISSLQSEDFAVYYCQQYNNWPPWTFGQGTKVEIKLSADDAK

KDAAKKDDAKKDDAKKDLQVQLQESGPGLVKPSQTLSLTCTVSGGSISSFNYYWSWIRHHPGKGLE
```

-continued

```
WIGYIYYSGSTYSNPSLKSRVTISVDTSKNQFSLTLSSVTAADTAVYYCARGYNWNYFDYWGQGTLV

TVSSGGGGSDIKLQQSGAELARPGASVKMSCKTSGYTFTRYTMHWVKQRPGQGLEWIGYINPSRGY

TNYNQKFKDKATLTTDKSSSTAYMQLSSLTSEDSAVYYCARYYDDHYCLDYWGQGTTLTVSSLSAD

DAKKDAAKKDDAKKDDAKKDLDIQLTQSPAIMSASPGEKVTMTCRASSSVSYMNWYQQKSGTSPK

RWIYDTSKVASGVPYRFSGSGSGTSYSLTISSMEAEDAATYYCQQWSSNPLTFGAGTKLELKASDYK

DDDDK
```

SEQ ID for CR011 x anti-CD3 (L4-L4-L4 linker set) bi-scFv—The Signal peptide of CR002 was used. There was a FLAG tag included at the C-terminus.

(SEQ ID NO: 358)
```
ATGGAAACCCCAGCGCAGCTTCTCTTCCTCCTGCTACTCTGGCTCCCAGATACCACCGGAGAAAT

AGTGATGACGCAGTCTCCAGCCACCCTGTCTGTGTCTCCAGGGGAAAGAGCCACCCTCTCCTGCA

GGGCCAGTCAGAGTGTTGACAACAACTTAGTCTGGTACCAGCAGAAACCTGGCCAGGCTCCCAG

GCTCCTCATCTATGGTGCATCCACCAGGGCCACTGGTATCCCAGCCAGGTTCAGTGGCAGTGGGT

CTGGGACAGAGTTCACTCTCACCATCAGTAGTCTGCAGTCTGAAGATTTTGCAGTTTATTACTGTC

AGCAGTATAATAACTGGCCTCCGTGGACGTTCGGCCAAGGGACCAAGGTGGAAATCAAACTTTC

CGCGGACGATGCGAAAAGGATGCTGCGAAGAAAGATGACGCTAAGAAAGACGATGCTAAAAA

GGACCTGCAGGTGCAGCTGCAGGAGTCGGGCCCAGGACTGGTGAAGCCTTCACAGACCCTGTCC

CTCACCTGCACTGTCTCTGGTGGCTCCATCAGCAGTTTTAATTACTACTGGAGCTGGATCCGCCAC

CACCCAGGGAAGGGCCTGGAGTGGATTGGGTACATCTATTACAGTGGGAGCACCTACTCCAACC

CGTCCCTCAAGAGTCGAGTTACCATATCAGTAGACACGTCTAAGAACCAGTTCTCCCTGACGCTG

AGCTCTGTGACTGCCGCGGACACGGCCGTGTATTACTGTGCGAGAGGGTATAACTGGAACTACTT

TGACTACTGGGGCCAGGGAACCCTGGTCACCGTCTCCTCATTATCAGCGGATGACGCCAAGAAA

GACGCAGCCAAAAAGGACGATGCAAAGAAGGATGACGCAAAGAAAGATTTAGATATCAAACTG

CAGCAGTCAGGGGCTGAACTGGCAAGACCTGGGGCCTCAGTGAAGATGTCCTGCAAGACTTCTG

GCTACACCTTTACTAGGTACACGATGCACTGGGTAAAACAGAGGCCTGGACAGGGTCTGGAATG

GATTGGATACATTAATCCTAGCCGTGGTTATACTAATTACAATCAGAAGTTCAAGGACAAGGCCA

CATTGACTACAGACAAATCCTCCAGCACAGCCTACATGCAACTGAGCAGCCTGACATCTGAGGA

CTCTGCAGTCTATTACTGTGCAAGATATTATGATGATCATTACTGCCTTGACTACTGGGGCCAAG

GCACCACTCTCACAGTCTCCTCACTTTCCGCGGACGATGCGAAAAGGATGCTGCGAAGAAAGA

TGACGCTAAGAAAGACGATGCTAAAAAGGACCTGGACATTCAGCTGACCCAGTCTCCAGCAATC

ATGTCTGCATCTCCAGGGGAGAAGGTCACCATGACCTGCAGAGCCAGTTCAAGTGTAAGTTACA

TGAACTGGTACCAGCAGAAGTCAGGCACCTCCCCCAAAAGATGGATTTATGACACATCCAAAGT

GGCTTCTGGAGTCCCTTATCGCTTCAGTGGCAGTGGGTCTGGGACCTCATACTCTCTCACAATCA

GCAGCATGGAGGCTGAAGATGCTGCCACTTATTACTGCCAACAGTGGAGTAGTAACCCGCTCAC

GTTCGGTGCTGGGACCAAGCTGGAGCTGAAAGATTATAAGGACGATGATGACAAATAGCTCGAG

CGG
```

(SEQ ID NO: 359)
```
METPAQLLFLLLLWLPDTTGEIVMTQSPATLSVSPGERATLSCRASQSVDNNLVWYQQKPGQAPRLLIY

GASTRATGIPARFSGSGSGTEFTLTISSLQSEDFAVYYCQQYNNWPPWTFGQGTKVEIKLSADDAKKDA

AKKDDAKKDDAKKDLQVQLQESGPGLVKPSQTLSLTCTVSGGSISSFNYYWSWIRHHPGKGLEWIGYI
```

-continued

```
YYSGSTYSNPSLKSRVTISVDTSKNQFSLTLSSVTAADTAVYYCARGYNWNYFDYWGQGTLVTVSSLS

ADDAKKDAAKKDDAKKDDAKKDLDIKLQQSGAELARPGASVKMSCKTSGYTFTRYTMHWVKQRPG

QGLEWIGYINPSRGYTNYNQKFKDKATLTTDKSSSTAYMQLSSLTSEDSAVYYCARYYDDHYCLDYW

GQGTTLTVSSLSADDAKKDAAKKDDAKKDDAKKDLDIQLTQSPAIMSASPGEKVTMTCRASSSVSYM

NWYQQKSGTSPKRWIYDTSKVASGVPYRFSGSGSGTSYSLTISSMEAEDAATYYCQQWSSNPLTFGAG

TKLELKDYKDDDDK
```

4. Testing of the 3 CR011 Engineered Antibodies by ELISA, Flow Cytometry and Determination of Cytotoxicity:

ELISA: The binding of the CR011 engineered antibodies to purified recombinant GPNMB (2 μg/mL) was measured using plates coated overnight at 4° C. Plates were then blocked and washed. Various dilutions of the CR011 engineered antibodies were added into the wells. Plates were incubated for 1 h and washed. HRP-conjugated anti-FLAG M2 mAb (Sigma, St. Louis, Mo.) was added into the wells for 1 h, washed and the reaction developed with the TMB substrate reagent as described by the manufacturer (Pharmingen, San Jose, Calif.).

Figure 18:
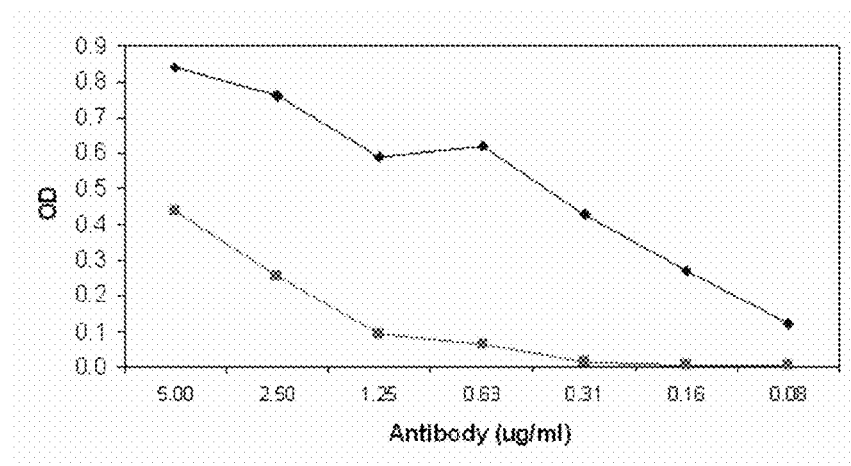
FIG. 18: A. ELISA results for CR011 scFv (squares) and CR011 x anti-CD3 (L4-L2-L4 linker set) bi-scFv (diamonds). Both engineered CR011 antibodies bound to the GPNMB target. B. Western blotting of 2 of the CR011 engineered antibody products (arrows). Clone 16 corresponded to the CHOK1 line expressing CR011 scFv (monomer), while clone 17 corresponded to the CHOK1 line expressing CR011 x anti-CD3 (L4-L2-L4 linker set) bi-scFv (dimer). Clones 16 and 17 are used to produce the engineered antibody products.
Figure 18:
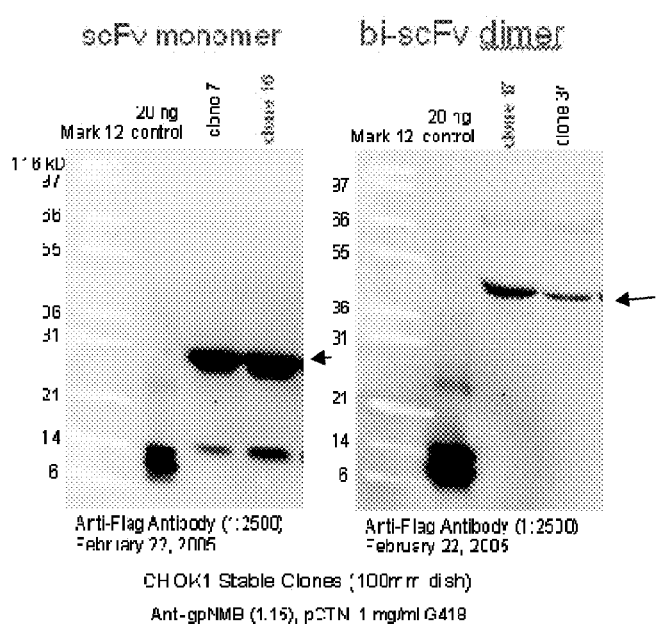

Binding of the CR011 scFv and CR011 x anti-CD3 (L4-L2-L4 linker set) bi-scFv product to GPNMB was first confirmed using ELISA, as shown in FIG. 18. Plates were coated with human GPNMB protein tagged with His and V5. Coated plates were incubated with either supernatants containing CR011 X anti-CD3 bi-scFv or purified CR011 scFv monomer. Binding of the recombinant mAbs (both monomer and dimer) was detected using anti-FLAG-HRP conjugated mAb M2 (Sigma). As can be seen in FIG. 18, both anti-GPNMB antibody species described bind to the recombinant GPNMB protein, indicating that the specificity and binding activity of the engineered anti-GPNMB antibody, using the methods described in this example, was preserved.

Flow Cytometry: The binding of the CR011 engineered antibodies to native proteins was analyzed by FACS. Briefly, human T cells and SK-Mel-5 cells were incubated with either the CR011 scFv or CR011 x anti-CD3 (L4-L2-L4 linker set) bi-scFv (5 μg/sample/100 μl) with subsequent staining with mouse anti-FLAG mAb (Sigma) and PE-conjugated goat anti-mouse Ig F(ab)$_2$. (Jackson ImmunoResearch, West Grove, Pa.) Ten thousand events were collected and analyzed on a FACSCalibur instrument (Becton Dickinson, Mountain View, Calif.).

Figure 19:
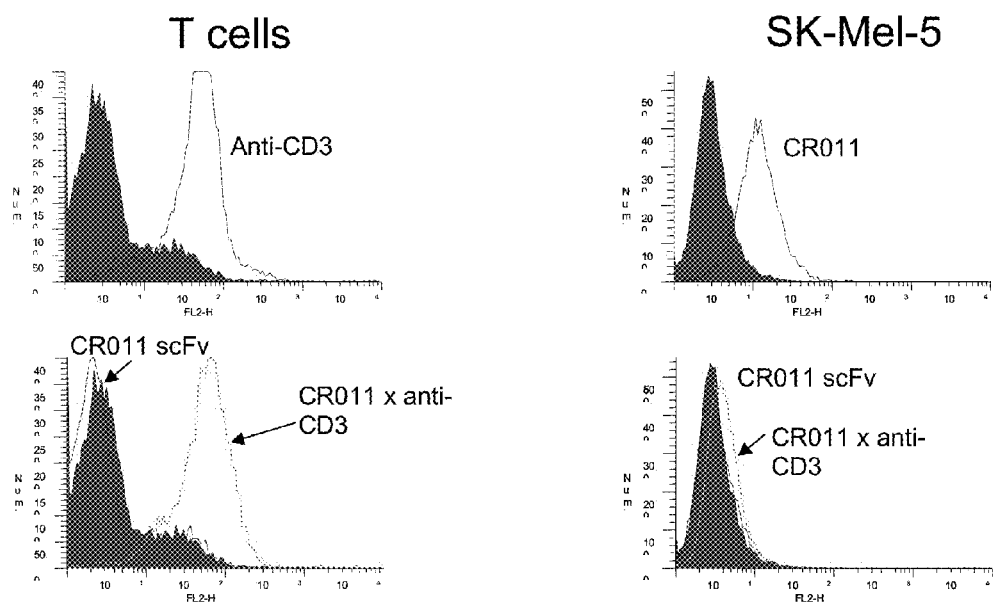
FIG. 19: Flow cytometry analysis of binding of CR011 scFv and CR011 x anti-CD3 (L4-L2-L4 linker set) bi-scFv products to native GPNMB protein expressed on the cell surface of target cells. Human T cells are used as a source of CD3, while SK-Mel-5 cells are used as a source of GPNMB.

To confirm binding of the CR011 scFv and CR011 x anti-CD3 (L4-L2-L4 linker set) bi-scFv products to native GPNMB protein expressed on the cell surface, we used SK-Mel-5 cells which naturally express GPNMB. To verify binding of the bi-scFv to human CD3 molecules, we used purified human T cells. As a positive control we used native PE conjugated anti-CD3-PE and CR011 mAb. Binding of the CR011 scFv was detected using anti-FLAG mAb M2 with subsequent staining with PE conjugated anti mouse IgG, while for detection of CR011 mAb binding we used anti-human IgG-PE. Control anti-CD3 mAb bound to T cells, and control anti-GPNMB mAb bound to SK-Mel-5 tumor cells. We found that only the CR011 x anti-CD3 (L4-L2-L4 linker set) bi-scFv stained T cells; the CR011 scFv monomer did not bind CD3 positive T cells, as expected (see FIG. 19). Binding to SK-Mel-5 cells by either the CR011 scFv monomer or CR011X anti-CD3 (L4-L2-L4 linker set) bi-scFv was present at a low level (FIG. 19).

Cytotoxicity: The ability of CR011 x anti-CD3 (L4-L2-L4 linker set) bi-scFv to redirect human T lymphocytes to kill relevant human tumor cells was measured by flow cytometry. Tumor cells were labeled with PKH2 green fluorescent linker kit (Sigma) and washed. Purified T cells were cultured O/N with PKH2-labeled tumor cells in the presence or absence of purified bi-scFv. Death of GPNMB positive tumor cells was measured by propidium iodine (PI) incorporation.

To evaluate the ability of the CR011 x anti-CD3 (L4-L2-L4 linker set) bi-scFv product to increase T cell mediated killing of GPNMB positive cells, we performed a cytotoxicity test. Purified T cells were cultured O/N with PKH2-labeled SK-Mel-5 (GPNMB positive) tumor cells in the presence of various doses of purified CR011 scFv and CR011 x anti-CD3 (L4-L2-L4 linker set) bi-scFv products.

Figure 20:
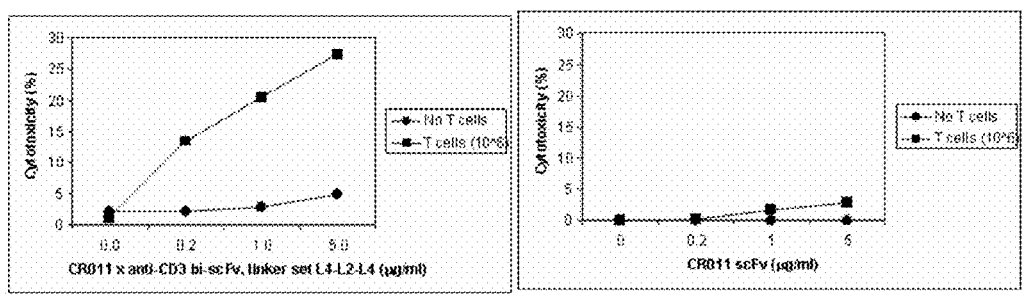
FIG. 20: Cytotoxicity analysis showed that purified CR011 x anti-CD3 (L4-L2-L4 linker set) bi-scFv, but not CR011 scFv, causes killing of GPNMB positive SK-Mel-5 tumor cells by T lymphocytes.

Conclusion:

The CR011 x anti-CD3 (L4-L2-L4 linker set) bi-scFv significantly increased killing of SK-Mel-5 tumor cells by T lymphocytes (FIG. 20). In contrast, the addition of mono-specific anti-GPNMB scFv did not increase killing of SK-Mel-5 tumors. In addition, no cytotoxicity was observed when the tumor cells were cultured with the CR011 x anti-CD3 (L4-L2-L4 linker set) bi-scFv without T lymphocytes (FIG. 20). These data indicate that the CR011 x anti-CD3 (L4-L2-L4 linker set) bi-scFv provided sufficient bridging between T cells and SK-Mel-5 cells to induce cell death and that both components of this engineered CR011 bi-specific antibody were biologically active. Therefore the CR011 x anti-CD3 (L4-L2-L4 linker set) bi-scFv engineered antibody of the present invention may be used as a therapeutic to treat diseases, such as melanoma and other cancers where there are upregulated levels of GPNMB and T cells present.

Other methods of cytotoxicity analysis, including fluorescence and chromium release assays can be used to demonstrate the usefulness of the CR011 x anti-CD3 (L4-L2-L4 linker set) bi-scFv in treating tumors. Other linkers may also be used to link the two scFv monomer components together, as in the CR011 xanti-CD3 (linker set L4-L4-L4) molecule described supra.

Example 29

Optimized Production Process of CR011-vcMMAE

CR011AE is an antibody-drug conjugate composed of the anti-GPNMB (CG56972) fully human antibody CR011 conjugated with the toxin Auristatin E through a protease-cleavable linker. The toxin-to-antibody ratio is approx. 4.0 but may vary between 3.5 and 4.2. While the CR011 antibody is IgG2, it is therefore possible to append up to 12 toxin molecules per antibody molecule using the free thiols as a reactive site.

Figure 21:
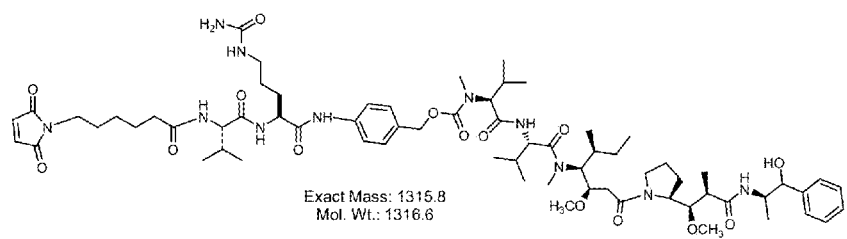
FIG. 21: The chemical structure of Maleimidocoaproyl-Valine-Citrullin-Monomethyl-Auristatin E (vcMMAE).

The structure of Maleimidocoaproyl-Valine-Citrullin-Monomethyl-Auristatin E (vcMMAE) is shown in FIG. 21.

Figure 22:
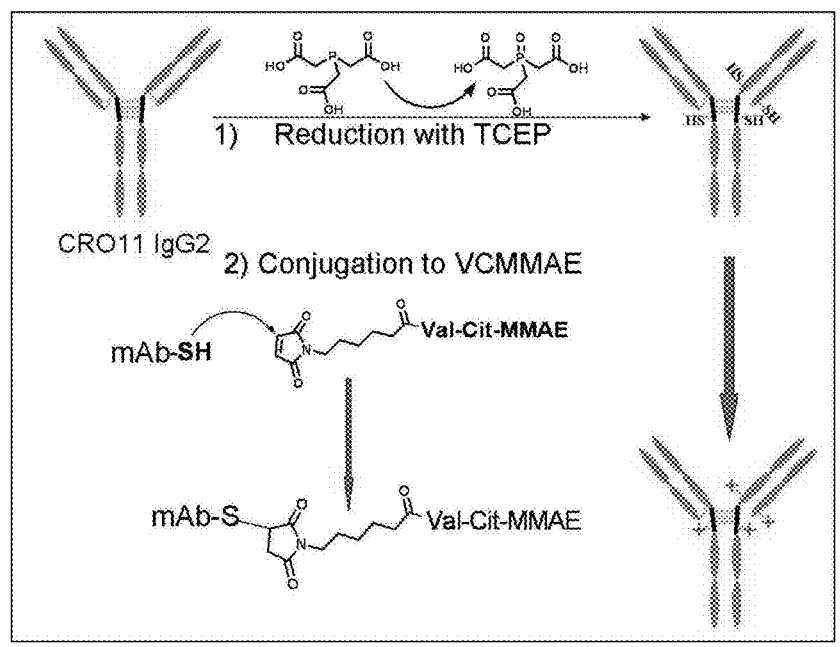
FIG. 22: Disulfides on CR011 antibody are gently reduced in the presence of TCEP to generate ~4 thiols per Ab. vcMMAE is then added to antibody solution. Nucleophilic attack of thiolates on maleimide-groups results in a stable thioester linkage. The resulting conjugate is purified from the mixture.

Conjugation: A process of generating the drug-substance consisting of CR011 mAb with VCMMAE attached. An overview of the conjugation process is summarized in FIG. 22.

Briefly, the conjugation process for CR011 fully human antibody consists of the following 4 steps. 1) Buffer exchange and sucrose removal by diafiltration, 2) Disulfides reduction, 3) Conjugation to vcMMAE and finally, 4) Purification of conjugated CR011-vcMMAE by diafiltration. There are several assays throughout the process, i.e. in-process assays, which include Ellman's assay and determination of protein concentration. At the end of the process, the drug substance, i.e. the conjugate, is analyzed for drug-to-antibody ratio, free drug content and protein concentration.

Diafiltration of the Bulk Antibody: The bulk antibody originally formulated in phosphate pH 7-10% sucrose was buffer exchanged into the conjugation buffer (borate pH 9.0-NaCl) by diafiltration over 10 diavolumes. At the end of diafiltration, CR011 was diluted to ~5.5 mg/mL and filtered through a set of two filters consisting of 1.2 and 0.22 jam. The buffer exchange is required because sucrose interferes with reduction. In addition, high pH improves CR011 solubility.

CR011 Reduction—General Considerations: CR011 is produced as an IgG2 isotype product and contains 6 disulfide bridges in the hinge region. These disulfides can be reduced under mild conditions to give rise to 12 cysteine residues. Therefore, it is possible to maximally attach 12 vcMMAE drug molecules per antibody. For the process, however, the bulk antibody is only partially reduced because the aim is to generate conjugates with an average of 4 vcMMAE molecules. The reason for this is two-fold. First, it broadens the therapeutic window by decreasing potential systemic toxicity associated with MMAE. Second, it is difficult and sometimes impossible to produce fully-loaded conjugates with low aggregation because of greatly reduced solubility imparted by the hydrophobic drug.

Process: Tris-(carboxyethyl)-phosphine or TCEP was added at the 4:1 molar ratio (TCEP:mAb) to CR011 at a concentration of ~5.5 mg/mL in the jacketed reactor equipped with an agitator set to 90 RPM. The reaction was allowed to proceed for 3 hours at 37° C. in the presence of 1 mM EDTA. At the end, Ellman's assay was used to determine the amount of free thiols. Typically, it was 4.2 thiols per antibody. The reactor was then chilled to 4° C.

CR011 Conjugation—General Considerations: TCEP was not fully consumed during the reduction. The left over TCEP was capable of reacting with vcMMAE. However, this spurious side reaction was slower compared to the conjugation reaction and can be mitigated by adding an excess of vcMMAE. The advantage of TCEP compared to DTT is that it does not require removal of the left-over reducing agent.

Process: vcMMAE was dissolved in DMSO and added at 20% molar excess to the reduced CR011 mAb. The reaction was allowed to proceed for 1 hour. The final concentration of DMSO is 4% (v/v). DMSO played a dual purpose in the process. It is required for solubilizing the drug and also it helps to solubilize the conjugate. At the end of conjugation, N-acetylcysteine was added to quench any unreacted drug.

CR011-vcMMAE Purification: The temperature in the reactor was brought to room temperature. A 40% sucrose stock solution was used to adjust the final sucrose concentration to 10% (w/v) followed by a pH adjustment using 300 mM histidine HCl pH 5.0 buffer to a final pH of 6.0. The conjugate was then purified by diafiltration into 20 mM histidine pH 6.0-10% sucrose (w/v) buffer and using 10 diavolumes. At the end of diafiltration, the conjugate was concentrated to ~7 mg/mL and filtered through a set of three filters consisting of 1.2, 0.45 and finally, 0.22 nm.

CR011-vcMMAE Formulation: The conjugate was formulated by adding Tween-20 to a final concentration of 0.02% and by diluting to 6 mg/mL (±10%) using formulation buffer (20 mM histidine pH 6.0, 10% sucrose, 0.02% Tween-20). The conjugate was then stored at 4° C. until pooling if more than one lot is being manufactured (a.k.a. staging time). After pooling, the final concentration was adjusted to 5.0 mg/mL (±5%) and the drug substance was stored frozen.

1. Pre-conjugation UF/DF: Removal of Sucrose

Experiments were performed to monitor the rate of removal of sucrose during UF/DF by Ellman's assay; and estimate the diavolumes needed to achieve the highest SH-per-Ab ratio.

It was found that it is desirable to conduct at least 6 diavolumes in order to remove sucrose to a level that does not impede CR011 reduction. To ensure robustness, at least 10 diavolumes should be utilized during the process.

2. The Effect of Percent DMSO on Aggregation in the Conjugation Reaction

Experiments were performed to determine the effect of DMSO in the conjugation reaction on: (1) aggregation; and (2) drug:Ab molar ratio (i.e. completeness of conjugation).

It was found that the percent aggregate in reaction with 12% DMSO was lower than in 15% DMSO, 4.4 and 3.0%, respectively. Formulation pH 9.0 buffer vs. pH 7.0 buffer did not have any effect on aggregation or yield, provided 10% sucrose was included in formulation. The percent aggregate in the 10%, 8%, 6%, and 4% (v/v) DMSO reactions were 2.7, 1.7, 1.0 and 0.5%, respectively. This suggests that CR011 and CR011 AE were very susceptible to aggregation when a higher percentage of DMSO is present.

All four conjugation reactions resulted in a final molar ratio of 4.0 drugs/Ab, suggesting that all four reactions went to completion. Safety margins for DMSO percentage in the conjugation reaction are 4-6%. This predicted to yield an aggregation level of 1% or less.

5. Investigation of Side Reaction During Conjugation of CR011 to vcMMAE

Experiments were performed to: (1) investigate the extent and the kinetics of the side reaction in which maleimide-drug is converted into an unreactive side product, which results in an incomplete conjugation and low drug-loading; (2) determine factors that influence the side reaction; and (3) determine whether the old vcMMAE lot (SGD1006-O-04) differed in reactivity compared to the new lot (SGD1006-0-06).

Figure 23:
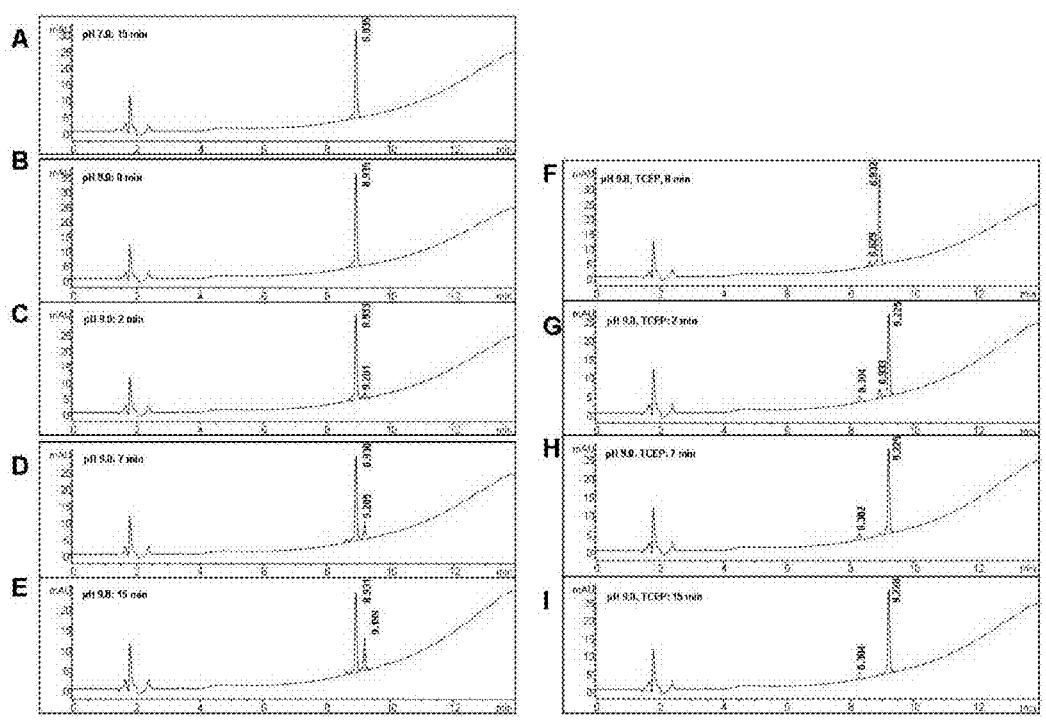
FIG. 23: Reaction of vcMMAE with NAcCys at pH 7.0 and pH 9.0 in the presence or absence of TCEP. 1A: VCMMAE converts fully into NAcCys-adduct following a incubation in phosphate pH 7 buffer. B-E: Appearance of a side product in a course of incubation of vcMMAE in borate buffer. F-I: Appearance of side products in borate pH 9 and in the presence of TCEP.

Reactions (100 μl) containing vcMMAE at 30 μM final concentration, were incubated in borate pH 9.0 buffer either in the absence or in the presence of 2-fold molar excess of TCEP (with respect to vcMMAE). The reactions were quenched at 0, 2, 7 or 15 min with excess NAcCys. The control consisted of vcMMAE in phosphate pH 7.0 buffer quenched at the 15 min time point. The chromatograms are shown on FIG. 23.

In pH 7 phosphate buffer 15 min and in pH 9.0 borate buffer 0 min after addition of the drug a single Cys-quenched product with (rt=9.0 min) is formed (Compare A and B). In borate buffer pH 9.0 an unreactive side product is formed (rt=9.2 min) in a time-dependent fashion (B, C, D and E). In borate buffer and in the presence of TCEP (such as CR011 conjugation conditions), formation of the unreactive product is catalyzed resulting in >90% conversion of maleimide into succinimide after only 2 min of incubation (F through I). Both the old vcMMAE lot (SGD-1006-0-06) and the new lot (SGD-1006-0-04) exhibited similar reactivity towards high pH and TCEP, as well as similar kinetics.

Figure 24:
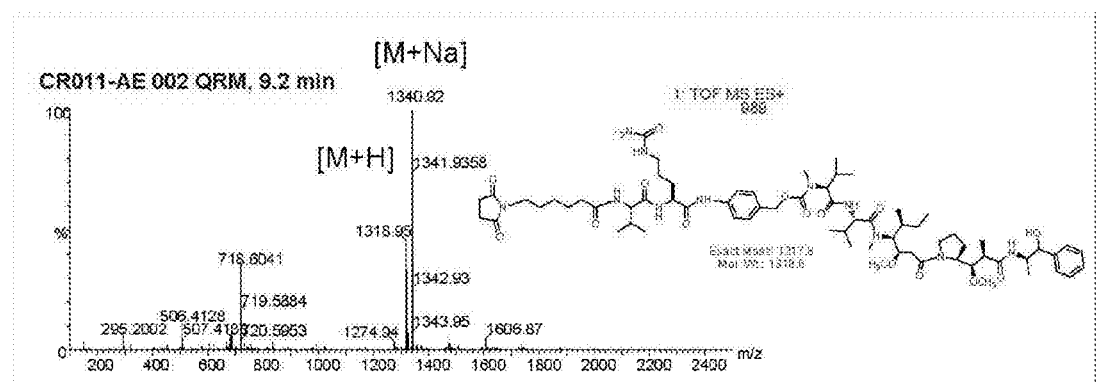
FIG. 24: LCMS identification of the side product with retention time of 9.2 min not capable of reaction with cystein and therefore, not capable of conjugation to CR011.
Figure 25:
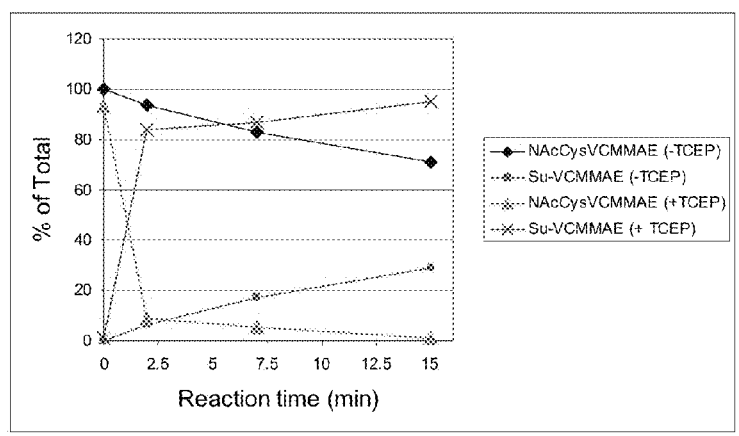
FIG. 25: Kinetics of the formation of NAcCys-vcMMAE and of the side product (succinimidyl-vcMMAE) following incubation in borate pH 9.0 buffer in the presence or absence of TCEP.

FIG. 24 shows the LC-MS identification of the unreactive product as succinimidyl-VCMMAE (rt=9.2 min, m/z=1318). FIG. 25 shows the relative kinetics of formation of the succinimide in the presence or absence of TCEP.

Conclusions:

The side product is a result of conjugation performed at pH 9 instead of pH 7.4 (PBS). Formation of the side product is greatly enhanced in the presence of TCEP. The major stable side product has been identified by LC-MS as succinimidyl-vcMMAE. Minor and less stable side-products remain to be identified. Both vcMMAE lots behaved similarly.

6. Overcoming the Side Reaction During Conjugation of CR011 to vcMMAE

Experiments were performed to investigate whether the side reaction can be overcome by providing a larger excess of the drug for conjugation.

Several ways to suppress the side reaction were proposed: (1) Conducting conjugation at lower pH, e.g. 8.5 instead of 9.0 (high risk due to reduced solubility of CR011); (2) Removal of the excess of TCEP by UF/DF (not practical); and (3) Elevation of the excess of VCMMAE added upfront (practical).

100 mg of CR011 that was previously buffer exchanged into 50 mM borate-50 mM NaCl, was reduced with TCEP to generate 4.35 free thiols per Ab. The reaction was divided into two halves. For the first 50 mg half, a 10% excess of VCM-MAE was added based on the 1 drug per thiol ratio. For the second half, a 20% excess was used. The conjugates were purified by UF/DF into 10 mM Histidine pH 6/10% sucrose solution. The results are summarized in Table 60.

TABLE 60

Preparation of CR011-VCMMAE conjugates using various excess of vcMMAE based on the 1 drug per thiol ratio. Drug-to-Ab ratios were determined by RP HPLC.

| | VCMMAE Excess, % | |
|---|---|---|
| | 10 | 20 |
| SH per Ab | 4.35 | 4.35 |
| Drug-to-Ab ratio (in reaction) | 3.9 | 4.1 |
| Drug-to-Ab ratio (in final product) | 3.7 | 4.0 |

Conclusions

Using 10% versus 20% excess of vcMMAE was compared in a 100 mg conjugation. The higher excess of vcMMAE afforded a drug-to-Ab ratio closer to the expected value, and therefore, has been determined to be optimal.

Equivalents

The foregoing description and Examples detail certain preferred embodiments of the antibodies and describes the best mode contemplated by the inventors. It will be appreciated, however, that no matter how detailed the foregoing may appear in text, the methods of making and using the antibodies described herein may be practiced in many ways and the invention should be construed in accordance with the appended claims and any equivalents thereof. The foregoing written specification is considered to be sufficient to enable one skilled in the art to practice the embodiments described herein.

What is claimed is:

1. An isolated monoclonal human antibody that specifically binds GPNMB comprising a combination of a variable heavy chain and a variable light chain selected from the group consisting of:
  (a) the variable heavy chain amino acid sequence of: SEQ ID NO:20, and the variable light chain amino acid sequence of SEQ ID NO: 29;
  (b) the variable heavy chain amino acid sequence of SEQ ID NO:74 and the variable light chain amino acid sequence of SEQ ID NO: 83;
  (c) the variable heavy chain amino acid sequence of SEQ ID NO: 164 and the variable light chain amino acid sequence of SEQ ID NO: 173;
  (d) the variable heavy chain amino acid sequence of SEQ ID NO: 38 and the variable light chain amino acid sequence of SEQ ID NO: 47; and
  (e) the variable heavy chain amino acid sequence of SEQ ID NO: 310 and the variable light chain amino acid sequence of SEQ ID NO: 319.

2. An isolated monoclonal human antibody that specifically binds GPNMB comprising a heavy chain polypeptide comprising an amino acid sequence comprising three complementarity determining regions (CDRs) and a light chain polypeptide comprising an amino acid sequence comprising three CDRs, where the three heavy chain CDRs and the three light chain CDRS are selected from the group consisting of:
  (a) a heavy chain CDR1 comprising the amino acid sequence of SEQ ID NO: 22, a heavy chain CDR2 comprising the amino acid sequence of SEQ ID NO: 24, a heavy chain CDR3 comprising the amino acid sequence of SEQ ID NO: 26, a light chain CDR1 comprising the amino acid sequence of SEQ ID NO: 31, a light chain CDR2 comprising the amino acid sequence 33, and a light chain CDR3 comprising the amino acid sequence of SEQ ID NO: 35;
  (b) a heavy chain CDR1 comprising the amino acid sequence of SEQ ID NO: 40, a heavy chain CDR2 comprising the amino acid sequence of SEQ ID NO: 42, a heavy chain CDR3 comprising the amino acid sequence of SEQ ID NO: 44, a light chain CDR1 comprising the amino acid sequence of SEQ ID NO: 49, a light chain CDR2 comprising the amino acid sequence 51, and a light chain CDR3 comprising the amino acid sequence of SEQ ID NO: 53;
  (c) a heavy chain CDR1 comprising the amino acid sequence of SEQ ID NO: 76, a heavy chain CDR2 comprising the amino acid sequence of SEQ ID NO: 78, a heavy chain CDR3 comprising the amino acid sequence of SEQ ID NO: 80, a light chain CDR1 comprising the amino acid sequence of SEQ ID NO: 85, a light chain CDR2 comprising the amino acid sequence 87, and a light chain CDR3 comprising the amino acid sequence of SEQ ID NO: 89;
  (d) a heavy chain CDR1 comprising the amino acid sequence of SEQ ID NO: 166, a heavy chain CDR2 comprising the amino acid sequence of SEQ ID NO: 168, a heavy chain CDR3 comprising the amino acid sequence of SEQ ID NO: 170, a light chain CDR1 comprising the amino acid sequence of SEQ ID NO: 175, a light chain CDR2 comprising the amino acid sequence 177, and a light chain CDR3 comprising the amino acid sequence of SEQ ID NO: 179; and (e) a heavy chain CDR1 comprising the amino acid sequence of SEQ ID NO: 312, a heavy chain CDR2 comprising the amino acid sequence of SEQ ID NO: 314, a heavy chain CDR3 comprising the amino acid sequence of SEQ ID NO: 316, a light chain CDR1 comprising the amino acid sequence of SEQ ID NO: 321, a light chain CDR2 comprising the amino acid sequence 323, and a light chain CDR3 comprising the amino acid sequence of SEQ ID NO: 325.

3. The antibody of claim 2, wherein the antibody is selected from the group consisting of: Mab1.15.1, Mab1.2.2,, Mab2.10.2, Mab2.22.1, and Mab2.6.1.

4. The antibody of claim 2, wherein said antibody is an IgG1 antibody.

5. An immunoconjugate comprising the antibody of claim 2 and a cytotoxic agent.

6. The immunoconjugate of claim 5, wherein said antibody comprises a heavy chain CDR1 comprising the amino acid sequence of SEQ ID NO: 22, a heavy chain CDR2 comprising the amino acid sequence of SEQ ID NO: 24, a heavy chain CDR3 comprising the amino acid sequence of SEQ ID NO: 26, a light chain CDR1 comprising the amino acid sequence of SEQ ID NO: 31, a light chain CDR2 comprising the amino acid sequence 33, and a light chain CDR3 comprising the amino acid sequence of SEQ ID NO: 35.

7. The immunoconjugate of claim 5, wherein the cytotoxic agent is auristatin E (dolastatin-10).

8. A pharmaceutical composition comprising the immunoconjugate of claim 5.

9. A single chain Fv antibody that specifically binds GPNMB, wherein the anti-GPNMB single chain Fv antibody comprises a $V_L$ domain of a monoclonal human anti-GPNMB antibody linked to a $V_H$ domain of said anti-GPNMB antibody, wherein the $V_L$ domain comprises an amino acid sequence comprising three complementarity determining regions (CDRs) and the $V_H$ domain comprises an amino acid sequence comprising three CDRs, where the three heavy chain CDRs and the three light chain CDRS are selected from the group consisting of:

(a) a heavy chain CDR1 comprising the amino acid sequence of SEQ ID NO: 22, a heavy chain CDR2 comprising the amino acid sequence of SEQ ID NO: 24, a heavy chain CDR3 comprising the amino acid sequence of SEQ ID NO: 26, a light chain CDR1 comprising the amino acid sequence of SEQ ID NO: 31, a light chain CDR2 comprising the amino acid sequence 33, and a light chain CDR3 comprising the amino acid sequence of SEQ ID NO: 35;

(b) a heavy chain CDR1 comprising the amino acid sequence of SEQ ID NO: 40, a heavy chain CDR2 comprising the amino acid sequence of SEQ ID NO: 42, a heavy chain CDR3 comprising the amino acid sequence of SEQ ID NO: 44, a light chain CDR1 comprising the amino acid sequence of SEQ ID NO: 49, a light chain CDR2 comprising the amino acid sequence 51, and a light chain CDR3 comprising the amino acid sequence of SEQ ID NO: 53;

(c) a heavy chain CDR1 comprising the amino acid sequence of SEQ ID NO: 76, a heavy chain CDR2 comprising the amino acid sequence of SEQ ID NO: 78, a heavy chain CDR3 comprising the amino acid sequence of SEQ ID NO: 80, a light chain CDR1 comprising the amino acid sequence of SEQ ID NO: 85, a light chain CDR2 comprising the amino acid sequence 87, and a light chain CDR3 comprising the amino acid sequence of SEQ ID NO: 89;

(d) a heavy chain CDR1 comprising the amino acid sequence of SEQ ID NO: 166, a heavy chain CDR2 comprising the amino acid sequence of SEQ ID NO: 168, a heavy chain CDR3 comprising the amino acid sequence of SEQ ID NO: 170, a light chain CDR1 comprising the amino acid sequence of SEQ ID NO: 175, a light chain CDR2 comprising the amino acid sequence 177, and a light chain CDR3 comprising the amino acid sequence of SEQ ID NO: 179; and (e) a heavy chain CDR1 comprising the amino acid sequence of SEQ ID NO: 312, a heavy chain CDR2 comprising the amino acid sequence of SEQ ID NO: 314, a heavy chain CDR3 comprising the amino acid sequence of SEQ ID NO: 316, a light chain CDR1 comprising the amino acid sequence of SEQ ID NO: 321, a light chain CDR2 comprising the amino acid sequence 323, and a light chain CDR3 comprising the amino acid sequence of SEQ ID NO: 325.

10. The single chain Fv antibody of claim 9 further comprising a single chain Fv antibody that specifically binds CD3, wherein the anti-CD3 single chain Fv antibody comprises a $V_H$ domain of an anti-CD3 antibody linked to a $V_L$ domain of said anti-CD3 antibody.

11. An immunoconjugate comprising a single chain Fv antibody of claim 9 and a cytotoxic agent.

12. The single chain Fv antibody of claim 9 comprising the amino acid sequence of SEQ ID NO: 355.

13. The single chain Fv antibody of claim 10 comprising the amino acid sequence of SEQ ID NO: 357 or SEQ ID NO: 359.

14. The pharmaceutical composition of claim 8, wherein said immunoconjugate has a concentration of 5 mg/ml.

15. The pharmaceutical composition of claim 8 further comprising sucrose, histidine, histidine hydrochloride monohydrate, and polysorbate 20.

16. A pharmaceutical composition comprising 5 mg/ml of the immunoconjugate of claim 7, 10% sucrose, 10 mM histidine, 10 mM histidine hydrochloride monohydrate, and 0.02% (w/v) polysorbate 20.

17. The immunoconjugate of claim 6, wherein the cytotoxic agent is auristatin E (dolastatin-10).

18. A pharmaceutical composition comprising the immunoconjugate of claim 6.

19. The pharmaceutical composition of claim 18, wherein said immunoconjugate has a concentration of 5 mg/ml.

20. The pharmaceutical composition of claim 18 further comprising sucrose, histidine, histidine hydrochloride monohydrate, and polysorbate 20.

21. A pharmaceutical composition comprising 5 mg/ml of the immunoconjugate of claim 6, 10% sucrose, 10 mM histidine, 10 mM histidine hydrochloride monohydrate, and 0.02% (w/v) polysorbate 20.

22. An isolated monoclonal human antibody that specifically binds GPNMB wherein said antibody comprises a heavy chain CDR1 comprising the amino acid sequence of SEQ ID NO: 22, a heavy chain CDR2 comprising the amino acid sequence of SEQ ID NO: 24, a heavy chain CDR3 comprising the amino acid sequence of SEQ ID NO: 26, a light chain CDR1 comprising the amino acid sequence of SEQ ID NO: 31, a light chain CDR2 comprising the amino acid sequence 33, and a light chain CDR3 comprising the amino acid sequence of SEQ ID NO: 35.

23. An isolated monoclonal human antibody that specifically binds GPNMB comprising the variable heavy chain amino acid sequence of SEQ ID NO: 20, and the variable light chain amino acid sequence of SEQ ID NO: 29.

24. An isolated monoclonal human antibody that specifically binds GPNMB which is Mab 1.15.1.

25. An immunoconjugate comprising the antibody of claim 22 and a cytotoxic agent.

26. An immunoconjugate comprising the antibody of claim 23 and a cytotoxic agent.

27. An immunoconjugate comprising the antibody of claim 24 and a cytotoxic agent.

* * * * *